(12) United States Patent
Chamberlain et al.

(10) Patent No.: US 11,840,495 B2
(45) Date of Patent: Dec. 12, 2023

(54) COMPOSITIONS AND METHODS RELATED TO DI-SUBSTITUTED BICYCLO[2.2.1] HEPTANAMINE-CONTAINING COMPOUNDS

(71) Applicants: The Broad Institute, Inc., Cambridge, MA (US); Instituto Carlos Slim de la Salud, A.C., Mexico City (MX); The Brigham and Women's Hospital, Inc., Boston, MA (US)

(72) Inventors: Brian T. Chamberlain, Cambridge, MA (US); David Kornfilt, Cambridge, MA (US); Florence F. Wagner, Cambridge, MA (US); Maria Alimova, Cambridge, MA (US); Anna Greka, Boston, MA (US); Joseph Growney, Cambridge, MA (US)

(73) Assignees: The Broad Institute, Inc., Cambridge, MA (US); Instituto Carlos Slim de la Salud, A.C., Mexico City (MX); Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 17/560,997

(22) Filed: Dec. 23, 2021

(65) Prior Publication Data

US 2022/0242815 A1 Aug. 4, 2022

Related U.S. Application Data

(60) Provisional application No. 63/270,335, filed on Oct. 21, 2021, provisional application No. 63/130,164, filed on Dec. 23, 2020.

(51) Int. Cl.

| | | |
|---|---|---|
| *C07C 211/38* | (2006.01) |
| *A61P 13/12* | (2006.01) |
| *C07C 209/22* | (2006.01) |
| *C07C 215/44* | (2006.01) |
| *C07C 217/52* | (2006.01) |
| *C07C 229/50* | (2006.01) |
| *C07D 295/185* | (2006.01) |
| *C07D 311/96* | (2006.01) |

(52) U.S. Cl.
CPC ............ *C07C 211/38* (2013.01); *A61P 13/12* (2018.01); *C07C 209/22* (2013.01); *C07C 215/44* (2013.01); *C07C 217/52* (2013.01); *C07C 229/50* (2013.01); *C07D 295/185* (2013.01); *C07D 311/96* (2013.01); *C07C 2602/42* (2017.05); *C07C 2603/97* (2017.05); *C07C 2603/98* (2017.05)

(58) Field of Classification Search
CPC .................................................. C07C 211/38
See application file for complete search history.

(56) References Cited

U.S. PATENT DOCUMENTS

| | | | |
|---|---|---|---|
| 3,514,486 A | 5/1970 | Hartzler | |
| 4,837,218 A | 6/1989 | Olney | |
| 6,130,217 A | 10/2000 | Arnold et al. | |
| 6,150,389 A | 11/2000 | Munk et al. | |
| 8,809,397 B2 | 8/2014 | Akireddy et al. | |
| 11,207,278 B2* | 12/2021 | Greka ................. | A61P 13/12 |
| 2003/0023098 A1 | 1/2003 | Chow et al. | |
| 2013/0310373 A1 | 11/2013 | Matsushima et al. | |

FOREIGN PATENT DOCUMENTS

| | | |
|---|---|---|
| CN | 103664639 A | 3/2014 |
| DE | 1110159 B | 7/1961 |
| DE | 2249397 A1 | 5/1974 |
| JP | H08333327 A | 12/1996 |
| WO | WO-96/01813 A1 | 1/1996 |
| WO | WO-2013/026852 A2 | 2/2013 |
| WO | WO-2017048720 A1 | 3/2017 |
| WO | WO-2022/140654 A1 | 6/2022 |
| WO | WO-2022/140677 A1 | 6/2022 |

OTHER PUBLICATIONS

Dvela-Levitt "Small Molecule Targets TMED9 and Promotes Lysosomal Degradation to Reverse Proteinopathy." Cell 178(3), 521-535, e1-e26, Published Jul. 25, 2019.*
Schönherr "Profound Methyl Effects in Drug Discovery and a Call for New C—H Methylation Reactions" Angew. Chem. Int. Ed. 2013, 52, 12256-12267.*
Certificate of Analysis for Product Name: AGN 192403 hydrochloride Catalog No. 1072, Online "https://documents.tocris.com/pdfs/tocris_coa/1072_3_coa.pdf?1677278640&_ga=2.52326827.30120129. 1677278642-821336995.1677278642" Print Date: Aug. 8, 2019 Accessed Feb. 24, 2023.*
Stone "Chemistry and Structure-Activity Relationships of Mecamylamine and Derivatives" J. Med. Chem. 1962, 5, 4, 665-690.*
Carmona et al., "Arene-Ruthenium Chemistry and Bronsted Acid Catalysis of a Chiral Phosphane-Hydroxyl Ligand," Organometallics, 33(3): 616-619 (2014).
Dvela-Levitt et al., "Small molecule targets TMED9 and promotes lysosomal degradation to reverse proteinopathy," Cell, 178(3): 521-535 and e1-e11 (2019).
International Search Report and Written Opinion for International Application No. PCT/US2021/065049 dated Mar. 28, 2022.
International Search Report and Written Opinion for International Application No. PCT/US2021/065090 dated Mar. 3, 2022.
Jones., "Pharmacological Correction of Proteinopathies via Lysosomal Degradation," Biochemistry, 59(6): 727-728 (2020).

(Continued)

*Primary Examiner* — David K O'Dell
(74) *Attorney, Agent, or Firm* — Foley Hoag LLP; David P. Halstead

(57) ABSTRACT

The present disclosure relates to compositions and methods related to bicyclo[2.2.1] heptanamine-containing compounds and salts.

16 Claims, 2 Drawing Sheets

(56) References Cited

OTHER PUBLICATIONS

Kawai et al., "A Method for Determining Absolute Configuration of Cycloalkanamines and Related Compounds by CD Spectra of Their 2,4-Dinitrophenyl Derivatives," Bull. Chem. Soc. Jpm., 58: 304-308 (1985).

Manetti et al., "New Rigid Nicotine Analogues, Carrying a Norbornane Moiety, Are Potent Agonists of α7 and α3* Nicotinic Receptors," J. Med. Chem., 62(4): 1887-1901 (2019).

Munk et al., "Synthesis and Pharmacologic Evaluationof 2-endo-Amino-3-exoisopropylbicyclo[2.2.1]heptane: A Potent Imidazoline1 Receptor Specific Agent," Journal of Medical Chemistry, 39(6): 1193-1195 (1996).

Novakov et al., "An improved synthesis of N-(3-phenylbicyclo[2.2.1]-y1)-N-ethylamine hydrochloride (Fencamfamine)," Pharmaceutical Chemistry Journal, 45(7): 419-422 (2011).

Novakov et al., "Soluble polyimides and copolyimides with increased hydrolytic stability that are based on [(2-amino)- and (2-aminomethyl)bicyclo[2.2.1]hept-3-yl]anilines," Polymer Science Series B vol. 52: 609-613 (2010).

Poos et al., "Bicyclic Bases. III. Isomeric 2-Amino-3-phenylnorbornanes," J. Org. Chem., 26(12): 4898-4904 (1961).

Rehse et al., "[Neuropsychotropic activity of bicyclo[2.2.1]-heptane dopamine analogs]," Archiv der Pharmazie, 320(10): 1042-1050 (1987).

Slobodchikova et al., "Nitro and trichloromethyl-functionalized norbornenes," Russian Journal of General Chemistry, 83(8): 1631-1632 (2013).

Stajer et al., "Application of t-2-benzoyl-t-5-phenylcyclohexane-r-1-carboxylic acid for the preparation of saturated isoindole-fused heterocycles," Journal of the Chemical Society, Perkin Transactions 2, 657-662 (2002).

Vaughan et al., Racemization in the Camphene Hydrochloride-Isobornyl Chloride Rearrangement, J. Am. Chem. Soc., 75(13): 3168-3172 (1953).

Wong et al., "2-Amino-2-oxazolines as Subtype Selective α2 Adrenoceptor Agonists," J. Med. Chem., 43(9): 1699-1704 (2000).

Zhou et al., "Moxonidine inhibits excitatory inputs to airway vagal preganglionic neurons via activation of both α2-adrenoceptors and imidazoline I1 receptors," Brain Research, 1732: 146695 (2020).

* cited by examiner

COMPOSITIONS AND METHODS RELATED TO DI-SUBSTITUTED BICYCLO[2.2.1] HEPTANAMINE-CONTAINING COMPOUNDS

RELATED APPLICATIONS

This application claims the benefit of U.S. Provisional Application No. 63/270,335 filed on Oct. 21, 2021 and U.S. Provisional Application No. 63/130,164 filed on Dec. 23, 2020, the contents of which are fully incorporated by reference herein.

BACKGROUND

BRD4780 also known as rac-3-exo-isopropylbicyclo [2.2.1]heptan-2-endo-amine hydrochloride or AGN192403 has been reported as a selective imidazoline 1 receptor agent and an alpha-2-adrenergic blocking agent. BRD4780 was subsequently found to clear mutant frameshift Mucin 1 protein (MUC1) in vitro and in vivo and was demonstrated to be effective at removing aberrant protein accumulation in a variety of proteinopathies. There is a need for additional compounds and methods for treating proteinopathies and other diseases.

SUMMARY OF THE INVENTION

In one aspect, the present disclosure provides compounds having a structure represented by formula I:

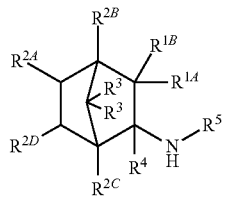

or a pharmaceutically acceptable salt thereof, wherein
$R^{1A}$ and $R^{1B}$ are each independently alkyl, cycloalkyl, aryl, heteroaryl, aralkyl, or heteroaralkyl; or $R^{1A}$ and $R^{1B}$ combine to form a cycloalkyl, cycloalkenyl, or heterocyclyl;
each $R^{2A}$, $R^{2B}$, $R^{2C}$, and $R_{2D}$, is independently selected from H or alkyl;
$R^3$ are both H or both alkyl;
$R^4$ is hydrogen, alkyl, cycloalkyl, aryl, heteroaryl, aralkyl, or heteroaralkyl;
$R^5$ is hydrogen, $C(O)OR^6$ (i.e., to form a carbamate); and
$R^6$ is aralkyl or heteroaralkyl.

Figure 1:
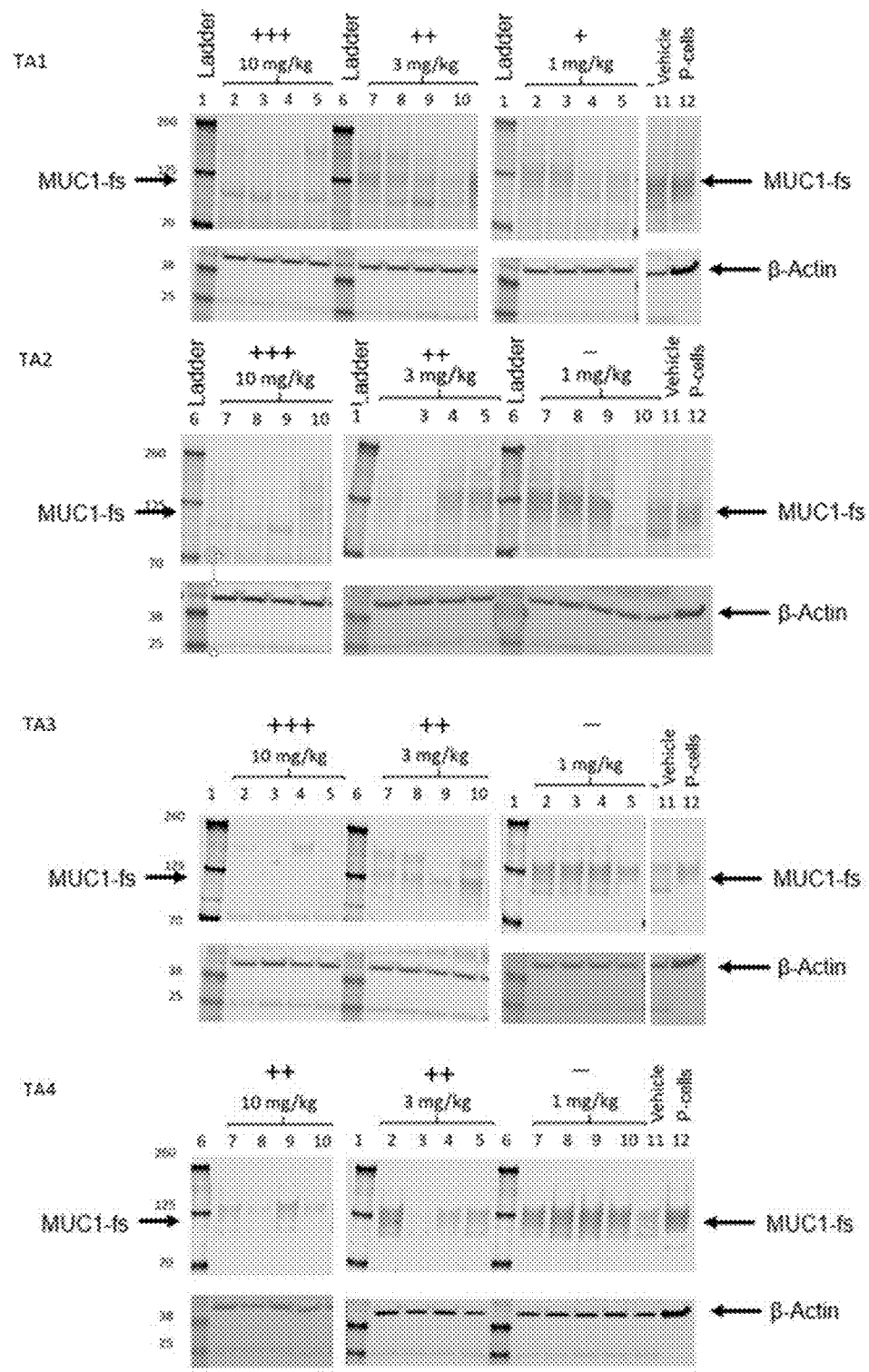
FIG. 1. Western blots probing for MUC1-fs from kidney collected at 4 hr post dose of MUC1-fs C57BL/6 transgenic mice treated with TA1, 2, 3, or 4, once daily for 7 days at doses of 1, 3, or 10 mg/kg. Vehicle and P-cells lanes for MUC1-fs expression are positive controls. Beta-actin is loading control. +++ indicates that the compound shows excellent efficacy at removing MUC1-fs; ++ indicates that the compound shows moderate efficacy at removing MUC1-fs; − indicates that the compound shows low efficacy.
Figure 2:
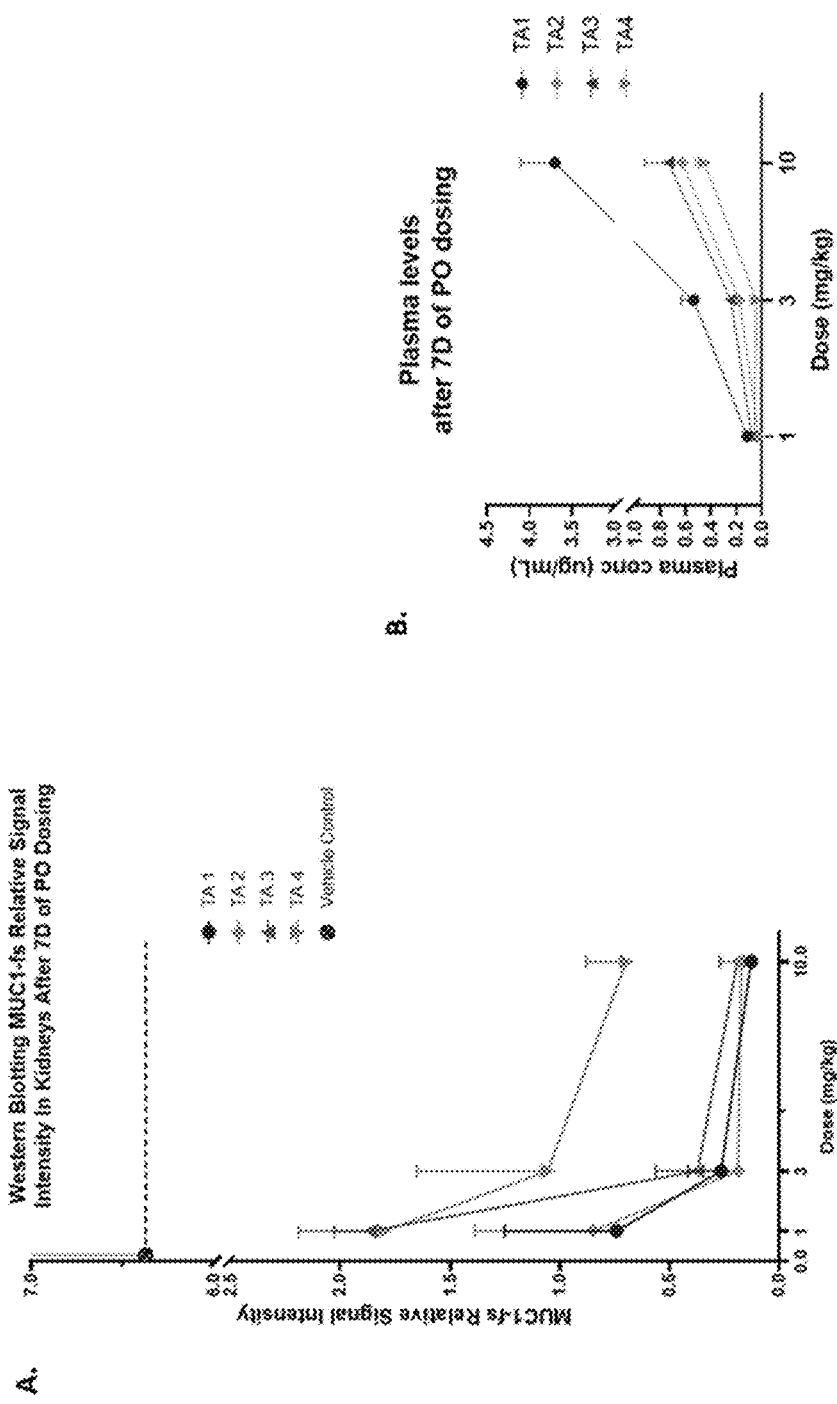
FIG. 2. Determination of levels of MUC1-fs in kidneys and of test article in plasma at 4 hr post dose after 7 days of oral dosing, once a day, at 1, 3 or 10 mg/kg (n=4 per treatment group)

A. C57BL/6 mice kidney MUC1-fs relative signal intensity to β-actin (loading control) signal intensity were determined by western blot analysis. Dotted line represents mean relative signal for vehicle control.

B. C57BL/6 mice plasma samples were analyzed by LC/MS to determine the concentrations of TA1, 2, 3 and 4, at each dose.

DETAILED DESCRIPTION OF THE INVENTION

In one aspect, the present disclosure provides compounds having a structure represented by formula I:

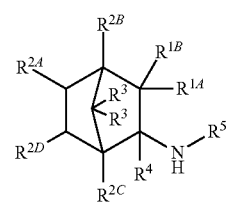

or a pharmaceutically acceptable salt thereof, wherein
$R^{1A}$ and $R^{1B}$ are each independently alkyl, cycloalkyl, aryl, heteroaryl, aralkyl, or heteroaralkyl; or $R^{1A}$ and $R^{1B}$ combine to form a cycloalkyl, cycloalkenyl, or heterocyclyl;
each $R^{2A}$, $R^{2B}$, $R^{2C}$, and $R^{2D}$ is independently selected from H or alkyl;
$R^3$ are both H or both alkyl;
$R^4$ is hydrogen, alkyl, cycloalkyl, aryl, heteroaryl, aralkyl, or heteroaralkyl;
$R^5$ is hydrogen, or $C(O)OR^6$ (i.e., to form a carbamate); and
$R^6$ is aralkyl or heteroaralkyl.

In certain embodiments, the compound is

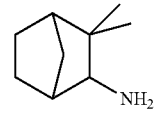

not or a hydrochloride salt thereof.
In certain embodiments, the compound is not any salt of

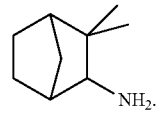

In certain embodiments, the compound has a structure represented by formula Ia or Ib:

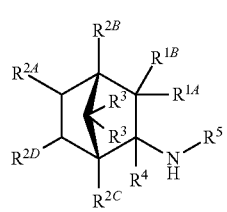

Ib

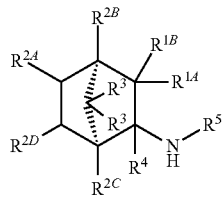

or a pharmaceutically acceptable salt thereof.

In certain embodiments, the compound has a structure represented by formula Iaa, Iab, Iac, or Iad:

Iaa

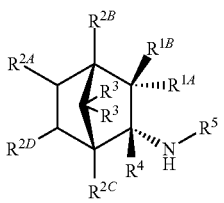

Iab

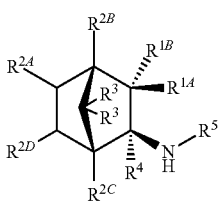

Iac

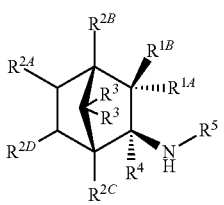

Iad

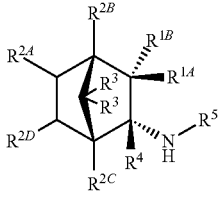

or a pharmaceutically acceptable salt thereof.

In certain embodiments, the compound has a structure represented by formula Iba, Ibb, Ibc, or Ibd:

Iba

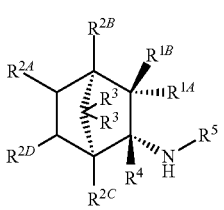

Ibb

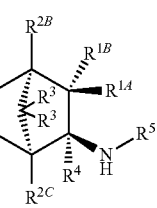

Ibc

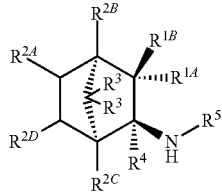

Ibd

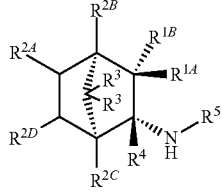

or a pharmaceutically acceptable salt thereof.

In certain embodiments, the compound has an enantiomeric excess (ee) or diastereomeric excess (de) greater than 95%, 96%, 97%, 98%, or 99%. In certain embodiments, the compound is substantially free of one enantiomer and/or substantially free of one or more (preferably all) other diastereomers. In certain embodiments, the compound is a single enantiomer or a single diastereomer.

In certain embodiments, $R^{1A}$ is alkyl. In certain embodiments, $R^{1A}$ is methyl, ethyl, propyl, isopropyl, butyl, or tertbutyl. In certain embodiments, $R^{1A}$ is aralkyl. In certain embodiments, $R^{1A}$ is benzyl. In certain embodiments, wherein $R^{1A}$ is cycloalkyl. In certain embodiments, $R^{1A}$ is cyclopropyl. In certain embodiments, $R^{1A}$ is aryl. In certain embodiments, $R^{1A}$ is phenyl. In certain embodiments, $R^{1B}$ is alkyl. In certain embodiments, $R^{1B}$ is methyl, ethyl, propyl, isopropyl, butyl, or tertbutyl. In certain embodiments, $R^{1B}$ is aralkyl. In certain embodiments, $R^{1B}$ is benzyl. In certain embodiments, $R^{1B}$ is cycloalkyl. In certain embodiments, $R^{1B}$ is cyclopropyl. In certain embodiments, $R^{1B}$ is aryl. In certain embodiments, $R^{1B}$ is phenyl.

In certain embodiments, $R^{1A}$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, alkylsulfonyl, or sulfonamide. In certain embodiments, $R^{1A}$ is substituted with alkyl (e.g., methyl), hydroxyl, amino, alkylamino (e.g., dimethylamino), amido, alkoxy (e.g., methoxy or ethoxy), heterocyclylamido (e.g., morpholinoamido or piperidinylamido), acyloxy (e.g., acetyloxy), or ester (e.g., ethylester). In certain embodiments, $R^{1B}$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, alkylsulfonyl, or sulfonamide. In certain embodiments, $R^{1B}$ is substituted with alkyl (e.g., methyl), hydroxyl, amino, alkylamino (e.g., dimethylamino), amido, alkoxy (e.g., methoxy or ethoxy), heterocyclylamido (e.g., morpholinoamido or piperidinylamido), acyloxy (e.g., acetyloxy), or ester (e.g., ethylester). In certain embodiments, $R^{1A}$ and $R^{1B}$ combine to form a cycloalkyl. In certain embodiments, $R^{1A}$ and $R^{1B}$ combine to form a cyclobutyl, cyclopently, cyclohexyl, cycloheptyl, bicycloheptanyl, cyclooctyl, or bicyclooctanyl.

In certain embodiments, $R^{1A}$ and $R^{1B}$ combine to form a cycloalkenyl. In certain embodiments, $R^{1A}$ and $R^{1B}$ combine to form a cyclopentenyl or cyclohexenyl. In certain embodiments, $R^{1A}$ and $R^{1B}$ combine to form a heterocyclyl. In certain embodiments, $R^{1A}$ and $R^{1B}$ combine to form a tetrahydrofuranyl, tetrahydropyranyl, tetrahydrocyclopentadioxolyl, oxabicycloheptanyl, piperidinyl, or azabicycloheptanyl. In certain embodiments, $R^{1A}$ and $R^{1B}$ combine to form a cycloalkyl, cycloalkenyl, or heterocyclyl and the cycloalkyl, cycloalkenyl, or heterocyclyl is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, alkylsulfonyl, or sulfonamide. In certain embodiments, $R^{1A}$ and $R^{1B}$ combine to form a cycloalkyl, cycloalkenyl, or heterocyclyl and the cycloalkyl, cycloalkenyl, or heterocyclyl is substituted with alkyl (e.g., methyl), hydroxyl, amino, alkylamino (e.g., dimethylamino), amido, alkoxy (e.g., methoxy or ethoxy), heterocyclylamido (e.g., morpholinoamido or piperidinylamido), acyloxy (e.g., acetyloxy), or ester (e.g., ethyl ester).

In certain embodiments, $R^{2A}$ is hydrogen. In certain embodiments, $R^{2B}$ is hydrogen. In certain embodiments, $R^{2C}$ is hydrogen. In certain embodiments, $R^{2D}$ is hydrogen. In certain embodiments, each $R^3$ is hydrogen. In certain embodiments, each $R^3$ is alkyl. In certain embodiments, each $R^3$ is the same. In certain embodiments, each $R^3$ is methyl.

In certain embodiments, $R^4$ is hydrogen. In certain embodiments, $R^4$ is alkyl. In certain embodiments, $R^4$ is methyl. In certain embodiments, $R^4$ is aryl. In certain embodiments, $R^4$ is phenyl. In certain embodiments, $R^4$ is heterocyclyl. In certain embodiments, pyridyl or thiophenyl. In certain embodiments, $R^5$ is hydrogen.

In one aspect, the present disclosure provides a compound represented by formula II:

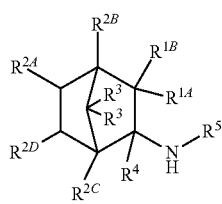

II or a stereoisomer or pharmaceutically acceptable salt thereof, wherein:
$R^{1A}$ and $R^{1B}$ are each independently $C_{1-6}$ alkyl, $C_{2-6}$ alkenyl, $C_{2-6}$ alkynyl, a 3-6 membered saturated or partially unsaturated monocyclic carbocyclic ring, phenyl, a 3-6 membered saturated or partially unsaturated monocyclic heterocyclic ring having 1-3 heteroatoms independently selected from nitrogen, oxygen, and sulfur, a 5-6 membered monocyclic heteroaryl ring having 1-4 heteroatoms independently selected from nitrogen, oxygen, and sulfur, an 8-10 membered bicyclic or bridged bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur;
or $R^{1A}$ and $R^{1B}$, taken together with the carbon atom to which they are attached, combine to form a 3, 4, 5, 6, 7, or 8 membered saturated or partially unsaturated monocyclic or bicyclic carbocyclic ring or a 3, 4, 5, 6, 7, or 8 membered saturated or partially unsaturated monocyclic or bicyclic heterocyclic ring having 1-3 heteroatoms independently selected from nitrogen, oxygen, and sulfur;
wherein $R^{1A}$ and $R^{1B}$ are each independently and optionally substituted with 1, 2, 3, 4, 5, or 6 deuterium or halogen atoms, or 1, 2, or 3 instances of $R^x$;
each $R^{2A}$, $R^{2B}$, $R^{2C}$, and $R^{2D}$ is independently H or $C_{1-6}$ alkyl;
both instances of $R^3$ are H or are $C_{1-6}$ alkyl;
$R^4$ is H;
$R^5$ is H or —C(O)OR$^6$;
$R^6$ is $C_{1-6}$ alkyl substituted with one instance of: phenyl, an 8-12 membered bicyclic aromatic ring, a 5-6 membered heteroaryl ring having 1-3 heteroatoms independently selected from nitrogen, oxygen, and sulfur, or an 8-12 membered bicyclic heteroaryl ring having 1-5 heteroatoms independently selected from nitrogen, oxygen, and sulfur;
each $R^x$ is independently oxo, halogen, —CN, —NO$_2$, —OR, —SR, —N(R)$_2$, —S(O)$_2$R, —S(O)$_2$NR$_2$, —S(O)R, —S(O)NR$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)S(O)$_2$R, —S(NR)(O)R, or $C_{1-6}$ alkyl, $C_{2-6}$ alkenyl, or $C_{2-6}$ alkynyl optionally substituted with one instance of oxo, halogen, —CN, —OR, —SR, —N(R)$_2$, or —C(O)OR; and
each R is independently H, $C_{1-6}$ aliphatic, phenyl, biphenyl, naphthalenyl, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, an 8-10 membered bicyclic heteroaryl ring having 1-4 heteroatoms independently selected from nitrogen, oxygen, and sulfur, a 7-12 membered saturated or partially unsaturated bicyclic heterocyclic ring having 1-4 heteroatoms independently selected from nitrogen, oxygen, and sulfur, a 8-12 membered saturated or partially unsaturated bridged bicyclic ring having 0-3 heteroatoms independently selected from nitrogen, oxygen, and sulfur, a 6-10 membered saturated or partially unsaturated spirocyclic ring having 0-3 heteroatoms independently selected from nitrogen, oxygen, and sulfur, or a 6-11 membered saturated or partially unsaturated bicyclic carbocyclic ring; or:
two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

wherein each R is independently and optionally substituted with one instance of $R^x$;

provided that $R^{1A}$ and $R^{1B}$ are not both methyl.

In another aspect, the present invention provides a compound represented by formula III:

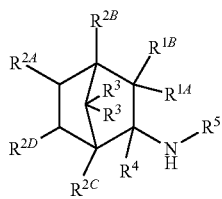

III or a stereoisomer or pharmaceutically acceptable salt thereof, wherein:

$R^{1A}$ and $R^{1B}$ are each independently $C_{1-6}$ alkyl, $C_{2-6}$ alkenyl, $C_{2-6}$ alkynyl, a 3-6 membered saturated or partially unsaturated monocyclic carbocyclic ring, phenyl, a 3-6 membered saturated or partially unsaturated monocyclic heterocyclic ring having 1-3 heteroatoms independently selected from nitrogen, oxygen, and sulfur, a 5-6 membered monocyclic heteroaryl ring having 1-4 heteroatoms independently selected from nitrogen, oxygen, and sulfur, an 8-10 membered bicyclic or bridged bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur;

or $R^{1A}$ and $R^{1B}$, taken together with the carbon atom to which they are attached, combine to form a 3, 4, 5, 6, 7, or 8 membered saturated or partially unsaturated monocyclic or bicyclic carbocyclic ring or a 3, 4, 5, 6, 7, or 8 membered saturated or partially unsaturated monocyclic or bicyclic heterocyclic ring having 1-3 heteroatoms independently selected from nitrogen, oxygen, and sulfur;

wherein $R^{1A}$ and $R^{1B}$ are each independently and optionally substituted with 1, 2, 3, 4, 5, or 6 deuterium or halogen atoms, or 1, 2, or 3 instances of $R^x$;

each $R^{2A}$, $R^{2B}$, $R^{2C}$, and $R^{2D}$ is independently H or $C_{1-6}$ alkyl;

both instances of $R^3$ are H or are $C_{1-6}$ alkyl;

$R^4$ is $C_{1-6}$ alkyl, $C_{2-6}$ alkenyl, $C_{2-6}$ alkynyl, a 3-6 membered saturated or partially unsaturated monocyclic carbocyclic ring, phenyl, a 5-6 membered monocyclic heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur;

wherein $R^4$ is optionally substituted with 1, 2, 3, 4, 5, or 6 deuterium or halogen atoms, or 1, 2, or 3 instances of $R^y$;

$R^5$ is H or —C(O)$OR^6$;

$R^6$ is $C_{1-6}$ alkyl substituted with one instance of: phenyl, an 8-12 membered bicyclic aromatic ring, a 5-6 membered heteroaryl ring having 1-3 heteroatoms independently selected from nitrogen, oxygen, and sulfur, or an 8-12 membered bicyclic heteroaryl ring having 1-5 heteroatoms independently selected from nitrogen, oxygen, and sulfur;

each $R^x$ is independently oxo, halogen, —CN, —NO$_2$, —OR, —SR, —N(R)$_2$, —S(O)$_2$R, —S(O)$_2$NR$_2$, —S(O)R, —S(O)NR$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)S(O)$_2$R, —S(NR)(O)R, or $C_{1-6}$ alkyl, $C_{2-6}$ alkenyl, or $C_{2-6}$ alkynyl optionally substituted with one instance of oxo, halogen, —CN, —OR, —SR, —N(R)$_2$, or —C(O)OR;

each $R^y$ is independently oxo, halogen, —CN, —NO$_2$, —OR, —SR, —N(R)$_2$, —S(O)$_2$R, —S(O)$_2$NR$_2$, —S(O)R, —S(O)NR$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)S(O)$_2$R, —S(NR)(O)R, or $C_{1-6}$ alkyl, $C_{2-6}$ alkenyl, or $C_{2-6}$ alkynyl optionally substituted with one instance of oxo, halogen, —CN, —OR, —SR, —N(R)$_2$, or —C(O)OR; and each R is independently H, $C_{1-6}$ aliphatic, phenyl, biphenyl, naphthalenyl, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, an 8-10 membered bicyclic heteroaryl ring having 1-4 heteroatoms independently selected from nitrogen, oxygen, and sulfur, a 7-12 membered saturated or partially unsaturated bicyclic heterocyclic ring having 1-4 heteroatoms independently selected from nitrogen, oxygen, and sulfur, a 5-8 membered saturated or partially unsaturated bridged bicyclic ring having 0-3 heteroatoms independently selected from nitrogen, oxygen, and sulfur, a 6-10 membered saturated or partially unsaturated spirocyclic ring having 0-3 heteroatoms independently selected from nitrogen, oxygen, and sulfur, or a 6-11 membered saturated or partially unsaturated bicyclic carbocyclic ring; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

wherein each R is independently and optionally substituted with one instance of $R^x$; provided that $R^{1A}$ and $R^{1B}$ are not both methyl, and that the compound is not

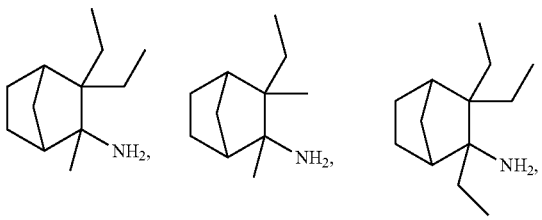

-continued

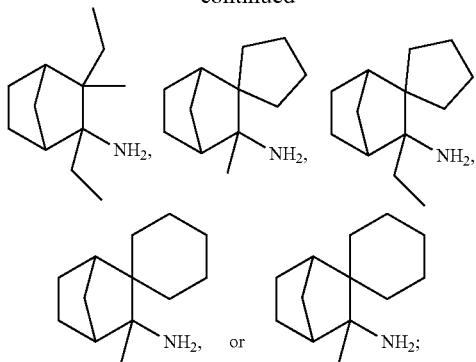

or a stereoisomer or salt thereof.

The following embodiments apply to compounds of formula II and III.

As defined generally above, $R^{1A}$ and $R^{1B}$ are each independently $C_{1-6}$ alkyl, $C_{2-6}$ alkenyl, $C_{2-6}$ alkynyl, a 3-6 membered saturated or partially unsaturated monocyclic carbocyclic ring, phenyl, a 3-6 membered saturated or partially unsaturated monocyclic heterocyclic ring having 1-3 heteroatoms independently selected from nitrogen, oxygen, and sulfur, a 5-6 membered monocyclic heteroaryl ring having 1-4 heteroatoms independently selected from nitrogen, oxygen, and sulfur, an 8-10 membered bicyclic or bridged bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur; or $R^{1A}$ and $R^{1B}$, taken together with the carbon atom to which they are attached, combine to form a 3, 4, 5, 6, 7, or 8 membered saturated or partially unsaturated monocyclic or bicyclic carbocyclic ring or a 3, 4, 5, 6, 7, or 8 membered saturated or partially unsaturated monocyclic or bicyclic heterocyclic ring having 1-3 heteroatoms independently selected from nitrogen, oxygen, and sulfur; wherein $R^{1A}$ and $R^{1B}$ are each independently and optionally substituted with 1, 2, 3, 4, 5, or 6 deuterium or halogen atoms, or 1, 2, or 3 instances of $R^x$.

In some embodiments, $R^{1A}$ is $C_{1-6}$ alkyl. In some embodiments, $R^{1A}$ is $C_{2-6}$ alkenyl. In some embodiments, $R^{1A}$ is $C_{2-6}$ alkynyl. In some embodiments, $R^{1A}$ is a 3-6 membered saturated or partially unsaturated monocyclic carbocyclic ring. In some embodiments, $R^{1A}$ is phenyl. In some embodiments, $R^{1A}$ is a 3-6 membered saturated or partially unsaturated monocyclic heterocyclic ring having 1-3 heteroatoms independently selected from nitrogen, oxygen, and sulfur. In some embodiments, $R^{1A}$ is a 5-6 membered monocyclic heteroaryl ring having 1-4 heteroatoms independently selected from nitrogen, oxygen, and sulfur. In some embodiments, $R^{1A}$ is an 8-10 membered bicyclic or bridged bicyclic saturated or partially unsaturated heterocyclic ring having 1-5 heteroatoms independently selected from nitrogen, oxygen, and sulfur. In some embodiments, $R^{1A}$ is an 8-10 membered bicyclic heteroaryl ring having 1-5 heteroatoms independently selected from nitrogen, oxygen, and sulfur.

In some embodiments, $R^{1A}$ and $R^{1B}$, taken together with the carbon atom to which they are attached, combine to form a 3, 4, 5, 6, 7, or 8 membered saturated or partially unsaturated monocyclic or bicyclic carbocyclic ring. In some embodiments, $R^{1A}$ and $R^{1B}$, taken together with the carbon atom to which they are attached, combine to form a 3, 4, 5, 6, 7, or 8 membered saturated or partially unsaturated monocyclic or bicyclic heterocyclic ring having 1-3 heteroatoms independently selected from nitrogen, oxygen, and sulfur.

As defined above, $R^{1A}$ is independently and optionally substituted with 1, 2, 3, 4, 5, or 6 deuterium or halogen atoms, or 1, 2, or 3 instances of $R^x$. In some embodiments, $R^{1A}$ is substituted with 1, 2, 3, 4, 5, or 6 deuterium atoms. In some embodiments, $R^{1A}$ is substituted with 1, 2, 3, 4, 5, or 6 halogen atoms. In some embodiments, $R^{1A}$ is substituted with 1 instance of $R^x$. In some embodiments, $R^{1A}$ is substituted with 2 instances of $R^x$. In some embodiments, $R^{1A}$ is substituted with 3 instances of $R^x$.

In some embodiments, $R^{1B}$ is $C_{1-6}$ alkyl. In some embodiments, $R^{1B}$ is $C_{2-6}$ alkenyl. In some embodiments, $R^{1B}$ is $C_{2-6}$ alkynyl. In some embodiments, $R^{1B}$ is a 3-6 membered saturated or partially unsaturated monocyclic carbocyclic ring. In some embodiments, $R^{1B}$ is phenyl. In some embodiments, $R^{1B}$ is a 3-6 membered saturated or partially unsaturated monocyclic heterocyclic ring having 1-3 heteroatoms independently selected from nitrogen, oxygen, and sulfur. In some embodiments, $R^{1B}$ is a 5-6 membered monocyclic heteroaryl ring having 1-4 heteroatoms independently selected from nitrogen, oxygen, and sulfur. In some embodiments, $R^{1B}$ is an 8-10 membered bicyclic or bridged bicyclic saturated or partially unsaturated heterocyclic ring having 1-5 heteroatoms independently selected from nitrogen, oxygen, and sulfur. In some embodiments, $R^{1B}$ is an 8-10 membered bicyclic heteroaryl ring having 1-5 heteroatoms independently selected from nitrogen, oxygen, and sulfur.

As defined above, $R^{1B}$ is independently and optionally substituted with 1, 2, 3, 4, 5, or 6 deuterium or halogen atoms, or 1, 2, or 3 instances of $R^x$. In some embodiments, $R^{1B}$ is substituted with 1, 2, 3, 4, 5, or 6 deuterium atoms. In some embodiments, $R^{1B}$ is substituted with 1, 2, 3, 4, 5, or 6 halogen atoms. In some embodiments, $R^{1B}$ is substituted with 1 instance of $R^x$. In some embodiments, $R^{1B}$ is substituted with 2 instances of $R^x$. In some embodiments, $R^{1B}$ is substituted with 3 instances of $R^x$.

In some embodiments, $R^{1A}$ and $R^{1B}$ are each independently $C_{1-4}$ alkyl, $C_{2-4}$ alkenyl, $C_{2-4}$ alkynyl, a 3-6 membered saturated or partially unsaturated monocyclic carbocyclic ring, phenyl, a 3-6 membered saturated or partially unsaturated monocyclic heterocyclic ring having 1 or 2 heteroatoms independently selected from nitrogen, oxygen, and sulfur, or a 5-6 membered monocyclic heteroaryl ring having 1 or 2 heteroatoms independently selected from nitrogen, oxygen, and sulfur; or $R^{1A}$ and $R^{1B}$, taken together with the carbon atom to which they are attached, combine to form a 3, 4, 5, 6, 7, or 8 membered saturated or partially unsaturated monocyclic or bicyclic carbocyclic ring or a 3, 4, 5, 6, 7, or 8 membered saturated or partially unsaturated monocyclic or bicyclic heterocyclic ring having 1-3 heteroatoms independently selected from nitrogen, oxygen, and sulfur; wherein $R^{1A}$ and $R^{1B}$ are each independently and optionally substituted with 1, 2, 3, 4, 5, or 6 deuterium or halogen atoms, or 1, 2, or 3 instances of $R^x$.

In some embodiments, $R^{1A}$ and $R^{1B}$ are each independently $C_{1-6}$ alkyl, $C_{2-6}$ alkenyl, $C_{2-6}$ alkynyl, cyclopropyl, cyclobutyl, or cyclopentyl; or $R^{1A}$ and $R^{1B}$, taken together with the carbon atom to which they are attached, combine to form a 3, 4, 5, or 6 membered saturated or partially unsaturated monocyclic carbocyclic ring or a 3, 4, 5, or 6 membered saturated or partially unsaturated monocyclic heterocyclic ring having 1-3 heteroatoms independently selected from nitrogen, oxygen, and sulfur; wherein $R^{1A}$ and $R^{1B}$ are each independently and optionally substituted with 1, 2, 3, 4, 5, or 6 deuterium or halogen atoms, or 1, 2, or 3 instances of $R^x$.

In some embodiments, $R^{1A}$ and $R^{1B}$ are each independently methyl, ethyl, propyl, isopropyl, n-butyl, sec-butyl, tert-butyl, n-pentyl, sec-pentyl, vinyl, allyl, ethynyl, propargyl, cyclopropyl, cyclobutyl, or cyclopentyl; or $R^{1A}$ and $R^{1B}$, taken together with the carbon atom to which they are attached, combine to form a 3, 4, 5, or 6 membered saturated monocyclic carbocyclic ring or a 3, 4, 5, or 6 membered saturated monocyclic heterocyclic ring having 1 or 2 heteroatoms independently selected from nitrogen, oxygen, and sulfur; wherein $R^{1A}$ and $R^{1B}$ are each independently and optionally substituted with 1, 2, 3, 4, 5, or 6 deuterium or halogen atoms, or 1, 2, or 3 instances of $R^x$.

In some embodiments, both $R^{1A}$ and $R^{1B}$ are ethyl. In some embodiments, one of $R^{1A}$ and $R^{1B}$ is methyl. In some embodiments, one of $R^{1A}$ and $R^{1B}$ is ethyl. In some embodiments, one of $R^{1A}$ and $R^{1B}$ is n-propyl or n-butyl. In some embodiments, one of $R^{1A}$ and $R^{1B}$ is methyl and one is ethyl.

As defined generally above, each $R^{2A}$, $R^{2B}$, $R^{2C}$, and $R^{2D}$ is independently H or $C_{1-6}$ alkyl.

In some embodiments, $R^{2A}$ is H. In some embodiments, $R^{2A}$ is $C_{1-6}$ alkyl. In some embodiments, $R^{2A}$ is methyl, ethyl, or propyl. In some embodiments, $R^{2A}$ is methyl.

In some embodiments, $R^{2B}$ is H. In some embodiments, $R^{2B}$ is $C_{1-6}$ alkyl. In some embodiments, $R^{2B}$ is methyl, ethyl, or propyl. In some embodiments, $R^{2B}$ is methyl.

In some embodiments, $R^{2C}$ is H. In some embodiments, $R^{2C}$ is $C_{1-6}$ alkyl. In some embodiments, $R^{2C}$ is methyl, ethyl, or propyl. In some embodiments, $R^{2C}$ is methyl.

In some embodiments, $R^{2D}$ is H. In some embodiments, $R^{2D}$ is $C_{1-6}$ alkyl. In some embodiments, $R^{2D}$ is methyl, ethyl, or propyl. In some embodiments, $R^{2D}$ is methyl.

In some embodiments, $R^{2A}$ and $R^{2B}$ are H. In some embodiments, $R^{2A}$ and $R^{2C}$ are H. In some embodiments, $R^{2A}$ and $R^{2D}$ are H. In some embodiments, $R^{2B}$ and $R^{2C}$ are H. In some embodiments, $R^{2B}$ and $R^{2D}$ are H. In some embodiments, $R^{2C}$ and $R^{2D}$ are H.

In some embodiments, $R^{2A}$, $R^{2B}$, and $R^{2C}$ are H. In some embodiments, $R^{2B}$, $R^{2C}$, and $R^{2D}$ are H. In some embodiments, $R^{2A}$, $R^{2C}$ and $R^{2D}$ are H. In some embodiments, $R^{2A}$, $R^{2B}$, and $R^{2D}$ are H.

In some embodiments, each of $R^{2A}$, $R^{2B}$, $R^{2C}$, and $R^{2D}$ is H. In some embodiments, one of $R^{2A}$, $R^{2B}$, $R^{2C}$, and $R^{2D}$ is $C_{1-6}$ alkyl. In some embodiments, one of $R^{2A}$, $R^{2B}$, $R^{2C}$, and $R^{2D}$ is methyl. In some embodiments, one of $R^{2A}$, $R^{2B}$, $R^{2C}$, and $R^{2D}$ is methyl and the others are H. In some embodiments, $R^{2A}$ and $R^{2B}$ are $C_{1-6}$ alkyl, such as methyl. In some embodiments, $R^{2A}$ and $R^{2C}$ are $C_{1-6}$ alkyl, such as methyl. In some embodiments, $R^{2A}$ and $R^{2D}$ are $C_{1-6}$ alkyl, such as methyl. In some embodiments, $R^{2B}$ and $R^{2C}$ are $C_{1-6}$ alkyl, such as methyl. In some embodiments, $R^{2B}$ and $R^{2D}$ are $C_{1-6}$ alkyl, such as methyl. In some embodiments, $R^{2C}$ and $R^{2D}$ are $C_{1-6}$ alkyl, such as methyl.

As defined generally above, both instances of $R^3$ are H or are $C_{1-6}$ alkyl.

In some embodiments, both instances of $R^3$ are H. In some embodiments, both instances of $R^3$ are $C_{1-6}$ alkyl.

In some embodiments, both instances of $R^3$ are methyl, ethyl, propyl, or n-butyl. In some embodiments, both instances of $R^3$ are methyl.

As defined generally above for formula II, $R^4$ is H.

As defined generally above for formula III, $R^4$ is $C_{1-6}$ alkyl, $C_{2-6}$ alkenyl, $C_{2-6}$ alkynyl, a 3-6 membered saturated or partially unsaturated monocyclic carbocyclic ring, phenyl, a 5-6 membered monocyclic heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur; wherein $R^4$ is optionally substituted with 1, 2, 3, 4, 5, or 6 deuterium or halogen atoms, or 1, 2, or 3 instances of R.

In some embodiments, $R^4$ is $C_{1-6}$ alkyl. In some embodiments, $R^4$ is $C_{3-6}$ alkyl. In some embodiments, $R^4$ is $C_4$-6 alkyl. In some embodiments, $R^4$ is not methyl or ethyl. In some embodiments, $R^4$ is $C_{2-6}$ alkenyl. In some embodiments, $R^4$ is $C_{2-6}$ alkynyl. In some embodiments, $R^4$ is a 3-6 membered saturated or partially unsaturated monocyclic carbocyclic ring. In some embodiments, $R^4$ is phenyl. In some embodiments, $R^4$ is a 5-6 membered monocyclic heteroaryl ring having 1-4 heteroatoms independently selected from nitrogen, oxygen, and sulfur. In some embodiments, $R^4$ is an 8-10 membered bicyclic heteroaryl ring having 1-5 heteroatoms independently selected from nitrogen, oxygen, and sulfur. In some embodiments, $R^4$ is unsubstituted. In some embodiments, $R^4$ is substituted with 1, 2, 3, 4, 5, or 6 deuterium or halogen atoms. In some embodiments, $R^4$ is substituted with 1, 2, or 3 instances of $R^y$.

As defined generally above, $R^5$ is H or —C(O)OR$^6$.

In some embodiments, $R^5$ is H. In some embodiments, $R^5$ is —C(O)OR$^6$.

As defined generally above, $R^6$ is $C_{1-6}$ alkyl substituted with one instance of: phenyl, an 8-12 membered bicyclic aromatic ring, a 5-6 membered heteroaryl ring having 1-3 heteroatoms independently selected from nitrogen, oxygen, and sulfur, or an 8-12 membered bicyclic heteroaryl ring having 1-5 heteroatoms independently selected from nitrogen, oxygen, and sulfur.

In some embodiments, $R^6$ is $C_{1-6}$ alkyl substituted with one instance of phenyl. In some embodiments, $R^6$ is $C_{1-6}$ alkyl substituted with one instance of an 8-12 membered bicyclic aromatic ring. In some embodiments, $R^6$ is $C_{1-6}$ alkyl substituted with one instance of a 5-6 membered heteroaryl ring having 1-3 heteroatoms independently selected from nitrogen, oxygen, and sulfur. In some embodiments, $R^6$ is $C_{1-6}$ alkyl substituted with one instance of an 8-12 membered bicyclic heteroaryl ring having 1-5 heteroatoms independently selected from nitrogen, oxygen, and sulfur.

As defined generally above, each $R^x$ is independently oxo, halogen, —CN, —NO$_2$, —OR, —SR, —N(R)$_2$, —S(O)$_2$R, —S(O)$_2$NR$_2$, —S(O)R, —S(O)NR$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)S(O)$_2$R, —S(NR)(O)R, or $C_{1-6}$ alkyl, $C_{2-6}$ alkenyl, or $C_{2-6}$ alkynyl optionally substituted with one instance of oxo, halogen, —CN, —OR, —SR, —N(R)$_2$, or —C(O)OR.

In some embodiments, $R^x$ is oxo. In some embodiments, $R^x$ is halogen. In some embodiments, $R^x$ is —CN. In some embodiments, $R^x$ is —NO$_2$. In some embodiments, $R^x$ is —OR. In some embodiments, $R^x$ is —SR. In some embodiments, $R^x$ is —N(R)$_2$. In some embodiments, $R^x$ is —S(O)$_2$R. In some embodiments, $R^x$ is —S(O)$_2$NR$_2$. In some embodiments, $R^x$ is —S(O)R. In some embodiments, $R^x$ is —S(O)NR$_2$. In some embodiments, $R^x$ is —C(O)R. In some embodiments, $R^x$ is —C(O)OR. In some embodiments, $R^x$ is —C(O)N(R)$_2$. In some embodiments, $R^x$ is —C(O)N(R)OR. In some embodiments, $R^x$ is —OC(O)R. In some embodiments, $R^x$ is —OC(O)N(R)$_2$. In some embodiments, $R^x$ is —N(R)C(O)OR. In some embodiments, $R^x$ is —N(R)C(O)R. In some embodiments, $R^x$ is —N(R)S(O)$_2$R. In some embodiments, $R^x$ is —S(NR)(O)R. In some embodiments, $R^x$ is $C_{1-6}$ alkyl, $C_{2-6}$ alkenyl, or $C_{2-6}$ alkynyl optionally substituted with one instance of oxo, halogen, —CN, —OR, —SR, —N(R)$_2$, or —C(O)OR. In some embodiments, R$^x$ is C$_{1-6}$ alkyl optionally substituted with one instance of oxo, halogen, —CN, —OR, —SR, —N(R)$_2$, or —C(O)OR. In some embodiments, R$^x$ is C$_{2-6}$ alkenyl optionally substituted with one instance of oxo, halogen, —CN, —OR, —SR, —N(R)$_2$, or —C(O)OR. In some embodiments, R$^x$ is C$_{2-6}$ alkynyl optionally substituted with one instance of oxo, halogen, —CN, —OR, —SR, —N(R)$_2$, or —C(O)OR.

As defined generally above for formula III, each R$^y$ is independently oxo, halogen, —CN, —NO$_2$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)S(O)$_2$R, —S(NR)(O)R, or C$_{1-6}$ alkyl, C$_{2-6}$ alkenyl, or C$_{2-6}$ alkynyl optionally substituted with one instance of oxo, halogen, —CN, —OR, —SR, —N(R)$_2$, or —C(O)OR.

In some embodiments, R$^y$ is oxo. In some embodiments, R$^y$ is halogen. In some embodiments, R$^y$ is —CN. In some embodiments, R$^y$ is —NO$_2$. In some embodiments, R$^y$ is —OR. In some embodiments, R$^y$ is —SR. In some embodiments, R$^y$ is —N(R)$_2$. In some embodiments, R$^y$ is —S(O)$_2$R. In some embodiments, R$^y$ is —S(O)$_2$N(R)$_2$. In some embodiments, R$^y$ is —S(O)R. In some embodiments, R$^y$ is —S(O)N(R)$_2$. In some embodiments, R$^y$ is —C(O)R. In some embodiments, R$^y$ is —C(O)OR. In some embodiments, R$^y$ is —C(O)N(R)$_2$. In some embodiments, R$^y$ is —C(O)N(R)OR. In some embodiments, R$^y$ is —OC(O)R. In some embodiments, R$^y$ is —OC(O)N(R)$_2$. In some embodiments, R$^y$ is —N(R)C(O)OR. In some embodiments, R$^y$ is —N(R)C(O)R. In some embodiments, R$^y$ is —N(R)S(O)$_2$R. In some embodiments, R$^y$ is —S(NR)(O)R. In some embodiments, R$^y$ is C$_{1-6}$ alkyl, C$_{2-6}$ alkenyl, or C$_{2-6}$ alkynyl optionally substituted with one instance of oxo, halogen, —CN, —OR, —SR, —N(R)$_2$, or —C(O)OR. In some embodiments, R$^y$ is C$_{1-6}$ alkyl optionally substituted with one instance of oxo, halogen, —CN, —OR, —SR, —N(R)$_2$, or —C(O)OR. In some embodiments, R$^y$ is C$_{2-6}$ alkenyl optionally substituted with one instance of oxo, halogen, —CN, —OR, —SR, —N(R)$_2$, or —C(O)OR. In some embodiments, R$^y$ is C$_{2-6}$ alkynyl optionally substituted with one instance of oxo, halogen, —CN, —OR, —SR, —N(R)$_2$, or —C(O)OR.

The following embodiments apply to compounds of formula III. In some embodiments, R$^4$ is not methyl. In some embodiments, R$^4$ is not ethyl. In some embodiments, R$^4$ is not methyl or ethyl.

In some embodiments, the present invention provides a compound represented by formula IVa, IVb, IVc, IVd, IVe, IVf, IVg, IVh, IVi, or IVj:

IVa
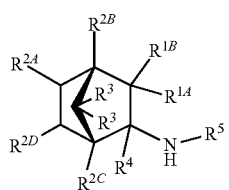

IVb
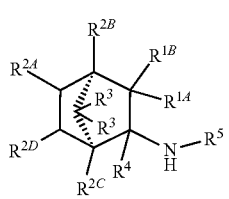

IVc
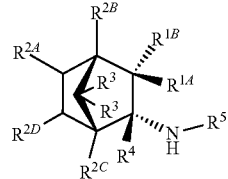

IVd
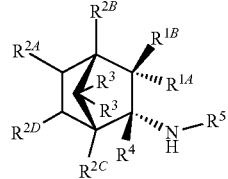

IVe
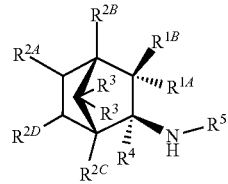

IVf
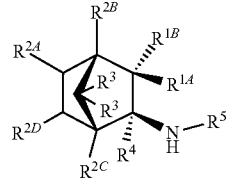

IVg
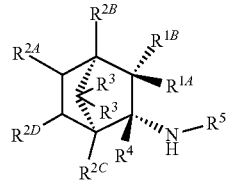

IVh
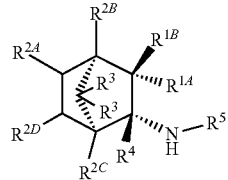

IVi
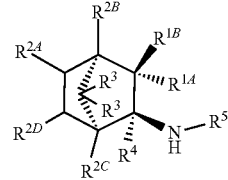

IVj
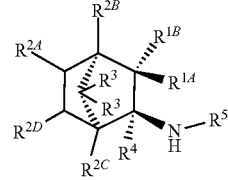

or a pharmaceutically acceptable salt thereof, wherein each variable is as defined above in formula II or III, both singly and in combinations of embodiments described herein.

In some embodiments, the present invention provides a compound represented by formula IVk, IVl, IVm, IVn, IVo, or IVp:

IVk
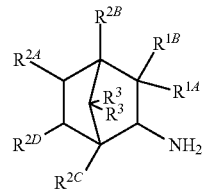

IVl
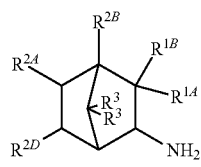

IVm
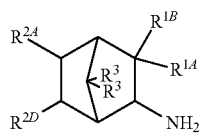

IVn
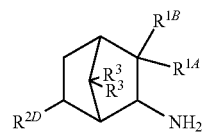

IVo
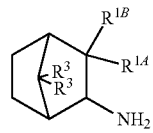

IVp
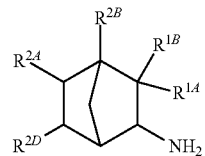

or a pharmaceutically acceptable salt thereof, wherein each variable is as defined above in formula II or III, both singly and in combinations of embodiments described herein.

In some embodiments, the present invention provides a compound represented by formula IVq, IVr, IVs, IVt, or IVu:

IVq
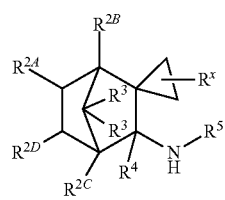

IVr
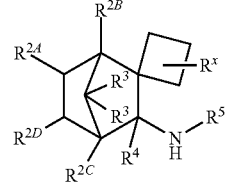

IVs
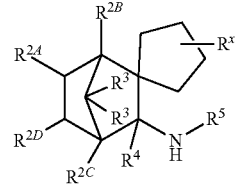

IVt
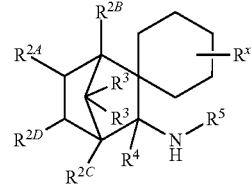

IVu
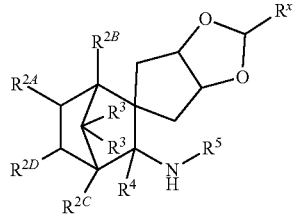

or a pharmaceutically acceptable salt thereof, wherein each variable is as defined above in formula II or III, both singly and in combinations of embodiments described herein.

In some embodiments, the present invention provides a method of treating or preventing a toxic proteinopathy, comprising administering to a subject in need thereof an effective amount of a compound of formula II, III, or IVa to IVu; or a pharmaceutically acceptable salt thereof.

In some embodiments, the toxic proteinopathy is selected from a neurodegenerative disease, autosomal dominant kidney disease caused by uromodulin mutations, and a form of retinitis pigmentosa (RP) caused by rhodopsin mutation.

In some embodiments, the toxic proteinopathy is MUC1-associated kidney disease.

In some embodiments, the subject has one or more of the following: end-stage renal disease, urinalysis revealing minimal protein and no blood, slowly progressive kidney failure, hyperglycemia and/or gout. In some embodiments, the subject has been identified to be in need of dialysis or kidney transplantation.

In some embodiments, the subject has one or more of the following symptoms of RP: night blindness, tunnel vision (due to loss of peripheral vision), latticework vision, photopsia (blinking/shimmering lights), photophobia (aversion to bright lights), development of bone spicules in the fundus, slow adjustment from dark to light environments and vice versa, blurring of vision, poor color separation, loss of central vision, and/or blindness.

In some embodiments, the present invention provides a method of treating or preventing a proteinopathy resulting from mutant protein accumulation in the early secretory pathway in a subject, the method comprising: identifying a subject as having or at risk of developing a proteinopathy resulting from mutant protein accumulation in the early secretory pathway in a subject, and administering a compound or pharmaceutical composition of the invention to the subject in an amount sufficient to cause reduction or improvement of a symptom of the proteinopathy resulting from mutant protein accumulation in the early secretory pathway in the subject, thereby treating or preventing the proteinopathy resulting from mutant protein accumulation in the early secretory pathway in the subject.

In some embodiments, the method comprises identifying the presence in the subject of a mutation in MUC1, UMOD and/or rhodopsin, optionally wherein the MUC1 mutation is a MUC1 frameshift mutation, the UMOD mutation is a C126R UMOD mutation and/or the rhodopsin mutation is a P23H rhodopsin mutation.

In some embodiments, the method comprises administering a compound of the invention, wherein said compound causes release of MUC1, UMOD and/or rhodopsin from the early secretory compartment, optionally wherein said compound causes release of MUC1, UMOD and/or rhodopsin from the endoplasmic reticulum (ER), from COPI-coated vesicles, from COPII-coated vesicles and/or from the Golgi apparatus. In some embodiments, the proteinopathy is selected from a neurodegenerative disease, MUC1-associated kidney disease, autosomal dominant kidney disease caused by uromodulin mutations, a form of retinitis pigmentosa (RP) caused by a rhodopsin mutation, pulmonary alveolar proteinosis or ApoL1-positive kidney disease, and type II diabetes, optionally wherein the neurodegenerative disease is selected from Alzheimer's disease (AD) and other dementias, Parkinson's disease (PD) and PD-related disorders, lysozyme amyloidosis, dialysis amyloidosis, cystic fibrosis, cataracts, odontogenic tumor amyloid, familial British dementia, hereditary cerebral hemorrhage with amyloidosis (Icelandic), familial amyloidotic neuropathy or senile systemic/cardiomyopathy, ApoAII amyloidosis, familial amyloidosis of the Finnish type (FAF), fibrinogen amyloidosis, inclusion body myositis/myopathy, hereditary lattice corneal dystrophy, prion disease (including, e.g., Creutzfeldt-Jakob Disease, variant Creutzfeldt-Jakob Disease, Bovine Spongiform Encephalopathy (BSE), Kuru, Gerstmann-Sträussler-Scheinker disease, fatal familial insomnia (FFI), scrapie, and other animal TSEs), motor neuron diseases (MND), including, e.g., Amyotrophic Lateral Sclerosis (ALS), Primary Lateral Sclerosis (PLS), Progressive Bulbar Palsy (PBP), Pseudobulbar Palsy, Progressive Muscular Atrophy, Spinal Muscular Atrophy (Type 1, Type 2, Type 3, Type 4), and Kennedy's Disease), and spinocerebellar ataxia (SCA). In some embodiments, the proteinopathy is MUC1-associated kidney disease.

In some embodiments, the symptom of the proteinopathy is selected from end-stage renal disease, urinalysis revealing minimal protein and no blood, slowly progressive kidney failure, hyperglycemia, gout, a need for dialysis or kidney transplantation, night blindness, tunnel vision (optionally due to loss of peripheral vision) latticework vision, photopsia (blinking/shimmering lights), photophobia (aversion to bright lights), development of bone spicules in the fundus, slow adjustment from dark to light environments and vice versa, blurring of vision, poor color separation, loss of central vision, and/or blindness.

In some embodiments, the subject has a mutation in MUC1, UMOD and/or rhodopsin, optionally wherein the MUC1 mutation is a MUC1 frameshift mutation, the UMOD mutation is a C126R UMOD mutation and/or the rhodopsin mutation is a P23H rhodopsin mutation.

In some embodiments, the present invention provides a method of reducing or eliminating accumulation of a mutant protein in the ER lumen of a cell, in COPI and/or COPII vesicles of a cell, in the cis-Golgi lumen of a cell, in the medial cisternae of the Golgi of a cell, and/or in the trans-Golgi network (TGN) of a cell, the method comprising administering a compound or pharmaceutical composition of the invention to the environment of a cell in an amount sufficient to reduce or eliminate accumulation of the mutant protein in the ER lumen of the cell, in COPI and/or COPII vesicles of the cell, in the cis-Golgi lumen of the cell, in the medial cisternae of the Golgi of the cell, and/or in the trans-Golgi network (TGN) of the cell, thereby reducing or eliminating accumulation of the mutant protein in the ER lumen of the cell, in COPI and/or COPII vesicles of the cell, in the cis-Golgi lumen of the cell, in the medial cisternae of the Golgi of the cell, and/or in the trans-Golgi network (TGN) of the cell. In some embodiments, the mutant protein is selected from a MUC1 frameshift mutant protein, a UMOD pathogenic variant and a rhodopsin mutant, optionally wherein the MUC1 mutation is a MUC1 frameshift mutation, the UMOD mutation is a C126R UMOD mutation and/or the rhodopsin mutation is a P23H rhodopsin mutation.

In certain embodiments, the compound is selected from:

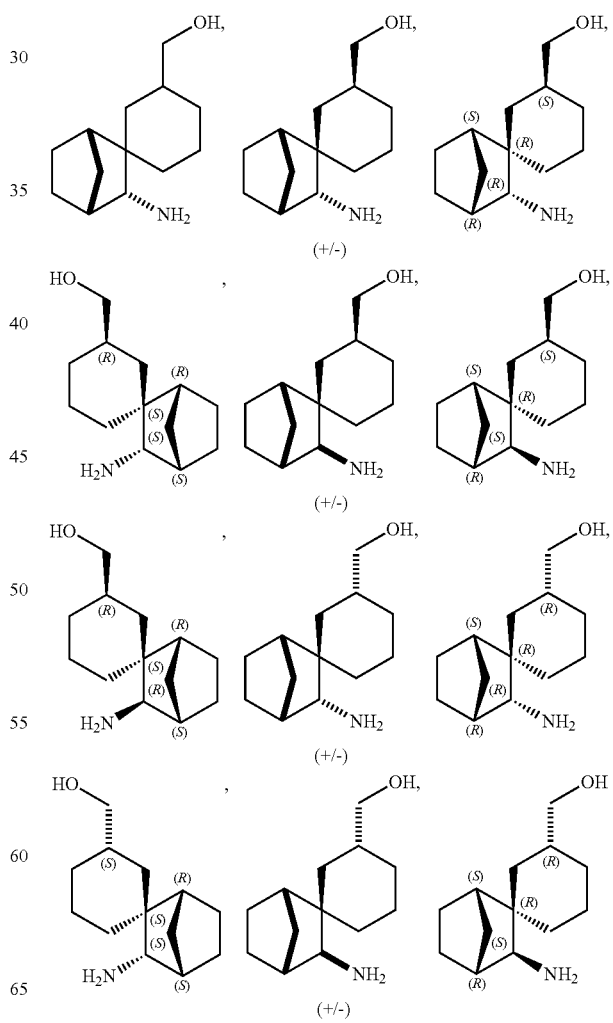

-continued
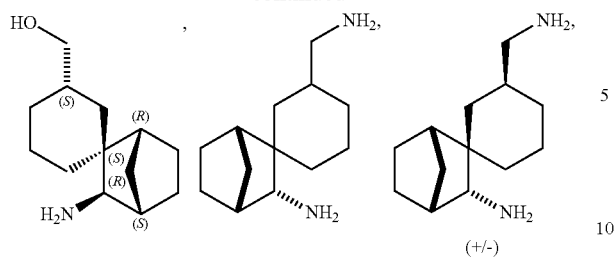
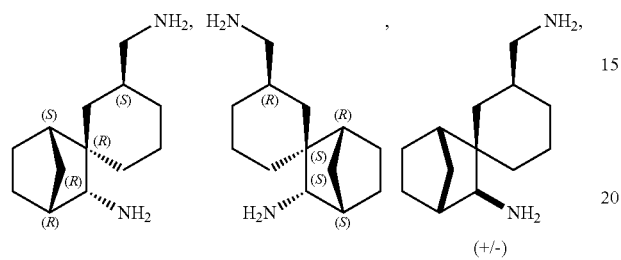
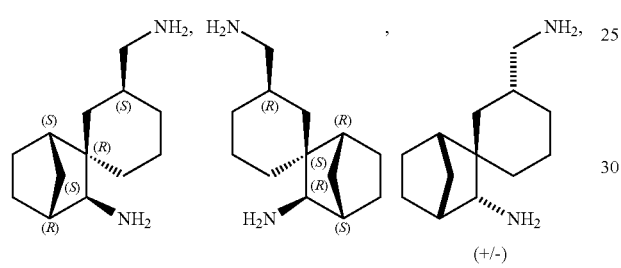
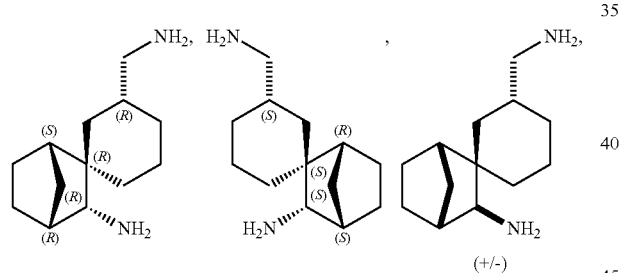
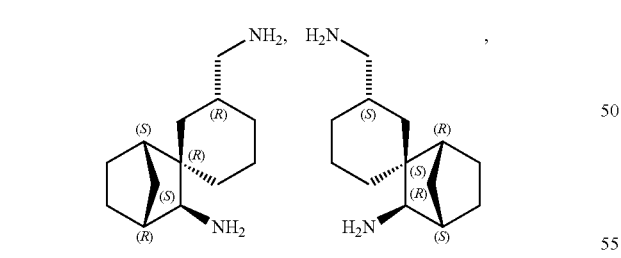
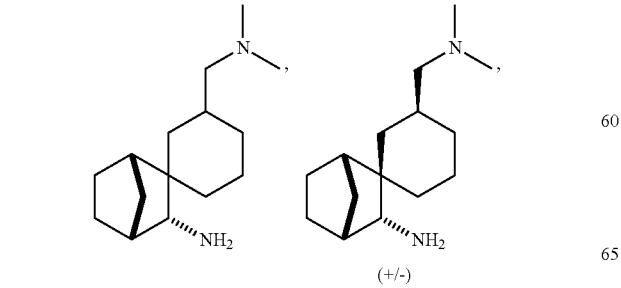
-continued
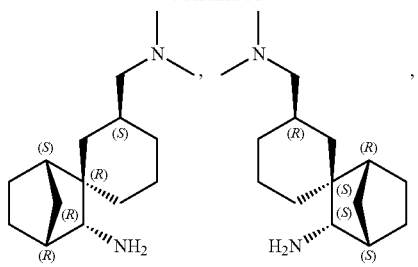
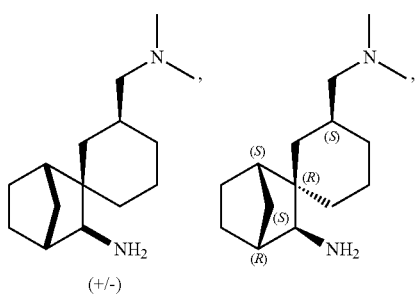
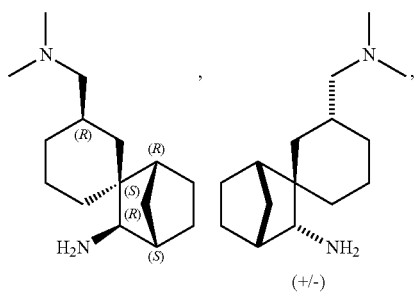
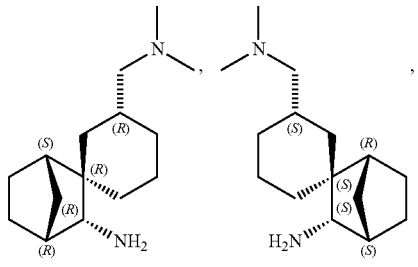
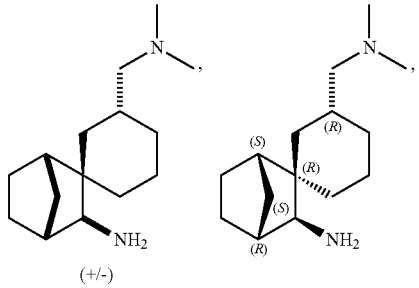
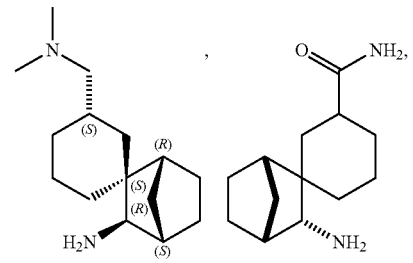

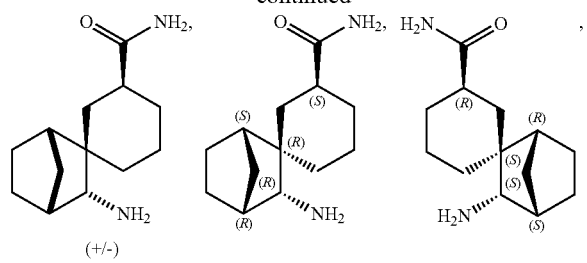
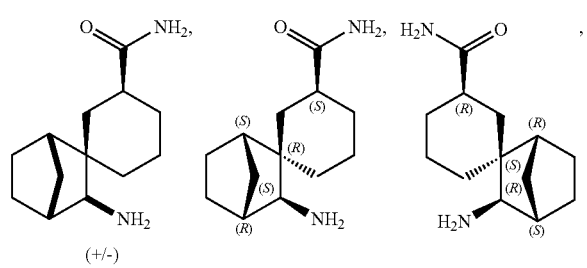
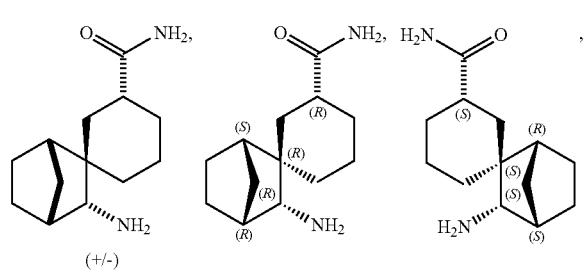
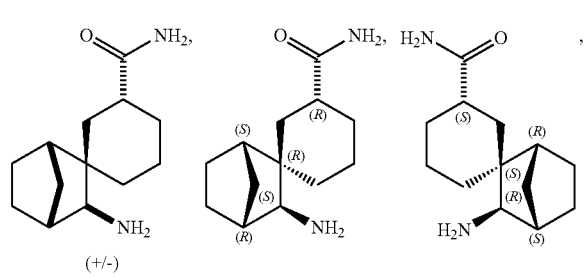
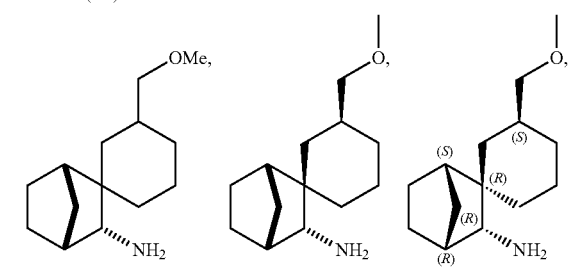
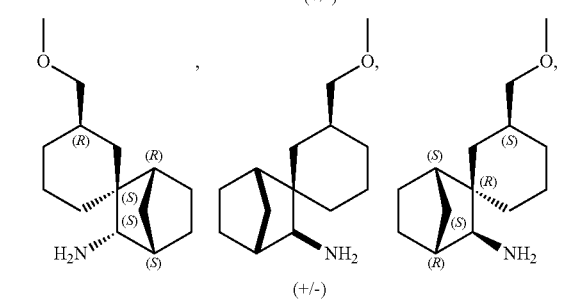
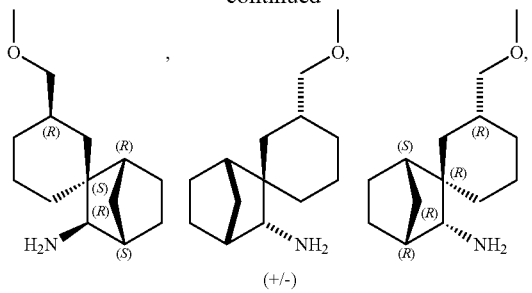
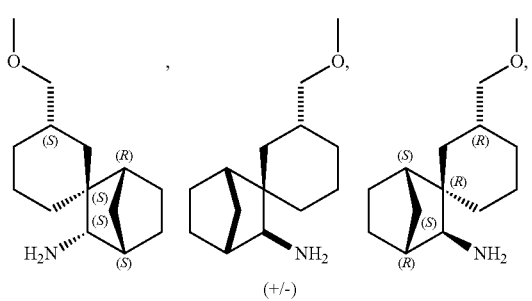
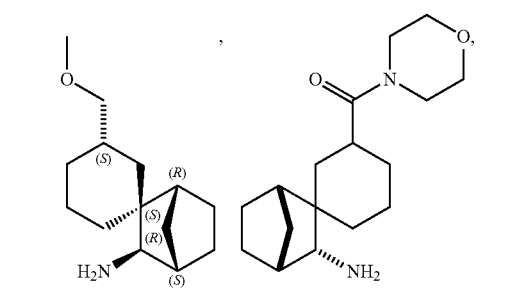
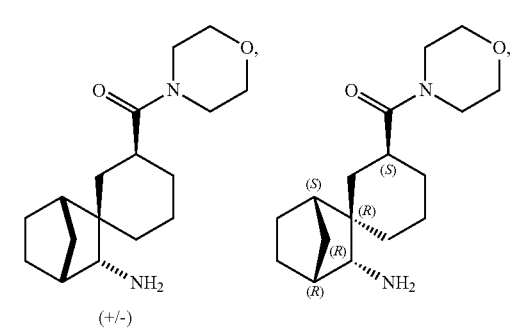
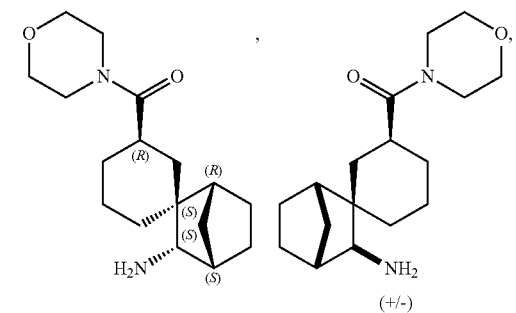

-continued
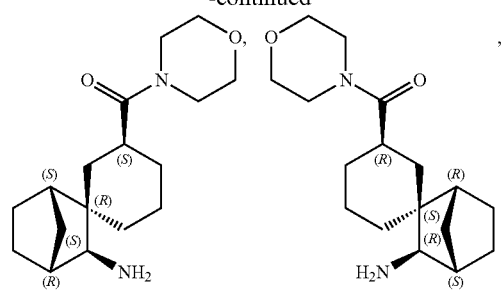
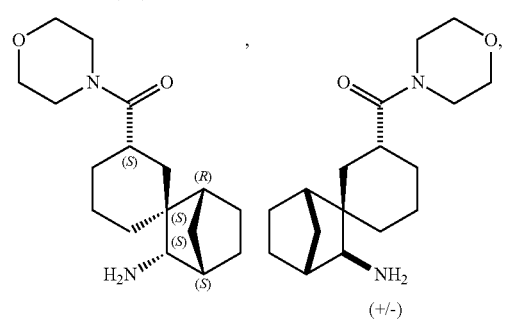
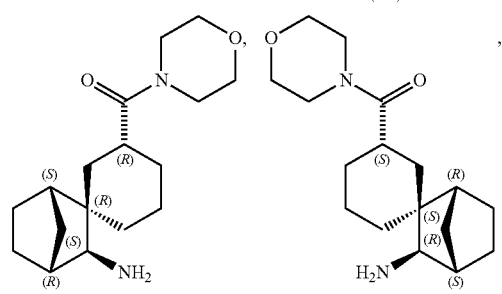
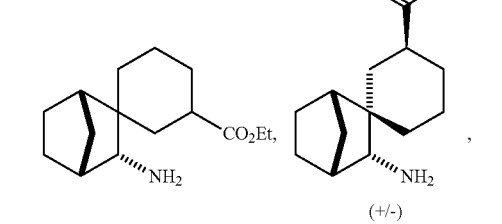
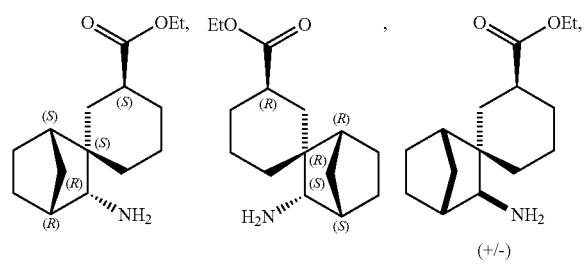
-continued
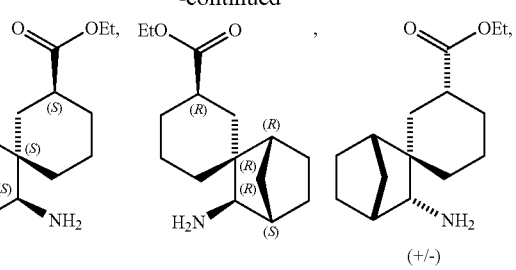
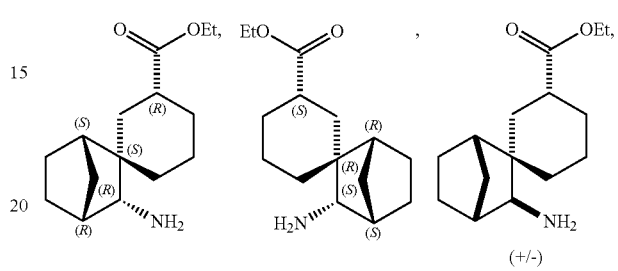
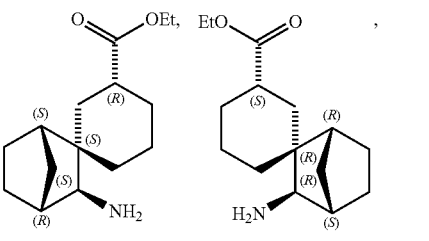
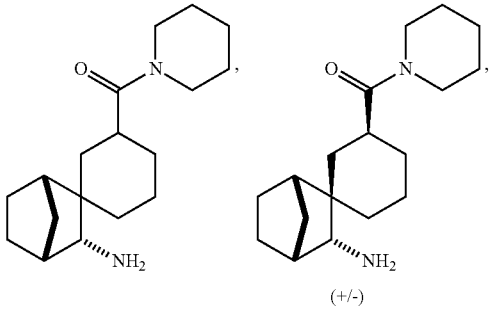
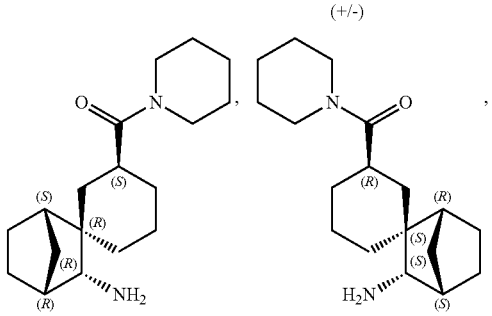
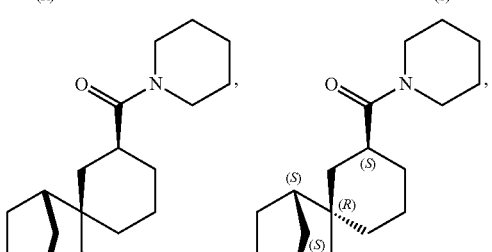

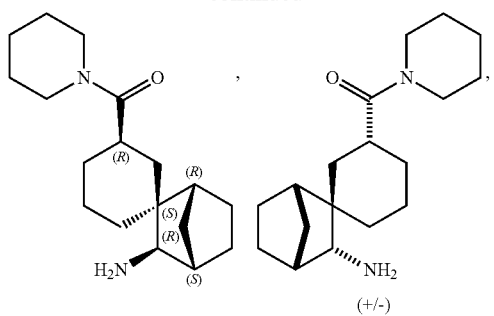
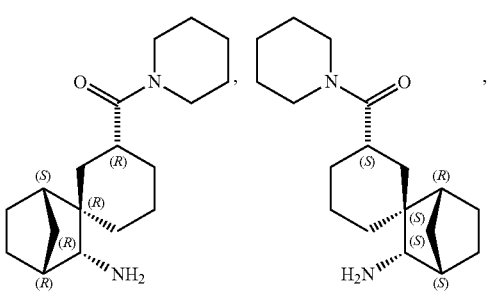
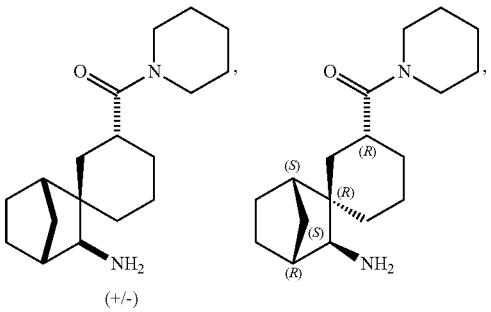
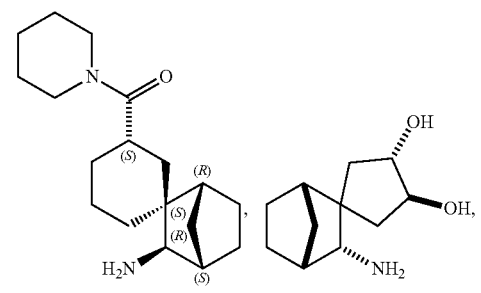
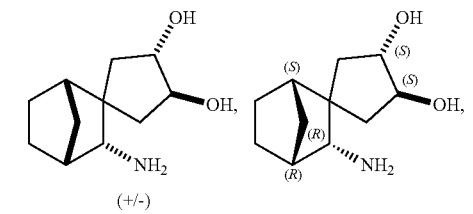
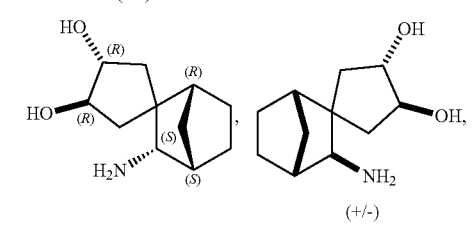
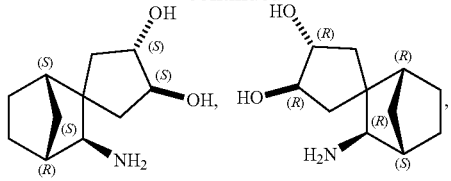
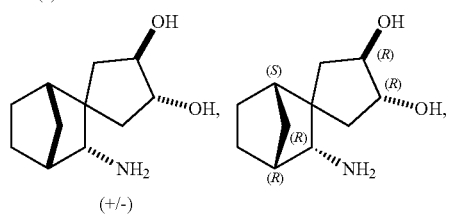
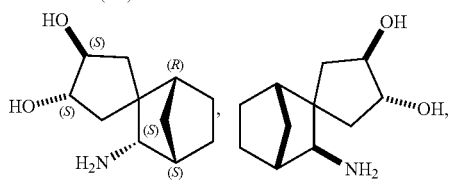
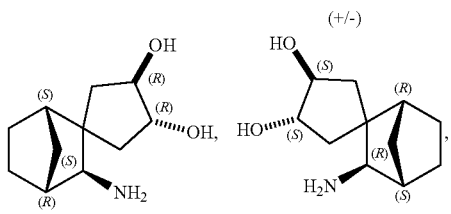
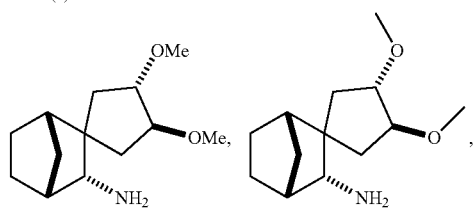
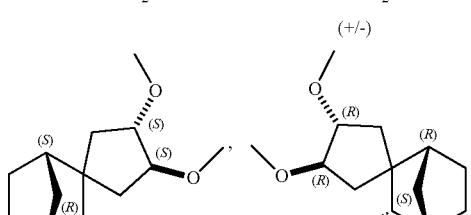
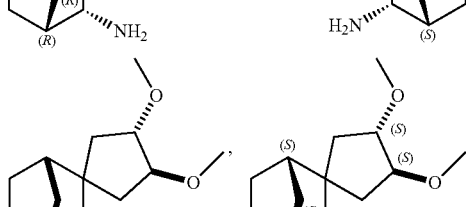
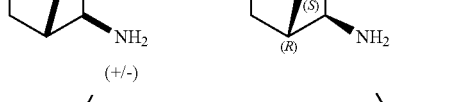
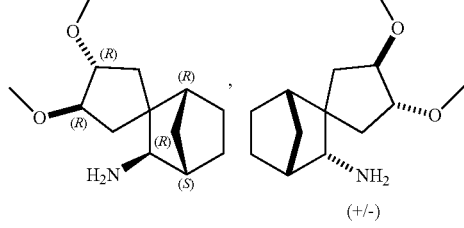

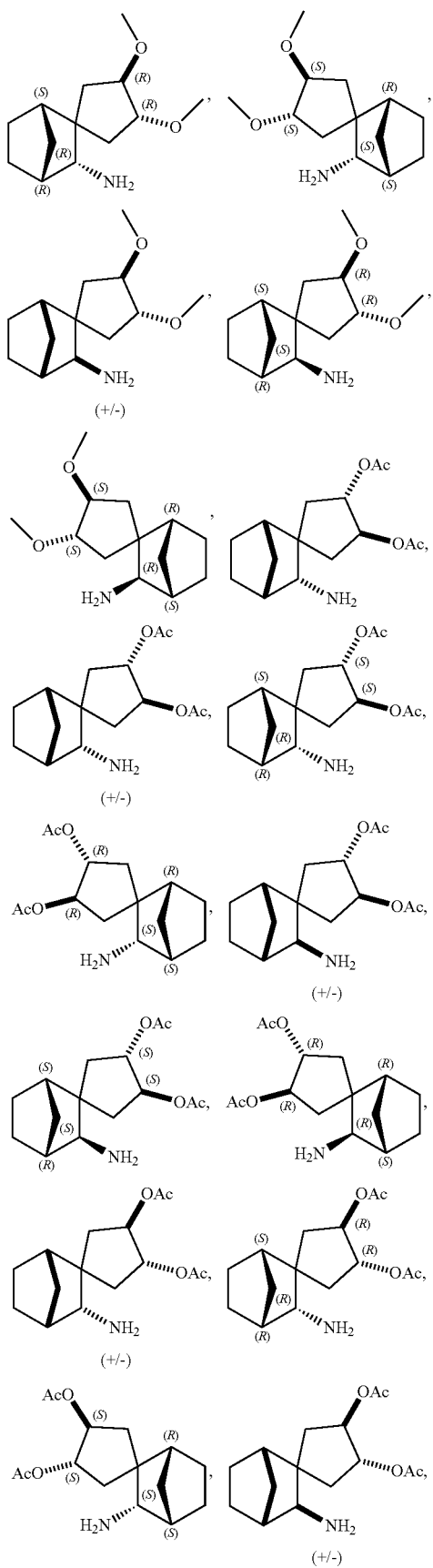
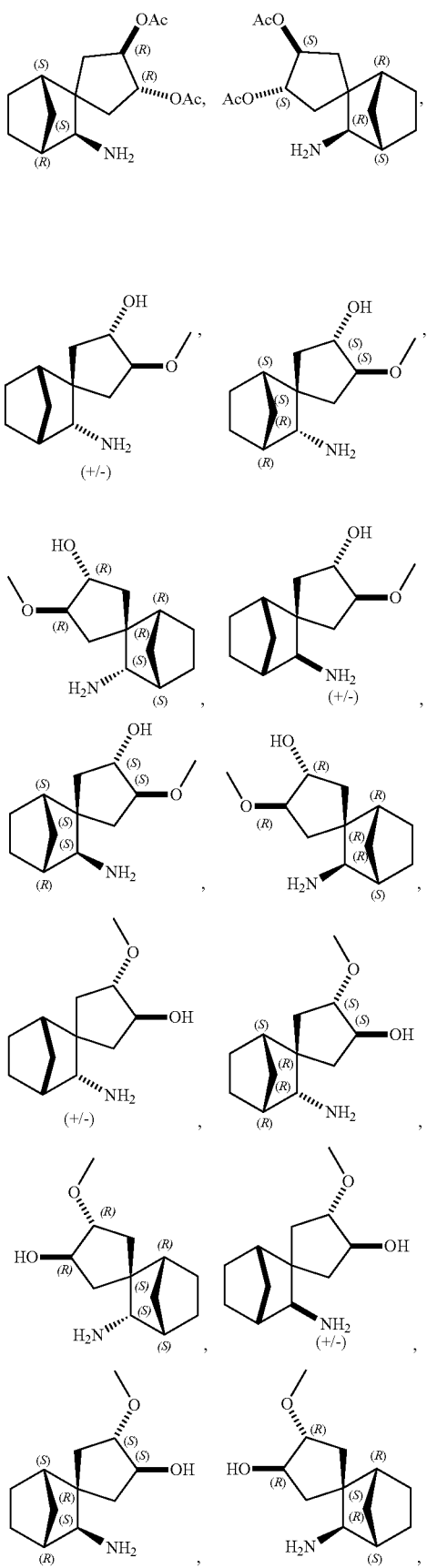

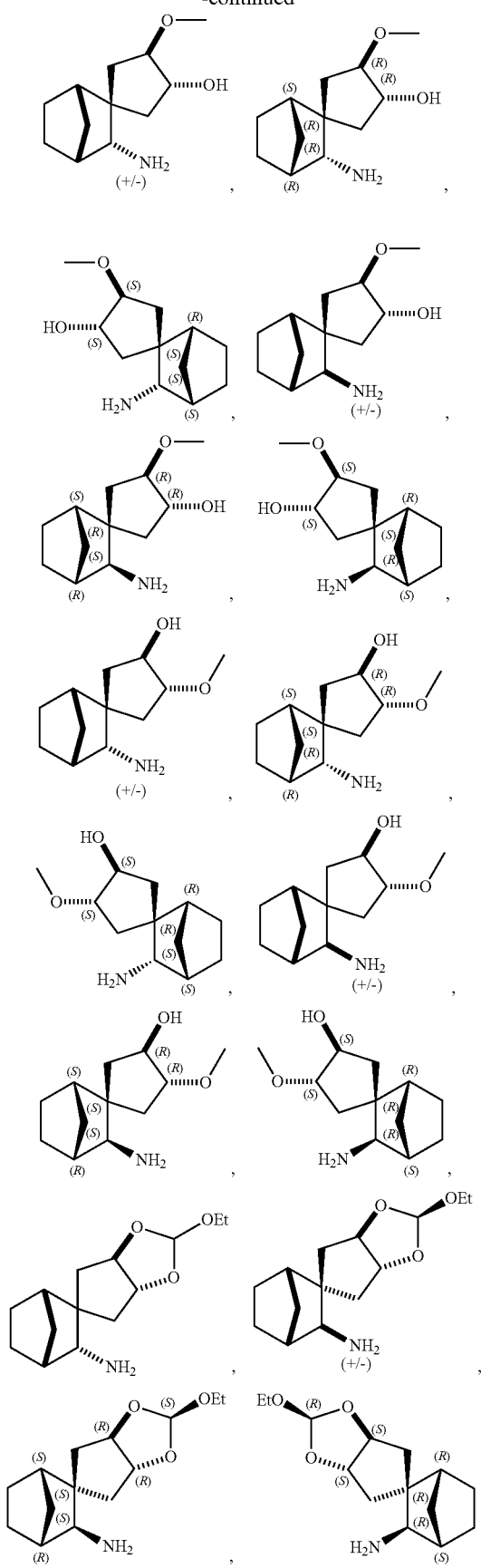
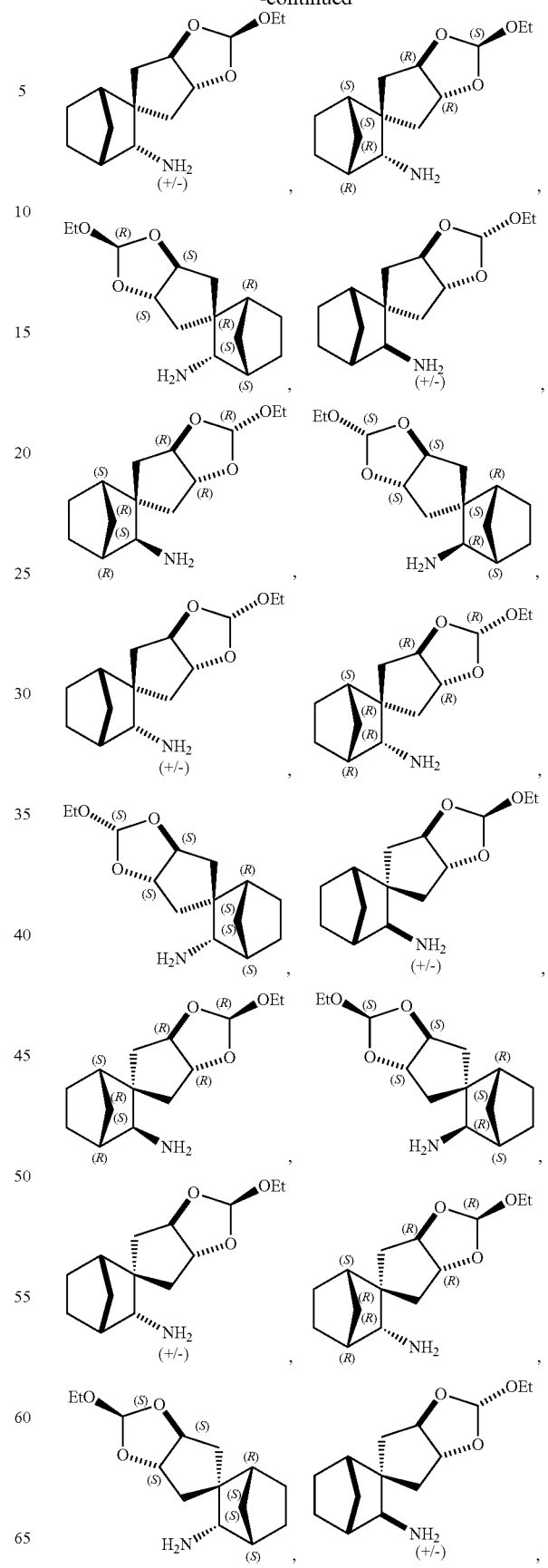

-continued
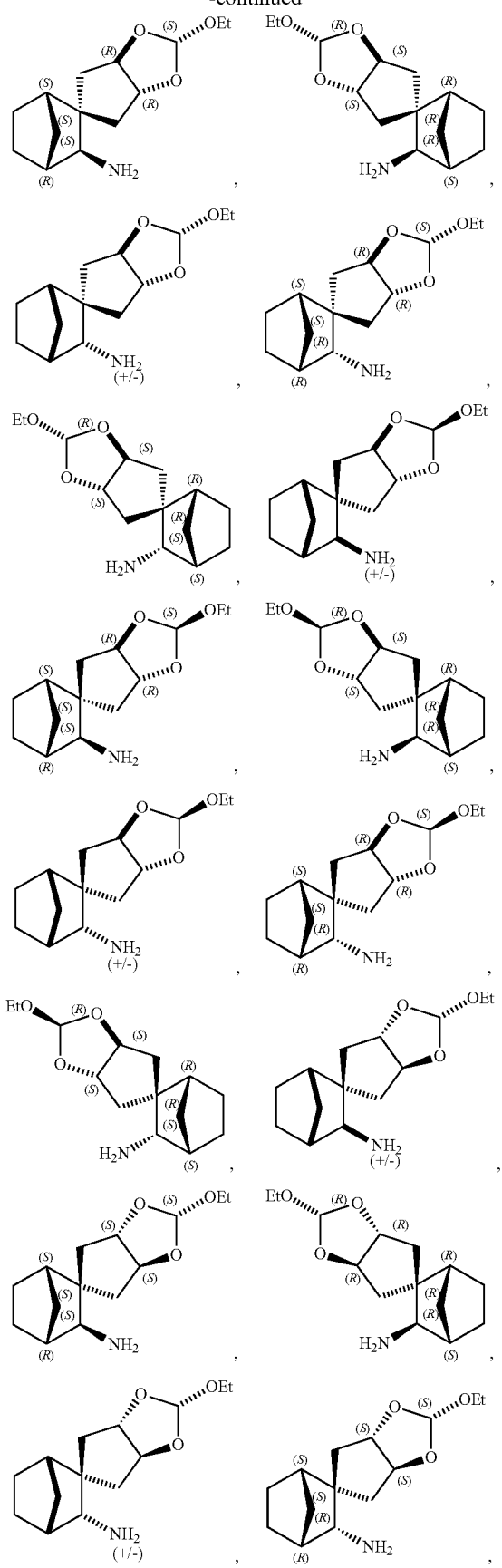
-continued
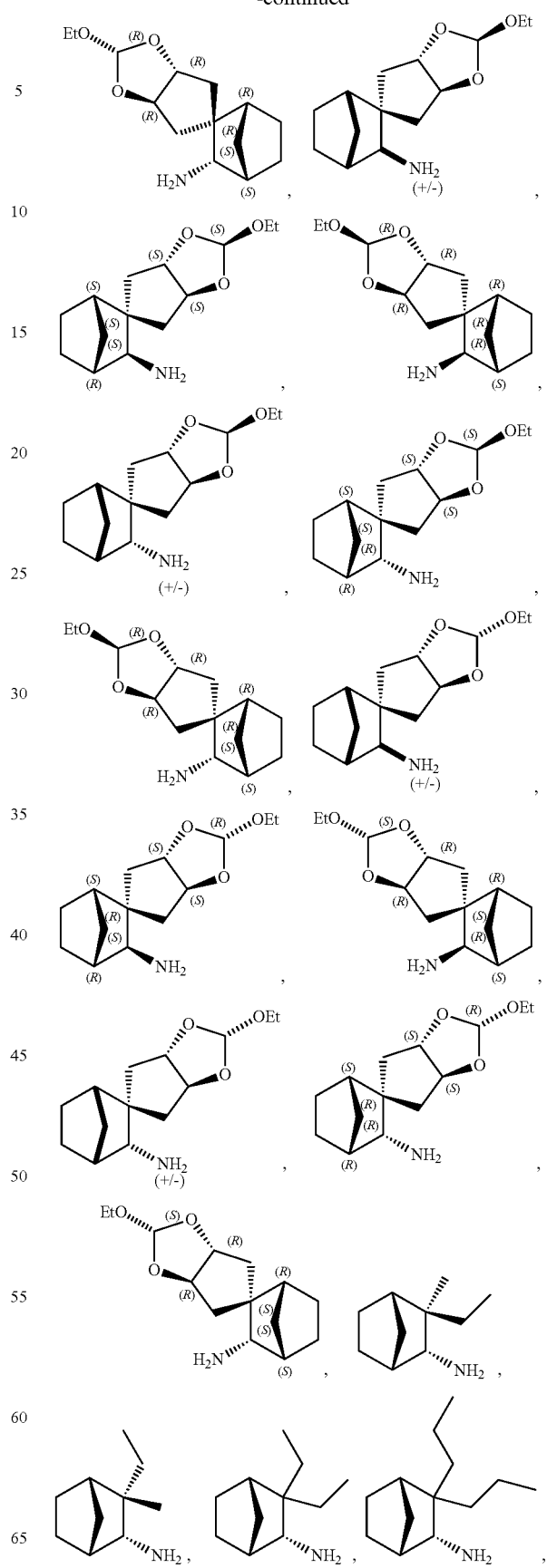
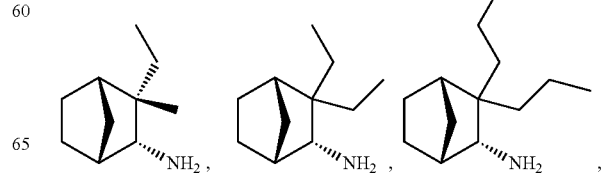

33
-continued
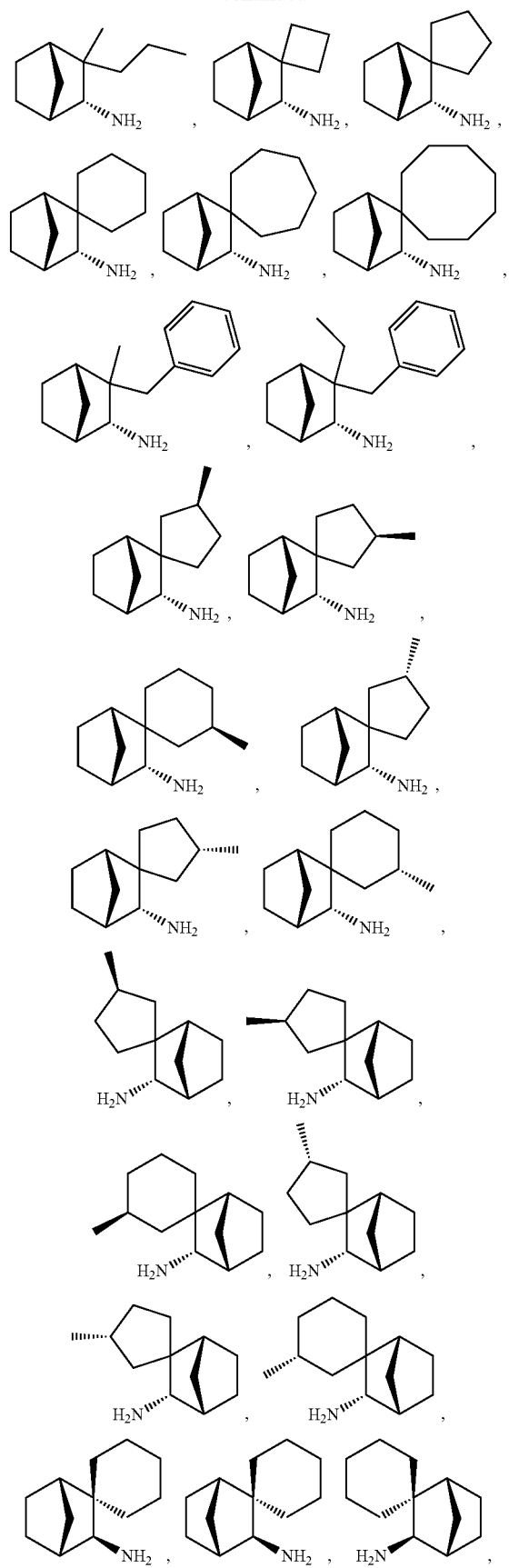
34
-continued
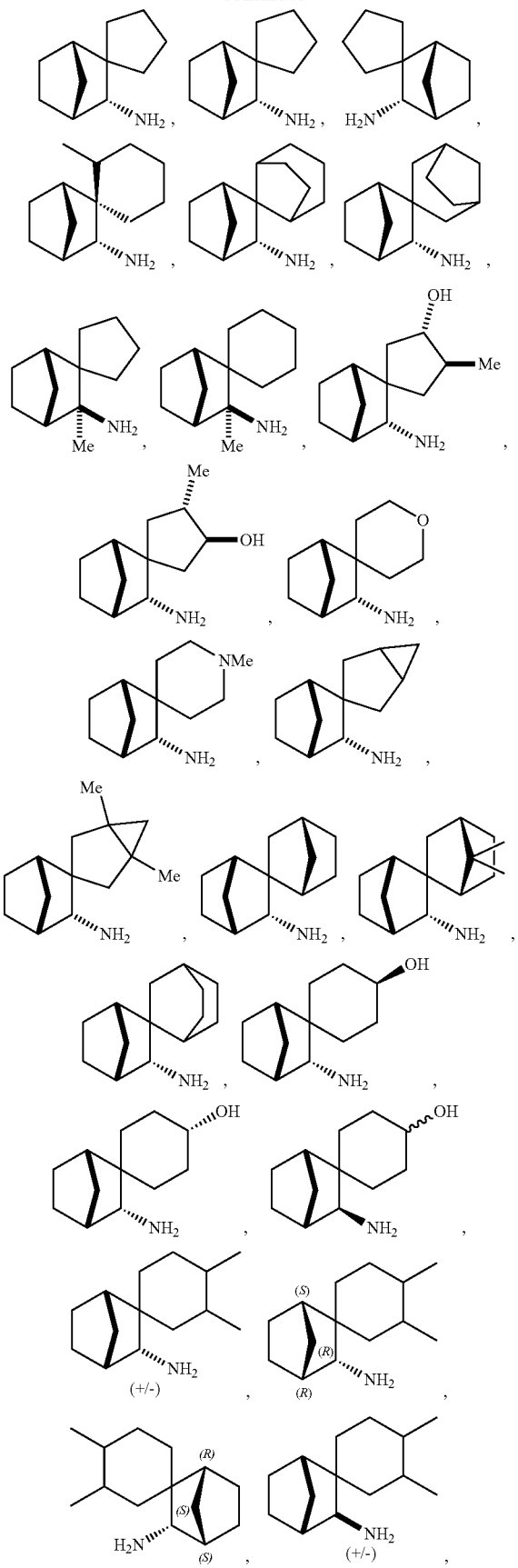

-continued
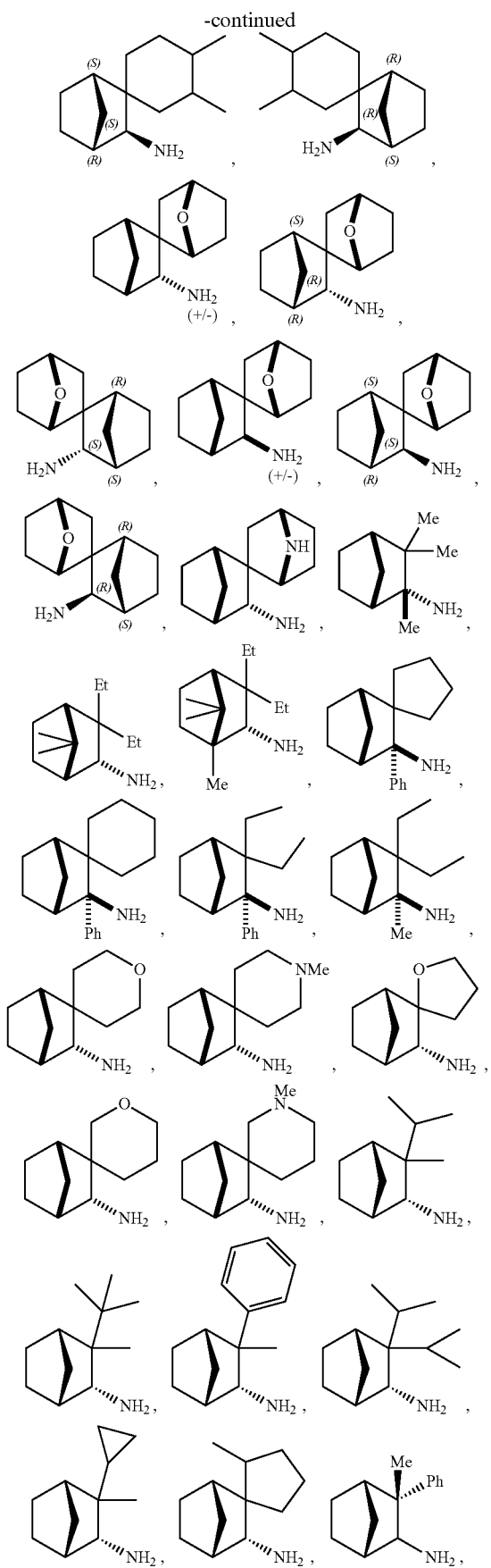
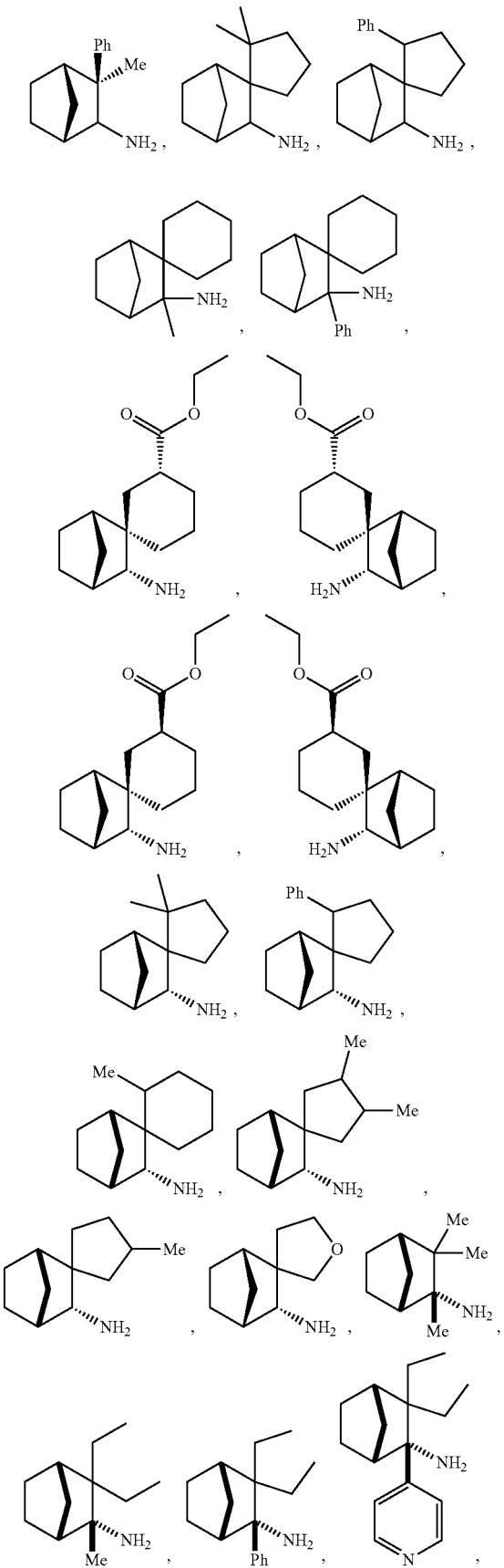

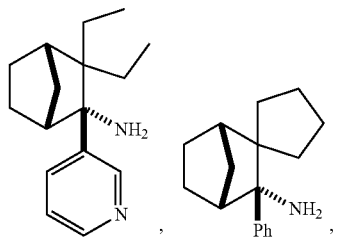

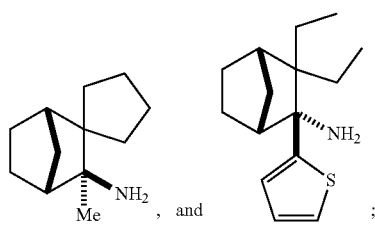

, and

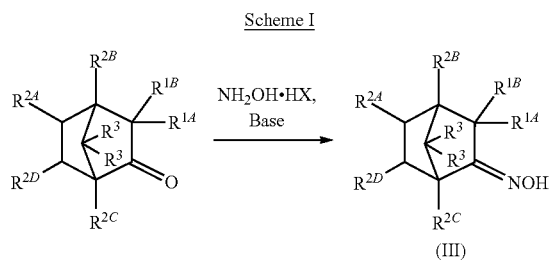

;

or a pharmaceutically acceptable salt thereof.

In certain embodiments, the compound is a pharmaceutically acceptable salt. In certain embodiments, the compound is a hydrochloride salt. In certain embodiments, the compound is a maleate salt.

In certain embodiments, the present disclosure provides a pharmaceutical composition comprising a compound of the invention wherein $R^5$ is H and a pharmaceutically acceptable excipient.

In certain embodiments, the present disclosure provides a method of making a compound represented by formula III according to Scheme I:

Scheme I

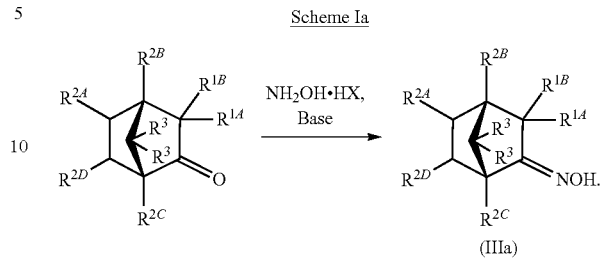

(III)

wherein $R^{1A}$ and $R^{1B}$ are each independently alkyl, cycloalkyl, aryl, heteroaryl, aralkyl, or heteroaralkyl; or $R^{1A}$ and $R^{1B}$ combine to form a cycloalkyl, cycloalkenyl, or heterocyclyl;

each $R^{2A}$, $R^{2B}$, $R^{2C}$, and $R_{2D}$, is independently selected from H or alkyl;

$R^3$ are both H or both alkyl;

X is an inorganic anion (e.g., chloride); and the base is an inorganic base (e.g., sodium acetate) or a nitrogenous base (e.g., pyridine).

In certain embodiments, the method is represented by Scheme Ia:

Scheme Ia

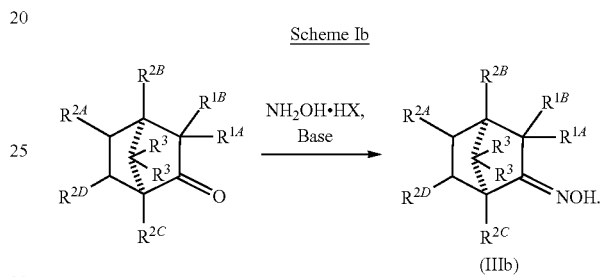

(IIIa)

In certain embodiments, the method is represented by Scheme Ib:

Scheme Ib

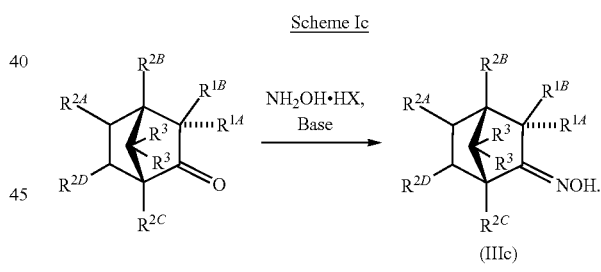

(IIIb)

In certain embodiments, the method is represented by Scheme Ic:

Scheme Ic

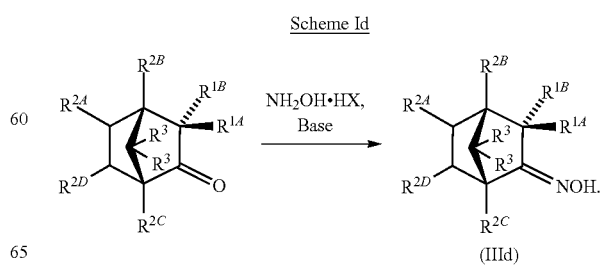

(IIIc)

In certain embodiments, the method is represented by Scheme Id:

Scheme Id (IIId)

In certain embodiments, the method is represented by Scheme Ie:

Scheme Ie

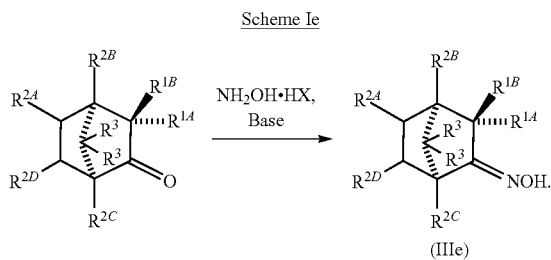

(IIIe)

In certain embodiments, the method is represented by Scheme If:

Scheme If

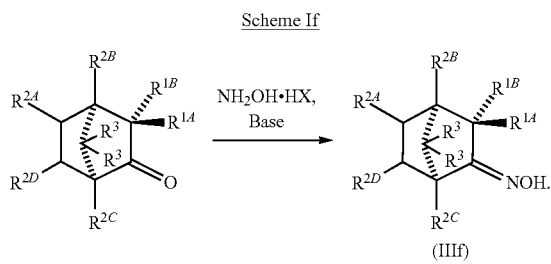

(IIIf)

In certain embodiments, the present disclosure provides a method represented by formula II according to Scheme II:

Scheme II

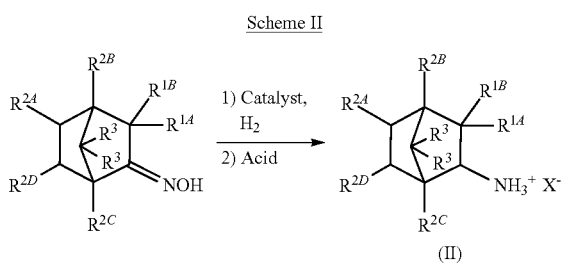

(II)

wherein
- $R^{1A}$ and $R^{1B}$ are each independently alkyl, cycloalkyl, aryl, heteroaryl, aralkyl, or heteroaralkyl; or $R^{1A}$ and $R^{1B}$ combine to form a cycloalkyl, cycloalkenyl, or heterocyclyl;
- each $R^{2A}$, $R^{2B}$, $R^{2C}$, and $R^{2D}$, is independently selected from H or alkyl;
- $R^3$ are both H or both alkyl;
- $X^-$ is an organic or inorganic anion;
- the catalyst is a noble metal oxide (e.g., platinum oxide); and
- the acid is a Brønsted acid (e.g., acetic acid).

In certain embodiments, the method is represented by Scheme IIa:

Scheme IIa

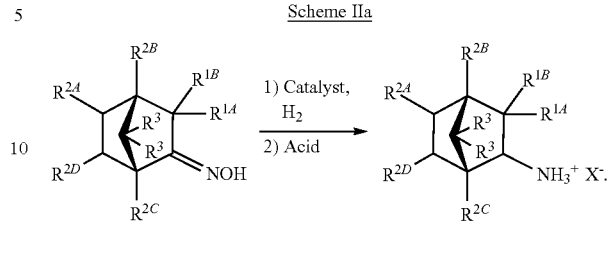

In certain embodiments, the method is represented by Scheme IIb:

Scheme IIb

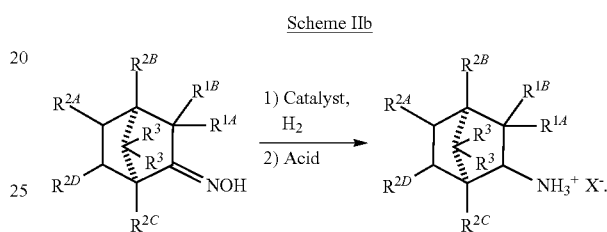

In certain embodiments, the method is represented by Scheme IIc:

Scheme IIc

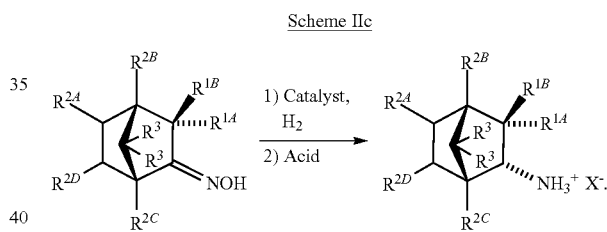

In certain embodiments, the method is represented by Scheme IId:

Scheme IId

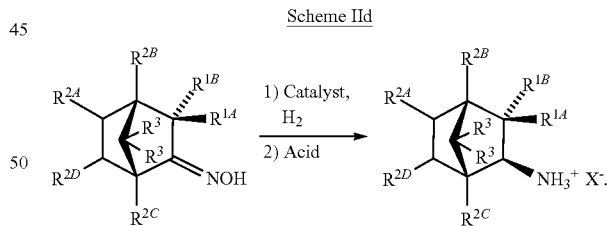

In certain embodiments, the method is represented by Scheme IIe:

Scheme IIe

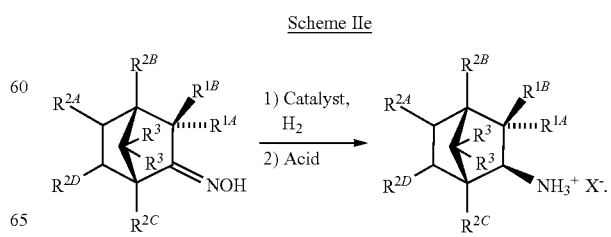

In certain embodiments, the method is represented by Scheme IIf:

Scheme IIf

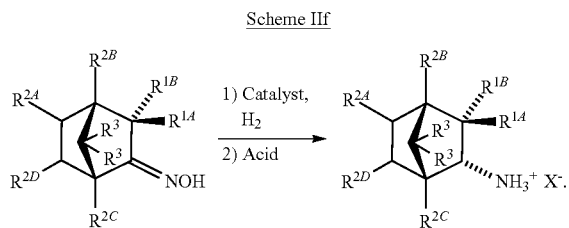

In certain embodiments, the method is represented by Scheme IIg:

Scheme IIg

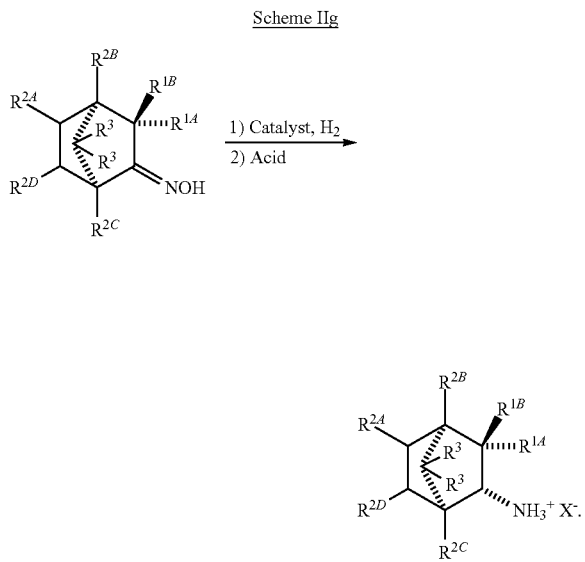

In certain embodiments, the method is represented by Scheme IIh:

Scheme IIh

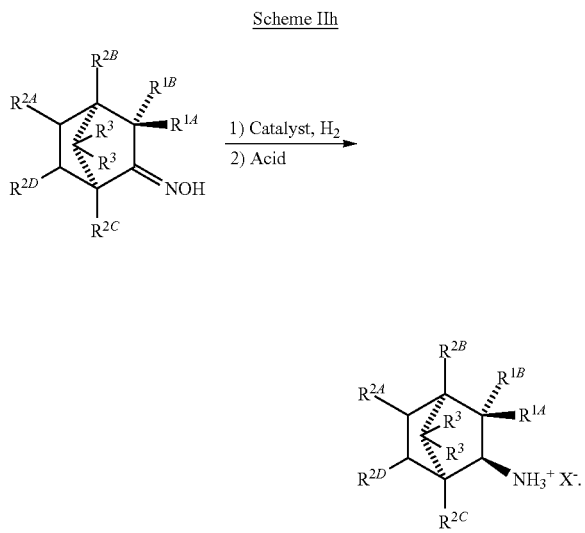

In certain embodiments, the method is represented by Scheme IIi:

Scheme IIi

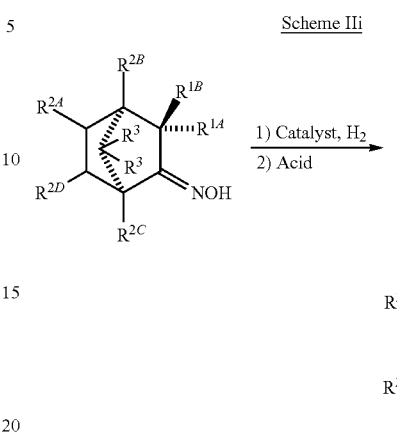

In certain embodiments, the method is represented by Scheme IIj:

Scheme IIj

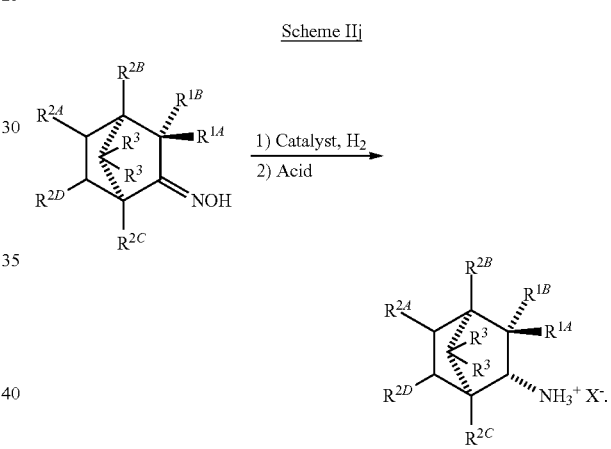

In certain embodiments of the method, the compound has an enantiomeric excess (ee) or diastereomeric excess (de) greater than 95%, 96%, 97%, 98%, or 99%. In certain embodiments of the method, the compound is substantially free of one enantiomer and/or substantially free of one or more (preferably all) other diastereomers. In certain embodiments of the method, the compound is a single enantiomer or a single diastereomer.

In certain embodiments of the method, $R^{1A}$ is alkyl. In certain embodiments of the method, $R^{1A}$ is methyl, ethyl, propyl, isopropyl, butyl, or tertbutyl. In certain embodiments of the method, $R^{1A}$ is aralkyl. In certain embodiments of the method, $R^{1A}$ is benzyl. In certain embodiments of the method, $R^{1A}$ is cycloalkyl. In certain embodiments of the method, $R^{1A}$ is cyclopropyl. In certain embodiments of the method, $R^{1A}$ is aryl. In certain embodiments of the method, $R^{1A}$ is phenyl. In certain embodiments of the method, $R^{1B}$ is alkyl. In certain embodiments of the method, $R^{1B}$ is methyl, ethyl, propyl, isopropyl, butyl, or tertbutyl. In certain embodiments of the method, $R^{1B}$ is aralkyl. In certain embodiments of the method, $R^{1B}$ is benzyl. In certain embodiments of the method, wherein $R^{1B}$ is cycloalkyl. In certain embodiments of the method, $R^{1B}$ is cyclopropyl. In certain embodiments of the method, $R^{1B}$ is aryl. In certain embodiments of the method, $R^{1B}$ is phenyl.

In certain embodiments of the method, $R^{1A}$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, alkylsulfonyl, or sulfonamide.

In certain embodiments of the method, $R^{1A}$ is substituted with alkyl (e.g., methyl), hydroxyl, amino, alkylamino (e.g., dimethylamino), amido, alkoxy (e.g., methoxy or ethoxy), heterocyclylamido (e.g., morpholinoamido or piperidinylamido), acyloxy (e.g., acetyloxy), or ester (e.g., ethyl-ester).

In certain embodiments of the method, $R^{1B}$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, alkylsulfonyl, or sulfonamide.

In certain embodiments of the method, $R^{1B}$ is substituted with alkyl (e.g., methyl), hydroxyl, amino, alkylamino (e.g., dimethylamino), amido, alkoxy (e.g., methoxy or ethoxy), heterocyclylamido (e.g., morpholinoamido or piperidinylamido), acyloxy (e.g., acetyloxy), or ester (e.g., ethyl-ester).

In certain embodiments of the method, $R^{1A}$ and $R^{1B}$ combine to form a cycloalkyl. In certain embodiments of the method, $R^{1A}$ and $R^{1B}$ combine to form a cyclobutyl, cyclopently, cyclohexyl, cycloheptyl, bicycloheptanyl, cyclooctyl, or bicyclooctanyl. In certain embodiments of the method, $R^{1A}$ and $R^{1B}$ combine to form a cycloalkenyl. In certain embodiments of the method, $R^{1A}$ and $R^{1B}$ combine to form a cyclopentenyl or cyclohexenyl. In certain embodiments of the method, $R^{1A}$ and $R^{1B}$ combine to form a heterocyclyl.

In certain embodiments of the method, $R^{1A}$ and $R^{1B}$ combine to form a tetrahydrofuranyl, tetrahydropyranyl, tetrahydrocyclopentadioxolyl, oxabicycloheptanyl, piperidinyl, or azabicycloheptanyl. In certain embodiments of the method, $R^{1A}$ and $R^{1B}$ combine to form a cycloalkyl, cycloalkenyl, or heterocyclyl and the cycloalkyl, cycloalkenyl, or heterocyclyl is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, alkylsulfonyl, or sulfonamide. In certain embodiments of the method, $R^{1A}$ and $R^{1B}$ combine to form a cycloalkyl, cycloalkenyl, or heterocyclyl and the cycloalkyl, cycloalkenyl, or heterocyclyl is substituted with alkyl (e.g., methyl), hydroxyl, amino, alkylamino (e.g., dimethylamino), amido, alkoxy (e.g., methoxy or ethoxy), heterocyclylamido (e.g., morpholinoamido or piperidinylamido), acyloxy (e.g., acetyloxy), or ester (e.g., ethyl ester).

In certain embodiments of the method, wherein $R^{2A}$ is hydrogen. In certain embodiments of the method, R' is hydrogen. In certain embodiments of the method, $R^{2C}$ is hydrogen. In certain embodiments of the method, $R^{2D}$ is hydrogen.

In certain embodiments of the method, each $R^3$ is hydrogen. In certain embodiments of the method, each $R^3$ is alkyl. In certain embodiments of the method, each $R^3$ is the same. In certain embodiments of the method, each $R^3$ is methyl.

In certain embodiments of the method, the compound is selected from

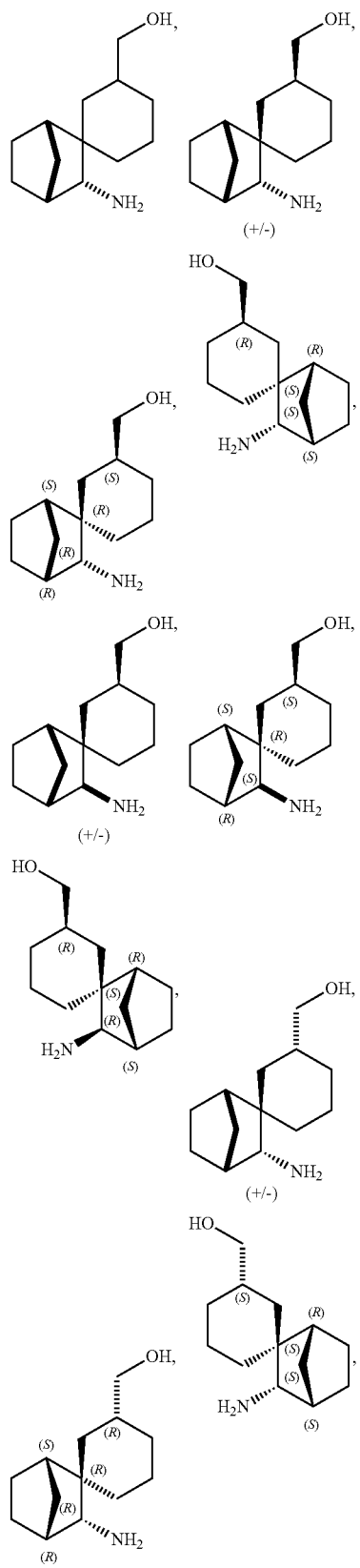

-continued
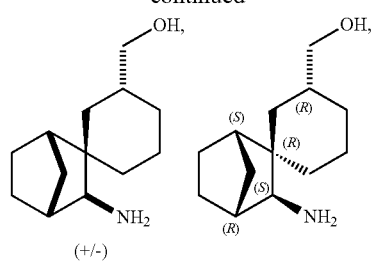
(+/-)
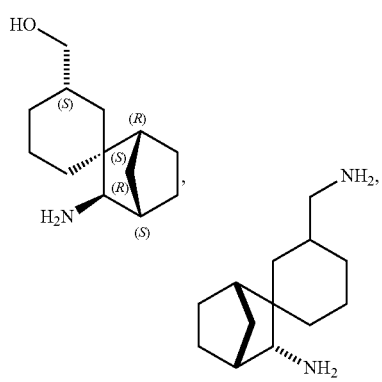
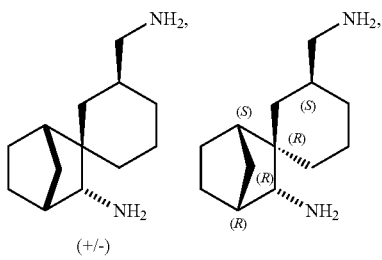
(+/-)
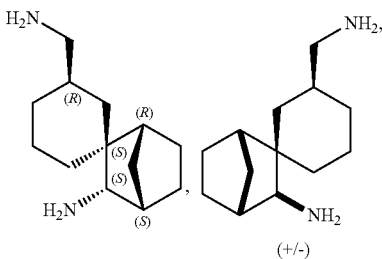
(+/-)
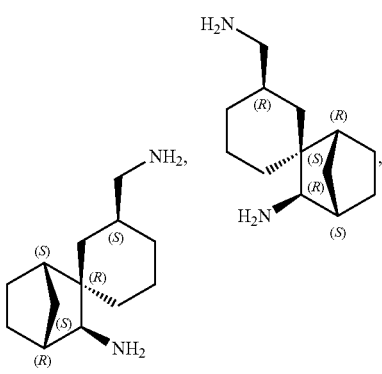
-continued
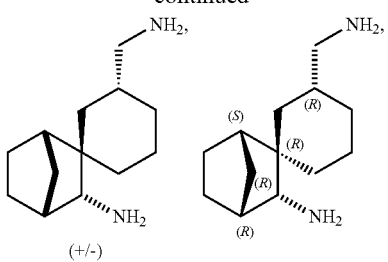
(+/-)
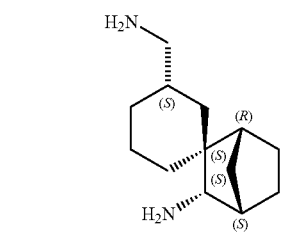
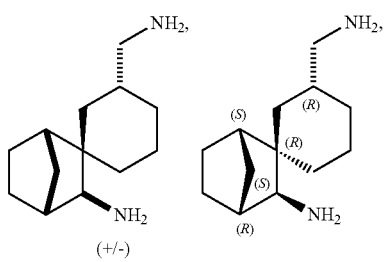
(+/-)
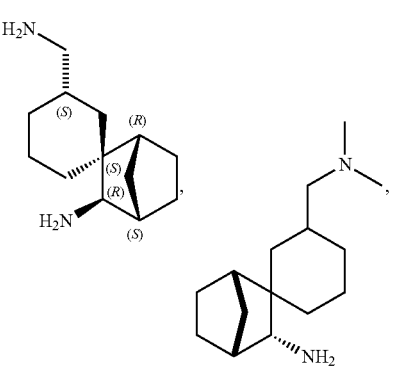
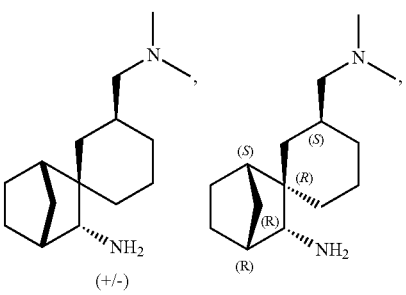
(+/-)

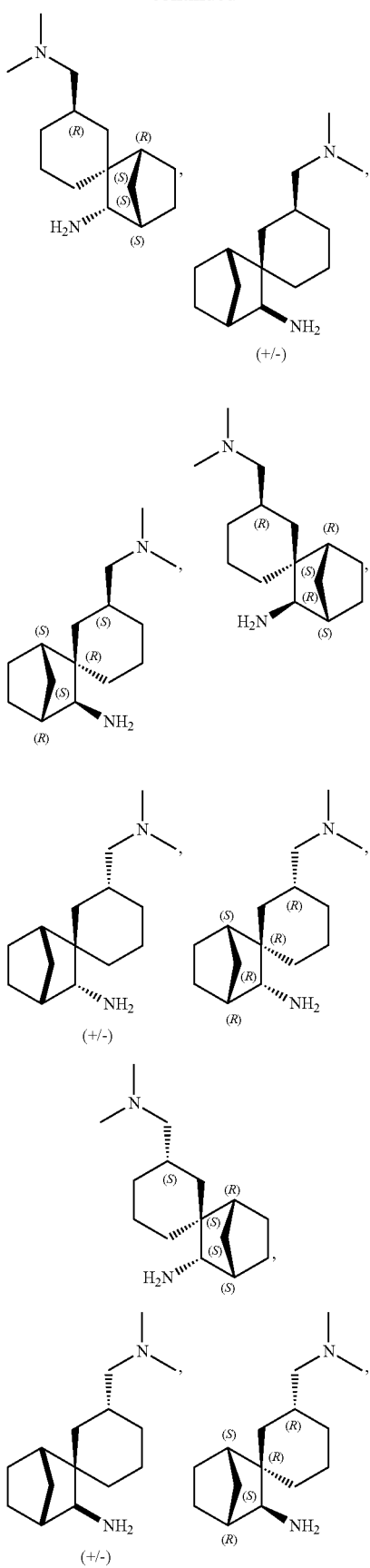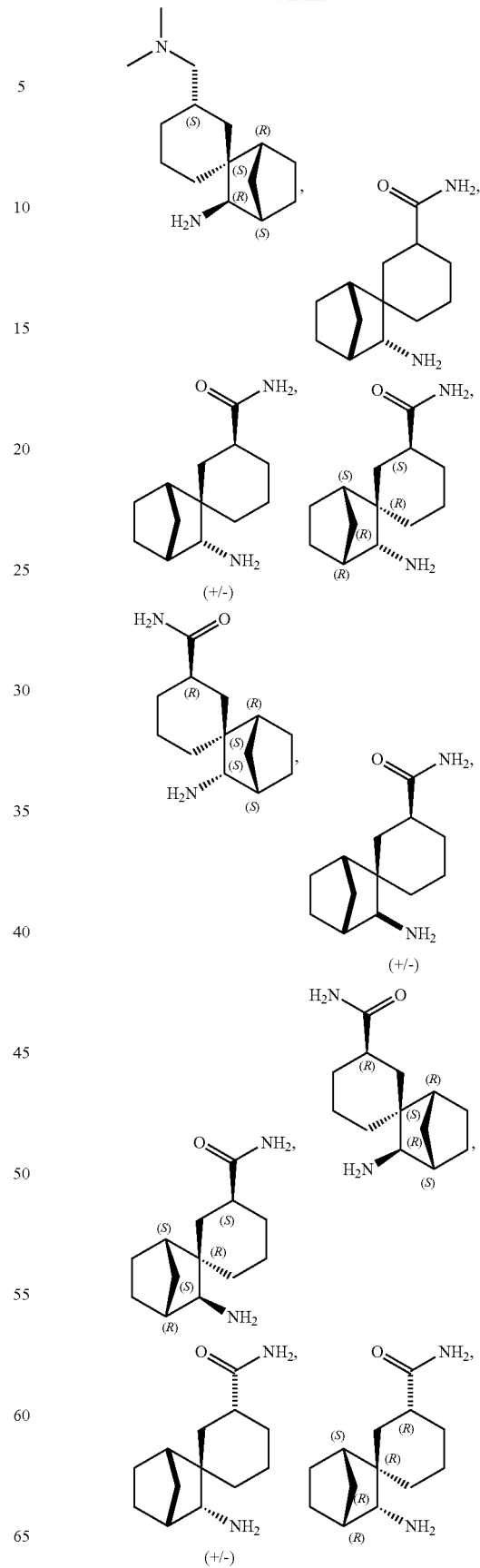

49
-continued
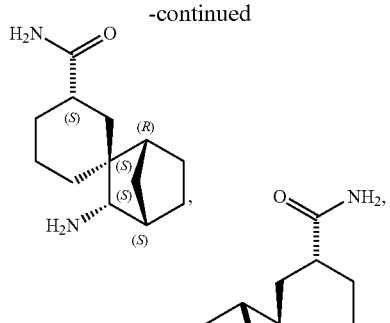
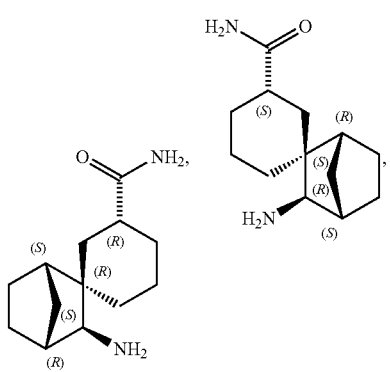
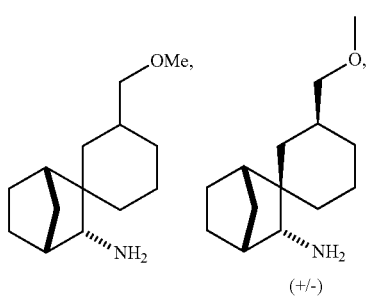
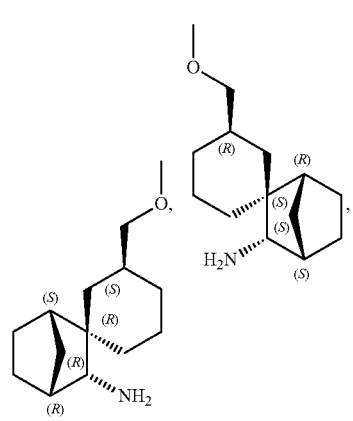
50
-continued
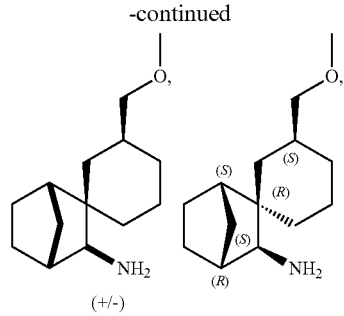
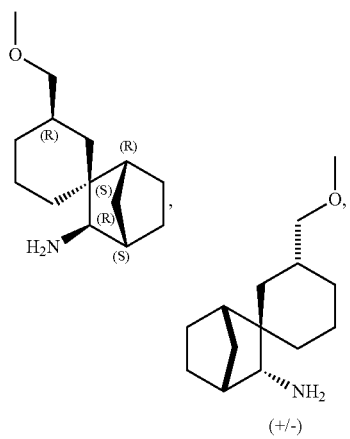
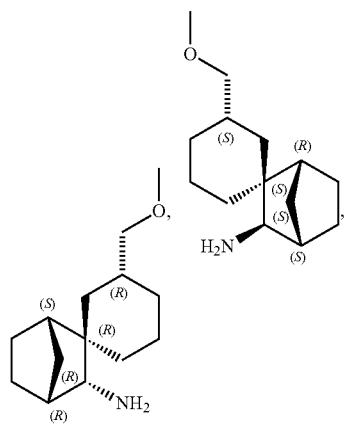
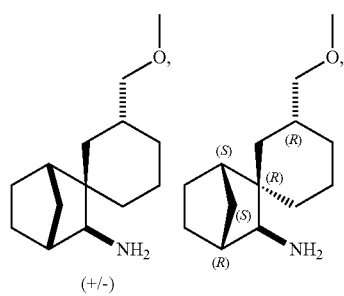
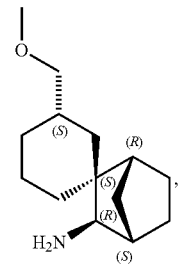

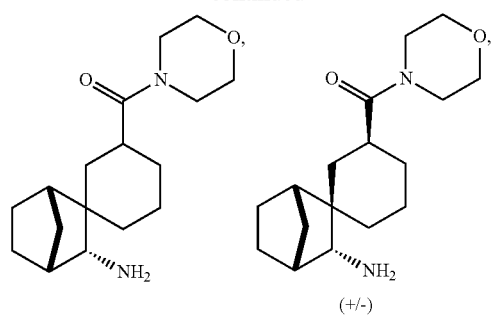
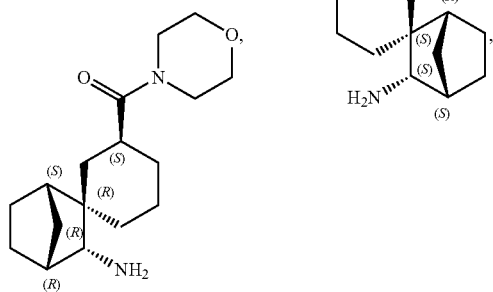
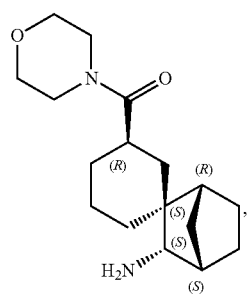
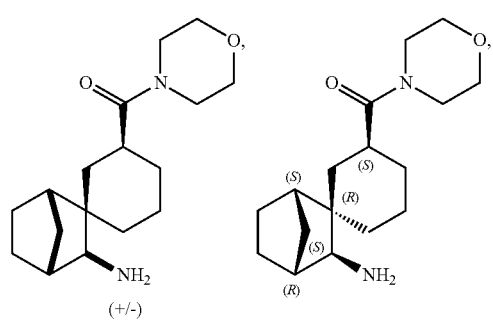
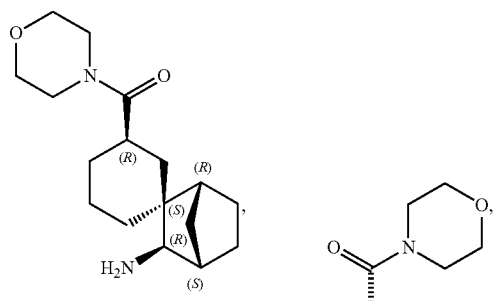
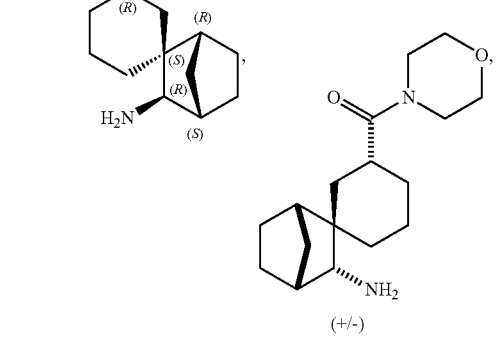
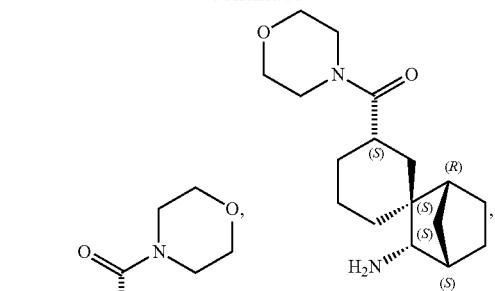
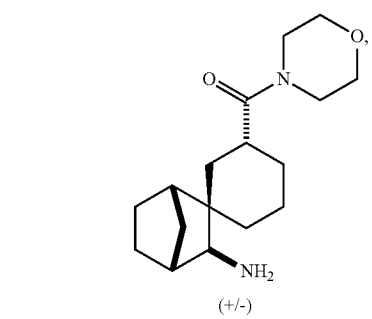
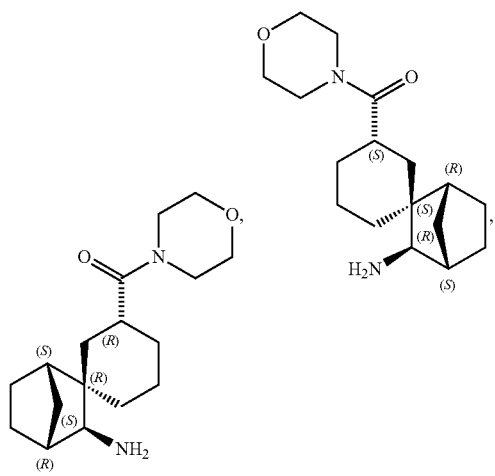
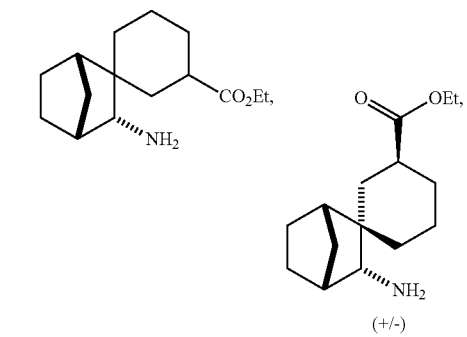

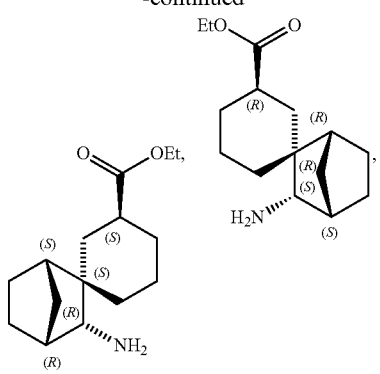
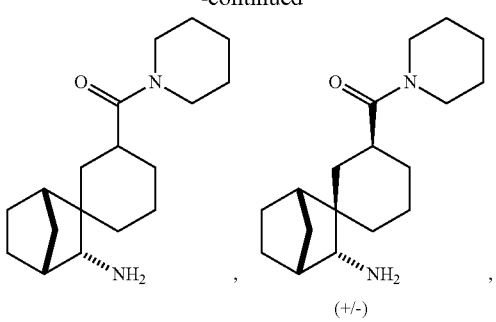
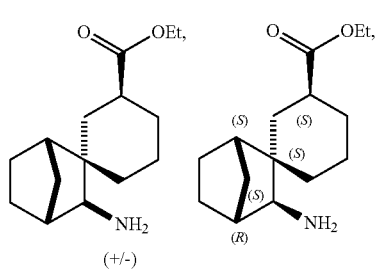
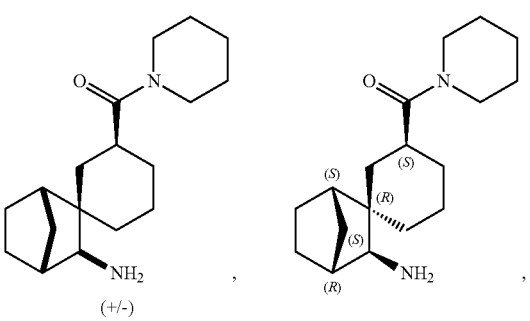
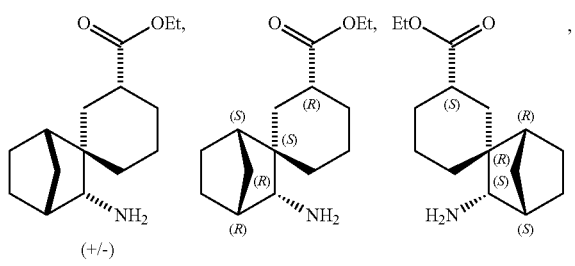
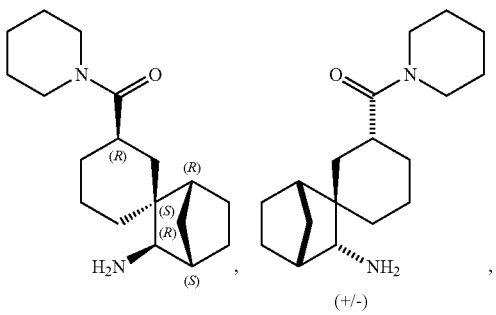
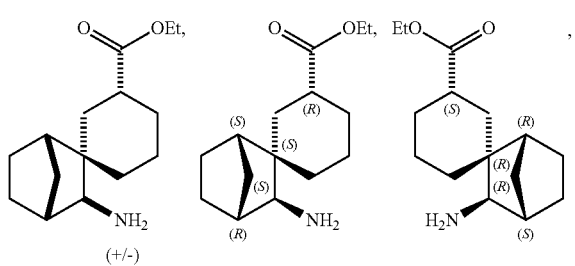
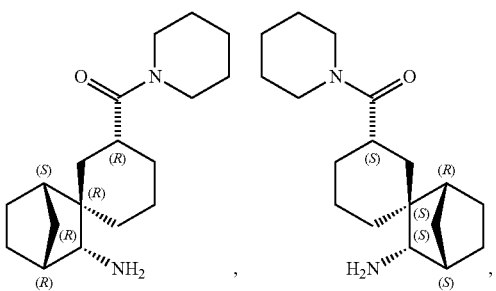

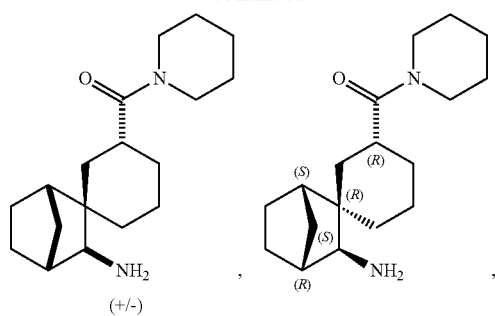
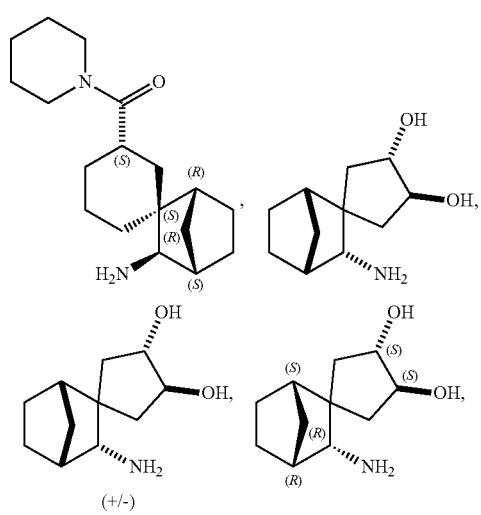
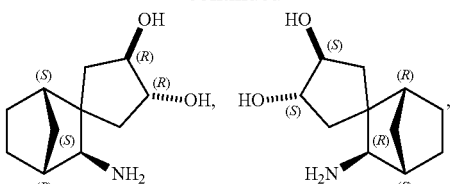
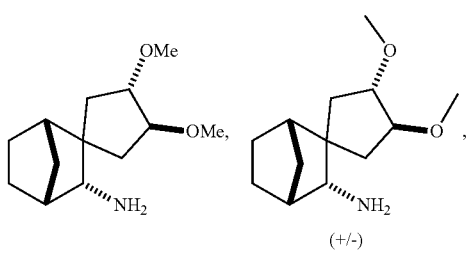
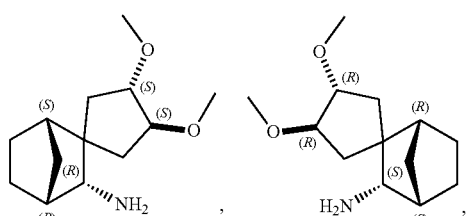
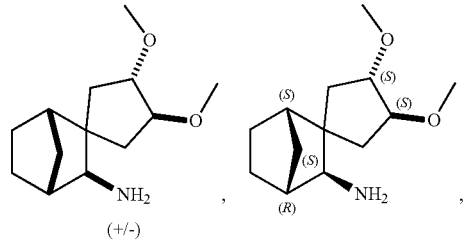
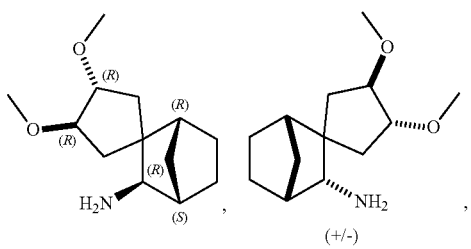
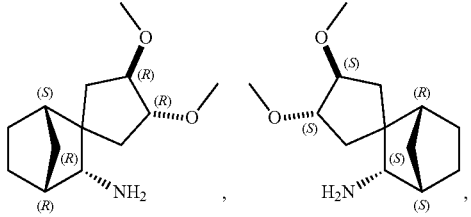
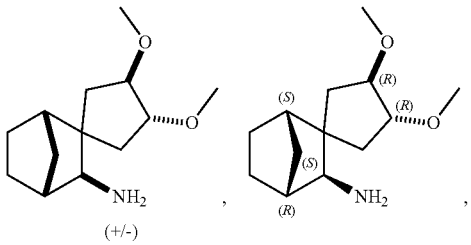

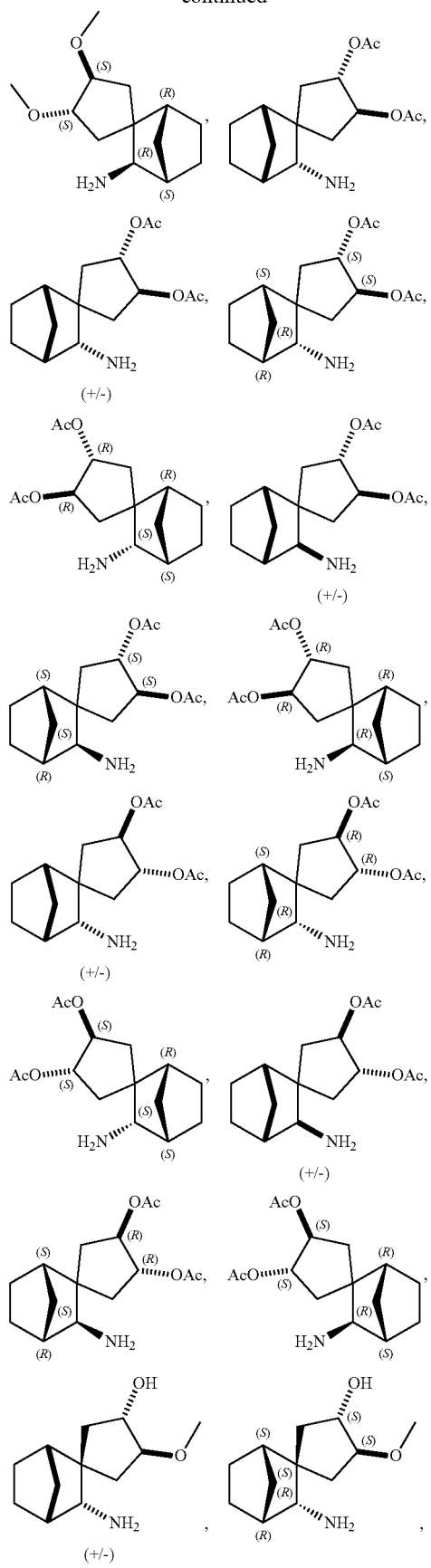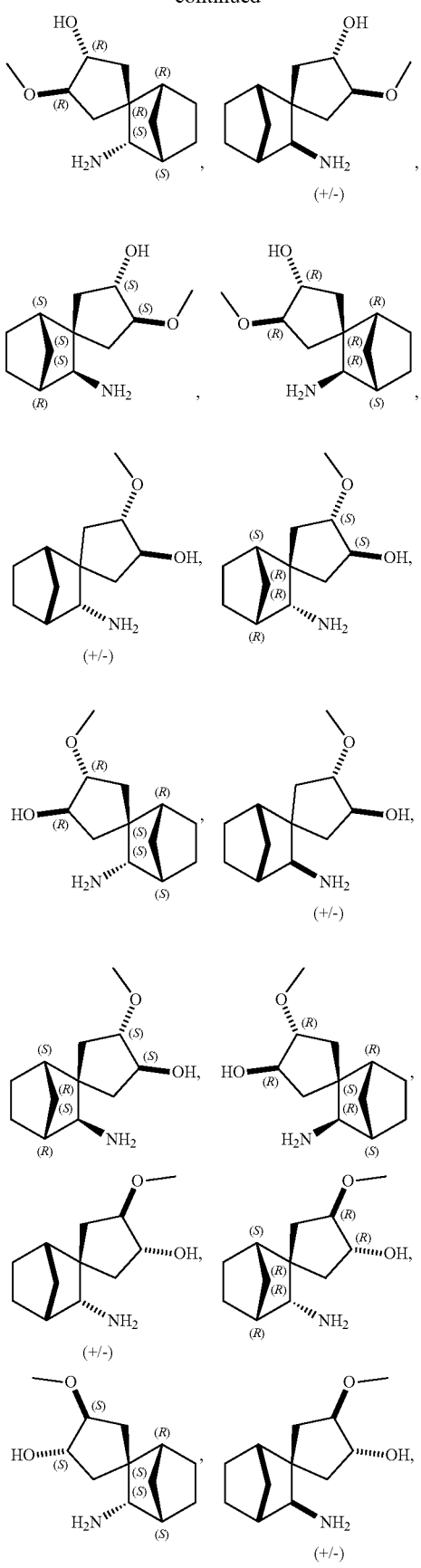

-continued
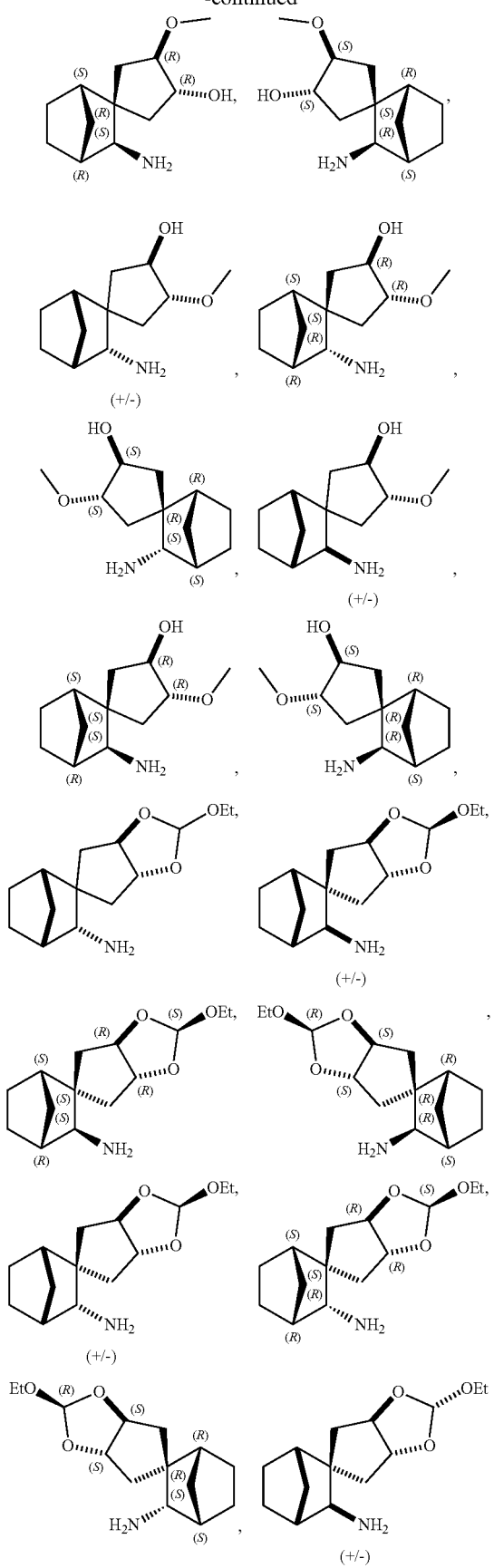
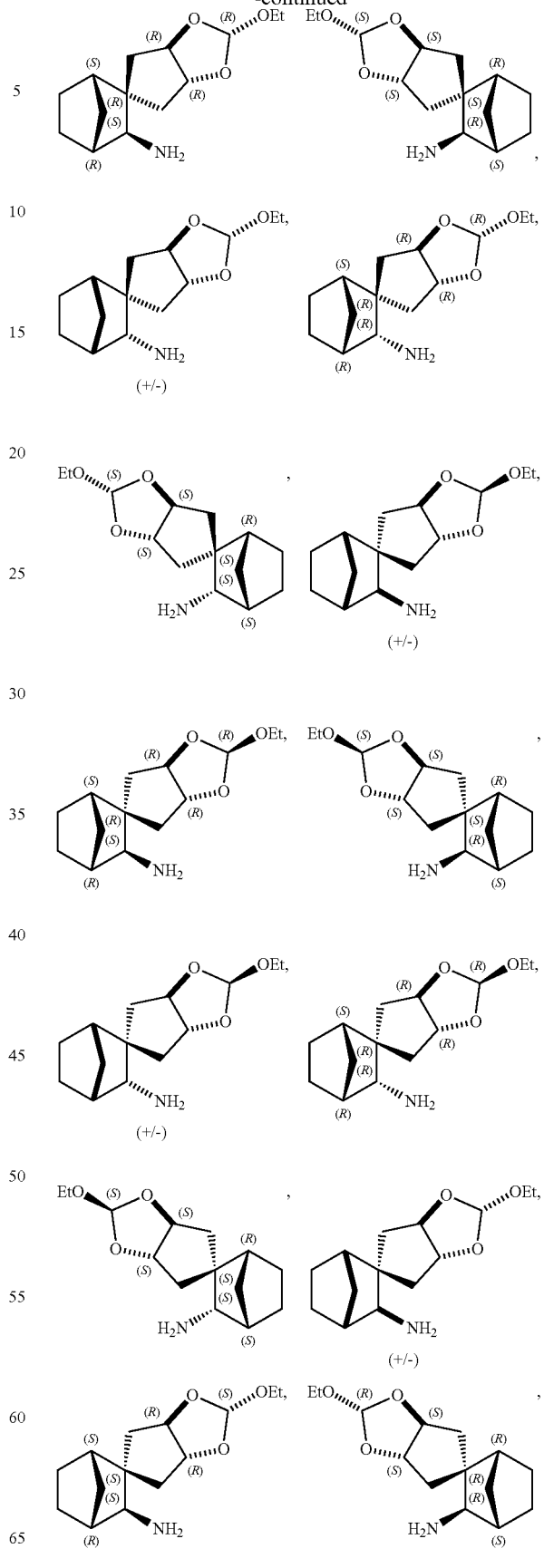

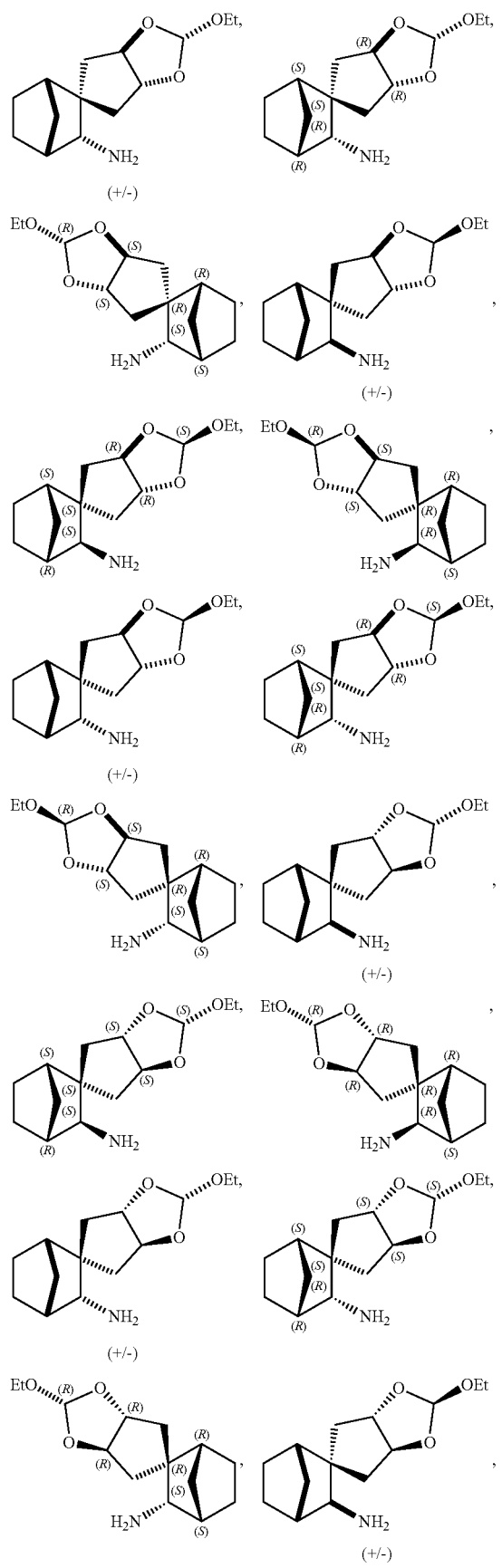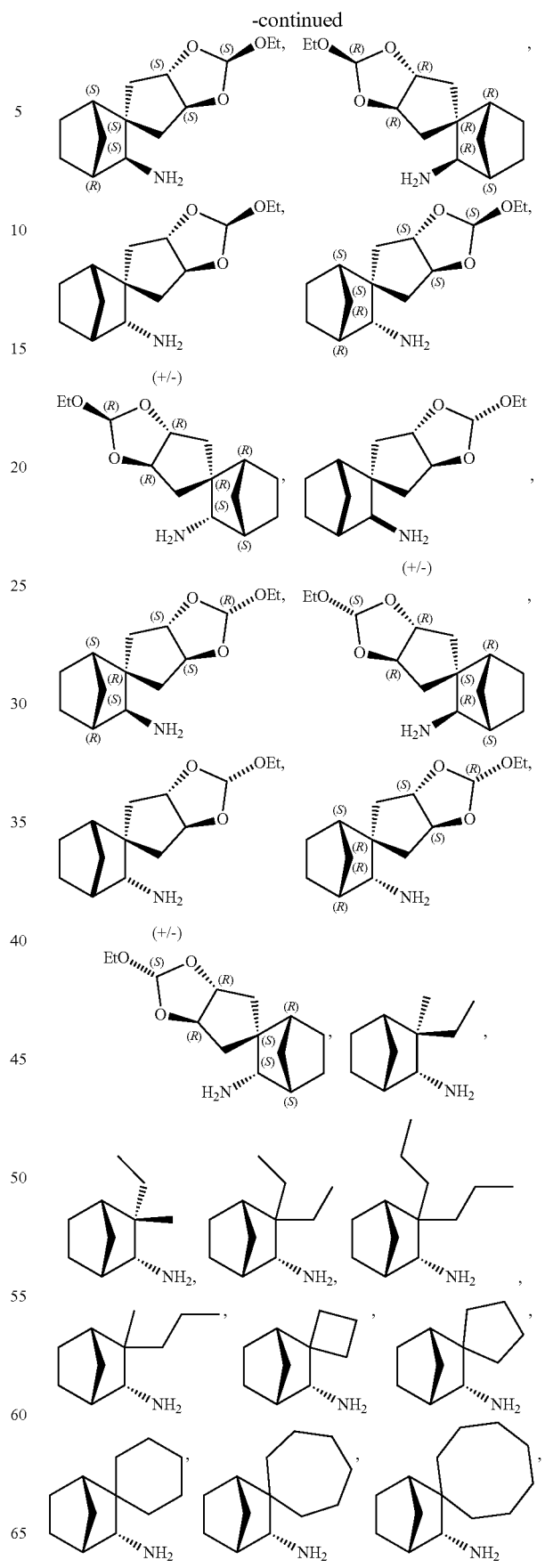

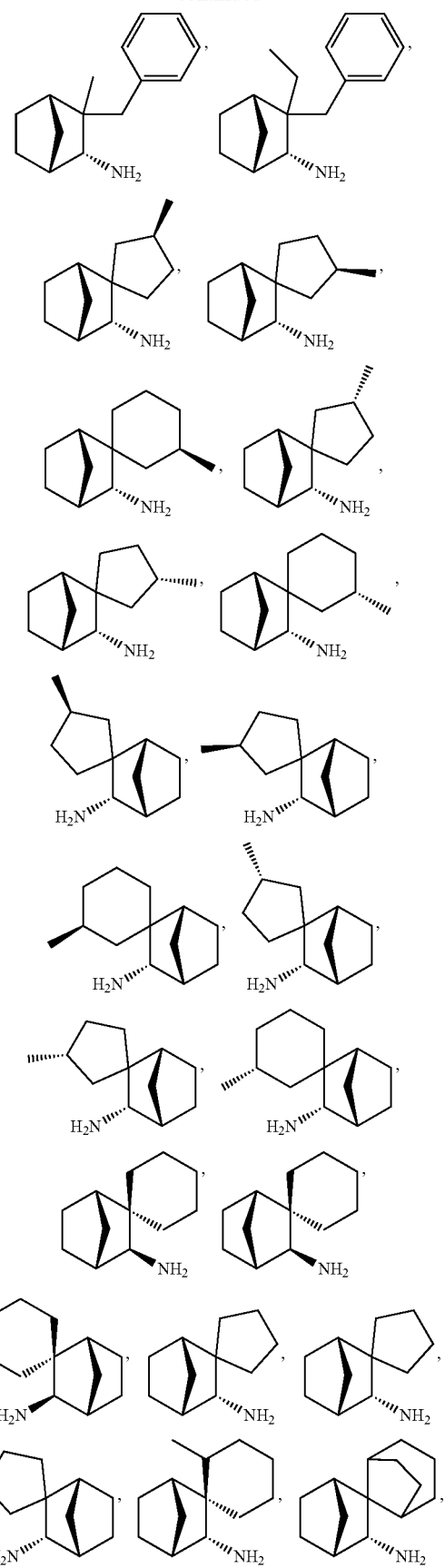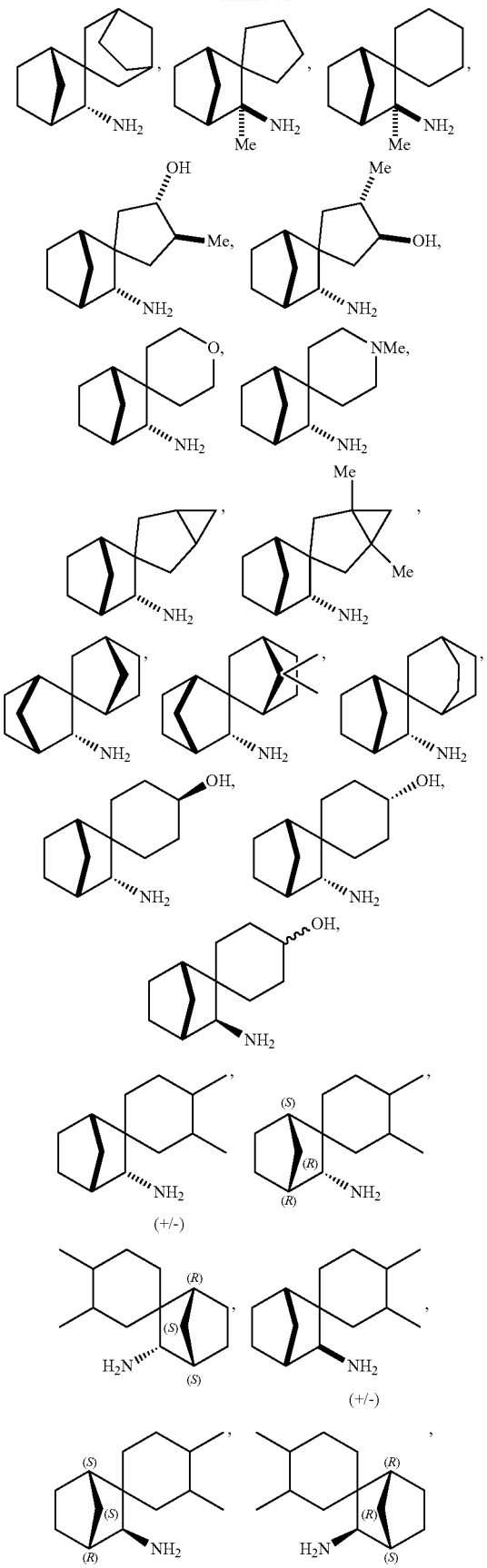

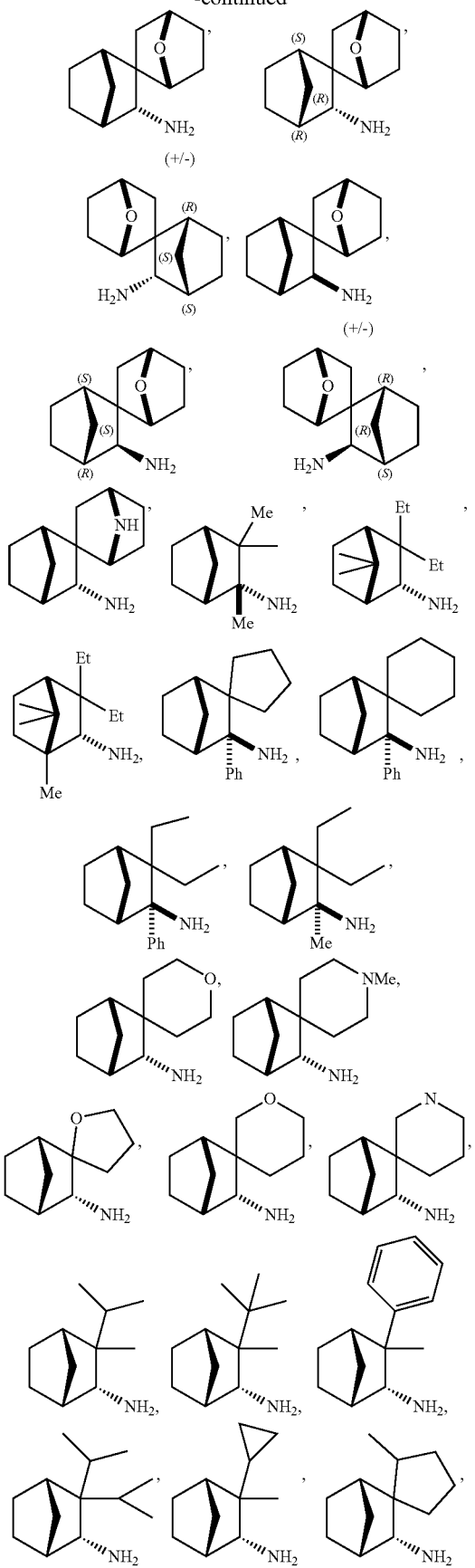
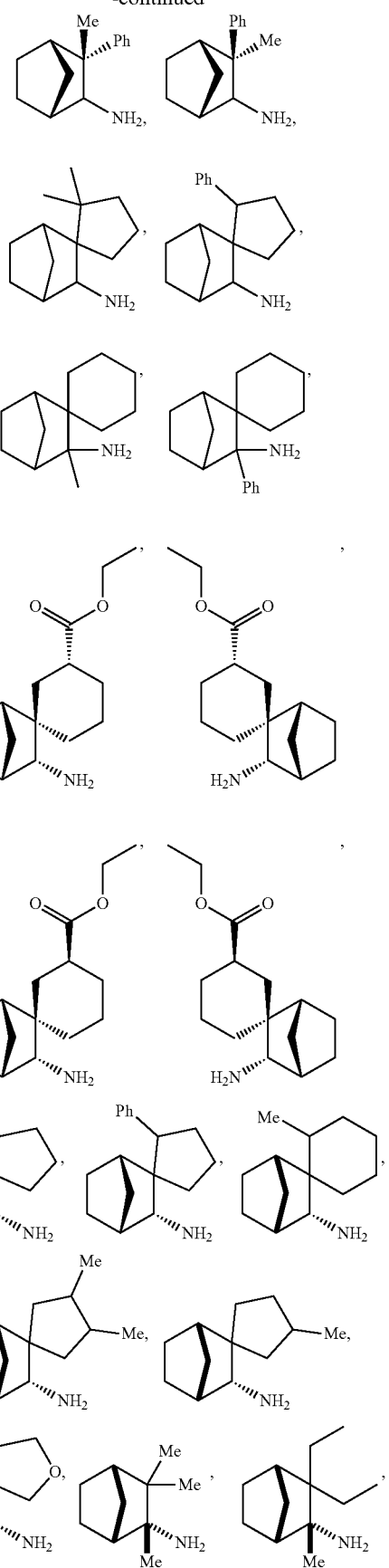

-continued

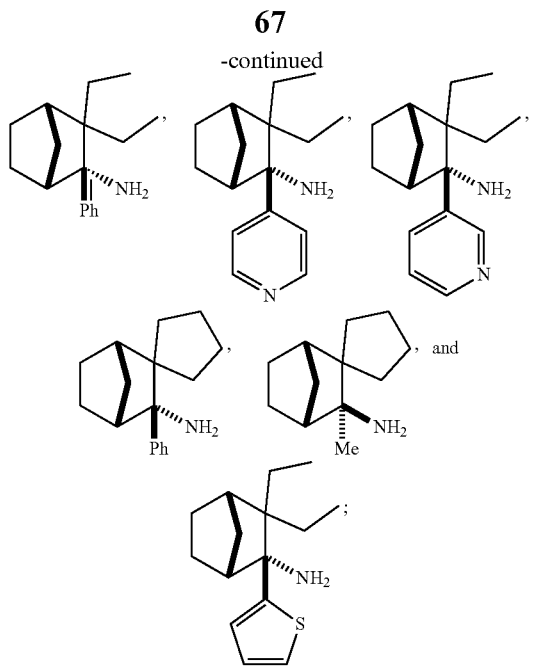

or a pharmaceutically acceptable salt thereof.

In certain embodiments, the method further comprises a step represented by Scheme II:

Scheme II

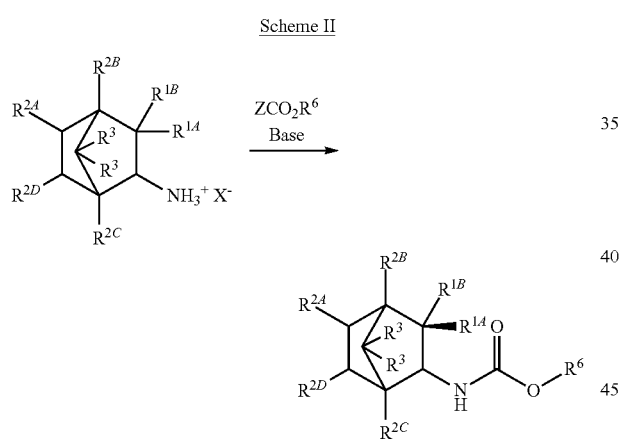

wherein
Z is halo;
$R^6$ is aralkyl or heteroaralkyl; and
base is a carbonate base or a nitrogenous base.

In certain embodiments, the method further comprises a step represented by Scheme IIIa:

Scheme IIIa

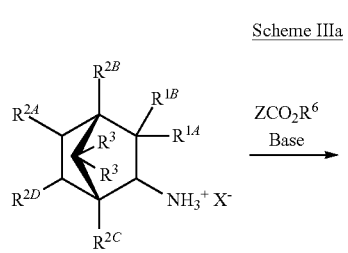

-continued

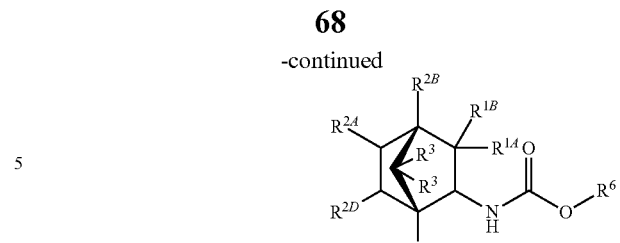

wherein
Z is halo;
$R^6$ is aralkyl or heteroaralkyl; and
base is a carbonate base or a nitrogenous base.

In certain embodiments, the method further comprises a step represented by Scheme IIIb:

Scheme IIIb

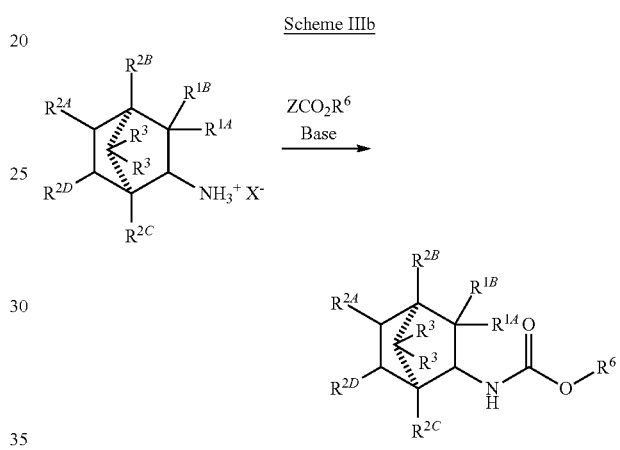

wherein
Z is halo;
$R^6$ is aralkyl or heteroaralkyl; and
base is a carbonate base or a nitrogenous base.

In certain embodiments, the method is represented by Scheme IIIc:

Scheme IIIc

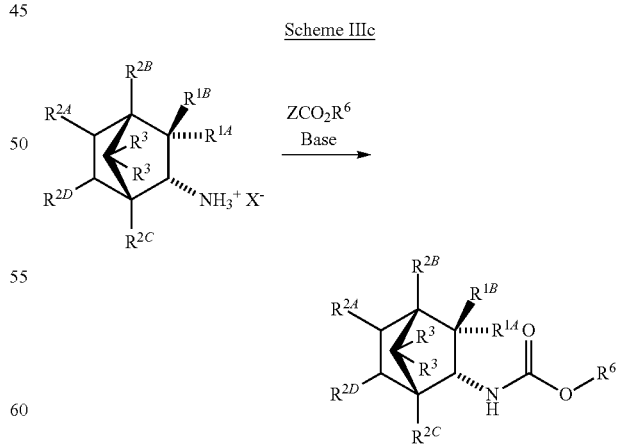

wherein
Z is halo;
$R^6$ is aralkyl or heteroaralkyl; and
base is a carbonate base or a nitrogenous base.

In certain embodiments, the method is represented by Scheme IIId:

Scheme IIId

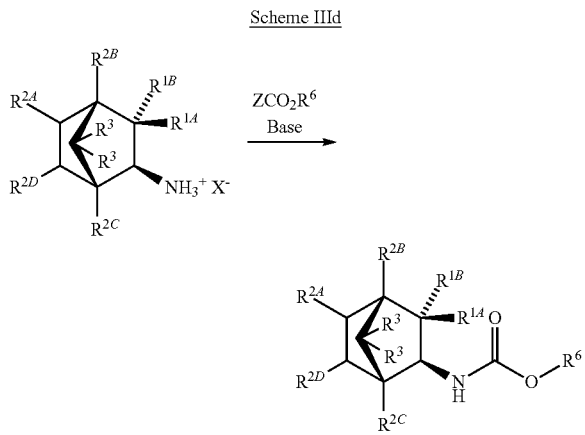

wherein
Z is halo;
$R^6$ is aralkyl or heteroaralkyl; and
base is a carbonate base or a nitrogenous base.

In certain embodiments, the method is represented by Scheme IIIe:

Scheme IIIe

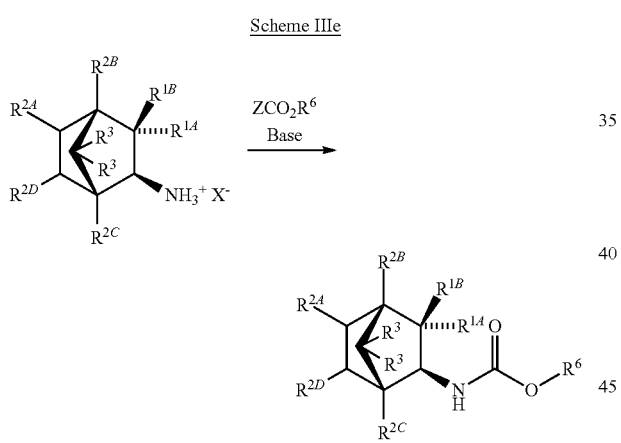

wherein
Z is halo;
$R^6$ is aralkyl or heteroaralkyl; and
base is a carbonate base or a nitrogenous base.

In certain embodiments, the method is represented by Scheme IIIf:

Scheme IIIf

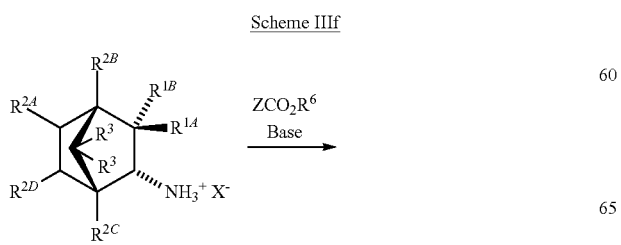

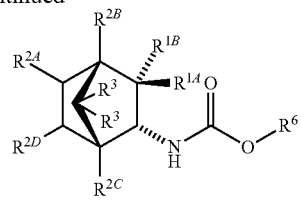

wherein
Z is halo;
$R^6$ is aralkyl or heteroaralkyl; and
base is a carbonate base or a nitrogenous base.

In certain embodiments, the method is represented by Scheme IIIg:

Scheme IIIg

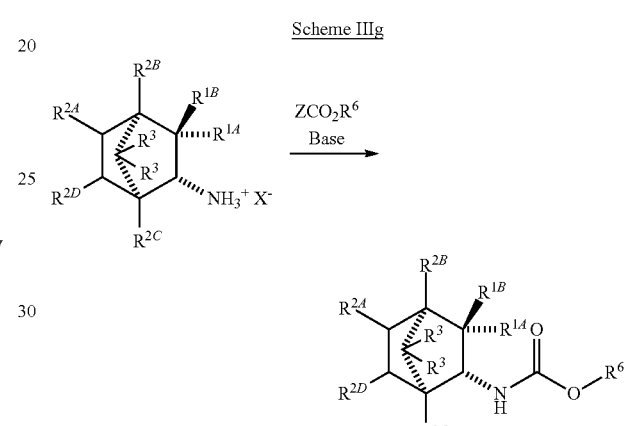

wherein
Z is halo;
$R^6$ is aralkyl or heteroaralkyl; and
base is a carbonate base or a nitrogenous base.

In certain embodiments, the method is represented by Scheme IIIh:

Scheme IIIh

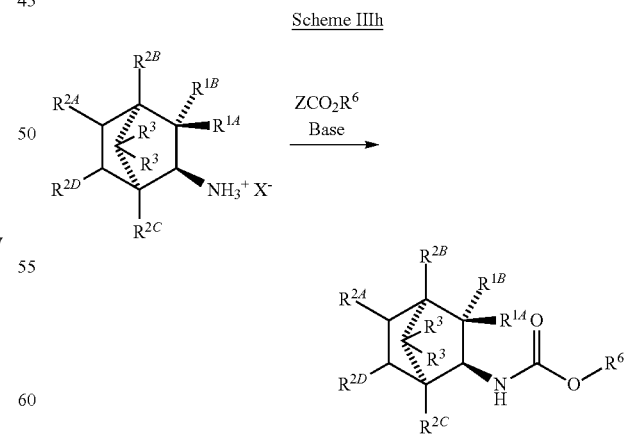

wherein
Z is halo;
$R^6$ is aralkyl or heteroaralkyl; and
base is a carbonate base or a nitrogenous base.

In certain embodiments, the method is represented by Scheme IIIi:

Scheme IIIi

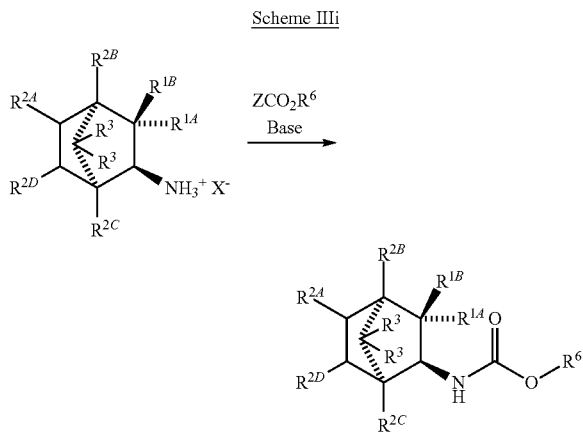

wherein
Z is halo;
$R^6$ is aralkyl or heteroaralkyl; and
base is a carbonate base or a nitrogenous base.

In certain embodiments, the method is represented by Scheme IIIj:

Scheme IIIj

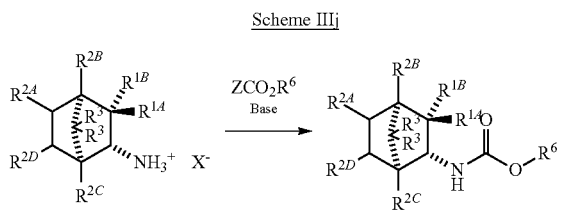

wherein
Z is halo;
$R^6$ is aralkyl or heteroaralkyl; and
base is a carbonate base or a nitrogenous base.

In certain embodiments of the method, Z is chloro. In certain embodiments of the method, $R^6$ is aralkyl. In certain embodiments of the method, $R^6$ is benzyl. In certain embodiments of the method, $R^6$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, alkylsulfonyl, or sulfonamide. In certain embodiments of the method, $R^6$ is substituted with nitro. In certain embodiments of the method, $R^6$ is substituted with nitro at the para-position.

In certain embodiments of the method, the nitrogenous base is a secondary or tertiary alkylamine (e.g., trimethylamine or diisopropylamine). In certain embodiments of the method, the carbonate base is sodium carbonate, potassium carbonate, calcium carbonate, or cesium carbonate. In certain embodiments of the method, the carbonate base is sodium carbonate. In certain embodiments of the method, the method further comprises a solvent. In certain embodiments of the method, the solvent is a mixture of water and a halogenated solvent. In certain embodiments of the method, the halogenated solvent is dichloromethane.

In certain embodiments, the present disclosure provides a method of treating or preventing a toxic proteinopathy with a compound, or pharmaceutical composition of the invention wherein $R^5$ is H.

In certain embodiments, the present disclosure provides a method for selecting a treatment for a toxic proteinopathy resulting from mutant protein accumulation in the early secretory pathway in a subject in need thereof, the method comprising: (a) identifying a subject as having or being at risk of developing a toxic proteinopathy resulting from mutant protein accumulation in the early secretory pathway; and (b) selecting a compound or pharmaceutical composition of the invention wherein $R^5$ is H as a treatment for the subject identified as having or being at risk of developing a toxic proteinopathy resulting from mutant protein accumulation in the early secretory pathway. In certain embodiments, the toxic proteinopathy is selected from a neurodegenerative disease, MUC1-associated kidney disease, autosomal dominant kidney disease caused by uromodulin mutations, and a form of retinitis pigmentosa (RP) caused by a rhodopsin mutation. In certain embodiments, the toxic proteinopathy is MUC1-associated kidney disease. In certain embodiments, the subject has one or more of the following: end-stage renal disease, urinalysis revealing minimal protein and no blood, slowly progressive kidney failure, hyperglycemia and/or gout. In certain embodiments, the subject has been identified to be in need of dialysis or kidney transplantation. In certain embodiments, the subject has one or more of the following symptoms of RP: night blindness; tunnel vision (due to loss of peripheral vision); latticework vision; photopsia (blinking/shimmering lights); photophobia (aversion to bright lights); development of bone spicules in the fundus; slow adjustment from dark to light environments and vice versa; blurring of vision; poor color separation; loss of central vision; and/or blindness.

In certain embodiments, step (b) comprises identifying the presence in the subject of a mutation in MUC1, UMOD and/or rhodopsin, optionally wherein the MUC1 mutation is a MUC1 frameshift mutation, the UMOD mutation is a C126R UMOD mutation and/or the rhodopsin mutation is a P23H rhodopsin mutation. In certain embodiments, the method further comprises: (c) administering the selected compound or pharmaceutical composition of the invention wherein $R^5$ is H to the subject. In certain embodiments, the subject is human.

In certain embodiments, the present disclosure provides a method for treating or preventing a proteinopathy resulting from mutant protein accumulation in the early secretory pathway in a subject, the method comprising: identifying a subject as having or at risk of developing a proteinopathy resulting from mutant protein accumulation in the early secretory pathway in a subject; and administering a compound or pharmaceutical composition of the invention wherein $R^5$ is H to the subject in an amount sufficient to cause reduction or improvement of a symptom of the proteinopathy resulting from mutant protein accumulation in the early secretory pathway in the subject, thereby treating or preventing the proteinopathy resulting from mutant protein accumulation in the early secretory pathway in the subject. In certain embodiments, said compound causes release of MUC1, UMOD and/or rhodopsin from the early secretory compartment, optionally wherein said compound causes release of MUC1, UMOD and/or rhodopsin from the endoplasmic reticulum (ER), from COPI-coated vesicles, from COPII-coated vesicles and/or from the Golgi apparatus. In certain embodiments, the proteinopathy is selected from a neurodegenerative disease, MUC1-associated kidney disease, autosomal dominant kidney disease caused by uromodulin mutations, a form of retinitis pigmentosa (RP) caused by a rhodopsin mutation, pulmonary alveolar proteinosis or ApoL1-positive kidney disease, and type II diabetes, optionally wherein the neurodegenerative disease is selected from Alzheimer's disease (AD) and other dementias; Parkinson's disease (PD) and PD-related disorders; lysozyme amyloidosis; dialysis amyloidosis; cystic fibrosis; cataracts; odontogenic tumor amyloid; familial British dementia; hereditary cerebral hemorrhage with amyloidosis (Icelandic); familial amyloidotic neuropathy or senile systemic/cardiomyopathy; ApoAII amyloidosis; familial amyloidosis of the Finnish type (FAF); fibrinogen amyloidosis; inclusion body myositis/myopathy; hereditary lattice corneal dystrophy; prion disease (including, e.g., Creutzfeldt-Jakob Disease, variant Creutzfeldt-Jakob Disease, Bovine Spongiform Encephalopathy (BSE), Kuru, Gerstmann-Sträussler-Scheinker disease, fatal familial insomnia (FFI), scrapie, and other animal TSEs); motor neuron diseases (MND; including, e.g., Amyotrophic Lateral Sclerosis (ALS), Primary Lateral Sclerosis (PLS), Progressive Bulbar Palsy (PBP), Pseudobulbar Palsy, Progressive Muscular Atrophy, Spinal Muscular Atrophy (Type 1, Type 2, Type 3, Type 4), and Kennedy's Disease); and spinocerebellar ataxia (SCA).

In certain embodiments, the proteinopathy is MUC1-associated kidney disease. In certain embodiments, the symptom of the proteinopathy is selected from end-stage renal disease, urinalysis revealing minimal protein and no blood, slowly progressive kidney failure, hyperglycemia, gout, a need for dialysis or kidney transplantation, night blindness; tunnel vision (optionally due to loss of peripheral vision); latticework vision; photopsia (blinking/shimmering lights); photophobia (aversion to bright lights); development of bone spicules in the fundus; slow adjustment from dark to light environments and vice versa; blurring of vision; poor color separation; loss of central vision; and/or blindness. In certain embodiments, the subject has a mutation in MUC1, UMOD and/or rhodopsin, optionally wherein the MUC1 mutation is a MUC1 frameshift mutation, the UMOD mutation is a C126R UMOD mutation and/or the rhodopsin mutation is a P23H rhodopsin mutation. In certain embodiments, the pharmaceutical composition comprising a compound of the invention wherein $R^5$ is H is administered to the subject via the oral route (P.O.). In certain embodiments, the pharmaceutical composition comprising a compound of the invention wherein $R^5$ is H comprises a pharmaceutically-acceptable carrier/excipient.

In certain embodiments, the present disclosure provides a method for reducing or eliminating accumulation of a mutant protein in the ER lumen of a cell, in COPI and/or COPII vesicles of a cell, in the cis-Golgi lumen of a cell, in the medial cisternae of the Golgi of a cell, and/or in the trans-Golgi network (TGN) of a cell, the method comprising administering a compound or pharmaceutical composition of the invention wherein $R^5$ is H to the environment of a cell in an amount sufficient to reduce or eliminate accumulation of the mutant protein in the ER lumen of the cell, in COPI and/or COPII vesicles of the cell, in the cis-Golgi lumen of the cell, in the medial cisternae of the Golgi of the cell, and/or in the trans-Golgi network (TGN) of the cell, thereby reducing or eliminating accumulation of the mutant protein in the ER lumen of the cell, in COPI and/or COPII vesicles of the cell, in the cis-Golgi lumen of the cell, in the medial cisternae of the Golgi of the cell, and/or in the trans-Golgi network (TGN) of the cell. In certain embodiments, the mutant protein is selected from a MUC1 frameshift mutant protein, a UMOD pathogenic variant and a rhodopsin mutant, optionally wherein the MUC1 mutation is a MUC1 frameshift mutation, the UMOD mutation is a C126R UMOD mutation and/or the rhodopsin mutation is a P23H rhodopsin mutation.

In certain embodiments, the present disclosure provides a pharmaceutical composition for treating a subject having or at risk of developing a proteinopathy comprising a therapeutically effective amount of a compound of the invention wherein $R^5$ is H and a pharmaceutically acceptable carrier. In certain embodiments, the proteinopathy is selected from a neurodegenerative disease, MUC1-associated kidney disease, autosomal dominant kidney disease caused by uromodulin mutations and a form of retinitis pigmentosa (RP) caused by a rhodopsin mutation. In certain embodiments, the subject is human.

In certain embodiments, the present disclosure provides a method of treating or preventing MUC1-associated kidney disease (MKD) in a subject in need thereof, the method comprising administering to the subject a compound or pharmaceutical composition of the invention wherein $R^5$ is H as a first agent and a second agent selected from vitamin D, a phosphate binder, a blood pressure medication and a diuretic, thereby treating or preventing MKD in the subject.

Pharmaceutical Compositions

The compositions and methods of the present invention may be utilized to treat an individual in need thereof. In certain embodiments, the individual is a mammal such as a human, or a non-human mammal. When administered to an animal (e.g., a mammal), such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to C1-C$_{10}$ straight-chain alkyl groups or C$_1$-C$_{10}$ branched-chain alkyl groups. Preferably, the "alkyl" group refers to C$_1$-C$_6$ straight-chain alkyl groups or C$_1$-C$_6$ branched-chain alkyl groups. Most preferably, the "alkyl" group refers to C$_1$-C$_4$ straight-chain alkyl groups or C$_1$-C$_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C$_{1-30}$ for straight chains, C$_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "C$_{x-y}$" or "C$_x$-C$_y$", when used in conjunction with a chemical moiety, such as, acyl, acyloxy, alkyl, alkenyl, alkynyl, or alkoxy is meant to include groups that contain from x to y carbons in the chain. Coalkyl indicates a hydrogen where the group is in a terminal position, a bond if internal. A C$_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

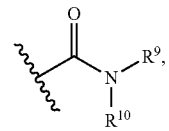

wherein R$^9$ and R$^{10}$ each independently represent a hydrogen or hydrocarbyl group, or R$^9$ and R$^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

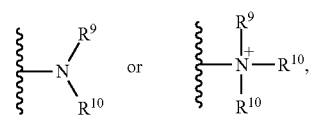

wherein R$^9$, R$^{10}$, and R$^{10\prime}$ each independently represent a hydrogen or a hydrocarbyl group, or R$^9$ and R$^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

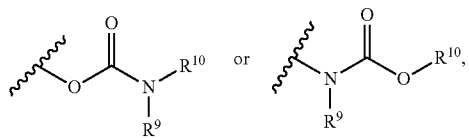

wherein R$^9$ and R$^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "cycloalkyl" includes substituted or unsubstituted non-aromatic single ring structures, preferably 4- to 8-membered rings, more preferably 4- to 6-membered rings. The term "cycloalkyl" also includes polycyclic ring systems having two or more cyclic rings in which two or more carbons are common to two adjoining rings wherein at least one of the rings is cycloalkyl and the substituent (e.g., $R^{100}$) is attached to the cycloalkyl ring, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, denzodioxane, tetrahydroquinoline, and the like.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

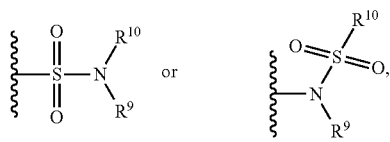

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group $SO_3H$, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

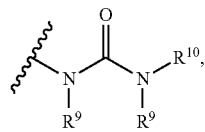

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

In certain embodiments, compounds of the disclosure may be racemic. In certain embodiments, compounds of the disclosure may be enriched in one enantiomer. For example, a compound of the disclosure may have greater than about 30% ee, 40% ee, 50% ee, 60% ee, 70% ee, 80% ee, 90% ee, 95%, 96%, 97% ee, 98% ee, 99% ee, or greater ee. In certain embodiments, compounds of the invention may have more than one stereocenter. In certain such embodiments, compounds of the invention may be enriched in one or more diastereomers. For example, a compound of the invention may have greater than about 30% de, about 40% de, about 50% de, about 60% de, about 70% de, about 80% de, about 90% de, or even about 95% or greater de.

In certain embodiments, a composition may be enriched to provide predominantly one enantiomer of a compound. An enantiomerically enriched composition may comprise, for example, at least about 60 mol percent of one enantiomer, or more preferably at least about 75, about 90, about 95, or even about 99 mol percent. In certain embodiments, the composition enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the composition may be enriched to provide predominantly one diastereomer of a compound, e.g., relative to other diastereomers. A diastereomerically enriched composition may comprise, for example, at least about 60 mol percent of one diastereomer, or more preferably at least about 75, about 90, about 95, or even about 99 mol percent.

One of ordinary skill in the art will understand that embodiments and dependent claims referencing variables that are part of a genus reciting "or a stereoisomer or pharmaceutically acceptable salt thereof" are to be construed as incorporating said "or a stereoisomer or pharmaceutically acceptable salt thereof." Notwithstanding, where stereochemistry is depicted in a genus, subgenus, or specific compound structure, the stereochemistry is to be construed as depicted.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

Treatment Selection

The compositions and methods described herein can be used for selecting, and then optionally administering, an optimal treatment (e.g., a compound as disclosed herein, alone (as a mixture of enantiomers (racemic or non-racemic) or diastereomers, or as one enantiomer or diastereomer) or in combination with other agents). Generally, the methods include administering a therapeutically effective amount of a treatment as described herein to a subject who is in need of, or who has been determined to be in need of, such treatment. Therapeutic applications and other uses for the compounds disclosed herein are expressly contemplated to include, without limitation, the full range of applications described in PCT/US2020/038847.

Methods of Treatment

As used in this context, to "treat" means to ameliorate at least one symptom of a proteinopathy. For example, a treatment can result in improved kidney function and/or amelioration in the rate of decline of kidney function that would occur in the absence of treatment, improved neurodegenerative disease and/or eye functions and/or amelioration in the rate of neurodegeneration and/or the rate of declining eye function in a subject having or at risk of a toxic proteinopathy resulting from mutant protein accumulation in the early secretory pathway, or in other organelles of the secretory pathway.

Exemplary neurodegenerative diseases of the instant disclosure include, without limitation, Alzheimer's disease (AD) and other dementias; Parkinson's disease (PD) and PD-related disorders; prion disease (including, e.g., Creutzfeldt-Jakob Disease, variant Creutzfeldt-Jakob Disease, Bovine Spongiform Encephalopathy, Kuru, Gerstmann-Sträussler-Scheinker disease, fatal familial insomnia (FFI), scrapie, and other animal TSEs); motor neuron diseases (MND; including, e.g., Amyotrophic Lateral Sclerosis (ALS), Primary Lateral Sclerosis (PLS), Progressive Bulbar Palsy (PBP), Pseudobulbar Palsy, Progressive Muscular Atrophy, Spinal Muscular Atrophy (Type 1, Type 2, Type 3, Type 4), and Kennedy's Disease); and spinocerebellar ataxia (SCA).

In certain embodiments, the methods of the instant disclosure can include selecting and/or administering a treatment that includes a therapeutically effective amount of a therapeutic compound disclosed herein. A therapeutic compound of the instant disclosure may be administered alone to a subject, or, optionally, the compound may be administered in combination with an additional therapeutic agent. Without limitation, specifically contemplated combination therapies for MUC1-associated kidney disease (MKD) include administration of a compound disclosed herein and any of the following: vitamin D in any or all of its forms (e.g., ergocalciferol, cholecalciferol, others), phosphate binders, blood pressure medications and diuretics. Specific examples of phosphate binders, blood pressure medications and diuretics include the following, with exemplary dosages also indicated:

Phosphate Binders:
Calcium Acetate (PhosLo, Calphron, Eliphos, PhosLo Gelcap, and Phoslyra)—667 mg or 667 mg in 5 ml (oral solution)
Sevelamer (Renagel and Renvela)—400 mg (Renagel tablet), 800 mg (Renagel tablet,
Renvela tablet, and Renvela powder packet), and 2400 mg (Renvela powder packet)
Ferric Citrate (Auryxia)—210 mg (tablet)
Lanthanum Carbonate (Fosrenol)—Tablet (500 mg, 750 mg, and 1000 mg) and Oral powder (750 mg and 1000 mg).
Sucroferric Oxyhydroxide (Velphoro)—500 mg
Aluminum Hydroxide (Amphojel)—320 mg/5 ml oral suspension Diuretics:
Bumetanide (Bumex)—0.5 mg (light green), 1 mg (yellow) and 2 mg (peach) tablets for oral administration.
Chlorthalidone (Thalitone)—Oral Tablet: 15 mg, 25 mg, 50 mg
Chlorothiazide (Diuril)—Adults (500 or 1000 mg IV/Tablet)
Ethacrynate (Edecrin)—25 mg tablets for oral use
Furosemide (Lasix)—Tablets 20, 40, and 80 mg
Hydrochlorothiazide HCTZ (Esidrix, Hydrodiuril, Microzide)—25 mg; 50 mg; 100 mg; 50 mg/5 mL; 12.5 mg
Indapamide (Lozol)—2.5 mg orally once a day.
Methyclothiazide (Enduron)—2.5 to 5 mg orally once a day
Metolazone (Mykroz, Zaroxolyn)—2.5 mg orally once a day (Zaroxolyn) or 0.5 mg orally once a day (Mykrox).
Torsemide (Demadex)—5 mg orally once a day; if diuresis remains inadequate after 4 to 6 weeks, titrate up to 10 mg orally once a day; if diuresis remains inadequate with 10 mg, an additional antihypertensive is added.

Blood Pressure Medications:
Beta Blockers:
acebutolol (Sectral)—200 mg or 400 mg tablet
atenolol (Tenormin)—25 mg, 50 mg, and 100 mg tablet.
betaxolol (Kerlone)—10 mg or 20 mg.
bisoprolol (Zebeta)—5 mg or 10 mg tablet.
bisoprolol/hydrochlorothiazide (Ziac)—Bisprolol (2.5 mg)/hydrochloride (6.25 mg) tablet.
metoprolol tartrate (Lopressor)—100 mg tablet daily
metoprolol succinate (Toprol-XL)—25 mg to 100 mg daily.
nadolol (Corgard)—40 mg tablet daily.
pindolol (Visken)—5 mg tablet initial dose.
propranolol (Inderal)—40 mg twice daily.
solotol (Betapace)—80 mg-240 mg tablets in 80 mg increments.
timolol (Blocadren)—5 mg, 10 mg, and 20 mg tablet.

ACE Inhibitors:
benazepril (Lotensin)—10 mg, 20 mg, and 40 mg tablets.
captopril (Capoten)—12.5 mg, 25 mg, 50 mg, and 100 mg tablet.
enalapril (Vasotec)—5 mg initial daily dose.
fosinopril (Monopril)—10 mg once a day
lisinopril (Prinivil, Zestril)—2.5 mg, 5 mg, 10 mg, 20 mg, 30 mg, 40 mg tablets 1 mg/ml oral solution.
moexipril (Univasc)—7.5 mg and 15 mg tablets.
perindopril (Aceon)—2 mg, 4 mg, and 8 mg tablets.
quinapril (Accupril)—5 mg, 10 mg, 20 mg, and 40 mg tablets.
ramipril (Altace)—1.25 mg tablet, 2.5 mg, and 5 mg tablet.
trandolapril (Mavik)—1 mg, 2 mg, and 4 mg tablet.

Calcium Channel Blockers
amlodipine (Norvasc, Lotrel)—10 mg orally
diltiazem (Cardizem CD, Cardizem SR, Dilacor XR, Tiazac)—20 mg average adult dose
felodipine (Plendil)—2.5 mg, 5 mg, and 10 mg oral tablet.
isradipine (DynaCirc, DynaCirc CR)—7.5 mg daily
nicardipine (Cardene SR)—20 mg and 30 mg capsule.
nifedipine (Adalat CC, Procardia XL)—10 mg, 20 mg, 30 mg, 60 mg, and 90 mg tablet.
nisoldipine (Sular)—17 mg orally daily.
verapamil (Calan SR, Covera HS, Isoptin SR, Verelan)—100 mg/200 mg daily.

Alpha Blockers
doxazosin (Cardura)—2 mg, 4 mg, and 8 mg daily.
prazosin (Minipress)—20 mg total daily dose.
terazosin (Hytrin)—1 mg at bedtime Alpha-Beta-Blockers
carvedilol (Coreg)—3.125 mg, 6.25 mg, 12.5 mg, and 25 mg tablet.
labetalol (Normodyne, Trandate)—100 mg, 200 mg, and 300 mg taken orally.

Central Agonists
methyldopa (Aldomet)—125 mg, 250 mg, and 500 mg tablet.
clonidine (Catapres)—0.1 mg, 0.2 mg, and 0.3 mg.
guanfacine (Tenex)—1 mg, 2 mg, 3 mg, and 4 mg.

Vasodilators
hydralazine (Apresoline)—25 mg, 50 mg, 10 mg, 100 mg, and 20 mg/ml.
minoxidil (Loniten)—2.5 mg and 10 mg tablet.

Without wishing to be bound by theory, though compounds of the instant disclosure have been primarily identified for effect upon the early secretory pathway, it is contemplated that actions of the compounds disclosed herein upon the late secretory pathway could also exert a beneficial effect. Thus, it is contemplated that the compositions and methods of the instant disclosure could also address proteinopathy and related effects in organelles of the late secretory pathway including, without limitation, post-Golgi trafficking vesicles (whether directed to the endosome, including, e.g., ESCRT-II complex vesicles, and/or endosome-bypassing lysosomal transport vesicles and/or cell surface-directed vesicles), the endosome, and/or post-endosomal transport vesicles, including, without limitation, endosome-to-lysosome vesicles, endosome-to-cell surface transport vesicles (including, e.g., synaptic vesicles) and cell surface-to-endosome vesicles, and the lysosome.

Combination Treatments

The compositions and methods of the present disclosure may be used in the context of a number of therapeutic or prophylactic applications. In order to increase the effectiveness of a treatment with the compositions of the present disclosure, e.g., a compound of the instant disclosure selected and/or administered as a single agent, can be selected and/or administered with another agent or therapy, optionally to augment the efficacy of another therapy (second therapy). Thus, it may be desirable to combine these compositions and methods with one another, or with other agents and methods effective in the treatment, amelioration, or prevention of diseases and pathologic conditions, for example, toxic proteinopathies resulting from mutant protein accumulation in the early secretory pathway, such as a neurodegenerative disease, MKD, an autosomal dominant kidney disease caused by uromodulin mutation, a form of retinitis pigmentosa caused by rhodopsin mutation, etc.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

EXAMPLES

The invention now being generally described, it will be more readily understood by reference to the following examples which are included merely for purposes of illustration of certain aspects and embodiments of the present invention, and are not intended to limit the invention.

Example 1: Preparation of Exemplary Compounds

General Overview of Synthetic Approaches

C3 disubstituted C2-endo-amine [2.2.1] bicycles are prepared through alkylation of the enolate of norcamphor followed oxime formation and reduction. The regiochemistry of C3 is known through the order of addition as alkylation of [2.2.1] enolates which provides exclusively the C3-exo alkylated product. Spirocyclic examples are synthesized by ring-closing metathesis reaction of alkenes introduced to C3 by enolate alkylation. Alternatively, spirocycles could be prepared through reaction of the enolate of norcamphor with dihaloalkanes, followed by a second formation of the enolate to provide the intramolecular alkylation and furnish the spriocycle, from which the endo-amine was prepared via oxime formation and reduction as described above. A representative synthesis of a spirocyclic compound is shown. Reduction of the oxime also reduces the alkene and furnishes the fully saturated compound. Enantio-pure compounds are prepared by functionalization of the amine as the Cbz carbamate to facilitate chiral separation by SFC chromatography.

Representative Procedure for C3-Disubstituted Analogs Prepared Through Alkylation of Norcamphor (Representative Procedure A)

Synthesis of (1R,2R,4S)-3,3-dimethylbicyclo[2.2.1]heptan-2-amine hydrochloride (201-P1), (1S,2S,4R)-3,3-dimethylbicyclo[2.2.1]heptan-2-amine hydrochloride (201-P2)

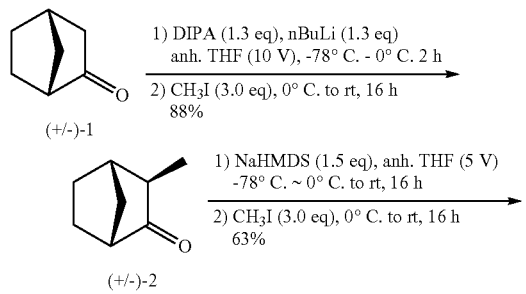

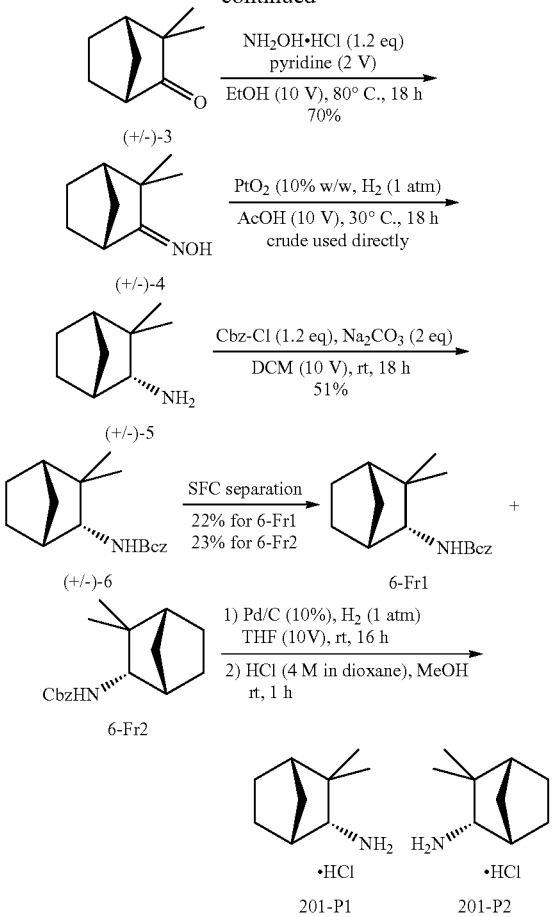

Note: absolute configuration is unassigned and the configuration of the C1 of P1 is arbitrarily shown as (R).

Step 1: To a stirred solution of diisopropylamine (12.0 g, 91 mmol, 1.3 eq) in anhydrous THF (10 mL) at −78° C. was added nBuLi (1.6 M in THF; 72 mL, 114 mmol, 1.25 eq) under $N_2$ protection. The reaction mixture was allowed to warm to 0° C. and a solution of rac-bicyclo[2.2.1]heptan-2-one (10.0 g) in anhydrous THF (5.0 mL) was added dropwise. The corresponding reaction mixture was then stirred at 0~5° C. for 2 hours under $N_2$ followed by the addition of $CH_3I$ (39 g, 273 mmol, 3.0 eq). The mixture was gradually warmed to room temperature and stirred overnight under $N_2$ protection. Once GC showed the reaction finished, the reaction mixture was poured into ice-water (300 mL; contain 10.0 mL conc. HCl) and stirred for 10 minutes followed by the extraction with EtOAc (3×100 mL). The organic phase was then washed with aq. sat. $NaHCO_3$ solution (100 mL), brine (100 mL), dried over $Na_2SO_4$, and filtered. The filtration was then concentrated under vacuum to give rac-3-exo-methylbicyclo[2.2.1]heptan-2-one (9.8 g, 88%) as a dark red oil. 1H NMR (400 MHz, $CDCl_3$) δ 2.56-2.54 (m, 1H), 2.32-2.31 (m, 1H), 1.90-1.76 (m, 4H), 1.54-1.42 (m, 3H), 1.05 (d, J=7.6 Hz, 3H).

Step 2: To a solution of rac-3-exo-methylbicyclo[2.2.1]heptan-2-one (5.0 g, 40 mmol, 1.0 eq) in anhydrous THF (5.0 mL) at −78° C. was added dropwise sodium bis(trimethylsilyl)amide (1 M in THF; 60 mL, 60 mmol, 1.5 eq) under nitrogen atmosphere. The reaction mixture was allowed to warm to 0° C. and stirred for 2 hours at 0° C. to 5° C. before the dropwise addition of $CH_3I$ (7.5 mL, 120 mmol, 3.0 eq). The corresponding reaction mixture was warmed to room temperature and stirred at room temperature overnight. Once GC showed the reaction finished, the reaction mixture was poured to ice-water (100 mL; contain 10.0 mL conc. HCl) and stirred for 10 minutes followed by the extraction with EtOAc (3×50 mL). The organic phase was then washed with aq. sat. NaHCO$_3$ solution (50 mL), brine (50 mL), dried over Na$_2$SO$_4$, and filtered. The filtration was then concentrated under vacuum to give rac-3,3-dimethylbicyclo[2.2.1]heptan-2-one (3.5 g, 63%) as a dark red oil.

Step 3: To a solution of rac-3,3-dimethylbicyclo[2.2.1]heptan-2-one (1.0 g, 7.23 mmol, 1.0 eq) in EtOH (10 mL) was added hydroxylamine hydrochloride (754 mg, 10.85 mmol, 1.5 eq) and pyridine (2 mL, 2V), and the reaction mixture was stirred at 80° C. overnight. Once LCMS showed the reaction finished, solvent was removed under vacuum to get a residue, which was diluted and extracted with EtOAc (3×50 mL). The organic phases were collected, washed with brine (20 mL), dried over Na$_2$SO$_4$, and filtered. The filtration was then concentrated under vacuum to get the crude, which was purified by prep-HPLC eluting with 0-90% ACN in water (0.1% TFA) to give rac-3,3-dimethylbicyclo[2.2.1]heptan-2-one oxime (770 mg, 70%) as a colorless semi-solid. LCMS [M+H]: 154.1.

Step 4: To a solution of rac-3,3-dimethylbicyclo[2.2.1]heptan-2-one oxime (770 mg, 5.0 mmol, 1.0 eq) in AcOH (10.0 mL) was added PtO$_2$ (77 mg, 10% wt), and the reaction mixture was stirred at room temperature under H$_2$ atmosphere (1 atm) overnight. Once LCMS showed the reaction finished, reaction mixture was filtered and the filtration was concentrated to get rac-3,3-dimethylbicyclo[2.2.1]heptan-2-endo-amine (370 mg crude) as a yellow oil. LCMS [M+H]: 140.3.

Step 5: To a solution of rac-3,3-dimethylbicyclo[2.2.1]heptan-2-endo-amine (370 mg, 2.66 mmol, 1.0 eq) in THF:H$_2$O=2:1 (10 mL) was added sodium bicarbonate (560 mg, 6.65 mmol, 2.5 eq) and benzyl chloroformate (910 mg, 5.32 mmol, 2.0 eq). The reaction mixture was then stirred at room temperature overnight. Once LCMS showed the reaction finished, solvent was removed under vacuum to get a residue, which was diluted and extracted with EtOAc (3×50 mL). The organic phases were collected, washed with brine (20 mL), dried over Na$_2$SO$_4$, and filtered. The filtration was then concentrated under vacuum to get the crude, which was purified by prep-HPLC eluting with 0-90% ACN in water (0.1% TFA) to give rac-benzyl (3,3-dimethylbicyclo[2.2.1]heptan-2-endo-yl)carbamate (370 mg, 51%) as a colorless semi-solid. 1H NMR (400 MHz, CDCl$_3$) δ 7.36 (dd, J=9.5, 4.3 Hz, 5H), 5.09 (d, J=1.3 Hz, 2H), 3.58 (dd, J=8.3, 3.7 Hz, 1H), 2.31 (s, 1H), 1.81 (s, 1H), 1.72 (d, J=10.3 Hz, 1H), 1.59 (dd, J=8.4, 6.0 Hz, 1H), 1.34-1.19 (m, 4H), 1.07 (d, J=13.8 Hz, 3H), 0.80 (s, 3H).

Step 6: Separation of enantiomers by SFC chromatography.

Analytical separation method: Instrument: Waters UPCC, Column: ChiralPak AY, 250×4.6 mm, 5 μm, Mobile phase: A for CO$_2$ and B for EtOH (0.04% DEA), Gradient: B 0-40%, Flow rate: 2.8 mL/min, Back pressure: 100 bar, Column temperature: 35° C., Wavelength: 214 nm Preparative separation method: Instrument: Waters SFC80, Column: ChiralPak AY, 250×25 mm, 10 μm, Mobile phase: A for CO$_2$ and B for EtOH (0.04% DEA), Gradient: B 40%, Flow rate: 70 g/min, Back pressure: 100 bar, Column temperature: 35° C., Wavelength: 214 nm, Cycle time: 8 min, Sample preparation: Compound was dissolved in 15 mL methanol, Injection: 3 ml per injection.

360 mg of racemic material was subjected to SFC separation. After separation, benzyl ((1R,2R,4S)-3,3-dimethylbicyclo[2.2.1]heptan-2-yl)carbamate (compound 6-Fr1; 80 mg, 22%, 100% ee) was obtained as a colorless solid, and benzyl ((1S,2S,4R)-3,3-dimethylbicyclo[2.2.1]heptan-2-yl)carbamate (compound 6-Fr2; 85 mg, 23%, 100% ee) was obtained as a colorless solid.

Step 7: To a solution of benzyl ((1R,2R,4S)-3,3-dimethylbicyclo[2.2.1]heptan-2-yl)carbamate (80 mg, 0.29 mmol, 1.0 eq) in EtOAc (5.0 mL) was added Pd/C (8 mg, 10% wt), and the reaction mixture was stirred at room temperature under H$_2$ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 201-P1 (13.1 mg, 26%) as a white solid. LCMS [M+H]: 140.3. 1H NMR (400 MHz, CD3OD) δ 3.04 (d, J=3.7 Hz, 1H), 2.44 (s, 1H), 1.91 (s, 1H), 1.81 (d, J=11.0 Hz, 1H), 1.71 (dd, J=8.1, 5.3 Hz, 1H), 1.55-1.42 (m, 3H), 1.37 (d, J=10.5 Hz, 1H), 1.11 (s, 3H), 1.00 (s, 3H).

To a solution of benzyl (1S,2S,4R)-3,3-dimethylbicyclo[2.2.1]heptan-2-yl)carbamate (85 mg, 0.31 mmol, 1.0 eq) in EtOAc (5.0 mL) was added Pd/C (8 mg, 10% wt), and the reaction mixture was stirred at room temperature under H$_2$ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 201-P2 (17.0 mg, 31%) as a white solid. LCMS [M+H]: 140.3. 1H NMR (400 MHz, MeOD) δ 3.04 (d, J=3.7 Hz, 1H), 2.44 (s, 1H), 1.91 (s, 1H), 1.81 (d, J=10.5 Hz, 1H), 1.76-1.63 (m, 1H), 1.58-1.42 (m, 3H), 1.37 (d, J=10.6 Hz, 1H), 1.11 (s, 3H), 0.98 (d, J=20.2 Hz, 3H).

TABLE 1

C2-amino-C3-disubstituted BRD4780 analogs. (Note, P1/P2 indicates a single enantiomer compound of undetermined absolute stereochemistry)

| Compound No. | Structure | 1H-NMR, 400 MHz | LCMS [M + H]+ | ee (%) | Procedure |
|---|---|---|---|---|---|
| 201-P1 | 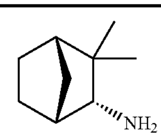 | (MeOD) δ 3.04 (d, J = 3.7 Hz, 1H), 2.44 (s, 1H), 1.91 (s, 1H), 1.81 (d, J = 10.5 Hz, 1H), 1.76-1.63 (m, 1H), 1.58-1.42 (m, 3H), 1.37 (d, J = 10.6 Hz, 1H), 1.11 (s, 3H), 0.98 (d, J = 20.2 Hz, 3H) | 140.3 | P1: 100% | A |
| 201-P2 | 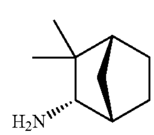 | | | P2: 100% | |

TABLE 1-continued

C2-amino-C3-disubstituted BRD4780 analogs. (Note, P1/P2 indicates a single
enantiomer compound of undetermined absolute stereochemistry)

| Compound No. | Structure | 1H-NMR, 400 MHz | LCMS [M + H]+ | ee (%) | Procedure |
|---|---|---|---|---|---|
| 202-rac | 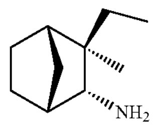 | (DMSO-d6) δ 8.17 (brs, 3H), 2.82 (brs, 1H), 2.36 (brs, 1H), 1.93 (brs, 1H), 1.70-1.63 (m, 2H), 1.52-1.48 (m, 1H), 1.43-1.27 (m, 4H), 1.18 (d, J = 10.0, 1H), 0.89 (s, 3H), 0.79 (t, J = 7.6 Hz, 3H). | 154.2 | NA | A |
| 202-P1 202-P2 | | (CDCl3) δ 8.28 (brs, 3H), 2.99 (brs, 1H), 2.51 (s, 1H), 1.92 (d, J = 2.0 Hz, 1H), 1.80-1.78 (m, 1H), 1.68-1.58 (m, 2H), 1.44-1.29 (m, 4H), 1.22-1.19 (m, 1H), 1.00 (s, 3H), 0.82 (t, J = 7.2 Hz, 3H). | 154.2 | P1: 100 P2: 100 | A |
| 203-P1 203-P2 | | (MeOD) δ 3.04 (d, J = 4.0 Hz, 1H), 2.45 (s, 1H), 2.03 (s, 1H), 1.79 (d, J = 10.6 Hz, 1H), 1.53 (ddd, J = 30.5, 20.7, 13.9 Hz, 5H), 1.38 (d, J = 10.6 Hz, 1H), 1.25-1.13 (m, 1H), 1.08 (s, 3H), 0.93 (t, J = 7.3 Hz, 3H). | 154.3 | P1: 100 P2: 88.5 | A |
| 204 | 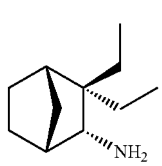 | (MeOD) δ 3.13 (d, J = 3.4 Hz, 1H), 2.46 (s, 1H), 2.01 (s, 1H), 1.78 (d, J = 10.5 Hz, 1H), 1.66-1.48 (m, 5H), 1.40-1.29 (m, 4H), 0.85 (q, J = 7.2 Hz, 6H). | 168.3 | NA | A |

TABLE 1-continued

C2-amino-C3-disubstituted BRD4780 analogs. (Note, P1/P2 indicates a single enantiomer compound of undetermined absolute stereochemistry)

| Compound No. | Structure | 1H-NMR, 400 MHz | LCMS [M + H]$^+$ | ee (%) | Procedure |
|---|---|---|---|---|---|
| 204-P1 | 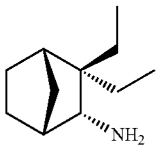 | (MeOD) δ 3.12 (d, J = 3.7 Hz, 1H), 2.45 (s, 1H), 2.00 (s, 1H), 1.78 (d, J = 10.4 Hz, 1H), 1.66-1.49 (m, 6H), 1.35 (dd, J = 12.8, 5.6 Hz, 6H), 0.85 (dd, J = 13.8, 7.0 Hz, 7H). | 168.3 | P1: 98.5 | A |
| 204-P2 | 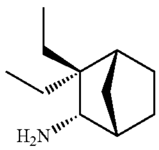 | | | P2: 94.2 | |
| 205 | 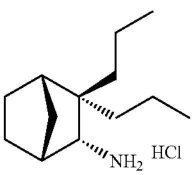 | (CDCl3) δ 8.33 (brs, 3H), 3.11 (s, 1H), 2.65 (s, 1H), 1.92 (s, 2H), 1.71-1.62 (m, 2H), 1.58-1.55 (m, 4H), 1.44-1.27 (m, 5H), 1.16-1.11 (m, 2H), 0.95-0.87 (m, 6H). | 196.2 | NA | A |
| 205-P1 | 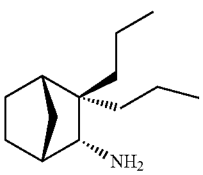 | (CDCl$_3$) δ 8.35 (brs, 3H), 3.12 (s, 1H), 2.66 (s, 1H), 1.93 (s, 2H), 1.70-1.62 (m, 2H), 1.45-1.36 (m, 4H), 1.34-1.27 (m, 5H), 1.17-1.12 (m, 2H), 0.96-0.92 (m, 3H), 0.91-0.88 (m, 3H). | 196.2 | P1: 98.8 | A |
| 205-P2 | 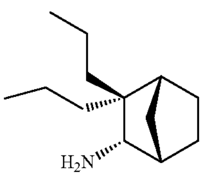 | | | P2: 95.1 | |
| 206-P1 | 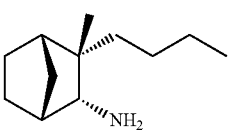 | (DMSO-d6) δ 8.09 (brs, 3H), 2.87 (t, J = 5.2, 1H), 2.37 (brs, 1H), 1.88 (brs, 1H), 1.68-1.56 (m, 2H), 1.43-1.26 (m, 7H), 1.22-1.15 (m, 3H), 0.99 (s, 3H), 0.90 (t, J = 7.2, 3H). | 182.3 | P1: 99 | A |
| 206-P2 | 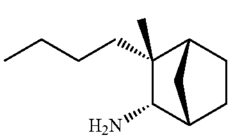 | | | P2: 100 | |

TABLE 1-continued

C2-amino-C3-disubstituted BRD4780 analogs. (Note, P1/P2 indicates a single enantiomer compound of undetermined absolute stereochemistry)

| Compound No. | Structure | 1H-NMR, 400 MHz | LCMS [M + H]+ | ee (%) | Procedure |
|---|---|---|---|---|---|
| 207 | 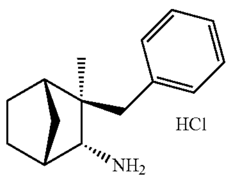 | (CDCl3) δ 7.28-7.22 (m, 3H), 7.15-7.13 (m, 2H), 3.18 (s, 1H), 2.72-2.66 (t, 2H), 2.20-2.19 (m, 1H), 1.84 (d, J = 3.8 Hz, 1H), 1.60-1.42 (m, 3 H), 1.38-1.35 (m, 2H), 1.02-0.96 (m, 3H) | 216.2 | NA | A |
| 207-P1 | 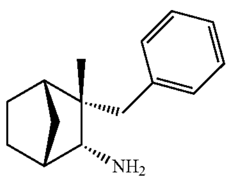 | (CD3OD) δ 7.30-7.21 (m, 5H), 3.08-3.05 (d, J = 12 Hz, 1H), 2.56 (s, 1H), 2.35-2.32 (d, J = 12 Hz, 1H), 2.15-2.12 (m, 1H), 1.93 (s, 1H), 1.84-1.81 (d, J = 12 Hz, 1H), 1.74-1.64 (m, 1H), 1.60-1.55 (m, 1H), 1.42-1.39 (d, J = 12 Hz, 1H), 0.93 (s, 3H) | 216.2 | P1: 95 | A |
| 207-P2 | 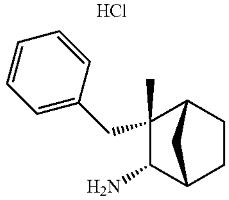 | | | P2: 100 | |

Representative procedure for synthesis of C3-spiro compounds through dialkylation of norcamphor enolate (Representative procedure B)

Synthesis of rac-spiro[bicyclo[2.2.1]heptane-3,1'-cyclobutan]-2-endo-amine hydrochloride (208)

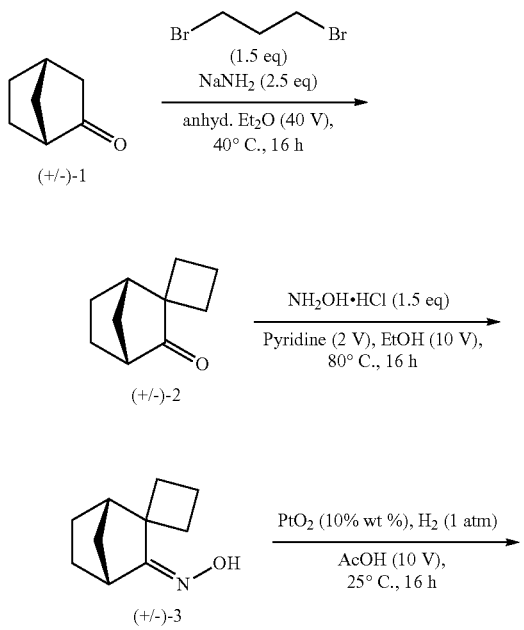

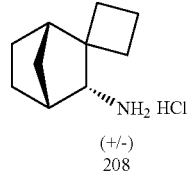

Step 1: To a magnetically stirred solution of norcamphor (0.5 g, 4.5 mmol, 1.0 eq) and 1,3-dibromopropane (1.4 g, 6.8 mmol, 1.5 eq) in anhydrous Et$_2$O (20.0 mL) was added NaNH$_2$ (438.8 mg, 11.3 mmol, 2.5 eq) in one portion. The whole reaction mixture was then stirred at 40° C. under N$_2$ for 16 hours. Once TLC showed no starting material left, and a new spot with a lower Rf value, the reaction mixture was cooled to room temperature. After that, the mixture was poured into ice-water (50 mL) and stirred for 5 minutes followed by extraction with EA (2×50 mL). All the organic phases were combined, washed with brine (3×30 mL), dried with Na$_2$SO$_4$, and filtered. The filtration was concentrated under vacuum to give crude rac-spiro[bicyclo[2.2.1]heptane-3,1'-cyclobutan]-2-one (0.7 g, crude) as a light yellow oil.

Step 2: To a solution of crude rac-spiro[bicyclo[2.2.1]heptane-3,1'-cyclobutan]-2-one (0.7 g, 4.7 mmol, 1.0 eq) in EtOH (7.0 mL) were added NH$_2$OH·HCl (486.5 mg, 7.0 mmol, 1.5 eq) and pyridine (1.4 mL, 2V). The reaction mixture was stirred at 80° C. overnight. Once LCMS showed the reaction finished, the reaction mixture was cooled to room temperature and solvent was removed under vacuum to provide the crude, which was extracted with EA (3×50 mL) and HCl (1N; 2×50 mL). All the organic phases were combined, washed with brine (3×50 mL), dried over Na$_2$SO$_4$, and filtered. The filtration was then concentrated under vacuum to get a residue which was purified by prep-HPLC eluting with 0-90% ACN in water (0.1% TFA) to give rac-spiro[bicyclo[2.2.1]heptane-3,1'-cyclobutan]-2-one oxime 335.6 mg. LCMS [M+H]: 166.1.

Step 3: To a solution of rac-spiro[bicyclo[2.2.1]heptane-3,1'-cyclobutan]-2-one (335.6 mg, 2.03 mmol, 1.0 eq) in AcOH (1.0 mL) was added PtO$_2$ (33.5 mg, 10% wt), and the reaction mixture was stirred at 25° C. under H$_2$ atmosphere (1 atm) overnight. Once LCMS showed the reaction finished, the mixture was filtered through celite and the filtration was concentrated under vacuum to provide the crude, which was then purified by prep-HPLC eluting with 0-90% ACN in water (0.1% TFA), and substituted with HCl to give rac-spiro[bicyclo[2.2.1]heptane-3,1'-cyclobutan]-2-endo-amine hydrochloride (144.5 mg, 0.77 mmol, 17.1% over 3 steps) as a white solid. LCMS [M+H]: 152.1. 1H NMR (400 MHz, DMSO-d6) δ 8.07 (brs, 3H), 3.00 (t, J=5.2 Hz, 1H), 2.33 (s, 1H), 2.17 (s, 1H), 2.00-1.98 (m, 1H), 1.87-1.74 (m, 5H), 1.39-1.25 (m, 6H).

Representative Procedure for Synthesis of C3-Spiro Compounds Through Ring-Closing Metathesis Approach (Representative Procedure C)

Synthesis of rac-spiro[bicyclo[2.2.1]heptane-3,1'-cyclopentan]-2-endo-amine hydrochloride (209) & (1R,3S,4S)-spiro[bicyclo[2.2.1]heptane-3,1'-cyclopentan]-2-amine hydrochloride (209-P1) & (1S,3R,4R)-spiro[bicyclo[2.2.1]heptane-3,1'-cyclopentan]-2-amine hydrochloride (209-P2)

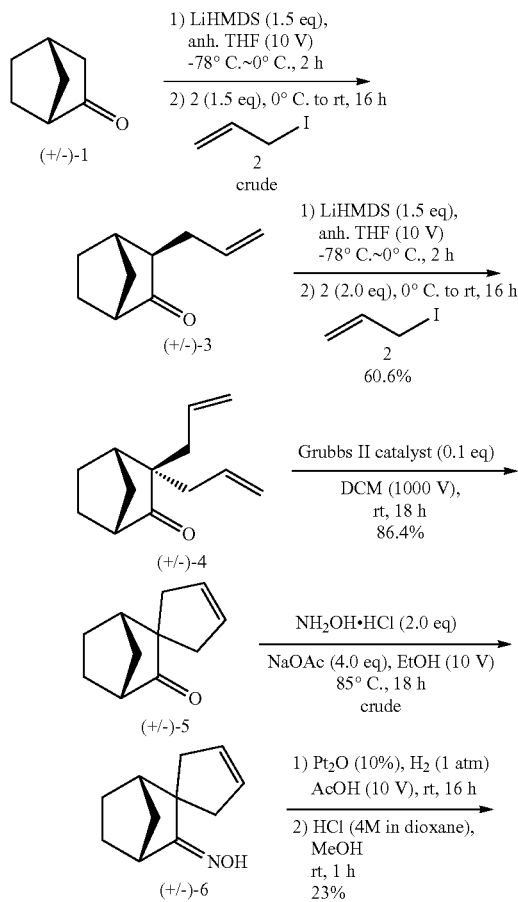

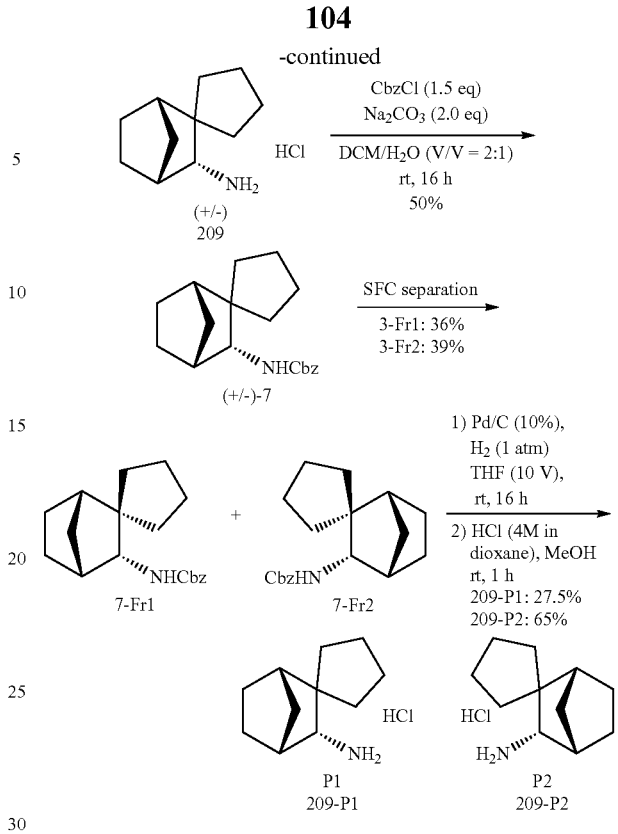

Step 1: To a stirred solution of rac-bicyclo[2.2.1]heptan-2-one (5.0 g, 45.4 mmol, 1.0 eq) in anhydrous THF (50 mL) at 0° C. was added LiHMDS (1.0 M in THF; 60 mL, 60 mmol, 1.5 eq) under N$_2$ protection. The corresponding reaction mixture was then stirred at 0-5° C. for 2 hours under N$_2$ followed by the addition of 3-iodoprop-1-ene (11.4 g, 67.5 mmol, 1.5 eq). The whole mixture was gradually warmed to room temperature and stirred overnight under N$_2$ protection. Once GC showed the reaction finished, the reaction mixture was poured into ice-water (300 mL; contain 10.0 mL conc. HCl) and stirred for 10 minutes followed by the extraction with EtOAc (3×100 mL). The organic phase was then washed with aq. sat. NaHCO$_3$ solution (100 mL), brine (100 mL), dried over Na$_2$SO$_4$, and filtered. The filtration was then concentrated under vacuum to give rac-3-exo-allylbicyclo[2.2.1]heptan-2-endo-one (8.94 g, crude) as a dark red oil.

Step 2: To a solution of rac-3-exo-allylbicyclo[2.2.1]heptan-2-endo-one (4 g, 24.3 mmol, 1.0 eq) in anhydrous DMF (93 mL) at 0° C. was added dropwise sodium bis(trimethylsilyl)amide (1 M in THF, 36 mL, 36 mmol, 1.5 eq) under nitrogen atmosphere. The reaction mixture was allowed to warm to 0° C. and stirred for 2 hours at 0° C. to 5° C. before the dropwise addition of 3-iodoprop-1-ene (8.1 g, 48.7 mmol, 2.0 eq). The corresponding reaction mixture was warmed to room temperature and stirred at room temperature overnight. Once TLC showed the reaction finished, the reaction mixture was poured to ice-water (100 mL; contain 10.0 mL conc. HCl) and stirred for 10 minutes followed by the extraction with EtOAc (3×50 mL). The organic phase was then washed with aq. sat. NaHCO$_3$ solution (50 mL), brine (50 mL), dried over Na$_2$SO$_4$, and filtered. The filtration was then concentrated under vacuum to give rac-3,3-diallylbicyclo[2.2.1]heptan-2-one (3.45 g, 18 mmol, 60.6%) as a brown oil. 1H NMR (400 MHz, CDCl$_3$) δ 5.90-5.75 (m, 2H), 5.11-4.99 (m, 4H), 2.58 (d, 1H), 2.40-2.35 (m, 2H), 2.29-2.43 (m, 1H), 2.20-2.14 (m, 1H), 2.05-1.99 (m, 2H), 1.90-1.82 (m, 2H), 1.81-1.77 (m, 2H), 1.69-1.58 (m, 1H), 1.52-1.46 (m, 2H).

Step 3: To a solution of rac-3,3-diallylbicyclo[2.2.1]heptan-2-one (1.0 g, 10.6 mmol, 1.0 eq) in anhydrous $CH_2Cl_2$ (1000 mL) was added Grubbs II catalyst (445 mg, 0.53 mmol, 0.1 eq) under $N_2$, and the reaction mixture was stirred at room temperature overnight. Once GC showed the reaction finished, evaporated to get a residue, which was then purified by silica gel column eluting with PE~PE:EA=10:1 to give rac-spiro[bicyclo[2.2.1]heptane-3,1'-cyclopentan]-3'-en-2-one (810 mg, 5 mmol, 86.4%) as a dark red solid. 1H NMR (400 MHz, $CDCl_3$) δ 5.68-5.85 (m, 1H), 5.58-5.55 (m, 1H), 2.62 (d, J=4.4 Hz, 1H), 2.54-2.43 (m, 3H), 2.37 (s, 1H), 2.32-2.27 (m, 1H), 1.88-1.80 (m, 2H), 1.66-1.61 (m, 3H), 1.56 (d, J=4.4 Hz, 1H), 1.53-1.46 (m, 1H).

Step 4: To a solution of rac-spiro[bicyclo[2.2.1]heptane-3,1'-cyclopentan]-3'-en-2-one (810 mg, 4.99 mmol, 1.0 eq) in EtOH (10 mL) was added hydroxylamine hydrochloride (693 mg, 9.98 mmol, 2.0 eq) and NaOAc (1.64 g, 19.97 mmol, 4.0 eq), and the reaction mixture was stirred at 80° C. overnight. Once LCMS showed the reaction finished, solvent was removed under vacuum to get a residue, which was diluted and extracted with EtOAc (3×50 mL). The organic phases were collected, washed with brine (3×10 mL), dried over $Na_2SO_4$, and filtered. The filtration was then concentrated under vacuum to give rac-spiro[bicyclo[2.2.1]heptane-3,1'-cyclopentan]-3'-en-2-one oxime (809 mg, crude) as a yellow oil. LCMS [M+H]: 178.2. 1H NMR (400 MHz, $CDCl_3$) δ 7.32 (brs, 1H), 5.75-5.72 (m, 1H), 5.68-5.63 (m, 1H), 3.50 (d, J=4 Hz, 1H), 2.57-2.53 (m, 3H), 2.41-2.35 (m. 1H), 2.21-2.20 (m, 1H), 1.76-1.65 (m, 4H), 1.59-1.55 (m, 2H), 1.50-1.44 (m, 1H), 1.42-1.39 (m. 1H).

Step 5: To a solution of rac-spiro[bicyclo[2.2.1]heptane-3,1'-cyclopentan]-3'-en-2-one oxime (809 mg, 4.57 mmol, 1.0 eq) in AcOH (10.0 mL) was added $PtO_2$ (80 mg, 10% wt), and the reaction mixture was stirred at room temperature under $H_2$ atmosphere (1 atm) overnight. Once LCMS showed the reaction finished, reaction mixture was filtered and the filtration was concentrated to get rac-spiro[bicyclo[2.2.1]heptane-3,1'-cyclopentan]-2-endo-amine hydrochloride (660 mg, crude). LCMS [M+H]: 166.1.

Step 6: To a solution of rac-spiro[bicyclo[2.2.1]heptane-3,1'-cyclopentan]-2-endo-amine hydrochloride (560 mg, 3.39 mmol, 1.0 eq) in DCM:$H_2O$=2:1 (15 mL) was added sodium bicarbonate (1058 mg, 10.17 mmol, 3.0 eq) and benzyl chloroformate (868 mg, 5.09 mmol, 1.5 eq). The whole reaction mixture was then stirred at room temperature overnight. Once LCMS showed the reaction finished, solvent was removed under vacuum to get a residue, which was diluted and extracted with DCM (3×50 mL). The organic phases were collected, washed with brine (20 mL), dried over $Na_2SO_4$, and filtered. The filtration was then concentrated under vacuum to get the crude, which was purified by prep-HPLC eluting with 0-90% ACN in water (0.1% TFA) to give rac-benzyl spiro[bicyclo[2.2.1]heptane-3,1'-cyclopentan]-2-endo-yl carbamate (600 mg, 50%) as a colorless semi-solid. 1H NMR (400 MHz, $CDCl_3$) δ 7.38-7.30 (m, 5H), 5.09 (s, 2H), 4.82 (d, J=8 Hz, 1H), 3.74 (dd, J=4, 8 Hz, 1H), 2.33 (s, 1H), 1.87 (s, 1H), 1.64-1.56 (m, 4H), 1.50-1.45 (m, 4H), 1.42-1.40 (m, 1H), 1.37-1.33 (m, 4H), 1.25 (d, J=8 Hz, 2H).

Step 7: To a solution of rac-benzyl spiro[bicyclo[2.2.1]heptane-3,1'-cyclopentan]-2-endo-yl carbamate (100 mg, 0.33 mmol, 1.0 eq) in EA (10.0 mL) was added Pd/C (20 mg, 10% wt), and the reaction mixture was stirred at room temperature under $H_2$ atmosphere (1 atm) overnight. Once LCMS showed the reaction finished, solvent was removed to get the crude, which was then purified by prep-HPLC eluting with 0-90% ACN in water (0.1% TFA), and substituted by HCl to give BM-108 (53 mg, 78.8%) as a white solid. 1H NMR (400 MHz, $CDCl_3$) δ 8.35 (s, 3H), 3.20 (s, 1H), 2.64 (s, 1H), 1.91 (s, 1H), 1.83-1.77 (m, 2H), 1.67-1.59 (m, 3H), 1.58-1.56 (m, 2H), 1.53-1.49 (m, 3H), 1.47-1.46 (m, 1H), 1.44-1.38 (m, 2H), 1.35-1.33 (m, 1H).

Step 8: 500 mg of rac-benzyl spiro[bicyclo[2.2.1]heptane-3,1'-cyclopentan]-2-endo-yl carbamate was separated by chiral SFC chromatography.

Analytical separation method: Instrument: Waters UPCC, Column: ChiralPak AY, 250×4.6 mm, 5 μm, Mobile phase: A for $CO_2$ and B for MeOH (0.04% DEA), Gradient: B 0-40%, Flow rate: 2.8 mL/min, Back pressure: 100 bar, Column temperature: 35° C., Wavelength: 214 nm Preparative separation method: Instrument: Waters SFC80, Column: ChiralPak AY, 250×25 mm, 10 μm, Mobile phase: A for $CO_2$ and B for MeOH (0.04% DEA), Gradient: B 40%, Flow rate: 2.8 mL/min, Back pressure: 100 bar, Column temperature: 35° C., Wavelength: 214 nm, Cycle time: 8 min, Sample preparation: Compound was dissolved in 15 mL methanol, Injection: 3 ml per injection.

After separation, benzyl (1R,3S,4S)-spiro[bicyclo[2.2.1]heptane-2,1'-cyclopentan]-3-ylcarbamate (compound 3-Fr1; 180 mg, 36%, 100% ee) was obtained as a colorless solid, and benzyl (1S,3R,4R)-spiro[bicyclo[2.2.1]heptane-2,1'-cyclopentan]-3-ylcarbamate (compound 3-Fr2; 197 mg, 39%, 100% ee) was obtained as a colorless solid.

Step 9: To a solution of benzyl (1R,3S,4S)-spiro[bicyclo[2.2.1]heptane-2,1'-cyclopentan]-3-ylcarbamate (180 mg, 0.60 mmol, 1.0 eq) in EA (10.0 mL) was added Pd/C (20 mg, 10% wt), and the reaction mixture was stirred at room temperature under $H_2$ atmosphere (1 atm) overnight. Once LCMS showed the reaction finished, solvent was removed to get the crude, which was then purified by prep-HPLC eluting with 0-90% ACN in water (0.1% TFA), and substituted by HCl to give BM-108-P1 (33 mg, 27.5%) as a white solid. 1H NMR (400 MHz, $CDCl_3$) δ 8.37-8.34 (m, 3H), 3.198 (m, 1H), 2.639 (m, 1H), 1.91 (m, 1H), 1.83-1.80 (m, 2H), 1.72-1.66 (m, 4H), 1.62-1.58 (m, 3H), 1.51-1.50 (m, 1H), 1.46-1.42 (m, 2H), 1.34 (d, J=8 Hz, 1H), 1.253 (s, 1H).

Synthesis of (1R,3S,4S)-spiro[bicyclo[2.2.1]heptane-3,1'-cyclohexan]-2-amine & (1S,3R,4R)-spiro[bicyclo[2.2.1]heptane-3,1'-cyclohexan]-2-amine (212-P1 & 212-P2)

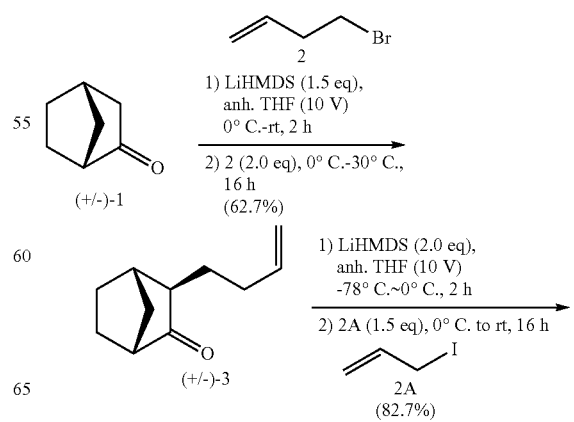

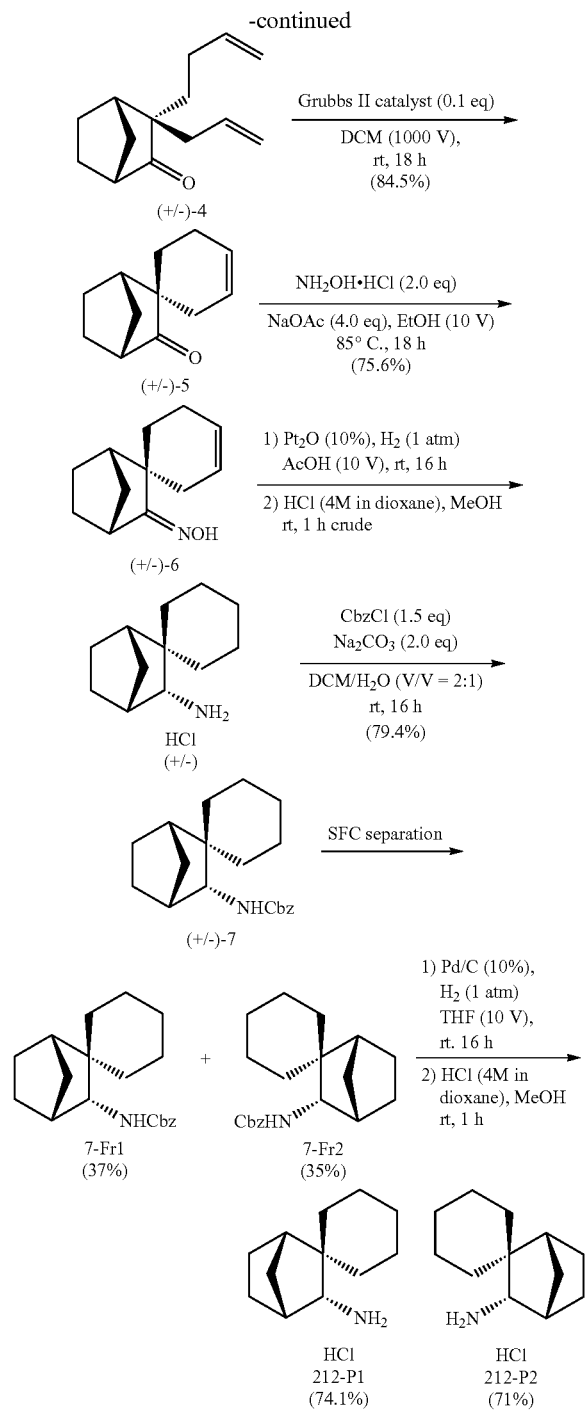

was then washed with aq. sat. NaHCO₃ solution (100 mL), brine (2×100 mL), dried over Na₂SO₄, and filtered. The filtration was then concentrated under vacuum to give rac-3-exo-(but-3-en-1-yl)bicyclo[2.2.1]heptan-2-one (4.67 g, 28.4 mmol, 62.7%) as a dark red oil. 1H NMR (400 MHz, CDCl₃) δ 5.83-5.76 (m, 1H), 5.09-4.98 (m, 2H), 2.64 (s, 1H), 2.43 (d, J=1.6 Hz, 1H), 2.43-2.05 (m, 2H), 1.87-1.79 (m, 3H), 1.75-1.70 (m, 1H), 1.68-1.64 (m, 1H), 1.59-1.47 (m, 2H), 1.46-1.44 (m, 1H), 1.41-1.30 (m, 1H).

Step 2: To a solution of rac-3-exo-(but-3-en-1-yl)bicyclo [2.2.1]heptan-2-one (4.47 g, 27.2 mmol, 1.0 eq) in anhydrous THF (50 mL) at 0° C. was added dropwise sodium bis(trimethylsilyl)amide (1 M in THF, 54 mL, 54 mmol, 2.0 eq) under nitrogen atmosphere. The reaction mixture was allowed to warm to 0° C. and stirred for 2 hours at 0° C. to 5° C. before the dropwise addition of 3-iodoprop-1-ene (6.86 g, 40.8 mmol, 1.5 eq). The corresponding reaction mixture was warmed to room temperature and stirred at room temperature overnight. Once TLC showed the reaction finished, the reaction mixture was poured to ice-water (100 mL; contain 10.0 mL conc. HCl) and stirred for 10 minutes followed by the extraction with EtOAc (3×50 mL). The organic phase was then washed with aq. sat. NaHCO₃ solution (50 mL), brine (50 mL), dried over Na₂SO₄, and filtered. The filtration was then concentrated under vacuum to give rac-3-exo-allyl-3-endo-(but-3-en-1-yl)bicyclo[2.2.1] heptan-2-one (4.6 g, 22.5 mmol, 82.7%) as a brown oil. 1H NMR (400 MHz, CDCl₃) δ 5.93-5.73 (m, 2H), 5.09-4.92 (m, 4H), 2.57 (d, J=4.4 Hz, 1H), 2.35 (s, 1H), 2.32-2.27 (m, 1H), 2.23-2.13 (m, 2H), 2.04-2.00 (m, 1H), 1.96-1.81 (m, 2H), 1.75-1.58 (m, 3H), 1.52-1.41 (m, 2H), 1.30-1.22 (m, 1H).

Step 3: To a solution of rac-3-exo-allyl-3-endo-(but-3-en-1-yl)bicyclo[2.2.1]heptan-2-one (1.0 g, 9.8 mmol, 1.0 eq) in anhydrous CH₂Cl₂ (1000 mL) was added Grubbs II catalyst (416 mg, 0.98 mmol, 0.1 eq) under N₂, and the reaction mixture was stirred at room temperature overnight. Once GC showed the reaction finished, evaporated to get a residue, which was then purified by silica gel column eluting with PE~PE:EA=10:1 to give compound 5 (729 mg, 4.14 mmol, 84.5%) as a dark red solid. 1H NMR (400 MHz, CDCl₃) δ 5.74-5.70 (m, 1H), 5.64-5.59 (m, 1H), 2.59-2.57 (m, 1H), 2.44 (d, J=1.6 Hz, 1H), 2.15-2.05 (m, 2H), 2.00-1.83 (m, 4H), 1.75-1.60 (m, 3H), 1.57-1.46 (m, 3H).

Step 4: To a solution of rac-spiro[bicyclo[2.2.1]heptane-3,1'-cyclohexan]-3'-en-2-one (370 mg, 2.1 mmol, 1.0 eq) in EtOH (8 mL) was added hydroxylamine hydrochloride (292 mg, 4.2 mmol, 2.0 eq) and NaOAc (689 mg, 8.4 mmol, 4.0 eq), and the reaction mixture was stirred at 80° C. overnight. Once LCMS showed the reaction finished, solvent was removed under vacuum to get a residue, which was diluted and extracted with EtOAc (3×15 mL). The organic phases were collected, washed with brine (3×15 mL), dried over Na₂SO₄, and filtered. The filtration was then concentrated under vacuum to give rac-spiro[bicyclo[2.2.1]heptane-3,1'-cyclohexan]-3'-en-2-one oxime (303 mg, 1.59 mmol, 75.6%) as a yellow oil. LCMS [M+H]: 192.1. 1H NMR (400 MHz, CDCl₃) δ 7.19 (s, 1H), 5.73-5.70 (m, 1H), 5.63-5.59 (m, 1H), 3.50-3.49 (m, 1H), 2.28 (d, J=2.0 Hz, 1H), 2.16-1.99 (m, 4H), 1.79-1.75 (m, 1H), 1.74-1.68 (m, 3H), 1.64-1.60 (m, 1H), 1.54-1.47 (m, 1H), 1.45-1.38 (m, 1H), 1.36-1.33 (m, 1H).

Step 5: To a solution of rac-spiro[bicyclo[2.2.1]heptane-3,1'-cyclohexan]-3'-en-2-one oxime (303 mg, 1.59 mmol, 1.0 eq) in AcOH (5.0 mL) was added PtO₂ (30 mg, 10% wt), and the reaction mixture was stirred at room temperature under H₂ atmosphere (1 atm) overnight. Once LCMS showed the reaction finished, reaction mixture was filtered and the filtration was concentrated to get rac-spiro[bicyclo [2.2.1]heptane-3,1'-cyclohexan]-2-endo-amine (342 mg, crude) as a white solid. LCMS [M+H]: 180.1. 1H NMR (400 MHz, CDCl₃) δ 2.61 (d, J=3.6 Hz, 1H), 2.23 (s, 1H), 2.16-2.04 (m, 3H), 1.59-1.56 (m, 2H), 1.54-1.53 (m, 1H), 1.51-1.39 (m, 6H), 1.35-1.30 (m, 2H), 1.27-1.18 (m, 4H), 1.16-1.13 (m, 2H).

Step 6: To a solution of rac-spiro[bicyclo[2.2.1]heptane-3,1'-cyclohexan]-2-endo-amine (342 mg, 1.92 mmol, 1.0 eq) in DCM:H₂O=2:1 (6 mL) was added sodium bicarbonate (611 mg, 5.76 mmol, 3.0 eq) and benzyl chloroformate (490 mg, 2.07 mmol, 1.5 eq). The whole reaction mixture was then stirred at room temperature overnight. Once LCMS showed the reaction finished, solvent was removed under vacuum to get a residue, which was diluted and extracted with DCM (3×25 mL). The organic phases were collected, washed with brine (20 mL), dried over Na₂SO₄, and filtered. The filtration was then concentrated under vacuum to get the crude, which was purified by silica gel column eluting with PE~PE:EA=100:1 to give rac-benzyl (spiro[bicyclo[2.2.1] heptane-3,1'-cyclohexan]-2-endo-yl)carbamate (475 mg, 79.4%) as a colorless semi-solid. LCMS [M+H]: 314.2. 1H NMR (400 MHz, CDCl₃) δ 7.37-7.36 (m, 4H), 7.35-7.31 (m, 1H), 5.13-5.06 (m, 2H), 4.91-4.89 (m, 1H), 3.50-3.47 (m, 1H), 2.26 (d, J=14.4 Hz, 1H), 1.54-1.48 (m, 6H), 1.40-1.32 (m, 3H), 1.24-1.20 (m, 2H), 1.18 (s, 1H), 1.13-1.05 (m, 1H).

Step 7: Chiral SFC separation. 475 of rac-benzyl (spiro [bicyclo[2.2.1]heptane-3,1'-cyclohexan]-2-endo-yl)carbamate was separated by chiral SFC chromatography.

Analytical separation method:Instrument: Waters UPCC, Column: ChiralPak AY, 250×4.6 mm, 5 µm, Mobile phase: A for CO₂ and B for EtOH (0.04% DEA), Gradient: B 0-40%, Flow rate: 2.8 mL/min, Back pressure: 100 bar, Column temperature: 35° C., Wavelength: 214 nm Preparative separation method: Instrument: Waters SFC80, Column: ChiralPak AY, 250×25 mm, 10 µm, Mobile phase: A for CO₂ and B for EtOH (0.04% DEA), Gradient: B 40%, Flow rate: 2.8 mL/min, Back pressure: 100 bar, Column temperature: 35° C., Wavelength: 214 nm, Cycle time: 8 min, Sample preparation: Compound was dissolved in 15 mL methanol, Injection: 3 ml per injection.

After separation, benzyl ((1R,3S,4S)-spiro[bicyclo[2.2.1] heptane-2,1'-cyclohexan]-3-yl)carbamate (compound 3-Fr1; 177 mg, 37%, 100% ee) was obtained as a colorless solid, and benzyl ((1S,3R,4R)-spiro[bicyclo[2.2.1]heptane-2,1'-cyclohexan]-3-yl)carbamate (compound 3-Fr2; 167 mg, 35%, 100% ee) was obtained as a colorless solid.

Step 8: To a solution of benzyl ((1R,3S,4S)-spiro[bicyclo [2.2.1]heptane-2,1'-cyclohexan]-3-yl)carbamate (177 mg, 0.57 mmol, 1.0 eq) in EA (10.0 mL) was added Pd/C (20 mg, 10% wt), and the reaction mixture was stirred at room temperature under H₂ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 212-P1 (90.28 mg, 74.2%) as a white solid. LCMS [M+H]: 180.2. 1H NMR (400 MHz, CD3OD) δ 2.87 (d, J=4.0 Hz, 1H), 2.44 (m, 1H), 1.73-1.63 (m, 5H), 1.61-1.52 (m, 3H), 1.52-1.45 (m, 3H), 1.39-1.33 (m, 2H), 1.32-1.25 (m, 2H), 1.17-1.12 (m, 1H).

To a solution of benzyl ((1S,3R,4R)-spiro[bicyclo[2.2.1] heptane-2,1'-cyclohexan]-3-yl)carbamate (167 mg, 0.53 mmol, 1.0 eq) in EA (10.0 mL) was added Pd/C (20 mg, 10% wt), and the reaction mixture was stirred at room temperature under H₂ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 212-P2 (81.44 mg, 71%) as a white solid. LCMS [M+H−HCl]: 180.2. 1H NMR (400 MHz, CD3OD) δ 2.87 (d, J=3.2 Hz, 1H), 2.44 (s, 2H), 1.74-1.61 (m, 5H), 1.59-1.52 (m, 3H), 1.52-1.45 (m, 3H), 1.39-1.35 (m, 2H), 1.33-1.25 (m, 2H), 1.17-1.12 (m, 1H).

Synthesis of rac-2,2'-spirobi[bicyclo[2.2.1]heptan]-3-amine hydrochloride 238

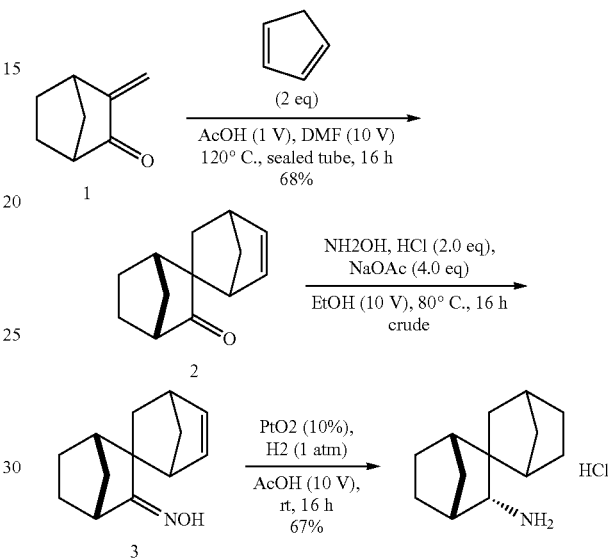

Note: absolute configuration is unassigned and the configuration of the C1 is arbitrarily shown as (R). The relative configuration of the [2,2,1]-bicycles is undefined.

Step 1:

To a solution of 3-methylenebicyclo[2.2.1]heptan-2-one (300 mg, 2.46 mmol. 1 eq) in AcOH (0.3 mL) and DMF (3 mL) was added cyclopenta-1,3-diene (487.3 mg, 7.37 mmol, 3 eq). The mixture was then stirred at 120° C. for 16 h in a sealed tube. Once TLC showed no starting material left, the mixture was cooled to room temperature and H₂O (15 mL) was added. The reaction mixture was then extracted with EtOAc (3×20 mL). All the organic phases were collected, washed with brine (3×20 mL), dried over Na₂SO₄ and concentrated. The residue was purified with column chromatography eluting with 0-10% EA in PE to give rac-2,2'-spirobi[bicyclo[2.2.1]heptan]-5'-en-3-one (2, 320 mg, 1.7 mmol, 68% yield) as a yellow oil.

¹H NMR (400 MHz, CDCl₃) δ 6.29-6.27 (m, 1H), 6.15-6.13 (m, 1H), 2.87 (brs, 1H), 2.79 (s, 1H), 2.66-2.65 (m, 1H), 2.08-2.03 (m, 3H), 1.84-1.78 (m, 2H), 1.62-1.56 (m, 1H), 1.50-1.42 (m, 3H), 1.28-1.25 (m, 1H), 1.08 (dd, J=11.2, 2.8 Hz, 1H).

Step 2:

To a stirred solution of rac-2,2'-spirobi[bicyclo[2.2.1] heptan]-5'-en-3-one (220 mg, 1.26 mmol, 1 eq) in EtOH (10 mL) was added NH₂OH·HCl (176.8 mg, 2.53 mmol, 2.0 eq) and NaOAc (404.4 mg, 5.05 mmol, 4.0 eq) in one portion at room temperature. The reaction mixture was stirred at 85° C. for 16 hours. Once LCMS showed finished, the mixture was concentrated to dryness. The residue was dissolved in EtOAc (50 mL). The organic layer was washed with water (50 mL) brine (60 mL), dried over Na$_2$SO$_4$, concentrated under vacuum to give crude product (282 mg, crude) which was used next step directly.

LCMS [M+H]:204.2

Step 3:

To a solution of rac-2,2'-spirobi[bicyclo[2.2.1]heptan]-5'-en-3-one oxime (282 mg, 1.39 mmol, 1.0 eq) in AcOH (5 mL) was added PtO$_2$ (28.2 mg, 10% wt) and stirred at rt under H$_2$ for 16 hours. Once LCMS showed the reaction finished, The mixture was filtered through a pad of celite to remove PtO$_2$ and then the filtrate was concentrated in vacuo to obtain a crude product, which was then purified by prep-HPLC eluting with 0-90% ACN in water (0.1% TFA), and substituted by HCl to give 238 (169 mg, 0.74 mmol, 67%) as a white solid.

LCMS [M+H]–HCl: 192.2

$^1$H NMR (400 MHz, CD$_3$OD) δ 3.31-3.30 (m, 1H), 3.08 (d, J=4.4 Hz, 1H), 2.53 (brs, 1H), 2.26 (brs, 2H), 1.94 (d, J=3.6 Hz, 1H), 1.72-1.69 (m, 2H), 1.63-1.53 (m, 2H), 1.51-1.34 (m, 7H), 1.28-1.26 (m, 1H), 1.22-1.10 (m, 2H).

Synthesis of rac-2,2'-spirobi[bicyclo[2.2.1]heptan]-3-amine & rac-2,2'-spirobi[bicyclo[2.2.1]heptan]-3-amine 238-A & 238-B

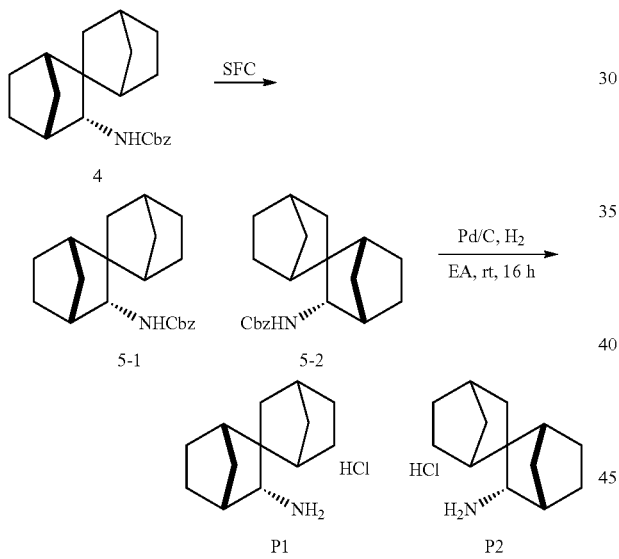

Note: absolute configuration is unassigned and the configuration of the C1 is arbitrarily shown as (R). The relative configuration of the [2,2,1]-bicycles is undefined.

Step 1

SFC separation was carried out for compound 4 (997 mg). The SFC separation information are shown as following:

Analytical separation method:

Instrument: Waters UPCC, Column: ChiralPak OZ, 250×4.6 mm, 5 μm, Mobile phase: A for CO$_2$ and B for EtOH (0.04% DEA), Gradient: B 15-40%, Flow rate: 2.5 mL/min, Back pressure: 100 bar, Column temperature: 35° C., Wavelength: 214 nm Preparative separation method:

Instrument: Waters SFC80, Column: DAICELCHIRALPAK®OZ, 250×25 mm 10 μm, Mobile phase: A for CO$_2$ and B for EtOH (0.1% NH$_3$·H$_2$O), Gradient: B 20%, Flow rate: 100 mL/min, Back pressure: 100 bar, Column temperature: RT, Wavelength: 214 nm, Cycle time: 11 min, Sample preparation: Compound was dissolved in 17 mL EtOH, Injection: 1 ml per injection.

After separation, rac-benzyl (2,2'-spirobi[bicyclo[2.2.1]heptan]-3-yl)carbamate (compound 5-1; 391 mg, 39%, 100% ee) was obtained as a colorless oil and rac-benzyl (2,2'-spirobi[bicyclo[2.2.1]heptan]-3-yl)carbamate (compound 5-2; 412 mg, 41%, 100% ee) was obtained as a colorless oil.

General procedure for preparation of rac-2,2'-spirobi[bicyclo[2.2.1]heptan]-3-amine 238-A (P1)

To a solution of rac-benzyl (2,2'-spirobi[bicyclo[2.2.1]heptan]-3-yl)carbamate (100 mg, 0.317 mmol, 1.0 eq) in EtOAc (10.0 mL) was added Pd/C (5 mg, 10% wt), and the reaction mixture was stirred at room temperature under H$_2$ atmosphere (1 atm) overnight. Once LCMS showed the reaction finished, the mixture was filtered through celite pad to get rid of Pd/C and the filtration was then concentrated to get the crude, which was then purified by prep-HPLC eluting with 0-90% ACN in water (0.1% TFA), and substituted by HCl to give 238-A (55 mg, yield 79%) as a white solid.

LCMS [M+H–HCl]: 192.1

$^1$H NMR (400 Hz, MeOD) δ 3.31-3.30 (m, 1H), 2.52 (s, 1H), 2.27-2.26 (d, J=4.4 Hz, 2H), 1.94-1.93 (d, J=3.2 Hz, 1H), 1.72-1.67 (m, 2H), 1.64-1.54 (m, 2H), 1.49-1.29 (m, 7H), 1.26-1.22 (m, 1H), 1.21-1.20 (m, 2H).

General procedure for preparation of rac-2,2'-spirobi[bicyclo[2.2.1]heptan]-3-amine 238-B (P2)

To a solution of rac-benzyl (2,2'-spirobi[bicyclo[2.2.1]heptan]-3-yl)carbamate (100 mg, 0.317 mmol, 1.0 eq) in EtOAc (10.0 mL) was added Pd/C (10 mg, 10% wt), and the reaction mixture was stirred at room temperature under H$_2$ atmosphere (1 atm) overnight. Once LCMS showed the reaction finished, the mixture was filtered through celite pad to get rid of Pd/C and the filtration was then concentrated to get the crude, which was then purified by prep-HPLC eluting with 0-90% ACN in water (0.1% TFA), and substituted by HCl to give 238-B (66 mg, yield 94%) as a white solid.

LCMS [M+H–HCl]: 192.1

$^1$H NMR (400 Hz, MeOD) δ 3.08-3.07 (d, J=4.4 Hz, 1H), 2.52 (s, 1H), 2.28-2.27 (m, 2H), 1.94-1.94 (d, J=3.2 Hz, 1H), 1.74-1.67 (m, 2H), 1.63-1.54 (m, 2H), 1.48-1.29 (m, 7H), 1.27-1.22 (m, 1H), 1.21-1.11 (m, 2H).

Synthesis of rac-spiro[bicyclo[2.2.1]heptane-2,1'-cyclopentan]-3'-en-3-amine hydrochloride 248

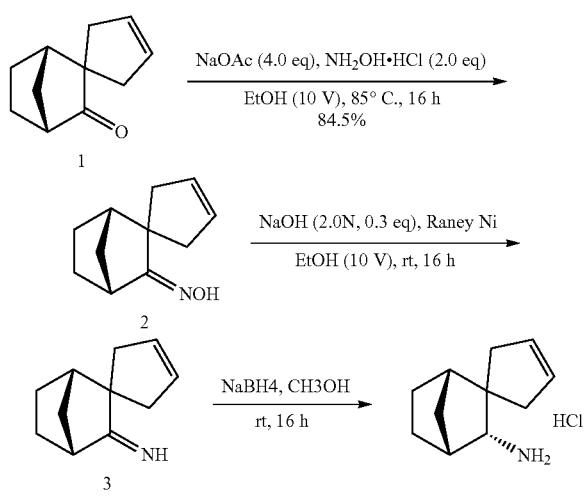

Note: absolute configuration is unassigned and the configuration of the C1 of P1 is arbitrarily shown as (R).

Step 1:

To a stirred solution of rac-spiro[bicyclo[2.2.1]heptane-2,1'-cyclopentan]-3'-en-3-one (1.3 g, 8.01 mmol, 1 eq) in EtOH (25 mL) was added NH$_2$OH·HCl (842 mg, 12.0 mmol, 1.5 eq) and NaOAc (1.97 g, 24.03 mmol, 3.0 eq) in one portion at room temperature. The reaction mixture was stirred at 85° C. for 16 hours. Once LCMS showed finished, the mixture was concentrated to dryness. The residue was dissolved in EtOAc (50 mL). The organic layer was washed with water (50 mL) brine (60 mL), dried over Na$_2$SO$_4$, concentrated under vacuum to give crude product, which was purified by silica column chromatography eluting with 10%~20% EtOAc in PE to give rac-spiro[bicyclo[2.2.1]heptane-2,1'-cyclopentan]-3'-en-3-one oxime (2, 1.2 g, 6.78 mmoL, 84.5% yield) as a white solid.

Step 2

To a stirred solution of rac-spiro[bicyclo[2.2.1]heptane-2,1'-cyclopentan]-3'-en-3-one oxime (1.2 g, 2.73 mmol, 1.0 eq) in EtOH (5 ml) was added NaOH (2.0 N, 3 mL) and Raney/Ni (0.5 mmol). The mixture was stirred at room temperature for 16 hours. LCMS showed the reaction was completed. The mixture was filtered and concentrated to get the crude, which was then purified by prep-HPLC eluting with 0-90% ACN in water (0.1% TFA), and substituted by HCl to give rac-spiro[bicyclo[2.2.1]heptane-2,1'-cyclopentan]-3'-en-3-imine (3, 50 mg, 0.310 mmol) as a white solid. LCMS [M+H]: 162.1

$^1$H NMR (400 MHz, MeOD$_3$) δ 5.79-5.78 (m, 1H), 5.70-5.69 (m, 1H), 3.36 (d, J=4.4 Hz, 1H), 2.88-2.82 (m, 1H), 2.66-2.59 (m, 3H), 2.47 (s, 1H), 2.26-2.21 (m, 1H), 2.01-1.98 (m, 1H), 1.81-1.65 (m, 3H), 1.55-1.49 (m, 1H).

Step 3

To a solution of rac-spiro[bicyclo[2.2.1]heptane-2,1'-cyclopentan]-3'-en-3-imine (50 mg, 0.31 mmol, 1.0 eq) in MeOH (3.0 mL) was added NaBH$_4$ (30 mg, 0.76 mmoL, 2.5 eq) and the reaction mixture was stirred at room temperature overnight. Once LCMS showed the reaction finished, solvent was removed to get the crude, which was then purified by prep-HPLC eluting with 0-90% ACN in water (0.1% TFA), and substituted with HCl to give 248 (16.82 mg, 0.084 mmol) as a white solid.

LCMS [M+H−HCl]: 164.2

$^1$H NMR (400 MHz, CD$_3$OD) δ 5.73-5.69 (m, 2H), 3.29-3.28 (m, 1H), 2.52-2.23 (m, 5H), 2.09 (s, 1H), 1.72-1.9 (m, 1H), 1.63-1.43 (m, 5H).

Synthesis of rac-3-aminospiro[bicyclo[2.2.1]heptane-2,1'-cyclopentane]-3',4'-diol hydrochloride 228

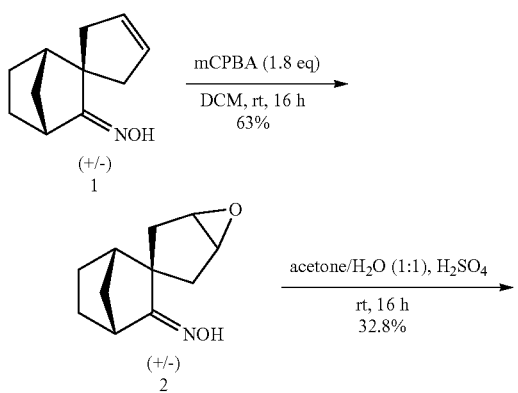

Note: absolute configuration is unassigned and the configuration of the C1 of P1 is arbitrarily shown as (R).

Step 1

To a stirred solution of rac-spiro[bicyclo[2.2.1]heptane-2,1'-cyclopentan]-3'-en-3-one oxime (6.7 g, 37.8 mmol, 1.0 eq.) in DCM (50 mL) was added m-CPBA (8.5 g, 41.6 mmol, 1.1 eq) at 0° C. The mixture was stirred at room temperature for 16 hrs. TLC (PE:EA=1:1) showed the reaction was completed. The mixture was adjusted pH=10 by sat.aq. NaHCO$_3$, extracted with EtOAc (3×20 mL). The organic phases were collected, washed with brine (2×30 mL), dried over Na$_2$SO$_4$, and concentrated under vacuum to get the crude, which was purified by silica column chromatography eluting with 30% EA in PE to give rac-6'-oxaspiro[bicyclo[2.2.1]heptane-2,3'-bicyclo[3.1.0]hexan]-3-one oxime (2, 4.6 g, 23.8 mmol, 63% yield) as a white solid.

LCMS [M+H]: 194.1

Step 2

To a stirred solution of rac-6'-oxaspiro[bicyclo[2.2.1]heptane-2,3'-bicyclo[3.1.0]hexan]-3-one oxime (2.5 g, 12.9 mmol, 1 eq) in acetone (40 mL) and H$_2$O (40 ml) was added H$_2$SO$_4$ (1.5 mL). The mixture was stirred at room temperature for 16 hours. TLC (MeOH:DCM=10:1) showed the reaction was completed. The mixture was concentrated, extracted with EtOAc (3×20 mL). The organic phases were collected, washed with brine (2×30 mL), dried over Na$_2$SO$_4$, and concentrated under vacuum to get the crude, which was purified by silica column chromatography eluting with 5% MeOH in DCM to give rac-3',4'-dihydroxyspiro[bicyclo[2.2.1]heptane-2,1'-cyclopentan]-3-one oxime (3, 886 mg, 4.20 mmol, 32.8% yield) as a white solid.

$^1$H NMR (400 MHz, MeOD$_3$) δ 4.08-4.03 (m, 1H), 3.86-3.82 (m, 1H), 3.38 (d, J=3.2 Hz, 1H), 2.23-1.97 (m, 3H), 1.74-1.53 (m, 7H), 1.44-1.33 (m, 1H).

Step 3

To a solution of rac-3',4'-dihydroxyspiro[bicyclo[2.2.1]heptane-2,1'-cyclopentan]-3-one oxime (100 mg, 0.47 mmol, 1.0 eq) in HOAc (3.0 mL) was added PtO$_2$ (10 mg), and the reaction mixture was stirred at room temperature under H$_2$ atmosphere (1 atm) overnight. Once LCMS showed the reaction finished, solvent was removed to get the crude, which was then purified by prep-HPLC eluting with 0-90% ACN in water (0.1% TFA), and substituted with HCl to give 228 (71.74 mg, 21.8%) as a white solid.

LCMS [M+H−HCl]: 198.2

$^1$H NMR (400 MHz, CD$_3$OD) δ 4.00-3.95 (m, 2H), 3.91-3.89 (m, 0.32H), 3.24 (d, J=3.6 Hz, 0.43H), 3.15 (d, J=3.2 Hz, 1H), 2.45 (s, 1H), 2.12-1.85 (m, 4H), 1.78-1.62 (m, 3H), 1.58-1.31 (m, 7H).

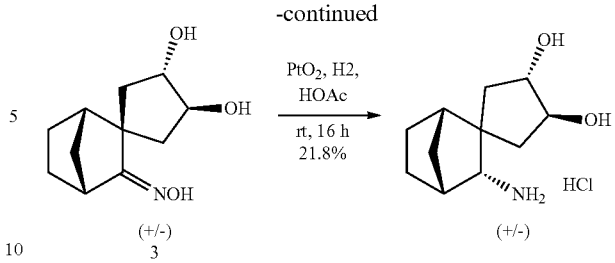

Synthesis of rac-tetrahydrospiro[bicyclo[2.2.1]heptane-2,4'-pyran]-3-amine hydrochloride 235

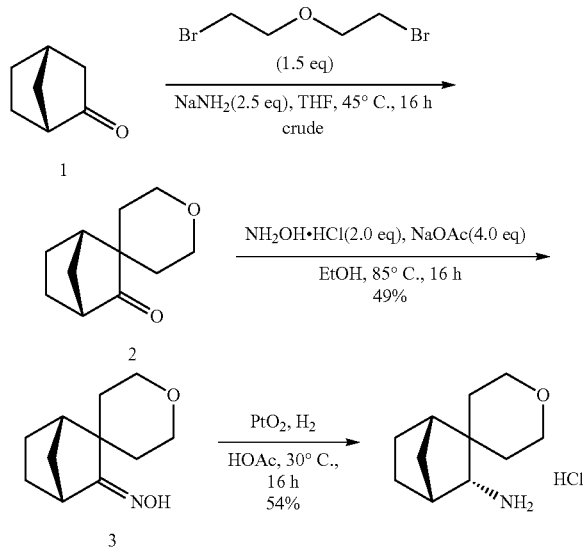

Note: absolute configuration is unassigned and the configuration of the C1 of P1 is arbitrarily shown as (R).

Step 1:
To a stirred solution of rac-bicyclo[2.2.1]heptan-2-one (950 mg, 8.60 mmol, 1.0 eq) and 1-bromo-2-(2-bromoethoxy) ethane (3 g, 12.94 mmol, 1.5 eq) in THF (20 mL) was added $NaNH_2$ (842 mg, 21.6 mmol, 2.5 eq) in one portion at room temperature under Ar. The resulting mixture was stirred at 45° C. for 16 hrs. LCMS showed the reaction was completed. The mixture was extracted with EtOAc (3×50 mL). The combined organic phase was washed with brine (1×60 mL), dried with anhydrous $Na_2SO_4$, and filtered. The filtration was then concentrated under vacuum to give rac-tetrahydrospiro[bicyclo[2.2.1]heptane-2,4'-pyran]-3-one (2, 2 g, crude)

LCMS [M+H]: 181.3

Step 2:
To a stirred solution of rac-tetrahydrospiro[bicyclo[2.2.1]heptane-2,4'-pyran]-3-one (2 g, 11.10 mmol, 1 eq) in EtOH (40 mL) was added $NH_2OH·HCl$ (1.53 g, 22.19 mmol, 2.0 eq) and NaOAc (3.64 g, 44.38 mmol, 4.0 eq) in one portion at room temperature. The reaction mixture was stirred at 85° C. for 16 hours. Once LCMS showed finished, the mixture was concentrated to dryness. The residue was dissolved in EtOAc (100 mL), washed with water (80 mL) brine (80 mL), dried over $Na_2SO_4$. The filtration was concentrated under vacuum to give crude product, which was purified by silica gel chromatography eluting with 10%-50% EA in PE to afford rac-tetrahydrospiro[bicyclo[2.2.1]heptane-2,4'-pyran]-3-one oxime (3, 830 mg, 4.25 mmol, 49%) as a white solid.

LCMS [M+H]:196.1

$^1$H NMR (400 MHz, $CDCl_3$) δ 6.91 (s, 1H), 3.93-3.83 (m, 2H), 3.73-3.61 (m, 2H), 3.52 (d, J=1.2 Hz, 1H), 2.30 (d, J=2.0 Hz, 1H), 1.76-1.68 (m, 6H), 1.51-1.47 (m, 1H), 1.41-1.32 (m, 3H).

Step 3:
To a stirred solution of rac-tetrahydrospiro[bicyclo[2.2.1]heptane-2,4'-pyran]-3-one oxime (200 mg, 1.02 mmol, 1 eq) in HOAc(5 mL) was added $PtO_2$ (35 mg, 0.15 mmol, 0.15 eq) in one portion at room temperature under nitrogen atmosphere. The suspension was degassed under vacuum and purged with $H_2$ several times. The mixture was stirred under $H_2$ (balloon) at 30° C. for 16 hours. Once LCMS showed the major formation of desired compound, the mixture was filtered to get rid of catalyst and the filtration was concentrated under vacuum to give the crude, which was then purified by prep-HPLC eluting with 0-90% ACN in water (0.1% TFA), and substituted by HCl to give 235 (103 mg, 0.57 mmol, 54% yield) as a white solid.

LCMS [M+H–HCl]: 182.1

$^1$H NMR (400 MHz, $CD_3OD$) δ 3.83-3.67 (m, 3H), 3.48-3.42 (m, 1H), 2.96 (d, J=3.6 Hz, 1H), 2.60 (s, 1H), 2.47 (s, 1H), 1.75-1.42 (m, 10H).

Synthesis of rac-3-aminospiro[bicyclo[2.2.1]heptane-2,1'-cyclopentane]-3',4'-diyl diacetate hydrochloride 230

Note: absolute configuration is unassigned and the configuration of the C1 of P1 is arbitrarily shown as (R).

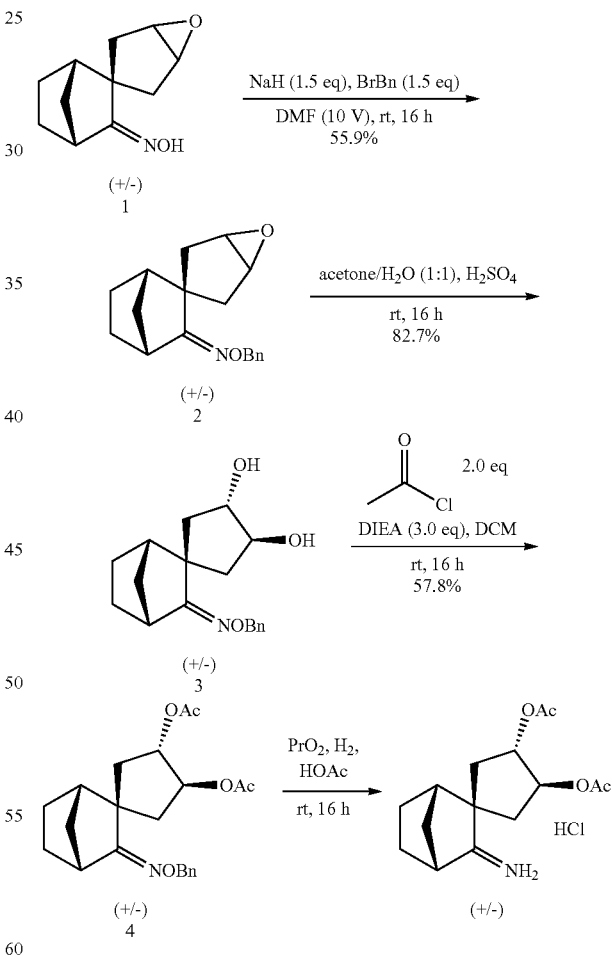

Step 1
To a stirred solution of rac-6'-oxaspiro[bicyclo[2.2.1]heptane-2,3'-bicyclo[3.1.0]hexan]-3-one oxime (1 g, 7.4 mmol, 1.0 eq.) in DMF (10 mL) was added NaH (444 mg, 11.1 mmol, 1.5 eq) at 0° C. in portions. The mixture was stirred at room temperature for 30 mints. BrBn (1.89 g, 1.11 mmol, 1.5 eq) was added. The mixture was stirred at room temperature for 16 hours. TLC (PE:EA=10:1) showed completed. The mixture was quenched with H₂O at 0° C., extracted with EtOAc (3×10 mL). The combined organic phase was washed with brine (2×20 mL), dried with anhydrous Na₂SO₄, and concentrated under vacuum to get the crude, which was purified by silica column chromatography eluting with 10% EA in PE to give rac-6'-oxaspiro[bicyclo[2.2.1]heptane-2,3'-bicyclo[3.1.0]hexan]-3-one O-benzyl oxime (2, 817 mg, 2.88 mmol, 55.9% yield) as a colorless oil.

¹H NMR (400 MHz, CDCl₃) δ 7.38-7.26 (m, 5H), 5.08 (s, 2H), 3.52-3.41 (m, 3H), 2.21-2.14 (m, 2H), 2.06-2.05 (m, 1H), 1.96-1.92 (m, 1H), 1.74-1.70 (m, 1H), 1.62-1.37 (m, 4H), 1.34-1.24 (m, 3H).

Step 2:

To a stirred solution of rac-6'-oxaspiro[bicyclo[2.2.1]heptane-2,3'-bicyclo[3.1.0]hexan]-3-one O-benzyl oxime (817 mg, 2.88 mmol, 1.0 eq) in acetone (15 mL) and H₂O (15 ml) was added H₂SO₄ (0.5 mL). The mixture was stirred at room temperature for 16 hours. TLC (MeOH:DCM=10:1) showed the reaction was completed. The mixture was concentrated, extracted with EtOAc (3×20 mL). The organic phases were collected, washed with brine (2×30 mL), dried over Na₂SO₄, and concentrated under vacuum to get the crude, which was purified by silica column chromatography eluting with 5% MeOH in DCM to give rac-3',4'-dihydroxyspiro[bicyclo[2.2.1]heptane-2,1'-cyclopentan]-3-one O-benzyl oxime (3, 718 mg, 2.38 mmol, 82.7% yield) as a white solid.

¹H NMR (400 MHz, MeOD₃) δ 7.30-7.20 (m, 5H), 4.95-4.88 (m, 2H), 4.77-4.75 (m, 0.55H), 4.18-4.10 (m, 1H), 3.84 (m, 1H), 3.34-3.30 (m, 1H), 2.15-2.05 (m, 3H), 1.97-1.90 (m, 1H), 1.72-1.41 (m, 7H), 1.34-1.16 (m, 3H).

Step 3:

To a solution of rac-3',4'-dihydroxyspiro[bicyclo[2.2.1]heptane-2,1'-cyclopentan]-3-one O-benzyl oxime (718 mg, 2.38 mmol, 1.0 eq) in DCM (10 mL) was added DIPEA (922 mg, 7.14 mmol, 3.0 eq) and acetyl chloride (374 mg, 4.77 mmol, 2.0 eq). The mixture was stirred at room temperature for 16 hours. TLC (PE:EA=3:1) showed the reaction was completed. The mixture was concentrated, extracted with EtOAc (3×20 mL). The organic phases were collected, washed with brine (2×30 mL), dried over Na₂SO₄, and concentrated under vacuum to get the crude, which was purified by silica column chromatography eluting with 10% EA in PE to give rac-3-((benzyloxy)imino)spiro[bicyclo[2.2.1]heptane-2,1'-cyclopentane]-3',4'-diyl diacetate (4, 531 mg, 1.38 mmol, 57.8%) as a colorless oil.

¹H NMR (400 MHz, CDCl₃) δ 7.36-7.23 (m, 5H), 5.35-5.24 (m, 1H), 5.04-4.98 (m, 3H), 3.35-3.30 (m, 1H), 2.34-2.13 (m, 3H), 2.01-1.97 (m, 6H), 1.80-1.49 (m, 6H), 1.38-1.21 (m, 2H).

Step 4:

To a solution of rac-3-((benzyloxy)imino)spiro[bicyclo[2.2.1]heptane-2,1'-cyclopentane]-3',4'-diyl diacetate (531 mg, 1.38 mmol, 1.0 eq) in HOAc (3.0 mL) was added PtO₂ (50 mg), and the reaction mixture was stirred at room temperature under H₂ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 230 (26.4 mg, 0.08 mmol) as a white solid.

LCMS [M+H−HCl]: 282.2

¹H NMR (400 MHz, CD₃OD) δ 4.03-4.12 (m, 1H), 4.02-3.99 (m, 1.3H), 3.28-3.18 (m, 2H), 2.49 (s, 1H), 2.29-2.24 (m, 1H), 2.15-2.02 (m, 5H), 2.01 (s, 6H), 1.98-1.84 (m, 2H), 1.81-1.66 (m, 5H), 1.63-1.41 (m, 11H).

Synthesis of (1R,2R,3S,4S)-3-benzyl-3-ethylbicyclo[2.2.1]heptane-2-amine hydrochloride 219-P1 & 219-P2

Note: absolute configuration is unassigned and the configuration of the C1 of P1 is arbitrarily shown as (R).

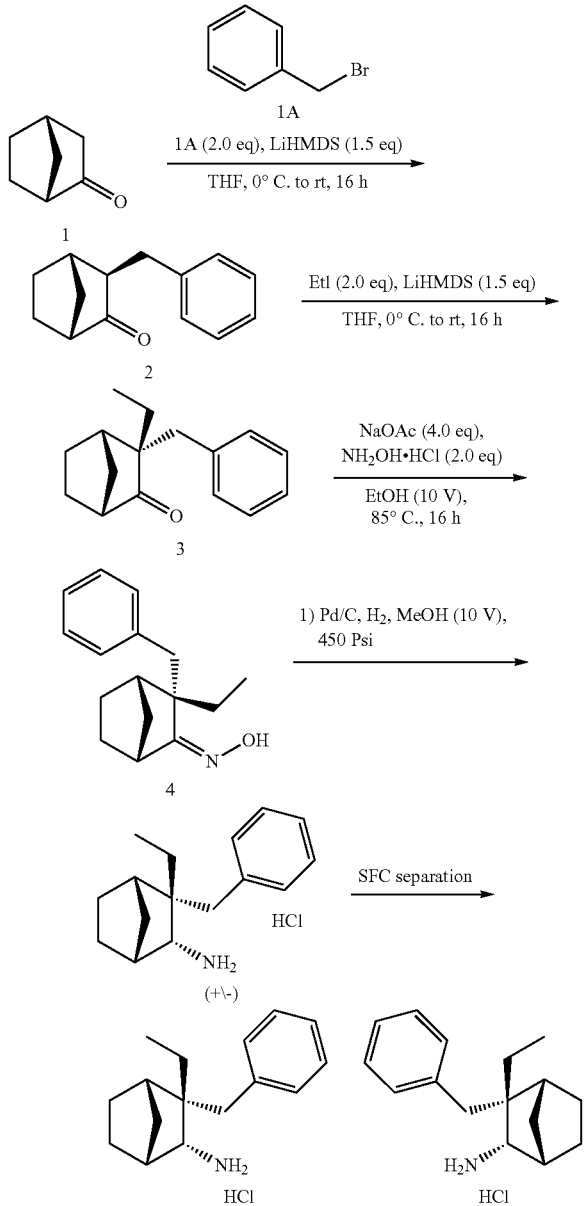

Step 1:

To a stirred solution of (1R,4S)-bicyclo[2.2.1]heptane-2-one (1.0 g, 9.07 mmol, 1.0 eq) in DMF (25 mL) at −5-5° C. was added HMDSLi (10 mL, 10.88 mmol, 1.2 eq) under N₂ protection. The corresponding reaction mixture was then stirred at −5-5° C. for 2 hours under N₂ followed by the addition of (bromomethyl)benzene (2.02 g, 11.79 mmol, 1.3 eq). The whole mixture was gradually warmed to room temperature and stirred overnight under N₂ protection. The reaction was quenched by sat. NH₄Cl (50 mL). The residue was then extracted with EtOAc (3×30 mL), dried over Na₂SO₄, and filtered. The filtration was concentrated under vacuum to give crude product, which was purified by silica gel chromatography eluting with 2%-10% EA in PE to afford (1R,3R,4S)-3-benzylbicyclo[2.2.1]heptan-2-one (2, 1.372 g, 6.86 mmol, 90%) as a yellow oil.

¹H NMR (400 MHz, MeOH) δ 7.20-7.16 (m, 5H), 3.00-2.96 (m, 1H), 2.61 (d, J=4 Hz 1H), 2.37-2.44 (m, 2H), 2.05-2.02 (m, 1H), 1.92-1.89 (m, 1H), 1.77-1.74 (m, 2H), 1.71-1.54 (m, 3H).

Step 2:

To a solution of (1R,3R,4S)-3-benzylbicyclo[2.2.1]heptan-2-one (4.25 g, 20.63 mmol, 1.0 eq) in DMF (20 mL) at −5-5° C. was added HMDSLi (31 mL, 30.9 mmol, 1.5 eq) under N₂ protection. The corresponding reaction mixture was then stirred at −5-5° C. for 2 hours under N₂ followed by the addition of CH₃CH₂I (9.64 g, 61.88 mmol, 3.0 eq). The corresponding reaction mixture was warmed to room temperature and stirred at room temperature overnight. The reaction was quenched by sat. NH₄Cl (100 mL). The residue was then extracted with EtOAc (3×60 mL), dried over Na₂SO₄. The filtration was concentrated under vacuum to give crude product, which was purified by silica gel chromatography eluting with 2%-10% EA in PE to afford (1R,3S,4S)-3-benzyl-3-ethylbicyclo[2.2.1]heptan-2-one (3, 3.65 g, 16.0 mmol, 76%) as a yellow oil.

¹H NMR (400 MHz, CDCl₃) δ 7.41-7.16 (m, 5H), 2.91-2.83 (m, 1H), 2.71-2.67 (m, 1H), 2.62-2.60 (m, 1H), 2.42-2.41 (m, 2H), 2.16-2.10 (m, 1H), 2.04-1.99 (m, 1H), 1.82-1.77 (m, 1H), 1.55-1.45 (m, 4H), 0.79-0.77 (m, 3H).

Step 3:

To a stirred solution of (1R,3S,4S)-3-benzyl-3-ethylbicyclo[2.2.1]heptan-2-one (1.86 g, 8.14 mmol, 1 eq) in EtOH (10 mL) was added NH₂OH·HCl (0.85 g, 12.21 mmol, 1.5 eq) and NaOAc (2.0 g, 24.42 mmol, 3.0 eq) in one portion at room temperature under nitrogen atmosphere. The reaction mixture was stirred at 85° C. for 2 hours. Once LCMS showed finished, the mixture was poured into water (50 mL) and stirred for 10 minutes. The aqueous was then extracted with EtOAc (3×50 mL). All the organic phases were collected, washed with brine 60 mL, dried over Na₂SO₄. The filtration was concentrated under vacuum to give crude product, which was purified by silica gel chromatography eluting with 2%-10% EA in PE to afford (1R,3S,4S,Z)-3-benzyl-3-ethylbicyclo[2.2.1]heptan-2-one oxime (4, 1.39 g, 5.70 mmol, 70%) as a yellow oil.

LCMS [M+H]:244.2

Step 4:

To a solution of (1R,3S,4S,Z)-3-benzyl-3-ethylbicyclo[2.2.1]heptan-2-one oxime (1.64 g, 6.70 mmol, 1.0 eq) in MeOH (20.0 mL) was added 10% Pd/C (655 mg, 10% wt) and 5 drops of HCl, and the reaction mixture was stirred at room temperature under H₂ atmosphere (450 psi) 48 hours. Once LCMS showed the reaction finished, The mixture was filtered through a pad of celite to remove Pd/C and then the filtrate was concentrated in vacuo to obtain a crude product to give (1R,2R,3S,4S)-3-benzyl-3-ethylbicyclo[2.2.1]heptan-2-amine hydrochloride (5, 1.2 g, 5.24 mmol, crude) as oil.

LCMS [M+H]:230.2

Step 5:

General procedure for preparation of (1R,2R,3S,4S)-3-benzyl-3-ethylbicyclo[2.2.1]heptan-2-amine hydrochloride 219-P1 & (1S,2S,3R,4R)-3-benzyl-3-ethylbicyclo[2.2.1]heptan-2-amine hydrochloride 219-P2

The SFC separation was carried out for compound the racemic mixture (850 mg).

The SFC separation information are shown as following:

Analytical separation method:

Instrument: Waters UPCC, Column: CHIRALCEL®OD 4.6*250 mm Sum, Mobile phase: A for N-Hexane and B for ETOH (0.2% DEA), Gradient: B 0-40%, Flow rate: 1.5 mL/min, Back pressure: 100 bar, Column temperature: 35° C., Wavelength: 214 nm Preparative separation method:

Instrument: Waters SFC80, Column: DAICELCHIRALPAK®AD, 250*25 mm 10 μm, Mobile phase: A for n-Hexane and B for EtOH(+N), Gradient: B 20%, Flow rate: 300 mL/min, Back pressure: 100 bar, Column temperature: 25° C., Wavelength: 214 nm, Cycle time: 14 min, Sample preparation: Compound was dissolved in about 300 mL EtOH, Injection: 4 ml per injection.

After separation, (1R,2R,3S,4S)-3-benzyl-3-ethylbicyclo[2.2.1]heptan-2-amine hydrochloride 219-P1 (48.57 mg, 5.7%, 98% ee) was obtained as a colorless solid, and (1S,2S,3R,4R)-3-benzyl-3-ethylbicyclo[2.2.1]heptan-2-amine hydrochloride 219-P2 (131.18 mg, 15.4%, 98% ee) was obtained as a colorless solid.

219-P1: LCMS [M+H]:230.2

¹H NMR (400 MHz, CD3OD) δ 7.30-7.20 (m, 5H) 3.34-3.29 (m, 2H), 2.92-2.89 (d, J=12 Hz, 1H), 2.54-2.50 (m, 1H), 2.16-2.11 (m, 1H), 2.02 (s, 1H), 1.82-1.60 (m, 4H), 1.43-1.40 (d, J=12 Hz, 1H), 1.31-1.16 (m, 1H), 0.94-0.91 (s, 3H)

219-P2: LCMS [M+H]:230.2

¹H NMR (400 MHz, CD3OD) δ 7.30-7.20 (m, 5H) 3.34-3.29 (m, 1H), 2.92-2.89 (d, J=12 Hz, 1H), 2.54-2.51 (m, 1H), 2.16-2.11 (m, 1H), 2.02 (s, 1H), 1.82-1.60 (m, 4H), 1.43-1.15 (m, 3H), 0.94-0.91 (m, 3H)

Synthesis of (1R,2R,3R,4S)-3-benzyl-3-ethylbicyclo[2.2.1]heptan-2-amine and (1S,2S,3S,4R)-3-benzyl-3-ethylbicyclo[2.2.1]heptan-2-amine 222-P1 & 222-P2

Note: absolute configuration is unassigned and the configuration of the C1 of P1 is arbitrarily shown as (R).

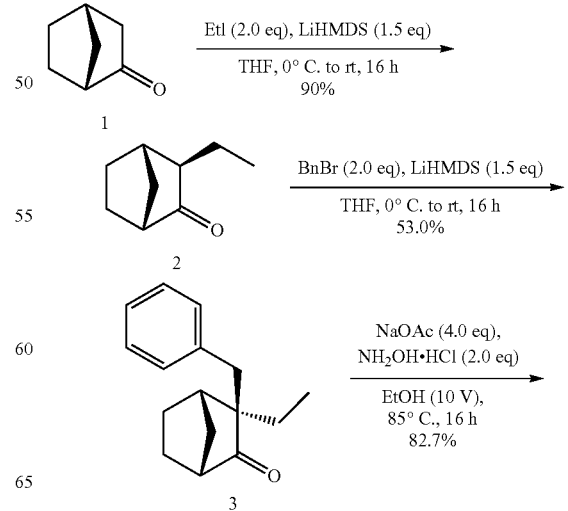

-continued

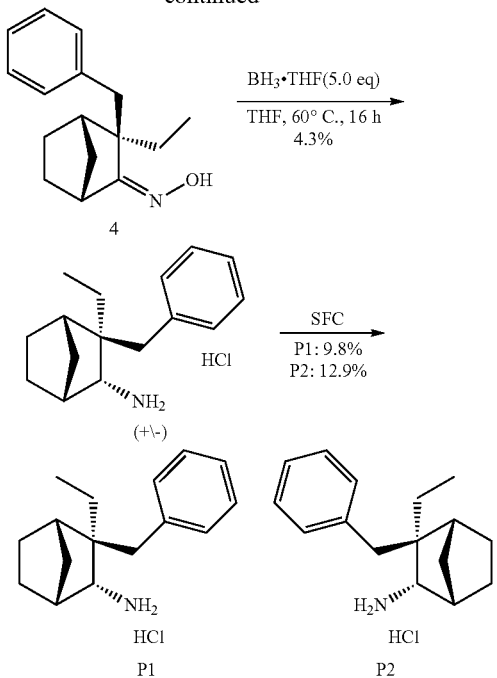

Step 1:

To a stirred solution of (1R,4S)-bicyclo[2.2.1]heptan-2-one (3.0 g, 27.2 mmol, 1.0 eq) in THF (200 mL) was added LiHMDS (1M solution in THF; 40.8 mmol, 40.8 mL, 1.5 eq) dropwise at 0° C. under nitrogen atmosphere. The corresponding reaction mixture was then stirred at 0-5° C. for 2 hours under $N_2$ followed by the addition of $CH_3CH_2I$ (8.5 g, 54.4 mmol, 2.0 eq). The whole mixture was gradually warmed to room temperature and stirred overnight under $N_2$ protection. Once GC showed the reaction finished, the reaction mixture was poured into ice-water (300 mL; contain 10.0 mL conc. HCl) and stirred for 10 minutes followed by the extraction with EtOAc (3×100 mL). The organic phase was then washed with aq. sat. $NaHCO_3$ solution (100 mL), brine (100 mL), dried over $Na_2SO_4$, and filtered. The filtration was then concentrated under vacuum to give (1R,3R,4S)-3-ethylbicyclo[2.2.1]heptan-2-one (2, 3.5 g, 25.36 mmol, 90%) as a brown oil.

Step 2:

To a solution of (1R,3R,4S)-3-ethylbicyclo[2.2.1]heptan-2-one (3.5 g, 25.36 mmol, 1.0 eq) in anhydrous THF (30 mL) at 0° C. was added dropwise LiHMDS (1 M in THF, 42 mL, 42 mmol, 1.5 eq) under nitrogen atmosphere. The reaction mixture was stirred for 2 hours at 0° C. to 5° C. before the dropwise addition of (bromomethyl)benzene (9.6 g, 56.4 mmol, 2.0 eq). The corresponding reaction mixture was warmed to room temperature and stirred at room temperature overnight. Once TLC showed the reaction finished, the reaction mixture was poured to ice-water (100 mL; contain 10.0 mL conc.HCl) and stirred for 10 minutes followed by the extraction with EtOAc (3×50 mL). The organic phase was then washed with aq. sat. $NaHCO_3$ solution (50 mL), brine (50 mL), dried over $Na_2SO_4$, and filtered. The filtration was then concentrated under vacuum and purified by silica gel column eluting with PE:EA=100:1 to give (1R,3R,4S)-3-benzyl-3-ethylbicyclo[2.2.1]heptan-2-one (3, 3.06 g, 13.42 mmol, 53.0%) as a yellow oil.

LCMS [M+H]: 229.2

Step 3:

To a stirred solution of (1R,3R,4S)-3-benzyl-3-ethylbicyclo[2.2.1]heptan-2-one (2.5 g, 10.96 mmol, 1.0 eq) in EtOH (30 mL) was added hydroxylamine hydrochloride (2.0 g, 29.0 mmol, 2.0 eq) and NaOAc (4.8 g, 58.0 mmol, 4.0 eq), and the reaction mixture was stirred at 85° C. overnight. Once LCMS showed the reaction finished, solvent was removed under vacuum to get a residue, which was diluted and extracted with EtOAc (3×50 mL). The organic phases were collected, washed with brine (3×50 mL), dried over $Na_2SO_4$, and filtered. The filtration was then concentrated under vacuum and purified by silica gel column eluting with PE:EA=20:1 to give (1R,3R,4S,Z)-3-benzyl-3-ethylbicyclo[2.2.1]heptan-2-one oxime (4, 2.2 g, 9.05 mmol, 82.7%) as a white solid.

LCMS [M+H]: 244.2

Step 4

To a solution of (1R,3R,4S,Z)-3-benzyl-3-ethylbicyclo[2.2.1]heptan-2-one oxime (2.2 g, 9.05 mmol, 1.0 eq) in THF (20.0 mL) was added BH3.THF (59.0 mL), and the reaction mixture was stirred at 60° C. under $N_2$ atmosphere (1 atm) overnight. Once LCMS showed the reaction finished, reaction mixture was filtered and the filtration was concentrated to give to get (1R,2R,3R,4S)-3-benzyl-3-ethylbicyclo[2.2.1]heptan-2-amine (1.58 g crude), which was then purified by prep-HPLC eluting with 0-90% ACN in water (0.1% TFA), and substituted by HCl to get (1R,2R,3R,4S)-3-benzyl-3-methylbicyclo[2.2.1]heptan-2-amine (5, 312 mg).

LCMS [M+H]: 230.2

$^1$H NMR (400 MHz, CDCL3) δ 7.30-7.19 (m, 5H), 7.15-7.13 (m, 2H), 3.44 (s, 1H), 2.80-2.77 (m, 1H), 2.59-2.40 (m, 4H), 2.14 (s, 1H), 1.66-1.21 (m, 9H), 1.10-1.00 (m, 3H).

General procedure for preparation of (1R,2R,3R,4S)-3-benzyl-3-ethylbicyclo[2.2.1]heptan-2-amine 222-P1 & (1S,2S,3S,4R)-3-benzyl-3-ethylbicyclo[2.2.1]heptan-2-amine 222-P2

SFC separation was carried out for the racemic mixture (100 mg).

The SFC separation information are shown as following:

Analytical separation method:

Instrument: Waters UPCC, Column: ChiralPak AY, 250×4.6 mm, 5 μm, Mobile phase: A for $CO_2$ and B for MeOH (0.04% DEA), Gradient: B 0-40%, Flow rate: 2.8 mL/min, Back pressure: 100 bar, Column temperature: 35° C., Wavelength: 214 nm Preparative separation method:

Instrument: Waters SFC80, Column: ChiralPak AY, 250×25 mm, 10 μm, Mobile phase: A for $CO_2$ and B for MeOH (0.04% DEA), Gradient: B 40%, Flow rate: 2.8 mL/min, Back pressure: 100 bar, Column temperature: 35° C., Wavelength: 214 nm, Cycle time: 8 min, Sample preparation: Compound was dissolved in 15 mL methanol, Injection: 3 ml per injection.

After separation, (1R,2R,3R,4S)-3-benzyl-3-methylbicyclo[2.2.1]heptan-2-amine 222-P1 (10.12 mg, 17%, 99% ee) was obtained as a colorless solid, and (1S,2S,3S,4R)-3-benzyl-3-methylbicyclo[2.2.1]heptan-2-amine 222-P2 (13.22 mg, 17%, 87% ee) was obtained as a colorless solid $^1$H NMR (400 MHz, $CD_3OD$) δ 7.35-7.32 (m, 2H), 7.28-7.23 (m, 3H), 3.51-3.50 (m, 1H), 2.86-2.83 (m, 1H), 2.65-2.62 (m, 1H), 2.47 (s, 1H), 2.20 (s, 1H), 1.78-1.75 (m, 1H), 1.69-1.63 (m, 1H), 1.58-1.53 (m, 3H), 1.44-1.28 (m, 4H), 1.10-1.07 (m, 3H).

¹H NMR (400 MHz, CD₃OD) δ 7.35-7.32 (m, 2H), 7.28-7.21 (m, 3H), 3.51-3.50 (m, 1H), 2.86-2.83 (m, 1H), 2.65-2.62 (m, 1H), 2.47 (s, 1H), 2.20 (s, 1H), 1.78-1.75 (m, 1H), 1.69-1.28 (m, 9H), 1.10-1.07 (m, 3H).

Synthesis of rac-3'-(aminomethyl)spiro[bicyclo [2.2.1]heptane-2,1'-cyclohexan]-3-amine hydrochloride 221

Note: absolute configuration is unassigned and the configuration of the C1 of P1 is arbitrarily shown as (R).

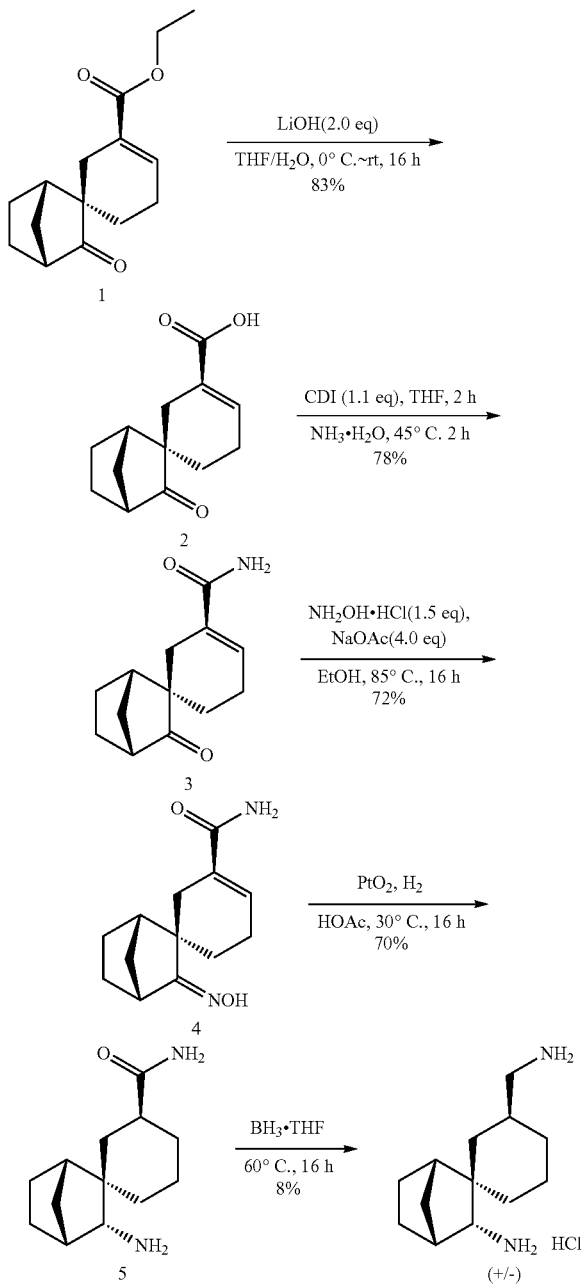

Step 1:
To a stirred solution of rac-ethyl 3-oxospiro[bicyclo [2.2.1]heptane-2,1'-cyclohexan]-3'-ene-3'-carboxylate (1.9 g, 7.60 mmol, 1.0 eq) in THF/H₂O (20 mL/20 mL) was added LiOH·H₂O (637 mg, 15.20 mmol, 2.0 eq). The mixture was warmed to 40° C. and stirred for 16 h. The reaction mixture was then extracted with EtOAc (2×50 mL). The combined organic layer, was washed with brine (50 mL), dried over Na₂SO₄, and filtered. The filtration was concentrated under vacuum to give crude product, which was purified by silica gel chromatography eluting with 10%-50% EA in PE to afford rac-3-oxospiro[bicyclo[2.2.1] heptane-2,1'-cyclohexan]-3'-ene-3'-carboxylic acid (2, 1.4 g, 6.36 mmol, 83%) as a white solid.

¹H NMR (400 MHz, CD₃OD) δ 7.04 (s, 1H), 2.56 (d, J=5.2 Hz, 1H), 2.5 (s, 1H), 2.36-2.32 (m, 2H), 2.19-2.07 (m, 2H), 2.01-1.91 (m, 2H), 1.76-1.72 (m, 2H), 1.68-1.53 (m, 3H), 1.53-1.46 (m, 1H).

Step 2:
To a stirred solution of rac-3-oxospiro[bicyclo[2.2.1]heptane-2,1'-cyclohexan]-3'-ene-3'-carboxylic acid (1 g, 4.50 mmol, 1.0 eq) in THF (15 mL) was added CDI (803 mg, 4.95 mmol, 1.1 eq) at room temperature. The reaction mixture was then stirred room temperature for 1 hour followed by the addition of NH₄OH (1.58 g, 45.05 mmol, 10 eq). The mixture was warmed to 45° C. and stirred for 2 h. The reaction was quenched by water (20 mL), extracted with EtOAc (3×20 mL), dried over Na₂SO₄, and filtered. The filtration was concentrated under vacuum to give crude product, which was purified by silica gel chromatography eluting with 10%-50% EA in PE to afford rac-3-oxospiro [bicyclo[2.2.1]heptane-2,1'-cyclohexan]-3'-ene-3'-carboxamide (3, 770 mg, 3.51 mmol, 78%) as a white solid.

LCMS [M+H]:220.0

¹H NMR (400 MHz, CD₃OD) δ 6.70 (s, 1H), 2.55 (d, J=5.2 Hz, 1H), 2.34-2.26 (m, 3H), 2.17-2.09 (m, 2H), 2.01-1.91 (m, 2H), 1.75-1.65 (m, 2H), 1.62-1.50 (m, 3H), 1.46-1.44 (m, 1H).

Step 3:
To a stirred solution of rac-3-oxospiro[bicyclo[2.2.1]heptane-2,1'-cyclohexan]-3'-ene-3'-carboxamide (770 mg, 3.51 mmol, 1.0 eq) in EtOH (15 mL) was added NH₂O.HCl (485 mg, 7.02 mmol, 2.0 eq) and NaOAc (1.15 g, 14.02 mmol, 4.0 eq) in one portion at room temperature. The reaction mixture was stirred at 85° C. for 16 hours. Once LCMS showed finished, the mixture was concentrated to dryness. The residue was dissolved in EtOAc (60 mL), washed with water (40 mL) brine (40 mL), dried over Na₂SO₄. The filtration was concentrated under vacuum to give crude product, which was purified by silica gel chromatography eluting with 10%-50% EA in PE to afford rac-3-(hydroxyimino) spiro[bicyclo[2.2.1]heptane-2,1'-cyclohexan]-3'-ene-3'-carboxamide (4, 590 mg, 21.52 mmol, 72%) as a white solid.

LCMS [M+H]:235.2

Step 4:
To a solution of rac-3-(hydroxyimino)spiro[bicyclo[2.2.1] heptane-2,1'-cyclohexan]-3'-ene-3'-carboxamide (590 mg, 2.52 mmol, 1.0 eq) in AcOH (5 mL) was added PtO₂ (59 mg, 10% wt) and stirred at 30° C. under H₂ for 16 hours. Once LCMS showed the reaction finished, The mixture was filtered through a pad of celite to remove PtO₂ and then the filtrate was concentrated to obtain a crude product, which was then purified by prep-HPLC eluting with 0-90% ACN in water (0.1% TFA), and substituted by HCl to give rac-3-aminospiro[bicyclo[2.2.1]heptane-2,1'-cyclohexane]-3'-carboxamide (5, 390 mg, 1.76 mmol, 70%) as a white solid.

LCMS [M+H]:223.3

¹H NMR (400 MHz, CD₃OD) δ 3.23 (s, 1H), 2.50-2.43 (m, 2H), 2.26-2.20 (m, 1H), 1.92-1.74 (m, 7H), 1.53-1.50 (m, 1H), 1.47-1.24 (m, 7H).

Step 5:

To a stirred solution of rac-3-aminospiro[bicyclo[2.2.1] heptane-2,1'-cyclohexane]-3'-carboxamide (390 mg, 1.66 mmol, 1.0 eq) in THF (2 mL) was added $BH_3$/THF(4.0 mL, 8.29 mmol, 1.0 mol/L).The reaction was stirred at 60° C. for 16 hours. Once LCMS showed the reaction finished. The reaction was concentrated and purified by Prep-HPLC eluting with 0-90% ACN in water (0.1% TFA), and substituted by HCl to give 221 (29 mg, 0.14 mmol, 8%) as a white solid.

LCMS [M+H−HCl]:209.2

$^1$H NMR (400 MHz, $CD_3OD$) δ 8.22-8.19 (m, 6H), 3.15 (s, 1H), 2.71-2.68 (m, 1H), 2.47 (s, 1H), 2.04-2.00 (m, 1H), 1.95-1.91 (m, 1H), 1.83-1.81 (m, 2H) 1.70 (s, 1H), 1.61-1.48 (m, 5H), 1.34-1.15 (m, 3H), 1.03-0.97 (m, 1H), 0.86-0.71 (m, 2H).

Synthesis of rac-3-aminospiro[bicyclo[2.2.1]heptane-2,1'-cyclohexane]-3'-carboxamide hydrochloride 224

Note: absolute configuration is unassigned and the configuration of the C1 of P1 is arbitrarily shown as (R).

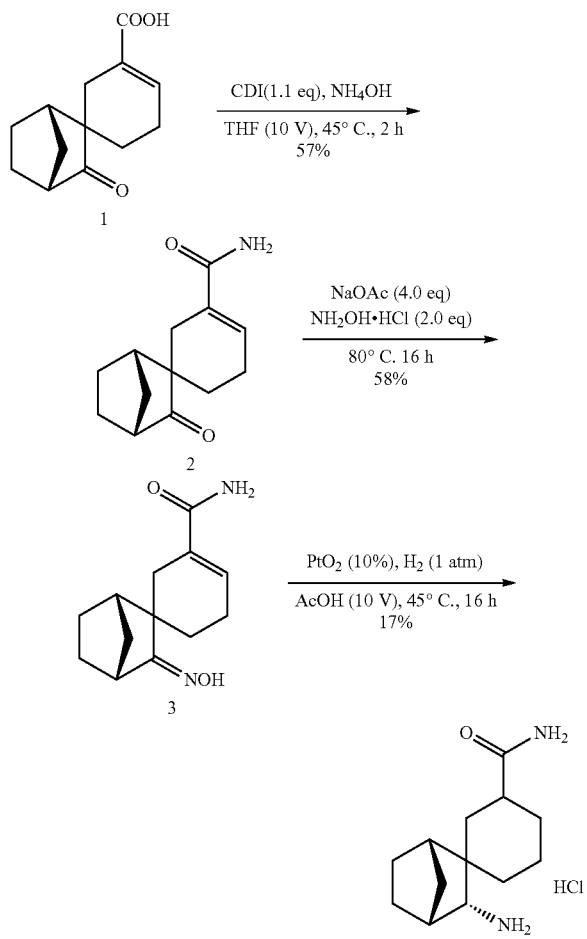

Step 1:

To a stirred solution of rac-3-oxospiro[bicyclo[2.2.1]heptane-2,1'-cyclohexan]-3'-ene-3'-carboxylic acid (300 mg, 1.36 mmol, 1.0 eq) in THF (5 mL) was added CDI (211 mg, 1.50 mmol, 1.1 eq) at rt. The reaction mixture was then stirred rt for 1 hours followed by the addition of $NH_4OH$ (477 mg, 13.6 mmol, 10 eq). The mixture was warmed to 45° C. and stirred for 2 h. The reaction was quenched by water (10 mL), extracted with EtOAc (3×10 mL), dried over $Na_2SO_4$, and filtered. The filtration was concentrated under vacuum to give crude product, which was purified by silica gel chromatography eluting with 10%-50% EA in PE to afford rac-3-oxospiro[bicyclo[2.2.1]heptane-2,1'-cyclohexan]-3'-ene-3'-carboxamide (2, 170 mg, 0.78 mmol, 57%) as a yellow oil.

LCMS [M+H]:220.2

Step 2:

To a stirred solution of rac-3-oxospiro[bicyclo[2.2.1]heptane-2,1'-cyclohexan]-3'-ene-3'-carboxamide (170 mg, 0.73 mmol, 1 eq) in EtOH (5 mL) was added $NH_2OH \cdot HCl$ (102.2 mg, 1.46 mmol, 2.0 eq) and NaOAc (239.4 mg, 2.92 mmol, 4.0 eq) in one portion at room temperature. The reaction mixture was stirred at 85° C. for 16 hours. Once LCMS showed finished, the mixture was concentrated to dryness. The residue was dissolved in EtOAc (50 mL), washed with water (50 mL) brine (60 mL), dried over $Na_2SO_4$. The filtration was concentrated under vacuum to give crude product (3, 106 mg, 0.45 mmol, 58%) which was used next step directly.

Step 3:

To a solution of rac-3-(hydroxyimino)spiro[bicyclo[2.2.1]heptane-2,1'-cyclohexan]-3'-ene-3'-carboxamide (106 mg, 0.45 mmol, 1.0 eq) in AcOH (2 mL) was added $PtO_2$ (10.6 mg, 10% wt) and stirred at 45° C. under $H_2$ for 16 hours. Once LCMS showed the reaction finished, The mixture was filtered through a pad of celite to remove $PtO_2$ and then the filtrate was concentrated in vacuo to obtain a crude product, which was then purified by prep-HPLC eluting with 0-90% ACN in water (0.1% TFA), and substituted by HCl to give 224 (20 mg, 0.08 mmol, 17%) as a white solid.

LCMS [M+H]:223.2

$^1$H NMR (400 MHz, $CD_3OD$) δ 3.24 (d, J=3.6 Hz, 1H), 2.5 (s, 1H), 2.44 (s, 1H), 2.29-2.22 (m, 1H), 1.93 (s, 1H), 1.89-1.71 (m, 6H), 1.59-1.25 (m, 9H).

Synthesis of rac-3',4'-dimethoxyspiro[bicyclo[2.2.1]heptane-2,1'-cyclopentan]-3-amine hydrochloride 229

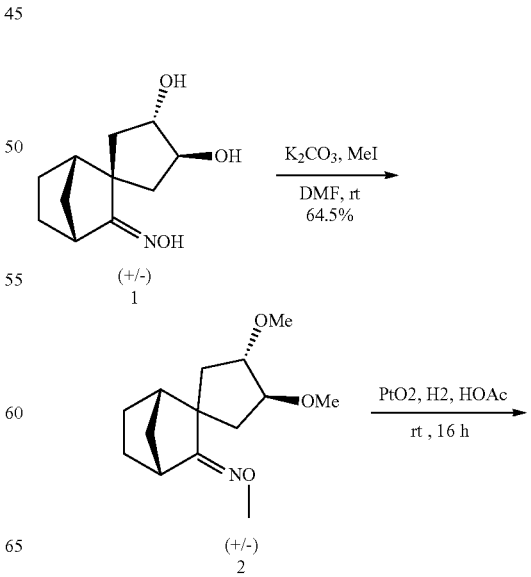

-continued

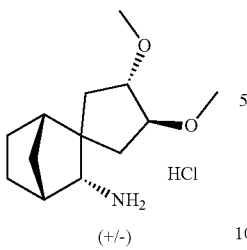

(+/-)

Note: absolute configuration is unassigned and the configuration of the C1 of P1 is arbitrarily shown as (R).

Step 1:

To a stirred solution of rac-3',4'-dihydroxyspiro[bicyclo[2.2.1]heptane-2,1'-cyclopentan]-3-one oxime (666 mg, 3.15 mmol, 1.0 eq,) in DMF (10 mL) was added NaH (631 mng, 15.78 mmol, 5.0 eq) at 0° C. in portions. The mixture was stirred at room temperature for 30 mins. CH₃I (2.23 g, 15.78 mmol, 5.0 eq) was added. The mixture was stirred at room temperature for 16 hours. TLC (PE:EA=10:1) showed completed. The mixture was quenched with H₂O at 0° C., extracted with EtOAc (3×10 mL). The combined organic phase was washed with brine (2×20 mL), dried with anhydrous Na₂SO₄, and concentrated under vacuum to get the crude, which was purified by silica column chromatography eluting with 10% EA in PE to give rac-3',4'-dimethoxyspiro[bicyclo[2.2.1]heptane-2,1'-cyclopentan]-3-one O-methyl oxime (2, 515 mg, 2.03 mmol, 64.5% yield) as a light yellow oil.

¹H NMR (400 MHz, CDCl₃) δ 3.89-3.75 (m, 3H), 3.69-3.63 (m, 1H), 3.39-3.37 (m, 3H), 3.36-3.35 (m, 3H), 3.32-3.31 (m, 1H), 2.20-2.04 (m, 3H), 1.82-1.77 (m, 1H), 1.70-1.50 (m, 7H), 1.35-1.25 (m, 2H).

Step 2:

To a solution of rac-3',4'-dimethoxyspiro[bicyclo[2.2.1]heptane-2,1'-cyclopentan]-3-one O-methyl oxime (515 mg, 0.35 mmol, 1.0 eq) in HOAc (3.0 mL) was added PtO₂ (50 mg), and the reaction mixture was stirred at room temperature under H₂ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 229 (71.74 mg, 0.272 mmol) as a white solid.

LCMS [M+H–HCl]: 226.2

¹H NMR (400 MHz, CD₃OD) δ 3.78 (t, J=3.2 Hz, 1H), 3.71 (t, J=2.4 Hz, 1H), 3.40 (s, 3H), 3.31 (s, 3H), 3.20 (d, J=4.0 Hz, 1H), 2.50 (s, 2H), 2.08-2.02 (m, 2H), 1.97-1.92 (m, 1H), 1.77-1.69 (m, 3H), 1.55-1.50 (m, 4H), 1.44-1.42 (m, 1H).

Synthesis of rac-3-(cyclopropylmethyl)-3-methylbicyclo[2.2.1]heptan-2-amine hydrochloride 244

Note: absolute configuration is unassigned and the configuration of the C1 of P1 is arbitrarily shown as (R).

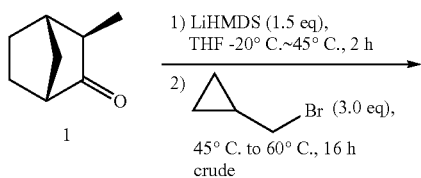

1) LiHMDS (1.5 eq),
THF -20° C.~45° C., 2 h

2)  Br (3.0 eq),

45° C. to 60° C., 16 h
crude

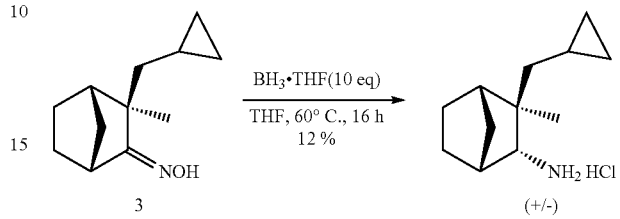

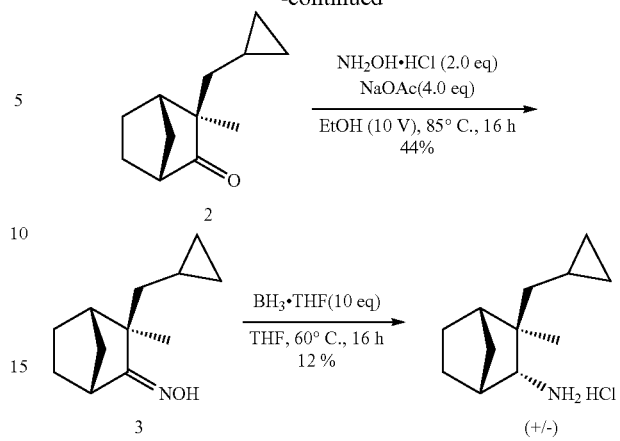

Step 1:

To a stirred solution of rac-3-methylbicyclo[2.2.1]heptan-2-one (2.0 g, 16.1 mmol, 1.0 eq) in anhydrous THF (40 mL) at −20° C. was added LiHMDS (1.0 M in THF; 24.18 mL, 24.18 mmol, 1.5 eq) under N₂ protection. The corresponding reaction mixture was then stirred at 45° C. for 2 hours under N₂ followed by the addition of (bromomethyl)cyclopropane (6.53 g, 48.35 mmol, 3.0 eq). The whole mixture was gradually warmed to 60° C. and stirred overnight under N₂ protection. Once TLC showed the reaction finished, the reaction mixture was poured into ice-water (80 mL; contain 4.0 mL conc.HCl) and stirred for 10 minutes followed by the extraction with EtOAc (3×50 mL). The organic phase was then washed with aq. sat. NaHCO₃ solution (80 mL), brine (80 mL), dried over Na₂SO₄, and filtered. The filtration was then concentrated under vacuum to give rac-3-(cyclopropylmethyl)-3-methylbicyclo[2.2.1]heptan-2-one (2, 3.1 g, crude).

Step 2:

To a stirred solution of rac-3-(cyclopropylmethyl)-3-methylbicyclo[2.2.1]heptan-2-one (3.1 g, 17.39 mmol, 1 eq) in EtOH (20 mL) was added NH₂OH·HCl (2.4 g, 34.77 mmol, 2.0 eq) and NaOAc (5.7 g, 69.56 mmol, 4.0 eq) in one portion at room temperature. The reaction mixture was stirred at 85° C. for 16 hours. Once LCMS showed finished, the mixture was concentrated to dryness. The residue was dissolved in EtOAc (80 mL), washed with water (60 mL) brine (60 mL), dried over Na₂SO₄. The filtration was concentrated under vacuum to give crude product, which was purified by silica gel chromatography eluting with 10%-50% EA in PE to afford rac-3-(cyclopropylmethyl)-3-methylbicyclo[2.2.1]heptan-2-one oxime (3, 1.4 g, 7.24 mmol, 44%) as a yellow oil.

LCMS [M+H]:194.1

¹H NMR (400 MHz, CDCl₃) δ 8.79 (brs, 1H), 3.49 (d, J=4.0 Hz, 1H), 2.42 (d, J=2.0 Hz, 1H), 1.85-1.68 (m, 4H), 1.58-1.51 (m, 1H), 1.43-1.34 (m, 5H), 1.24 (s, 3H), 0.77-0.69 (m, 1H), 0.52-0.44 (m, 3H).

Step 3:

To a stirred solution of rac-3-(cyclopropylmethyl)-3-methylbicyclo[2.2.1]heptan-2-one oxime (640 mg, 3.32 mmol, 1 eq) in THF (5 mL) was added BH₃/THF (33.2 mL, 33.2 mmol, 1.0 mol/L). The reaction was stirred at 60° C. for 16 hours. Once LCMS showed the reaction finished. The reaction was concentrated and purified by Prep-HPLC eluting with 0-90% ACN in water (0.1% TFA), and substituted by HCl to give 244 (70.59 mg, 0.39 mmol, 12%) as a white solid.

LCMS [M+H−HCl]: 180.3

¹H NMR (400 MHz, CDCl₃) δ 8.37 (brs, 3H), 3.19 (s, 1H), 2.57 (s, 1H), 2.08 (s, 1H), 1.88-1.73 (m, 2H), 1.66-1.58 (m, 1H), 1.47-1.38 (m, 2H), 1.33-1.27 (m, 3H), 1.21 (s, 3H), 0.75-0.23 (m, 1H), 0.51 (d, J=8.0 Hz, 2H), 0.04-0.02 (m, 2H).

Synthesis of rac-3-(cyclopropylmethyl)-3-methylbicyclo[2.2.1]heptan-2-amine hydrochloride 243-A Note: absolute configuration is unassigned and the configuration of the C1 of P1 is arbitrarily shown as (R).

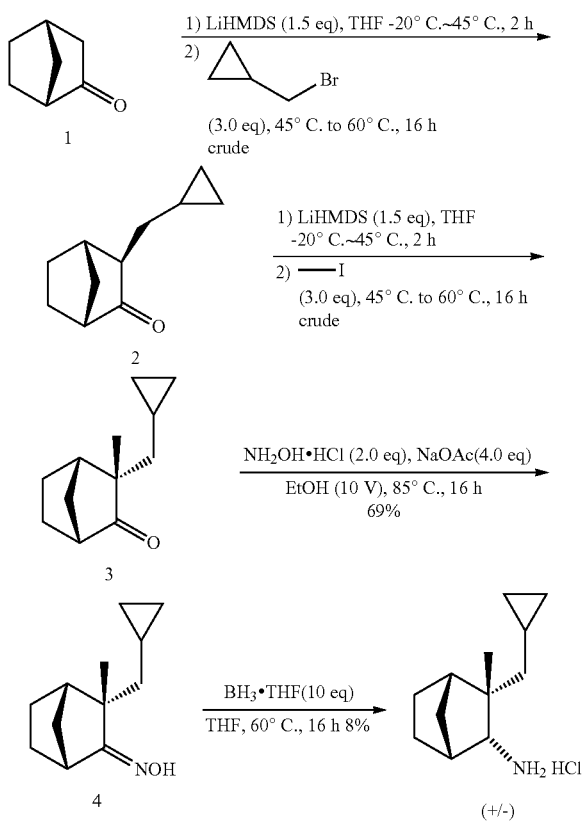

Step 1:

To a stirred solution of rac-bicyclo[2.2.1]heptan-2-one (500 mg, 4.55 mmol, 1.0 eq) in anhydrous THF (10 mL) at −20° C. was added LiHMDS (1.0 M in THF; 6.82 mL, 6.82 mmol, 1.5 eq) under N₂ protection. The corresponding reaction mixture was then stirred at 45° C. for 2 hours under N₂ followed by the addition of (bromomethyl)cyclopropane (1.23 g, 9.01 mmol, 2.0 eq). The whole mixture was gradually warmed to 60° C. and stirred overnight under N₂ protection. Once TLC showed the reaction finished, the reaction mixture was poured into ice-water (50 mL; contain 2.0 mL conc.HCl) and stirred for 10 minutes followed by the extraction with EtOAc (2×40 mL). The organic phase was then washed with aq. sat. NaHCO₃ solution (60 mL), brine (60 mL), dried over Na₂SO₄, and filtered. The filtration was then concentrated under vacuum to give crude rac-3-(cyclopropylmethyl)bicyclo[2.2.1]heptan-2-one (2, 600 mg, crude).

Step 2:

To a stirred solution of rac-3-(cyclopropylmethyl)bicyclo[2.2.1]heptan-2-one (600 mg, 3.65 mmol, 1.0 eq) in anhydrous THF (10 mL) at −20° C. was added LiHMDS (1.0 M in THF; 5.48 mL, 5.48 mmol, 1.5 eq) under N₂ protection. The corresponding reaction mixture was then stirred at 45° C. for 2 hours under N₂ followed by the addition of iodomethane (1.04 g, 7.31 mmol, 2.0 eq). The whole mixture was gradually warmed to 60° C. and stirred overnight under N₂ protection. Once TLC showed the reaction finished, the reaction mixture was poured into ice-water (40 mL; contain 2.0 mL conc.HCl) and stirred for 10 minutes followed by the extraction with EtOAc (3×50 mL). The organic phase was then washed with aq. sat. NaHCO₃ solution (50 mL), brine (40 mL), dried over Na₂SO₄, and filtered. The filtration was then concentrated under vacuum to give crude rac-3-(cyclopropylmethyl)-3-methylbicyclo[2.2.1]heptan-2-one (3, 680 mg, crude).

Step 3:

To a stirred solution of rac-3-(cyclopropylmethyl)-3-methylbicyclo[2.2.1]heptan-2-one (680 mg, 3.63 mmol, 1 eq) in EtOH (15 mL) was added NH₂OH·HCl (501 mg, 7.26 mmol, 2.0 eq) and NaOAc (1.19 g, 14.52 mmol, 4.0 eq) in one portion at room temperature. The reaction mixture was stirred at 85° C. for 16 hours. Once LCMS showed finished, the mixture was concentrated to dryness. The residue was dissolved in EtOAc (60 mL), washed with water (40 mL) brine (40 mL), dried over Na₂SO₄. The filtration was concentrated under vacuum to give crude product, which was purified by silica gel chromatography eluting with 10%-50% EA in PE to afford rac-3-(cyclopropylmethyl)-3-methylbicyclo[2.2.1]heptan-2-one oxime (4, 510 mg, 2.64 mmol, 69%) as a white oil.

LCMS [M+H]:194.3

¹H NMR (400 MHz, CDCl₃) δ 3.40 (d, J=4.0 Hz, 1H), 2.18 (d, J=2.4 Hz, 1H), 1.74-1.61 (m, 3H), 1.50-1.41 (m, 2H), 1.31-1.24 (m, 3H), 1.47 (s, 3H), 0.81-0.76 (m, 1H), 0.59-0.56 (m, 1H), 0.46-0.30 (m, 3H), 0.07-0.01 (m, 1H).

Step 5

To a stirred solution of rac-3-(cyclopropylmethyl)-3-methylbicyclo[2.2.1]heptan-2-one oxime (510 mg, 2.64 mmol, 1 eq) in THF (2 mL) was added BH₃/THF (26.42 mL, 26.42 mmol, 1.0 mol/L).The reaction was stirred at 60° C. for 16 hours. Once LCMS showed the reaction finished. The reaction was concentrated and purified by Prep-HPLC eluting with 0-90% ACN in water (0.1% TFA), and substituted by HCl to give 243-A (37.49 mg, 0.21 mmol, 8%) as a white solid.

LCMS [M+H−HCl]: 180.1

¹H NMR (400 MHz, CDCl₃) δ 8.25 (brs, 3H), 3.04 (s, 1H), 2.58 (s, 1H), 2.10 (s, 1H), 1.91-1.88 (m, 1H), 1.73-1.67 (m, 3H), 1.59-1.46 (m, 2H), 1.34-1.32 (m, 1H), 1.20 (s, 3H), 1.05-1.02 (m, 1H), 0.56-0.51 (m, 2H), 0.42-0.41 (m, 1H), 0.16-0.05 (m, 2H).

Synthesis of rac-3-isopropyl-3-methylbicyclo[2.2.1]heptan-2-amine hydrochloride 245

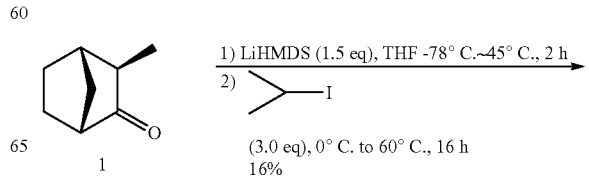

131

-continued

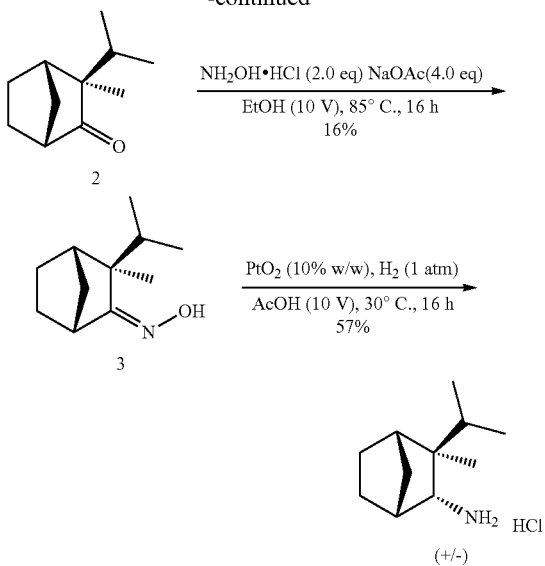

Step 1:

To a stirred solution of rac-3-methylbicyclo[2.2.1]heptan-2-one (2.0 g, 16.1 mmol, 1.0 eq) in anhydrous THF (40 mL) at 0° C. was added LiHMDS (1.0 M in THF; 24.15 mL, 24.15 mmol, 1.5 eq) under N$_2$ protection. The corresponding reaction mixture was then stirred at 45° C. for 2 hours under N$_2$ followed by the addition of 2-iodopropane (8.2 g, 48.3 mmol, 3.0 eq). The whole mixture was gradually warmed to 60° C. and stirred overnight under N$_2$ protection. Once TLC showed the reaction finished, the reaction mixture was poured into ice-water (80 mL; contain 4.0 mL conc.HCl) and stirred for 10 minutes followed by the extraction with EtOAc (50 mL×3). The organic phase was then washed with aq. sat. NaHCO$_3$ solution (80 mL), brine (80 mL), dried over Na$_2$SO$_4$, and filtered. The filtration was concentrated under vacuum to give crude product, which was purified by silica gel chromatography eluting with 10%-50% EA in PE to afford rac-3-isopropyl-3-methylbicyclo[2.2.1]heptan-2-one (2, 420 mg, 2.52 mmol, 16%) as a white oil.

$^1$H NMR (400 MHz, CDCl$_3$) δ 2.53 (d, J=5.2 Hz, 1H), 2.31 (d, J=1.6 Hz, 1H), 2.13-2.03 (m, 1H), 1.89-1.78 (m, 3H), 1.51-1.40 (m, 3H), 1.23 (s, 3H), 1.06-1.01 (m, 3H), 0.94-0.87 (m, 3H).

Step 2:

To a stirred solution of rac-3-isopropyl-3-methylbicyclo[2.2.1]heptan-2-one (420 mg, 2.53 mmol, 1 eq) in EtOH (10 mL) was added NH$_2$OH·HCl (349 mg, 5.05 mmol, 2.0 eq) and NaOAc (829 mg, 10.1 mmol, 4.0 eq) in one portion at room temperature. The reaction mixture was stirred at 85° C. for 16 hours. Once LCMS showed finished, the mixture was concentrated to dryness. The residue was dissolved in EtOAc (50 mL), washed with water (40 mL) brine (40 mL), dried over Na$_2$SO$_4$. The filtration was concentrated under vacuum to give crude product, which was purified by silica gel chromatography eluting with 10%-50% EA in PE to afford rac-3-isopropyl-3-methylbicyclo[2.2.1]heptan-2-one oxime (3, 110 mg, 0.61 mmol, 16%) as a white solid.

LCMS [M+H]:182.1

$^1$H NMR (400 MHz, DMSO) δ 10.11 (s, 1H), 3.38 (s, 1H), 2.31 (s, 1H), 1.87-1.78 (m, 2H), 1.71-1.63 (m, 2H), 1.54-1.47 (m, 1H), 1.35-1.34 (m, 2H), 1.25 (d, J=26.8 Hz, 3H), 0.98-0.90 (m, 6H).

132

Step 3:

To a stirred solution of rac-3-isopropyl-3-methylbicyclo[2.2.1]heptan-2-one oxime (110 mg, 0.61 mmol, 1 eq) in HOAc(5 mL) was added PtO$_2$ (21 mg, 0.09 mmol, 0.15 eq) in one portion at room temperature under nitrogen atmosphere. The suspension was degassed under vacuum and purged with H$_2$ several times. The mixture was stirred under H$_2$ (balloon) at 40° C. for 16 hours. Once LCMS showed the major formation of desired compound, the mixture was filtered to get rid of catalyst and the filtration was concentrated under vacuum to give the crude, which was then purified by prep-HPLC eluting with 0-90% ACN in water (0.1% TFA), and substituted by HCl to give 245 (63 mg, 0.38 mmol, 57% yield) as a white solid.

LCMS [M+H−HCl]: 168.6

$^1$H NMR (400 MHz, CDCl$_3$) δ 8.32 (brs, 3H), 3.16 (s, 1H), 2.61 (s, 1H), 2.17 (s, 1H), 1.95-1.94 (m, 1H), 1.72-1.60 (m, 2H), 1.46-1.34 (m, 2H), 1.25-1.23 (m, 1H), 0.97-0.96 (m, 6H), 0.85 (d, J=6.8 Hz, 3H).

Synthesis of (1R,2R,3S,4S)-3-isopropyl-3-methylbicyclo[2.2.1]heptan-2-amine hydrochloride & (1R, 2S,3S,4S)-3-isopropyl-3-methylbicyclo[2.2.1]heptan-2-amine hydrochloride 246-A & 246-B Note: absolute configuration is unassigned and the configuration of the C1 of P1 is arbitrarily shown as (R). In this instance, since diastereomers at C1 were produced, the (S)-diastereomer is shown independently.

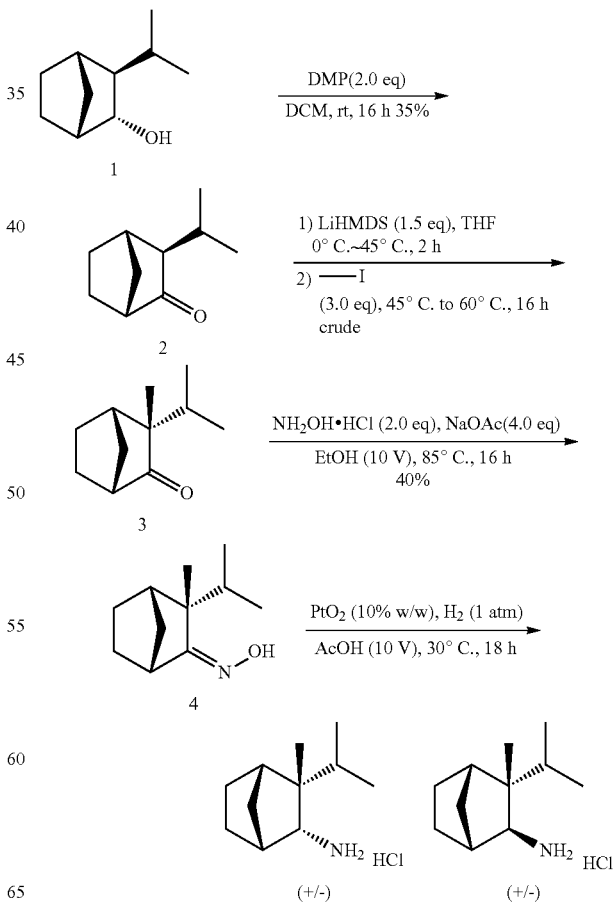

Step 1:

To a stirred solution of rac-3-isopropylbicyclo[2.2.1]heptan-2-ol (4.2 g, 27.2 mmol, 1.0 eq) in DCM (50 mL) was added DMP (23 g, 54.4 mmol, 2.0 eq) in one portion at room temperature. The reaction mixture was stirred at room temperature for 16 hours. Once TLC showed finished, the mixture was dissolved in aq. sat. NaHCO$_3$ solution (100 mL). The residue was extracted with EtOAc (50 mL×3), washed with brine (80 mL×2), dried over Na$_2$SO$_4$. The filtration was concentrated under vacuum to give crude product, which was purified by silica gel chromatography eluting with 10%-50% EA in PE to afford rac-3-isopropylbicyclo[2.2.1]heptan-2-one (2, 1.6 g, 10.51 mmol, 35%) as a white oil.

$^1$H NMR (400 MHz, CDCl$_3$) δ 2.55-2.51 (m, 2H), 1.87-1.84 (m, 1H), 1.82-1.74 (m, 3H), 1.53-1.35 (m, 4H), 1.06 (d, J=6.8 Hz, 3H), 0.94 (d, J=6.4 Hz, 3H).

Step 2:

To a stirred solution of rac-3-isopropylbicyclo[2.2.1]heptan-2-one (300 mg, 1.80 mmol, 1.0 eq) and HMAP (322 mg, 1.80 mmol, 1.0 eq) in anhydrous THF (6 mL) at 0° C. was added LiHMDS (1.0 M in THF; 2.7 mL, 2.7 mmol, 1.5 eq) under N$_2$ protection. The corresponding reaction mixture was then stirred at 45° C. for 2 hours under N$_2$ followed by the addition of iodomethane (765 mg, 5.39 mmol, 3.0 eq). The whole mixture was gradually warmed to 60° C. and stirred overnight under N$_2$ protection. Once TLC showed the reaction finished, the reaction mixture was poured into ice-water (50 mL; contain 4.0 mL conc.HCl) and stirred for 10 minutes followed by the extraction with EtOAc (50 mL×3). The organic phase was then washed with aq. sat. NaHCO$_3$ solution (50 mL), brine (40 mL), dried over Na$_2$SO$_4$, and filtered. The filtration was then concentrated under vacuum to give crude rac-3-isopropyl-3-methylbicyclo[2.2.1]heptan-2-one (3, 400 mg, crude)

Step 3:

To a stirred solution of rac-3-isopropyl-3-methylbicyclo[2.2.1]heptan-2-one (400 mg, 2.41 mmol, 1 eq) in EtOH (10 mL) was added NH$_2$OH·HCl (332 mg, 4.81 mmol, 2.0 eq) and NaOAc (789 mg, 9.62 mmol, 4.0 eq) in one portion at room temperature. The reaction mixture was stirred at 85° C. for 16 hours. Once LCMS showed finished, the mixture was concentrated to dryness. The residue was dissolved in EtOAc (30 mL), washed with brine (20 mL), dried over Na$_2$SO$_4$. The filtration was concentrated under vacuum to give crude product, which was then purified by prep-HPLC eluting with 0-90% ACN in water (0.1% TFA) to give rac-3-isopropyl-3-methylbicyclo[2.2.1]heptan-2-one oxime (4, 160 mg, 0.88 mmol, 40% yield) as a white solid.

LCMS [M+H]:182.2

$^1$H NMR (400 MHz, CDCl$_3$) δ 3.54 (d, J=2.0 Hz, 1H), 2.12 (d, J=5.2 Hz, 1H), 1.82-1.67 (m, 4H), 1.51-1.29 (m, 3H), 1.09 (d, J=6.8 Hz, 3H), 0.97 (s, 3H), 0.87 (d, J=6.8 Hz, 3H).

Step 4:

To a stirred solution of rac-3-isopropyl-3-methylbicyclo[2.2.1]heptan-2-one oxime (160 mg, 0.88 mmol, 1 eq) in HOAc (5 mL) was added PtO$_2$ (30 mg, 0.15 mmol, 0.15 eq) in one portion at room temperature under nitrogen atmosphere. The suspension was degassed under vacuum and purged with H$_2$ several times. The mixture was stirred under H$_2$ (balloon) at 40° C. for 16 hours. Once LCMS showed the major formation of desired compound, the mixture was filtered to get rid of catalyst and the filtration was concentrated under vacuum to give the crude, which was then purified by prep-HPLC eluting with 0-90% ACN in water (0.1% TFA), and substituted by HCl to give 246-A (11.48 mg, 0.07 mmol) and 246-B (11.7 mg, 0.07 mmol) as white solids.

246-A:

LCMS [M+H−HCl]: 168.1

$^1$H NMR (400 MHz, CDCl$_3$) δ 8.32 (brs, 3H), 3.05 (s, 1H), 2.74 (s, 1H), 2.08-2.04 (m, 1H), 1.92 (s, 1H), 1.73-1.68 (m, 2H), 1.46-1.38 (m, 2H), 1.26-1.25 (m, 2H), 1.01 (d, J=6.4 Hz, 3H), 0.93 (s, 3H), 0.88 (d, J=6.4 Hz, 3H).

246-B

LCMS [M+H−HCl]: 168.1

$^1$H NMR (400 MHz, CDCl$_3$) δ 8.18 (brs, 3H), 2.66 (s, 1H), 2.32 (d, J=4.4 Hz, 1H), 2.20-2.17 (m, 1H), 1.86 (s, 1H), 1.46-1.41 (m, 1H), 1.24-1.11 (m, 6H), 0.96 (s, 3H), 0.93 (d, J=6.4 Hz, 3H), 0.77 (d, J=6.4 Hz, 3H).

Synthesis of rac-(1R,2R,3R,4S)-3-methyl-3-phenylbicyclo[2.2.1]heptan-2-amine 218

Note: absolute configuration is unassigned and the configuration of the C1 of P1 is arbitrarily shown as (R).

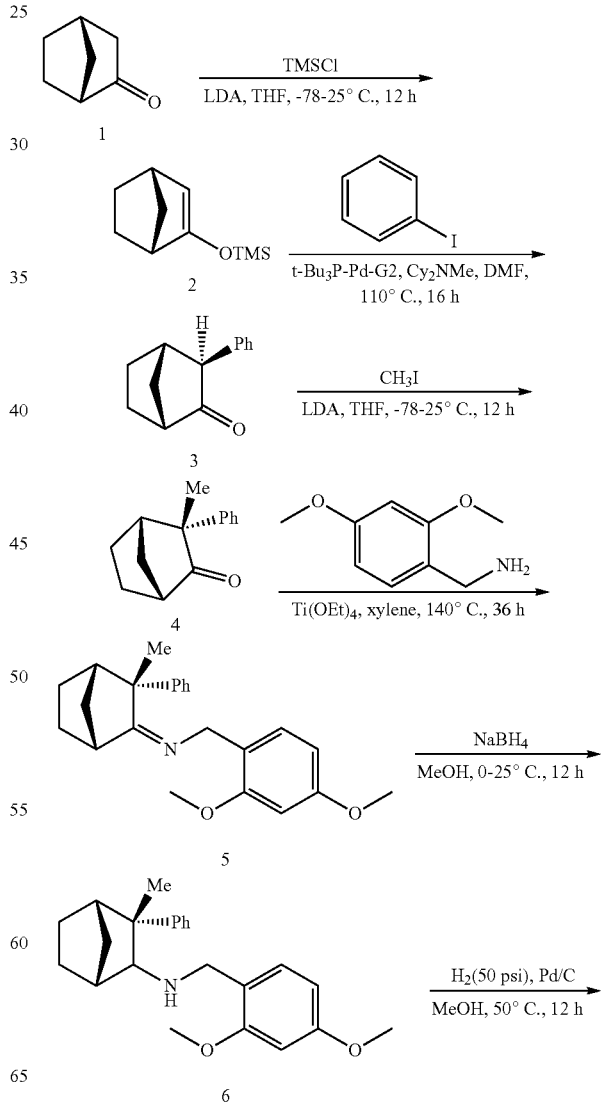

-continued

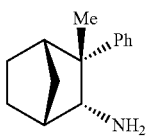

Step 1:

Rac-(1R,4S)-norbornan-2-one (10000 mg, 90.8 mmol, 1.0 eq) in 200 mL of anhydrous THF was added LDA (2 M, 54.5 mL, 109 mmol, 1.2 eq) at −78° C. under the $N_2$. The mixture was stirred at −78° C. for 1 hour and then TMSCl (9863 mg, 90.8 mmol, 1.0 eq) was added into the mixture by dropwise. The mixture was slowly warmed to 25° C. and stirred for 12 hours. TLC (Petroleum ether/EtOAc=10/1, Rf=0.60, Twist molybdate) indicated reactant 1 was consumed completely. The mixture was quenched with 200 ml of saturated $NH_4Cl$ solution, extracted with 500 ml of EA for once, the organic layer was dried over with $Na_2SO_4$ (200 g), concentrated at 45° C. under vacuum to give rac-(((1R,4S)-bicyclo[2.2.1]hept-2-en-2-yl)oxy)trimethylsilane (2, 12000 mg, 65.8 mmol) as yellow oil and used for next step directly. The structure was supported by HNMR.

$^1$H NMR (400 MHz, CHLOROFORM-d) δ: 4.69 (d, J=3.2 Hz, 1H), 2.77 (s, 1H), 2.56 (s, 1H), 1.89-1.76 (m, 1H), 1.75-1.58 (m, 3H), 1.37-1.09 (m, 3H), 1.04 (br d, J=8.0 Hz, 1H), 0.20 (s, 9H) ppm.

Step 2:

Rac-[(1R,4S)-2-bicyclo[2.2.1]hept-2-enyl]oxy-trimethylsilane (630 mg, 3.46 mmol, 1.0 eq), iodobenzene (705 mg, 3.46 mmol, 1.0 eq), (t-Bu)$_3$Pd-G2 (177 mg, 0.346 mmol, 0.1 eq) and Cy2NMe (742 mg, 3.80 mmol, 1.1 eq) in 25 mL of anhydrous DMF was stirred at 110° C. for 12 h under $N_2$. TLC (Petroleum ether/EtOAc=10/1, Rf=0.40, Twist molybdate) indicated reactant 1 was consumed completely. The reaction mixture was diluted with 20 mL of water and extracted with 20 mL of EA for three times. The combined organic layers were washed with 15 mL of brine for twice, dried over with $Na_2SO_4$ (100 g), filtered and concentrated under reduced pressure to give a residue. The residue was purified by column chromatography ($SiO_2$, Petroleum ether/Ethyl acetate=1/0 to 100/1). The fraction of column was concentrated at 40° C. under vacuum. Combined the products to give rac-(1R,4S)-3-phenylbicyclo[2.2.1]heptan-2-one (180 mg, 0.966 mmol) as colorless oil. The structure was supported by HNMR and LCMS.

$^1$H NMR (400 MHz, CHCl$_3$-d) δ: 7.36-7.27 (m, 4H), 7.26-7.19 (m, 1H), 3.13 (d, J=3.2 Hz, 1H), 2.90 (s, 1H), 2.68 (d, J=2.4 Hz, 1H), 2.11-2.02 (m, 1H), 2.01-1.88 (m, 2H), 1.74-1.63 (m, 2H), 1.62-1.59 (m, 1H) ppm.

MS (ESI): m/z for $C_{13}H_{14}O$ [M+H]+ calcd. 187.1, [M+H]+ found. 187.1

Step 3:

Rac-(1R,4S)-3-phenylnorbornan-2-one (560 mg, 3.01 mmol, 1.0 eq) in 28 mL of anhydrous THF was added LDA (2 M, 1.95 mL, 3.91 mmol, 1.3 eq) at −70° C. The mixture was stirred at 25° C. for 0.5 hour and then cooled to −70° C. CH$_3$I (555 mg, 3.91 mmol, 1.30 eq) was dropwise into mixture slowly. The mixture was slowly warmed to 25° C. and stirred for 12 hours. TLC (Petroleum ether/EtOAc=10/1, Rf=0.40, Twist molybdate) indicated reactant 1 was consumed completely. The reaction mixture was quenched with 30 mL of saturated $NH_4Cl$ solution and extracted with 40 mL of EA by three times. The combined organic layers were washed with 15 mL of brine by twice, dried over with $Na_2SO_4$ (100 g), filtered and concentrated at 45° C. under vacuum to give a residue. The residue was purified by prep-TLC ($SiO_2$, PE: EA=10:1) to give the crude product rac-(1R,3R,4S)-3-methyl-3-phenylbicyclo[2.2.1]heptan-2-one (280 mg, 1.40 mmol) as colorless oil. The structure was supported by HNMR and LCMS.

$^1$H NMR (400 MHz, CHLOROFORM-d) δ: 7.37-7.28 (m, 4H), 7.26-7.19 (m, 1H), 2.78-2.69 (m, 2H), 2.13 (d, J=10.4 Hz, 1H), 1.84-1.72 (m, 1H), 1.65-1.60 (m, 1H), 1.59-1.49 (m, 1H), 1.45-1.38 (m, 4H), 1.30-1.21 (m, 1H) ppm.

MS (ESI): m/z for $C_{14}H_{16}O$ [M+H]+ calcd. 201.1, [M+H]+ found. 201.1

Step 4:

To a solution of rac-(1R,3R,4S)-3-methyl-3-phenyl-norbornan-2-one (180 mg, 0.899 mmol, 1.00 eq), (2,4-dimethoxyphenyl)methanamine (180 mg, 1.08 mmol, 1.20 eq) and (EtO)$_4$Ti (718 mg, 3.15 mmol, 3.50 eq) in 9 mL of anhydrous o-xylene was stirred at 140° C. for 12 h. LCMS indicated that the desired mass was formed and reactant 1 was consumed. The reaction mixture was diluted with 20 mL of water and extracted with 20 mL of EA by three times. The combined organic layers were washed with 15 mL of brine by twice, dried over with $Na_2SO_4$ (20 g), filtered and concentrated at 45° C. under reduced pressure to give a residue rac-(1R,3R,4S,Z)-N-(2,4-dimethoxybenzyl)-3-methyl-3-phenylbicyclo[2.2.1]heptan-2-imine (330 mg, 0.944 mmol) as colorless oil. The structure was supported by LCMS.

MS (ESI): m/z for $C_{23}H_{27}NO_2$ [M+H]+ calcd. 350.2, [M+H]+ found. 350.2

Step 5:

To a solution of rac-(Z,1R,3R,4S)-N-[(2,4-dimethoxyphenyl)methyl]-3-methyl-3-phenyl-norbornan-2-imine (300 mg, 0.858 mmol, 1.0 eq) in 3.5 mL of anhydrous MeOH was added NaBH$_4$ (195 mg, 5.15 mmol, 6.0 eq) at 0° C. The mixture was stirred at 25° C. for 12 h. LCMS indicated that the desired mass was formed, and the reactant 1 was consumed. The mixture was quenched with 50 mL of saturated $NH_4Cl$, extracted with 30 ml of EA by twice, the combined organic layers were washed with 15 mL of brine by twice, dried over with $Na_2SO_4$ (20 g), filtered and concentrated at 45° C. under reduced pressure to give a residue. The mixture was purified by prep-HPLC (FA condition) to give a residue rac-(1R,3R,4S)-N-(2,4-dimethoxybenzyl)-3-methyl-3-phenylbicyclo[2.2.1]heptan-2-amine (7.0 mg, 0.0199 mmol) as colorless oil. The structure was supported by HNMR and LCMS.

$^1$H NMR (400 MHz, CHLOROFORM-d) δ: 9.84 (s, 1H), 7.60-7.53 (m, 2H), 7.52-7.45 (m, 1H), 7.44-7.35 (m, 2H), 7.26-7.20 (m, 1H), 7.09-6.83 (m, 1H), 6.61-6.47 (m, 1H), 6.41-6.31 (m, 1H), 4.29 (s, 1H), 4.08 (br s, 1H), 3.80 (s, 3H), 3.77-3.68 (m, 1H), 3.53 (s, 3H), 2.78 (s, 1H), 2.54 (s, 1H), 2.14-1.98 (m, 2H), 1.82-1.61 (m, 3H), 1.60-1.52 (m, 1H), 1.41 (s, 3H) ppm.

MS (ESI): m/z for $C_{23}H_{29}NO_2$ [M+H]+ calcd. 352.2, [M+H]+ found. 352.0

Step 6:

Rac-(1R,3R,4S)-N-[(2,4-dimethoxyphenyl)methyl]-3-methyl-3-phenyl-norbornan-2-amine (7.0 mg, 0.0199 mmol, 1.0 eq) in 10 mL of anhydrous MeOH was added Pd/C (1 mg) under the $N_2$.

The mixture was purged with $H_2$ for 3 times and stirred at 50° C. for 12 h under 50 PSI. TLC (Petroleum ether/EtOAc=10/1, Rf=0.40, Twist molybdate) indicated reactant 1 was consumed completely. The mixture was filter and concentrated at 45° C. in vacuo to remove solvent. The mixture was purified by prep-HPLC (HCl condition) to give a residue to give HCl salt of 218 (2.9 mg, 0.0143 mmol) as yellow oil. The structure was supported by HNMR.

LCMS [M+H]: 202.2

$^1$H NMR (400 MHz, DMSO-d6) δ: 8.00 (s, 3H), 7.44-7.33 (m, 4H), 7.29-7.21 (m, 1H), 3.49-3.44 (m, 1H), 2.61-2.56 (m, 2H), 1.98 (d, J=10.4 Hz, 1H), 1.78-1.68 (m, 1H), 1.67-1.54 (m, 1H), 1.41-1.31 (m, 3H), 1.22 (s, 3H) ppm.

Synthesis of rac-3'-((dimethylamino)methyl)spiro[bicyclo[2.2.1]heptane-2,1'-cyclohexan]-3-amine hydrochloride 223

Note: The absolute configuration of the product is unknown. The stereocenter at C1 is arbitrarily assigned as (R). The relative stereochemistry of the substitutent on the cyclohexane ring is undefined.

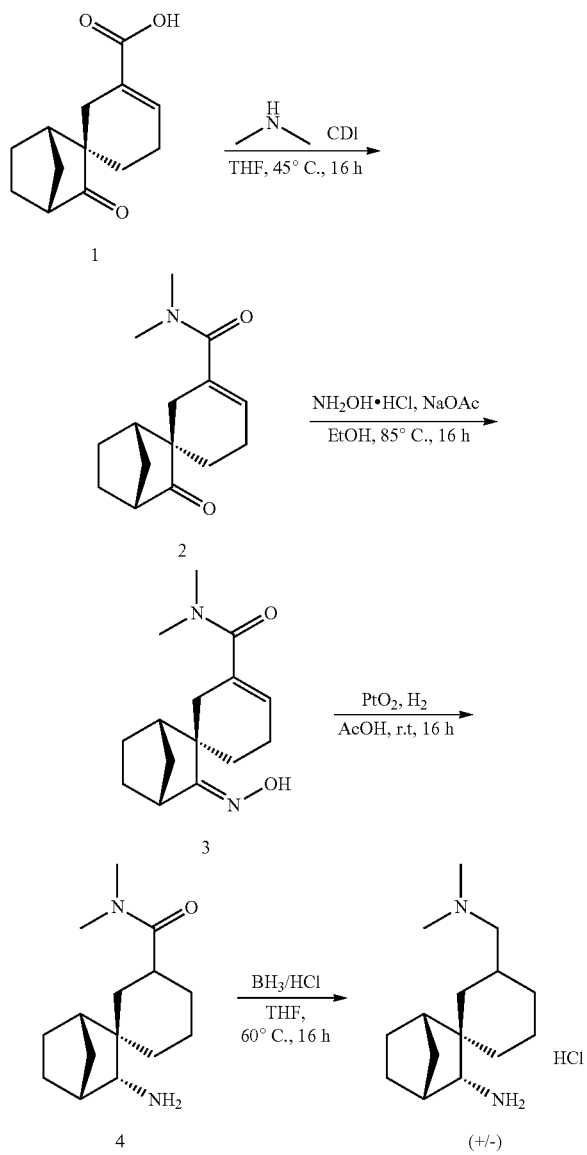

Step 1:

To a solution of rac-3-oxospiro[bicyclo[2.2.1]heptane-2,1'-cyclohexan]-3'-ene-3'-carboxylic acid (400 mg, 1.8 mmol, 1.0 eq) in THF (8 mL) was added dimethylamine (325 mg, 2.0 mmol, 1.1 eq) and CDI (2 mL, 3.6 mmol, 2.0 eq).The reaction mixture was stirred at 45° C. for 16 hours. Once LCMS showed the reaction finished, the reaction was purified by prep-HPLC eluting with 0-90% ACN in water (0.1% TFA) to give rac-N,N-dimethyl-3-oxospiro[bicyclo[2.2.1]heptane-2,1'-cyclohexan]-3'-ene-3'-carboxamide (300 mg, 67%) as a colorless oil.

$^1$H NMR (400 MHz, CDCl$_3$) δ 5.98-5.84 (m, 1H), 3.04 (d, J=51.4 Hz, 6H), 2.60-2.45 (m, 2H), 2.34-1.91 (m, 7H), 1.81-1.42 (m, 6H).

Step 2:

To a solution of rac-N,N-dimethyl-3-oxospiro[bicyclo[2.2.1]heptane-2,1'-cyclohexan]-3'-ene-3'-carboxamide (320 mg, 1.3 mmol, 1.0 eq) in EtOH (10 mL) was added hydroxylamine hydrochloride (182 mg, 2.6 mmol, 2.0 eq) and Sodium acetate trihydrate (426.4 mg, 5.2 mmol, 4.0 eq), the reaction mixture was stirred at 80° C. for 16 hours. Once LCMS showed the reaction finished, the reaction was purified by prep-HPLC eluting with 0-90% ACN in water (0.1% TFA) to give rac-3-(hydroxyimino)-N,N-dimethylspiro[bicyclo[2.2.1]heptane-2,1'-cyclohexan]-3'-ene-3'-carboxamide (320 mg, 93%) as a colorless oil $^1$H NMR (400 MHz, MeOD) δ 5.86 (d, J=2.7 Hz, 1H), 3.47 (d, J=3.6 Hz, 1H), 3.02 (d, J=54.7 Hz, 7H), 2.37-2.04 (m, 6H), 1.85-1.63 (m, 6H), 1.61-1.46 (m, 1H), 1.39 (q, J=11.8 Hz, 3H).

Step 3:

To a solution of rac-3-(hydroxyimino)-N,N-dimethylspiro[bicyclo[2.2.1]heptane-2,1'-cyclohexan]-3'-ene-3'-carboxamide (260 mg, 1.0 mmol, 1.0 eq) in AcOH (10.0 mL) was added PtO$_2$ (26 mg, 10% wt), and the reaction mixture was stirred at room temperature under H$_2$ atmosphere (1 atm) for 16 hours. Once LCMS showed the reaction finished, reaction mixture was filtered and the filtration was concentrated to get rac-3-amino-N,N-dimethylspiro[bicyclo[2.2.1]heptane-2,1'-cyclohexane]-3'-carboxamide (260 mg, crude) as a yellow oil Step 4:

rac-3-amino-N,N-dimethylspiro[bicyclo[2.2.1]heptane-2,1'-cyclohexane]-3'-carboxamide (260 mg, 1.0 mmol, 1.0 eq) was added to a solution of THF/BH$_3$ (10 ml).The reaction mixture was stirred at 80° C. for 16 hours. Once LCMS showed the reaction finished, the reaction was purified by prep-HPLC eluting with 0-90% ACN in water (0.1% HCl) to give rac-3'-((dimethylamino)methyl)spiro[bicyclo[2.2.1]heptane-2,1'-cyclohexan]-3-amine hydrochloride (223, 13.2 mg, 5%) as a white solid.

LCMS [M+H–HCl]: 237.2

$^1$H NMR (400 MHz, MeOD) δ 2.98 (d, J=6.9 Hz, 2H), 2.91 (d, J=4.2 Hz, 6H), 2.53 (s, 1H), 2.05 (s, 1H), 1.96-1.77 (m, 7H), 1.64-1.16 (m, 7H), 1.03-0.93 (m, 2H).

Synthesis of rac-3'-(methoxymethyl)spiro[bicyclo[2.2.1]heptane-2,1'-cyclohexan]-3-amine hydrogen chloride & rac-3'-(methoxymethyl)spiro[bicyclo[2.2.1]heptane-2,1'-cyclohexan]-3-amine hydrogen chloride 225-1 & 225-2

Note: absolute configuration is unassigned and the configuration of the C1 of P1 is arbitrarily shown as (R).

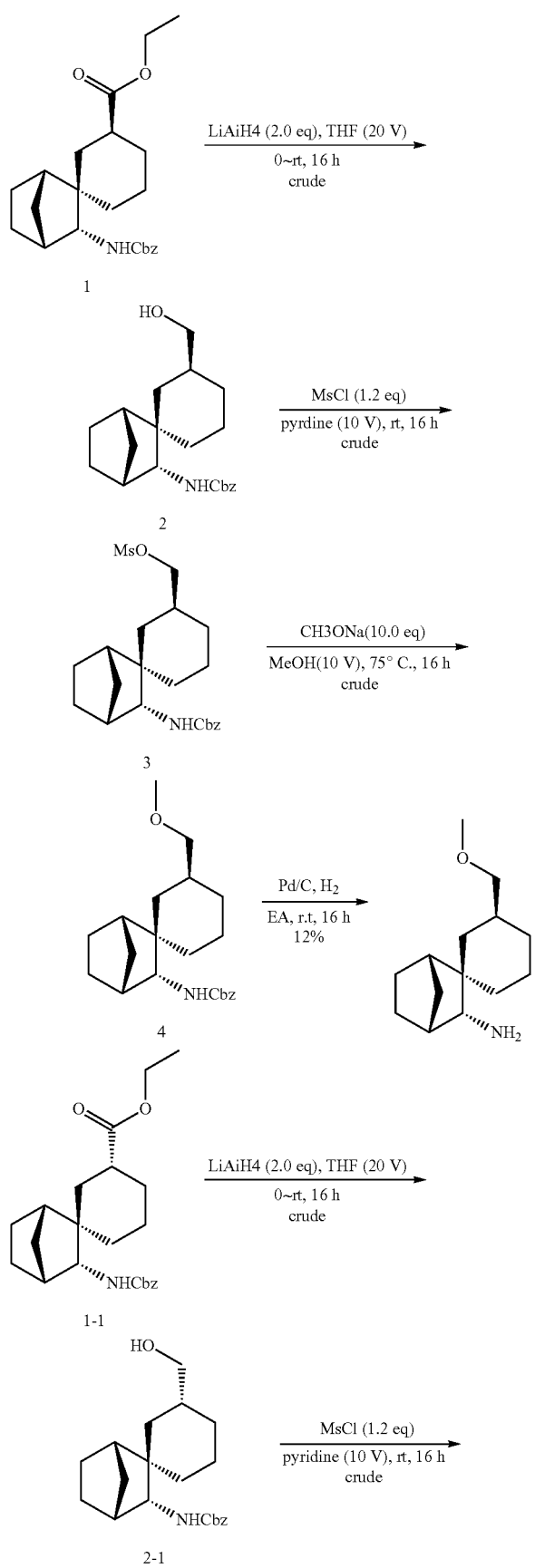

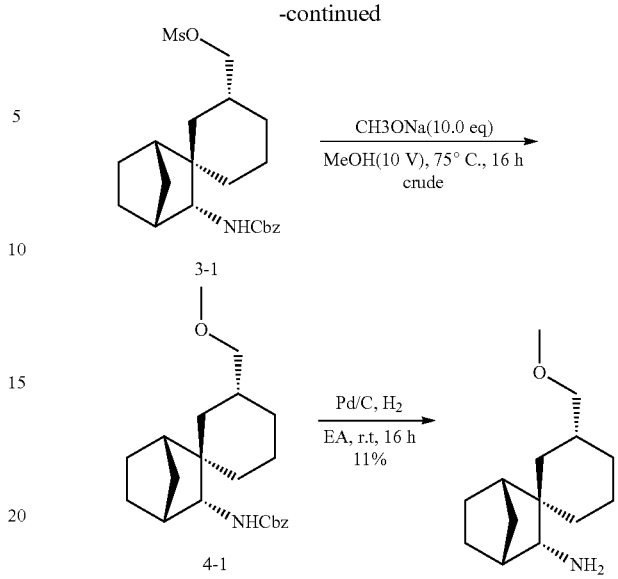

Step 1:

To a solution of rac-ethyl 3-(((benzyloxy)carbonyl)amino)spiro[bicyclo[2.2.1]heptane-2,1'-cyclohexane]-3'-carboxylate (350 mg, 0.91 mmol, 1.0 eq) in THF (10 mL) was added LiAlH$_4$ (70 mg, 1.83 mmol, 2.0 eq) at 0° C. The mixture was stirred at room temperature for 16 hours. TLC was done to detect the process of the reaction. Once the reaction finished, 79 uL of H$_2$O, 79 uL of NaOH (15%) and 240 uL of H$_2$O was added in sequence at 0° C. to quench the reaction and the corresponding mixture was then stirred at room temperature for another 30 mins. Solid was filtered, and the filtration was dried over Na$_2$SO$_4$ to get rid of residual water and filtered. The filtration was then concentrated under vacuum to give rac-benzyl (3'-(hydroxymethyl)spiro[bicyclo[2.2.1]heptane-2,1'-cyclohexan]-3-yl)carbamate (241 mg, crude) as a colorless oil.

$^1$H NMR (400 Hz, CD$_3$OD) δ 8.02 (s, 1H), 7.33-7.31 (m, 3H), 4.59 (s, 1H), 4.00 (d, J=4.0 Hz, 1H), 2.21 (s, 1H), 1.87-1.68 (m, 6H), 1.65-1.51 (m, 6H), 1.40-1.28 (m, 7H), 1.10-1.02 (m, 1H), 0.84-0.72 (m, 3H).

Step 2:

To a stirred solution of rac-benzyl (3'-(hydroxymethyl)spiro[bicyclo[2.2.1]heptane-2,1'-cyclohexan]-3-yl)carbamate (241 mg, 0.70 mmol, 1 eq) in pyridine (10 mL) was added MSCl (127 mg, 1.05 mmol, 1.5 eq) dropwise at room temperature under nitrogen atmosphere. The reaction mixture was stirred at room temperature for 18 hours. Once TLC showed the reaction finished, the mixture was quenched by cold water (50 mL) at 0° C. The mixture was poured into water (100 mL) and the aqueous was then extracted with EtOAc (3×100 mL). All the organic phases were washed with sat.NaHCO$_3$ (2×100 mL), CuSO$_4$ (aq, 8×60 mL) and sat.NaHCO$_3$ (2×100 mL), dried over Na$_2$SO$_4$, and filtered. The filtration was concentrated under vacuum to give rac-(3-(((benzyloxy)carbonyl)amino)spiro[bicyclo[2.2.1]heptane-2,1'-cyclohexan]-3'-yl)methyl methanesulfonate (362 mg, crude).

Step 3:

To a solution of rac-(3-(((benzyloxy)carbonyl)amino)spiro[bicyclo[2.2.1]heptane-2,1'-cyclohexan]-3'-yl)methyl methanesulfonate (362 mg, 0.86 mmol, 1 eq) in MeOH (10 mL) was added NaOAc (464 mg, 8.7 mmol, 10.0 eq) in one portion at room temperature. The reaction was heated at 75°

C. and stirred for 16 hours. Once TLC showed the reaction finished, the mixture was cooled to room temperature and water (20 mL) was added. The reaction mixture was then extracted with EtOAc (3×10 mL). All the organic phases were collected, washed with brine (20 mL), dried over $Na_2SO_4$, and filtered. The filtration was concentrated under vacuum to give rac-benzyl (3'-(methoxymethyl)spiro[bicyclo[2.2.1]heptane-2,1'-cyclohexan]-3-yl)carbamate (201 mg, crude) as a yellow oil.

Step 4:
To a solution of rac-benzyl (3'-(methoxymethyl)spiro[bicyclo[2.2.1]heptane-2,1'-cyclohexan]-3-yl)carbamate (201 mg, crude) in EA (10.0 mL) was added Pd/C (30 mg, 10% wt), and the reaction mixture was stirred at room temperature under $H_2$ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 225-1 (20.0 mg, 0.09 mmol, 12%) as a white solid.

LCMS [M+H−HCl]: 224.2
$^1$H NMR (400 Hz, $CD_3OD$) δ 3.34-3.32 (m, 3H), 3.31-3.15 (m, 6H), 3.01-3.01 (m, 2H), 2.87 (s, 2H), 2.68-2.64 (m, 2H), 2.50 (s, 1H), 1.98-1.76 (m, 13H), 1.53-1.23 (m, 13H), 0.99-0.90 (m, 4H).

Step 1:
To a solution of ethyl rac-3-(((benzyloxy)carbonyl)amino)spiro[bicyclo[2.2.1]heptane-2,1'-cyclohexane]-3'-carboxylate (200 mg, 0.519 mmol, 1.0 eq) in THF (10 mL) was added $LiAlH_4$ (39 mg, 1.04 mmol, 2.0 eq) at 0° C. The mixture was stirred at room temperature for 16 hours. TLC was done to detect the process of the reaction. Once the reaction finished, 39 uL of $H_2O$, 39 uL of NaOH (15%) and 120 uL of $H_2O$ was added in sequence at 0° C. to quench the reaction and the corresponding mixture was then stirred at room temperature for another 30 mins. Solid was filtered, and the filtration was dried over $Na_2SO_4$ to get rid of residual water and filtered. The filtration was then concentrated under vacuum to give rac-benzyl (3'-(hydroxymethyl)spiro[bicyclo[2.2.1]heptane-2,1'-cyclohexan]-3-yl)carbamate (compound 2-1) (141 mg, crude) as a colorless oil.

Step 2:
To a stirred solution of rac-benzyl (3'-(hydroxymethyl)spiro[bicyclo[2.2.1]heptane-2,1'-cyclohexan]-3-yl)carbamate (141 mg, 0.41 mmol, 1 eq) in pyridine (10 mL) was added MsCl (75 mg, 0.61 mmol, 1.5 eq) dropwise at room temperature under nitrogen atmosphere. The reaction mixture was stirred at room temperature for 18 hours. Once TLC showed the reaction finished, the mixture was quenched by cold water (10 mL) at 0° C. The mixture was poured into water (10 mL) and the aqueous was then extracted with EtOAc (3×10 mL). All the organic phases were washed with sat.$NaHCO_3$ (2×10 mL), $CuSO_4$ (aq, 8×15 mL) and sat.$NaHCO_3$ (2×10 mL), dried over $Na_2SO_4$, and filtered. The filtration was concentrated under vacuum to give rac-(3-(((benzyloxy)carbonyl)amino)spiro[bicyclo[2.2.1]heptane-2,1'-cyclohexan]-3'-yl)methyl methanesulfonate (196 mg, crude).

Step 3:
To a solution of rac-(3-(((benzyloxy)carbonyl)amino)spiro[bicyclo[2.2.1]heptane-2,1'-cyclohexan]-3'-yl)methyl methanesulfonate (196 mg, 0.55 mmol, 1 eq) in MeOH (10 mL) was added NaOAc (296 mg, 5.5 mmol, 10.0 eq) in one portion at room temperature. The reaction was heated at 75° C. and stirred for 16 hours. Once TLC showed the reaction finished, the mixture was cooled to room temperature and water (20 mL) was added. The reaction mixture was then extracted with EtOAc (3×10 mL). All the organic phases were collected, washed with brine (20 mL), dried over $Na_2SO_4$, and filtered. The filtration was concentrated under vacuum to give rac-benzyl (3'-(methoxymethyl)spiro[bicyclo[2.2.1]heptane-2,1'-cyclohexan]-3-yl)carbamate (134 mg, crude) as a yellow oil.

Step 4:
To a solution of benzyl (rac-3'-(methoxymethyl)spiro[bicyclo[2.2.1]heptane-2,1'-cyclohexan]-3-yl)carbamate (200 mg, crude) in EA (10.0 mL) was added Pd/C (20 mg, 10% wt), and the reaction mixture was stirred at room temperature under $H_2$ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 225-2 (20.0 mg, 0.09 mmol, 12%) as a white solid.

LCMS [M+H−HCl]: 224.2
$^1$H NMR (400 Hz, $CD_3OD$) δ 7.48-7.34 (m, 1H), 3.32-3.31 (m, 4H), 3.32-3.15 (m, 1H), 3.00 (s, 1H), 2.88-2.87 (d, J=5.6 Hz 1H), 2.43 (s, 1H), 1.99 (s, 1H), 1.88-1.77 (m, 3H), 1.62-1.58 (m, 6H).

Synthesis of ((1S,3R,4R)-3-aminospiro[bicyclo[2.2.1]heptane-2,1'-cyclohexan]-3'-yl)(morpholino)methanone hydrochloride 226

Note: absolute configuration is unassigned and the configuration of the C1 of P1 is arbitrarily shown as (R). The relative stereochemistry of the cyclohexane substituent is unknown.

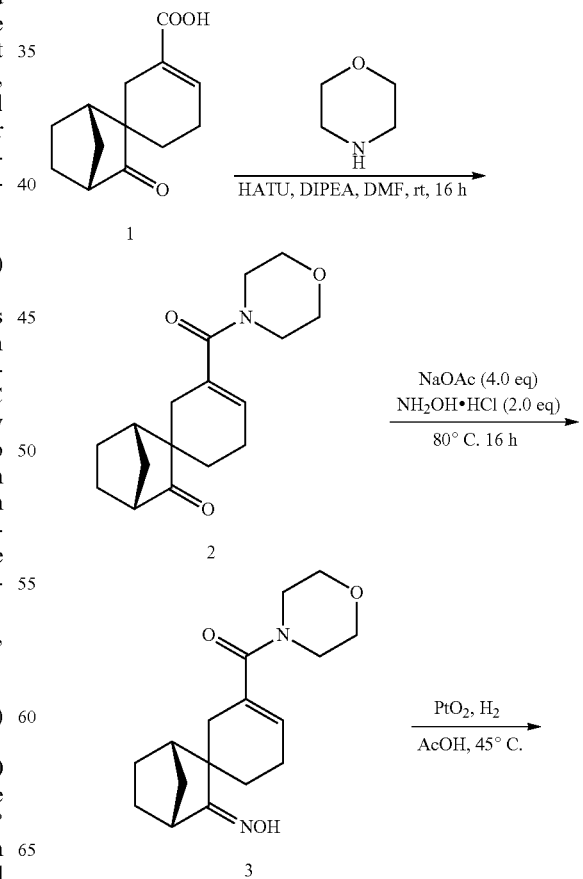

-continued

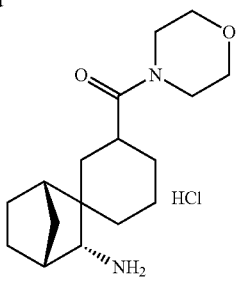

Step 1:
To a stirred solution of ethyl (1S,4R)-3-oxospiro[bicyclo[2.2.1]heptane-2,1'-cyclohexan]-3'-ene-3'-carboxylic acid (500 mg, 2.25 mmol, 1.0 eq),in DMF (10 mL) was added morpholine (196 mg 2.25 mmol 1.0 eq), HATU (1.28 g, 3.38 mmol, 1.5 eq) and DIPEA (582 mg 4.5 mmol 2.0 eq) at rt. The resulting mixture was stirred at rt for 16 hours. Extracted with EtOAc (3×20 mL), washed with water (1×50 mL), dried over $Na_2SO_4$, and filtered. The filtration was concentrated under vacuum to give crude product, which was purified by silica gel chromatography eluting with 2%-10% EA in PE to afford (1S,4R)-3'-(morpholine-4-carbonyl)spiro[bicyclo[2.2.1]heptane-2,1'-cyclohexan]-3'-en-3-one (Compound 1; 334 mg 1.09 mmol 49%) as a oil.

$^1$H NMR (400 MHz, MeOH) δ 5.86 (S, 1H), 3.65-3.54 (m, 8H), 2.62-2.60 (m, 1H), 2.44 (s, 1H), 2.23-2.19 (m, 3H), 2.04 (s, 1H), 1.96-1.93 (m, 2H), 1.70-1.56 (m, 3H), 1.54-1.49 (m, 3H).

Step 2:
To a stirred solution of (1S,4R)-3'-(morpholine-4-carbonyl)spiro[bicyclo[2.2.1]heptane-2,1'-cyclohexan]-3'-en-3-one (300 mg, 0.98 mmol, 1.0 eq) in EtOH (10 mL) was added $NH_2OH·HCl$ (102.02 mg, 1.47 mmol, 1.5 eq) and NaOAc (241.17 mg, 2.94 mmol, 3.0 eq) in one portion at room temperature under nitrogen atmosphere. The reaction mixture was stirred at 80° C. for 16 hours. Once LCMS showed finished, the mixture was poured into water (50 mL) and stirred for 10 minutes. The aqueous was then extracted with EtOAc (3×20 mL). All the organic phases were collected, washed with brine 60 mL, dried over $Na_2SO_4$. and filtered The filtration was concentrated under vacuum to give ((1S,4R,Z)-3-(hydroxyimino)spiro[bicyclo[2.2.1]heptane-2,1'-cyclohexan]-3'-en-3'-yl)(morpholino)methanone (260 mg, 0.81 mmol, 82%) as a yellow oil.

LCMS [M+H]:305.2

Step 3:
To a stirred solution of ((1S,4R,Z)-3-(hydroxyimino)spiro[bicyclo[2.2.1]heptane-2,1'-cyclohexan]-3'-en-3'-yl)(morpholino)methanone (260 mg, 0.81 mmol, 1.0 eq, crude), in HOAc (4 mL) was added $PtO_2$ (26 mg, 0.089 mmol, 0.1 eq) in one portion at room temperature under nitrogen atmosphere. The suspension was degassed under vacuum and purged with $H_2$ several times. The mixture was stirred under $H_2$ (balloon) at 45° C. for 16 hours. LCMS showed major of desired compound. The residue was concentrated under vacuum to give crude product, which was purified by prep-HPLC eluting with 0-95% ACN in water (0.1% TFA), substituted with conc. HCl to afford ((1S,3R,4R)-3-aminospiro[bicyclo[2.2.1]heptane-2,1'-cyclohexan]-3'-yl)(morpholino)methanone hydrochloride 226 (14 mg, 0.05 mmol, 5.6% yield) as a white solid.

LCMS: [M+H]:293.2

$^1$H NMR (400 MHz, MeOD) δ 3.70-3.54 (m, 8H), 3.23 (S, 1H), 2.89 (s, 1H), 2.53 (s, 1H), 1.96-1.91 (m, 2H), 1.78 (s, 5H), 1.53-1.28 (m, 8H).

Synthesis of ((1S,3R,4R)-3-aminospiro[bicyclo[2.2.1]heptane-2,1'-cyclohexan]-3'-yl)(piperidin-1-yl)methanone hydrochloride 227

Note: absolute configuration is unassigned and the configuration of the C1 of P1 is arbitrarily shown as (R). The relative stereochemistry of the cyclohexane substituent is unknown.

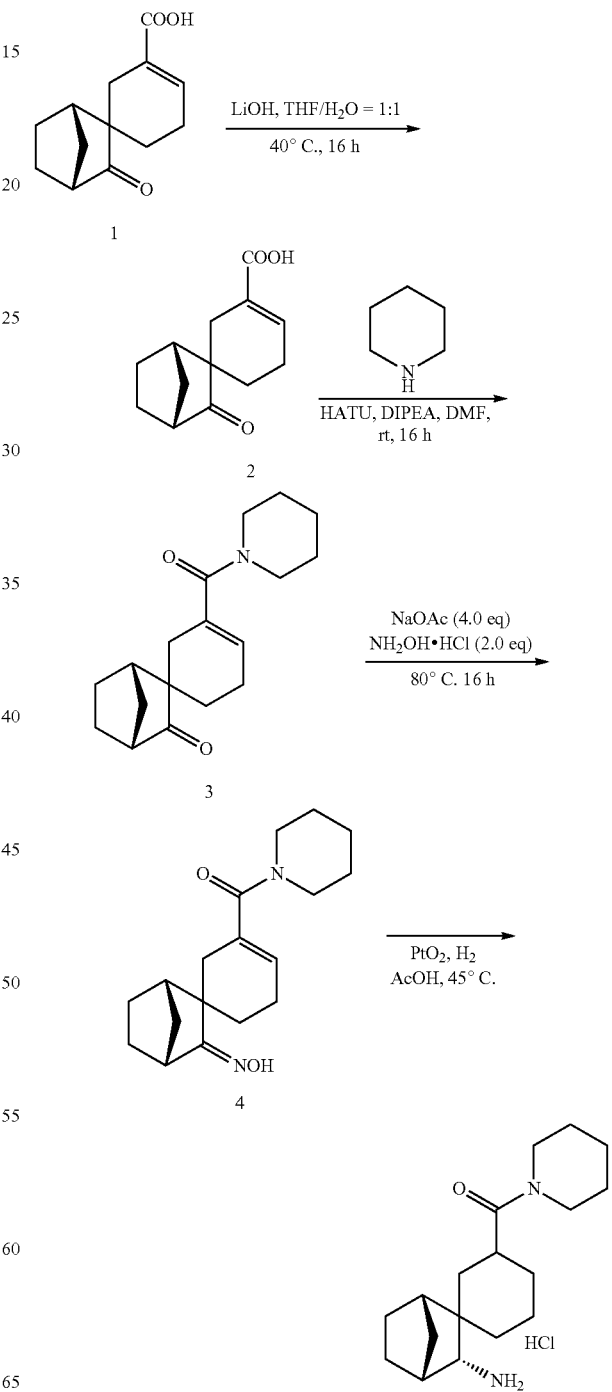

Step 1

To a stirred solution of ethyl (1S,4R)-3-oxospiro[bicyclo[2.2.1]heptane-2,1'-cyclohexan]-3'-ene-3'-carboxylate (2 g, 8.0 mmol, 1.0 eq) in THF and H$_2$O mixture solution (5 mL:5 mL) was added LiOH (670 mg, 16 mmol, 2.0 eq) at 40° C. under N$_2$. The resulting mixture was stirred at 40° C. for 16 hours. The mixture was adjusted pH=3 by HCl (10%), extracted with EtOAc (3×20 mL), washed with water (1×50 mL), dried over Na$_2$SO$_4$, and filtered. The filtration was concentrated under vacuum to afford (1S,4R)-3-oxospiro[bicyclo[2.2.1]heptane-2,1'-cyclohexan]-3'-ene-3'-carboxylic acid (Compound 2 1.5 g, 6.75 mmol 87%) as a brown solid.

$^1$H NMR (400 MHz, MeOH) δ 7.04-7.03 (m, 1H), 2.56-2.55 (m, 1H), 2.36-2.32 (d, J=16H, 3H), 2.11-2.10 (m, 1H), 1.98-1.94 (m, 2H), 1.72-1.67 (m, 2H), 1.61-1.59 (m, 3H), 1.51-1.44 (m, 1H), 1.28-1.23 (m, 1H).

Step 2

To a stirred solution of (1S,4R)-3-oxospiro[bicyclo[2.2.1]heptane-2,1'-cyclohexan]-3'-ene-3'-carboxylic acid (180 mg, 0.81 mmol, 1.0 eq) in DMF (7 mL) was added piperidine (69 mg 0.81 mmol 1.0 eq), HATU (463.8 mg, 1.22 mmol, 1.5 eq) and DIPEA (209 mg 1.62 mmol 2.0 eq) at rt. The resulting mixture was stirred at rt for 16 hours. Extracted with EtOAc (3×20 mL), washed with water (1×50 mL), dried over Na$_2$SO$_4$, and filtered. The filtration was concentrated under vacuum to give crude product, which was purified by silica gel chromatography eluting with 2%-10% EA in PE to afford (1S,4R)-3'-(piperidine-1-carbonyl)spiro[bicyclo[2.2.1]heptane-2,1'-cyclohexan]-3'-en-3-one (Compound 2, 200 mg 0.66 mmol, 67%) as a yellow oil.

$^1$H NMR (400 MHz, MeOH) δ 5.84 (s, 1H), 4.10-4.08 (m, 1H), 2.55-2.46 (m, 2H), 2.28-2.24 (m, 1H), 2.15-2.14 (m, 3H), 2.00-1.94 (m, 3H), 1.75-1.56 (m, 13H), 1.25-1.21 (m, 1H).

Step 3:

To a stirred solution of (1S,4R)-3'-(piperidine-1-carbonyl)spiro[bicyclo[2.2.1]heptane-2,1'-cyclohexan]-3'-en-3-one (160 mg, 0.55 mmol, 1.0 eq) in EtOH (5 mL) was added NH$_2$OH·HCl (55.2 mg, 0.79 mmol, 1.5 eq) and NaOAc (130.4 mg, 1.59 mmol, 3.0 eq) in one portion at room temperature under nitrogen atmosphere. The reaction mixture was stirred at 85° C. for 16 hours. Once LCMS showed finished, the mixture was poured into water (50 mL) and stirred for 10 minutes. The aqueous was then extracted with EtOAc (3×20 mL). All the organic phases were collected, washed with brine 60 mL, dried over Na$_2$SO$_4$. and filtered The filtration was concentrated under vacuum to give ((1S,4R,Z)-3-(hydroxyimino)spiro[bicyclo[2.2.1]heptane-2,1'-cyclohexan]-3'-en-3'-yl)(piperidin-1-yl)methanone (160 mg, 0.53 mmol, 94%) as a yellow oil.

LCMS [M+H]:303.2

Step 4:

To a stirred solution of ((1S,4R,Z)-3-(hydroxyimino)spiro[bicyclo[2.2.1]heptane-2,1'-cyclohexan]-3'-en-3'-yl)(piperidin-1-yl)methanone (150 mg, 0.5 mmol, 1.0 eq, crude), in HOAc (3 mL) was added PtO$_2$ (15 mg, 0.066 mmol, 0.1 eq) in one portion at room temperature under nitrogen atmosphere. The suspension was degassed under vacuum and purged with H$_2$ several times. The mixture was stirred under H$_2$ (balloon) at 45° C. for 16 hours. LCMS showed major of desired compound. The residue was concentrated under vacuum to give crude product, which was purified by prep-HPLC eluting with 0-95% ACN in water (0.1% TFA), substituted with conc. HCl to afford ((1S,3R,4R)-3-aminospiro[bicyclo[2.2.1]heptane-2,1'-cyclohexan]-3'-yl)(piperidin-1-yl)methanone hydrochloride 227 (14 mg, 0.05 mmol, 9.6% yield) as a white solid.

LCMS [M+H]:291.2

$^1$H NMR (400 MHz, MeOD) δ 3.60-3.56 (m, 3H), 3.49-3.48 (m, 1H), 3.19 (s, 1H), 2.83 (s, 1H), 2.53 (s, 1H), 1.93-1.85 (m, 2H), 1.82-1.69 (m, 9H), 1.53 (s, 3H), 1.46-1.40 (m, 3H), 1.35-1.28 (m, 4H)

Synthesis of rac-spiro[bicyclo[2.2.1]heptane-2,3'-bicyclo[3.1.0]hexan]-3-amine 236

Note: absolute configuration is unassigned and the configuration of the C1 of P1 is arbitrarily shown as (R). The relative stereochemistry of the cyclopentane substituent is unknown.

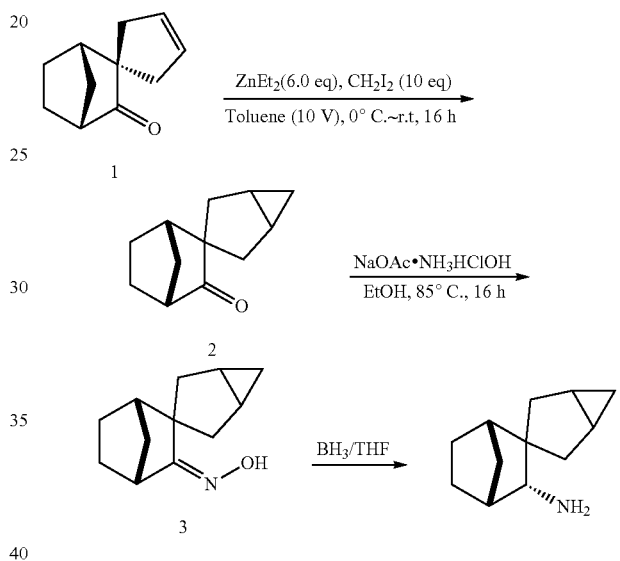

Step 1:

To a solution of rac-spiro[bicyclo[2.2.1]heptane-2,1'-cyclopentan]-3'-en-3-one (1.0 g, 6.2 mmol, 1.0 eq) and Diiodomethane (16.6 g, 6.2 mmol, 10.0 eq) in Toluene (30 mL) was added Diethylzinc (37.2 mL, 37.2 mmol, 6.0 eq) at 0° C. The reaction mixture was stirred at r.t for 16 hours. Once LCMS showed the reaction finished, the reaction was purified by prep-HPLC eluting with 0-90% ACN in water (0.1% TFA) to give rac-spiro[bicyclo[2.2.1]heptane-2,3'-bicyclo[3.1.0]hexan]-3-one (500 mg, 45%) as a colorless oil.

$^1$H NMR (400 MHz, CDCl$_3$) δ 2.53 (d, J=4.2 Hz, 1H), 2.25 (d, J=1.8 Hz, 1H), 1.93 (dd, J=13.3, 5.2 Hz, 1H), 1.86-1.69 (m, 5H), 1.64-1.42 (m, 4H), 1.34-1.18 (m, 2H), 0.94 (q, J=4.1 Hz, 1H), 0.40 (td, J=8.2, 4.6 Hz, 1H).

Step 2:

To a solution of rac-spiro[bicyclo[2.2.1]heptane-2,3'-bicyclo[3.1.0]hexan]-3-one (300 mg, 1.7 mmol, 1.0 eq) in EtOH (10 mL) was added hydroxylamine hydrochloride (238 mg, 3.4 mmol, 2.0 eq) and Sodium acetate trihydrate (558 mg, 6.8 mmol, 4.0 eq), the reaction mixture was stirred at 80° C. for 16 hours. Once LCMS showed the reaction finished, the reaction was purified by prep-HPLC eluting with 0-90% ACN in water (0.1% TFA) to give rac-spiro[bicyclo[2.2.1]heptane-2,3'-bicyclo[3.1.0]hexan]-3-one oxime (210 mg, 64%) as a colorless oil Step 3:

To a solution of (1S,4R,Z)-spiro[bicyclo[2.2.1]heptane-2,3'-bicyclo[3.1.0]hexan]-3-one oxime (210 mg, 1.08 mmol, 1.0 eq) in THF/BH$_3$ (10 mL). The reaction mixture was stirred at 80° C. for 16 hours. Once LCMS showed the reaction finished, the reaction was purified by prep-HPLC eluting with 0-90% ACN in water (0.1% HCl) to give rac-spiro[bicyclo[2.2.1]heptane-2,3'-bicyclo[3.1.0]hexan]-3-amine 236 (10 mg, 5%) as a white solid.

LCMS [M+H−HCl]: 178.1

1H NMR (400 MHz, MeOD) δ 3.12 (d, J=4.3 Hz, 1H), 2.46 (s, 1H), 2.11-1.96 (m, 3H), 1.67 (d, J=10.5 Hz, 1H), 1.57-1.30 (m, 9H), 0.72 (dd, J=13.3, 8.0 Hz, 1H).

Synthesis of rac-1',5'-dimethylspiro[bicyclo[2.2.1]heptane-2,3'-bicyclo[3.1.0]hexan]-3-amine hydrochloride 237

Note: absolute configuration is unassigned and the configuration of the C1 of P1 is arbitrarily shown as (R). The relative stereochemistry of the cyclopentane substituents is unknown.

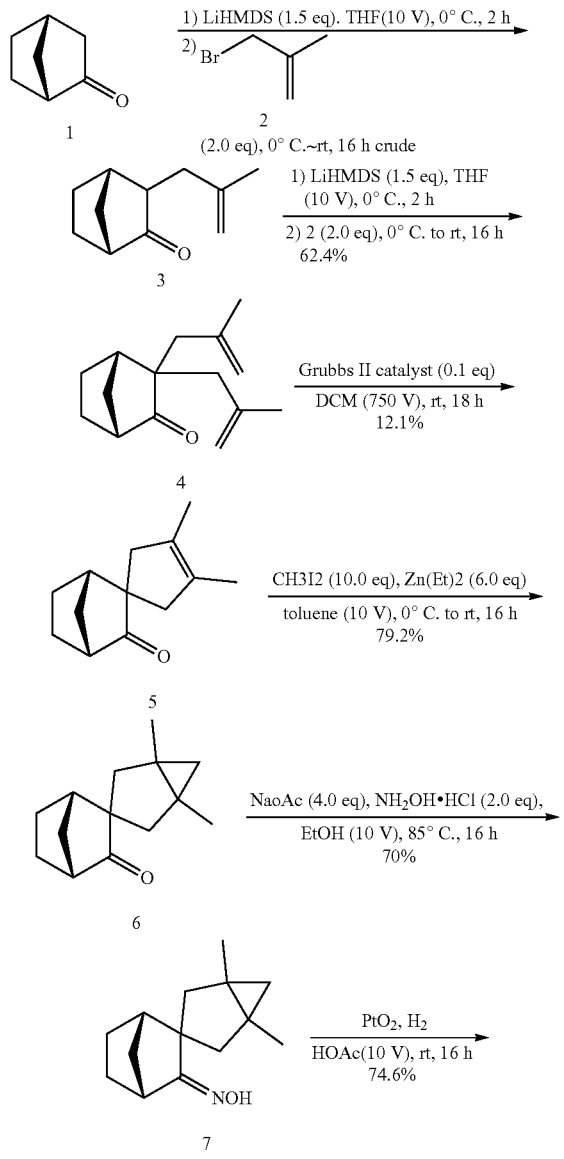

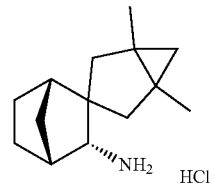

Step 1:

To a stirred solution of rac-bicyclo[2.2.1]heptan-2-one (2.0 g, 18.2 mmol, 1.0 eq) in anhydrous THF (20 mL) at 0° C. was added LiHMDS (1.0 M in THF; 27.2 mL, 27.2 mmol, 1.5 eq) under N$_2$ protection. The corresponding reaction mixture was then stirred at 0-5° C. for 2 hours under N$_2$ followed by the addition of 3-bromo-2-methylprop-1-ene (4.9 g, 36.3 mmol, 2.0 eq). The whole mixture was gradually warmed to room temperature and stirred overnight under N$_2$ protection. Once TLC showed the reaction finished, the reaction mixture was poured into ice-water (300 mL; contain 10.0 mL conc.HCl) and stirred for 10 minutes followed by the extraction with EtOAc (3×100 mL). The organic phase was then washed with brine (100 mL), dried over Na$_2$SO$_4$, and filtered. The filtration was then concentrated under vacuum and purified by column chromatography eluting with 0-1% EA in PE to give rac-3-(2-methylallyl)bicyclo[2.2.1]heptan-2-one (3.5 g, crude) as a dark red oil.

Step 2:

To a solution of rac-3-(2-methylallyl)bicyclo[2.2.1]heptan-2-one (3.5 g, 21.3 mmol, 1.0 eq) in anhydrous THF (50 mL) at 0° C. was added dropwise sodium bis(trimethylsilyl)amide (1 M in THF, 32 mL, 32 mmol, 1.5 eq) under nitrogen atmosphere. The reaction mixture was allowed to warm to 0° C. and stirred for 2 hours at 0° C. to 5° C. before the dropwise addition of 3-bromo-2-methylprop-1-ene (5.7 g, 42.7 mmol, 2.0 eq). The corresponding reaction mixture was warmed to room temperature and stirred at room temperature overnight. Once TLC showed the reaction finished, the reaction mixture was poured to ice-water (100 mL; contain 10.0 mL conc.HCl) and stirred for 10 minutes followed by the extraction with EtOAc (3×50 mL). The organic phase was then washed with brine (50 mL), dried over Na$_2$SO$_4$, and filtered. The filtration was then concentrated under vacuum and purified by column chromatography eluting with 0-1% EA in PE to give rac-3,3-bis(2-methylallyl)bicyclo[2.2.1]heptan-2-one (2.9 g, 13.3 mmol, 62%) as a brown oil.

$^1$H NMR (400 Hz, CDCl$_3$) δ 4.79-4.79 (m, 1H), 4.72 (s, 1H), 4.87-4.86 (m, 1H), 4.82 (s, 1H), 2.52-2.52 (m, 1H), 2.38-2.36 (m, 1H), 2.30-3.22 (m, 2H), 2.13-2.10 (m, 1H), 2.02-1.92 (m, 2H), 1.80-1.73 (m, 2H), 1.65 (s, 3H), 1.58 (s, 3H), 1.44-1.41 (m, 1H), 1.31-1.27 (m, 1H).

Step 3:

To a solution of rac-3,3-bis(2-methylallyl)bicyclo[2.2.1]heptan-2-one (2.0 g, 9.2 mmol, 1.0 eq) in anhydrous CH$_2$Cl$_2$ (1500 mL) was added Grubbs 2 catalyst (1.17 mg, 1.38 mmol, 0.15 eq) under N$_2$, and the reaction mixture was stirred at room temperature overnight. Once TLC showed the reaction finished, evaporated to get a residue, which was purified by silica gel chromatography eluting with 1% EA in PE to afford rac-3',4'-dimethylspiro[bicyclo[2.2.1]heptane-2,1'-cyclopentan]-3'-en-3-one (211 mg, 5.25 mmol, 12%) as a dark red solid.

Step 4:

To a solution of rac-3',4'-dimethylspiro[bicyclo[2.2.1]heptane-2,1'-cyclopentan]-3'-en-3-one (200 mg, 1.05 mmol, 1.0 eq) in toluene (5 mL) was added CH$_2$I$_2$ (2.8 g, 10.5 mmol, 10.0 eq) and Zn(Et)$_2$ (778 mg, 6.3 mmol, 6.0 eq), and the reaction mixture was stirred at rt overnight. Once TLC showed the reaction finished, the reaction mixture was poured to ice-water (100 mL) and stirred for 10 minutes followed by the extraction with EtOAc (3×50 mL). The organic phase was then washed with brine (50 mL), dried over Na$_2$SO$_4$, and filtered. The filtration was then concentrated under vacuum and purified by column chromatography eluting with 0-1% EA in PE to give crude rac-1',5'-dimethylspiro[bicyclo[2.2.1]heptane-2,3'-bicyclo[3.1.0]hexan]-3-one (129 mg, crude) that was used directly.

Step 5:

To a solution of rac-1',5'-dimethylspiro[bicyclo[2.2.1]heptane-2,3'-bicyclo[3.1.0]hexan]-3-one (129 mg, 0.62 mmol, 1.0 eq) in EtOH (10 mL) was added hydroxylamine hydrochloride (86 mg, 1.25 mmol, 2.0 eq) and NaOAc (204 mg, 2.49 mmol, 4.0 eq), and the reaction mixture was stirred at 85° C. overnight. Once LCMS showed the reaction finished, solvent was removed under vacuum to get a residue, which was diluted and extracted with EtOAc (3×20 mL). The organic phases were collected, washed with brine (2×20 mL), dried over Na$_2$SO$_4$, and filtered. The filtration was then concentrated under vacuum and purified by column chromatography eluting with 0-10% EA in PE to give rac-1',5'-dimethylspiro[bicyclo[2.2.1]heptane-2,3'-bicyclo[3.1.0]hexan]-3-one oxime (96 mg, 70.0%) as a white solid.

LCMS [M+H]:220.2

Step 6:

To a solution of rac-1',5'-dimethylspiro[bicyclo[2.2.1]heptane-2,3'-bicyclo[3.1.0]hexan]-3-one oxime (96 mg, 0.44 mmol, 1.0 eq) in AcOH (5 mL) was added PtO$_2$ (9.6 mg, 10% wt) and stirred at room temperature under H$_2$ for 16 hours. Once LCMS showed the reaction finished, The mixture was filtered through a pad of celite to remove PtO$_2$ and then the filtrate was concentrated in vacuo to obtain a crude product, which was then purified by prep-HPLC eluting with 0-90% ACN in water (0.1% TFA), and substituted by HCl to give 237 (97 mg, 0.47 mmol, 74%) as a white solid.

LCMS [M+H−HCl]: 206.2

$^1$H NMR (400 Hz, CD$_3$OD) δ 3.15-3.14 (d, J=4.4 Hz, 1H), 2.48 (s, 1H), 2.03-2.02 (m, 1H), 1.84-1.82 (m, 3H), 1.77-1.73 (m, 1H), 1.66-1.64 (m, 2H), 1.39-1.37 (m, 2H), 1.36-1.36 (m, 1H), 1.13-1.10 (m, 6H), 0.30-0.29 (m, 1H), 0.23-0.21 (m, 1H).

Synthesis of rac-3',4'-dimethylspiro[bicyclo[2.2.1]heptane-2,1'-cyclohexan]-3-amine 240

Note: absolute configuration is unassigned and the configuration of the C1 of P1 is arbitrarily shown as (R). The relative stereochemistry of the cyclohexane substituents is unknown. They are syn relative to each other.

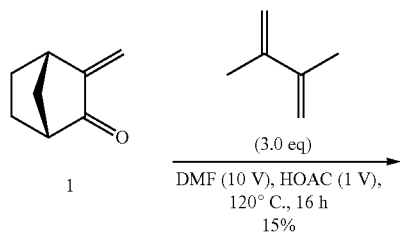

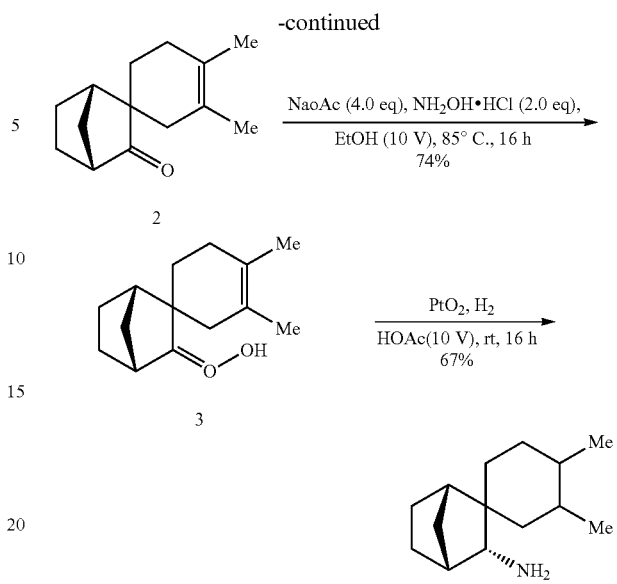

Step 1:

To a solution of rac-3-methylenebicyclo[2.2.1]heptan-2-one (1.0 g, 8.6 mmol. 1 eq) in AcOH (1.0 mL) and DMF (10 mL) was added 2,3-dimethylbuta-1,3-diene (2.0 mg, 24.6 mmol, 3 eq). The mixture was then stirred at 120° C. for 16 h in a sealed tube. Once TLC showed no starting material left, the mixture was cooled to room temperature and H$_2$O (15 mL) was added. The reaction mixture was then extracted with EtOAc (3×20 mL). All the organic phases were collected, washed with brine (3×20 mL), dried over Na$_2$SO$_4$ and concentrated. The residue was purified with column chromatography eluting with 0-10% EA in PE to give rac-3',4'-dimethylspiro[bicyclo[2.2.1]heptane-2,1'-cyclohexan]-3'-en-3-one (250 mg, 1.6 mmol, 15% yield) as a yellow oil.

Step 2:

To a stirred solution of rac-3',4'-dimethylspiro[bicyclo[2.2.1]heptane-2,1'-cyclohexan]-3'-en-3-one (350 mg, 1.6 mmol, 1 eq) in EtOH (10 mL) was added NH$_2$OH·HCl (225 mg, 3.24 mmol, 2.0 eq) and NaOAc (531 mg, 6.48 mmol, 4.0 eq) in one portion at room temperature. The reaction mixture was stirred at 85° C. for 16 hours. Once LCMS showed finished, the mixture was concentrated to dryness. The residue was dissolved in EtOAc (50 mL). The organic layer was washed with water (50 mL) brine (60 mL), dried over Na$_2$SO$_4$, concentrated under vacuum to give rac-3',4'-dimethylspiro[bicyclo[2.2.1]heptane-2,1'-cyclohexan]-3'-en-3-one oxime (198 mg, 74%) which was used next step directly.

LCMS [M+H]: 220.2

Step 3:

To a solution of rac-3',4'-dimethylspiro[bicyclo[2.2.1]heptane-2,1'-cyclohexan]-3'-en-3-one oxime (198 mg, 0.2 mmol, 1.0 eq) in AcOH (5 mL) was added PtO$_2$ (19.8 mg, 10% wt) and stirred at rt under H$_2$ for 16 hours. Once LCMS showed the reaction finished, The mixture was filtered through a pad of celite to remove PtO$_2$ and then the filtrate was concentrated in vacuo to obtain a crude product, which was then purified by prep-HPLC eluting with 0-90% ACN in water (0.1% TFA), and substituted by HCl to give 240 (126 mg, 0.61 mmol, 67%) as a white solid.

LCMS [M+H]−HCl: 208.2

¹H NMR (400 Hz, CD₃OD) δ 2.99 (d, J=3.6 Hz, 1H), 2.37 (s, 1H), 1.88 (s, 1H), 1.76-1.58 (m, 5H), 1.52-1.20 (m, 15H), 0.81 (d, J=6.8 Hz, 3H), 0.75 (d, J=7.2 Hz, 3H).

Synthesis of rac-2,3,3-trimethylbicyclo[2.2.1]heptan-2-amine hydrochloride 242

Note: absolute configuration is unassigned and the configuration of the C1 of P1 is arbitrarily shown as (R).

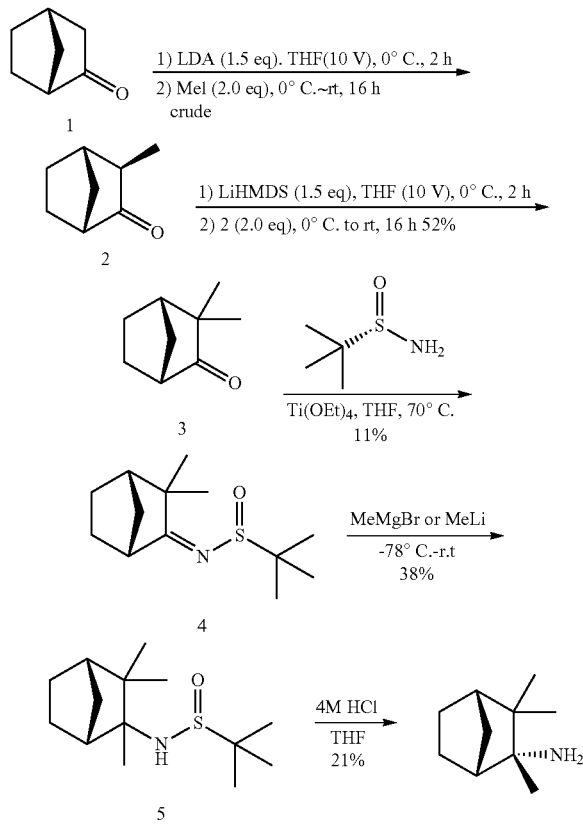

Step 1:

To a stirred solution of diisopropylamine (5.0 g, 45 mmol, 1.0 eq) in anhydrous THF (50 mL) at 0° C. was added LDA (2.0 M in THF; 34 mL, 68 mmol, 1.5 eq) under N₂ protection. The reaction mixture was then stirred at 0-5° C. for 2 hours under N₂ followed by the addition of CH₃I (13 g, 90.9 mmol, 2.0 eq). The whole mixture was gradually warmed to room temperature and stirred overnight under N₂ protection. Once GC showed the reaction finished, the reaction mixture was poured into ice-water (300 mL; contain 10.0 mL conc.HCl) and stirred for 10 minutes followed by the extraction with EtOAc (3×100 mL). The organic phase was then washed with aq. sat. NaHCO₃ solution (100 mL), brine (100 mL), dried over Na₂SO₄, and filtered. The filtration was then concentrated under vacuum to give rac-3-methylbicyclo[2.2.1]heptan-2-one crude as a dark red oil.

Step 2

To a solution of rac-3-methylbicyclo[2.2.1]heptan-2-one (5.0 g, 40 mmol, 1.0 eq) in anhydrous THF (50.0 mL) at 0° C. was added dropwise LiHMDS (1 M in THF; 60 mL, 60 mmol, 1.5 eq) under nitrogen atmosphere. The reaction mixture was allowed to warm to 0° C. and stirred for 2 hours at 0° C. to 5° C. before the dropwise addition of CH₃I (7.5 mL, 120 mmol, 3.0 eq). The corresponding reaction mixture was warmed to room temperature and stirred at room temperature overnight. Once GC showed the reaction finished, the reaction mixture was poured to ice-water (100 mL; contain 10.0 mL conc.HCl) and stirred for 10 minutes followed by the extraction with EtOAc (3×50 mL). The organic phase was then washed with aq. sat. NaHCO₃ solution (50 mL), brine (50 mL), dried over Na₂SO₄, and filtered. The filtration was then concentrated under vacuum to give rac-3,3-dimethylbicyclo[2.2.1]heptan-2-one (3.5 g, 52%) as a dark red oil.

¹H NMR (400 Hz, CD₃OD) δ 2.51-2.49 (m, 1H), 2.24 (d, J=1.6 Hz, 1H), 2.02-1.38 (m, 17H), 1.39 (s, 3H), 1.25-1.11 (m, 2H), 1.03 (s, 3H), 0.99 (s, 3H).

Step 3

To a solution of rac-3,3-dimethylbicyclo[2.2.1]heptan-2-one (1.5 g, 10.8 mmol, 1.0 eq) in anhydrous THF (15 mL) was added (S)-2-methylpropane-2-sulfinamide (1.9 g, 16.3 mmol, 1.5 eq) and Ti(OEt)₄ (4.6 g, 21.7 mmol, 2.0 eq). The reaction mixture was stirred for 16 hours at 70° C. Once LCMS showed the reaction finished, the reaction mixture was poured to aq.NaHCO₃ (100 mL) and stirred for 10 minutes followed by the extraction with EtOAc (3×50 mL). The organic phase was then washed with aq. sat. NaHCO₃ solution (50 mL), brine (50 mL), dried over Na₂SO₄, and filtered. The filtration was then concentrated under vacuum to give rac-3,3-dimethylbicyclo[2.2.1]heptan-2-ylidene)-2-methylpropane-2-sulfinamide (300 mg, 11%) as a yellow oil.

LCMS [M+H]: 242.1

Step 4

To a solution of rac-3,3-dimethylbicyclo[2.2.1]heptan-2-ylidene)-2-methylpropane-2-sulfinamide (300 mg, 1.17 mmol, 1.0 eq) in anhydrous THF (10 mL) was added MeLi (1.6 M, 5.84 mmol, 2.0 eq). The reaction mixture was stirred for 16 hours at room temperature. Once LCMS showed the reaction finished, the reaction mixture was poured to ice-water (20 mL) and stirred for 10 minutes followed by the extraction with EtOAc (3×10 mL). The organic phase was then washed with brine (20 mL), dried over Na₂SO₄, and filtered. The filtration was then concentrated under vacuum to give rac-2-methyl-N-2,3,3-trimethylbicyclo[2.2.1]heptan-2-yl)propane-2-sulfinamide (121 mg, 38%) as a yellow solid.

LCMS [M+H]: 258.2

¹H NMR (400 Hz, CDCl₃) δ 3.87 (s, 1H), 2.28 (s, 1H), 1.86 (d, J=10.4 Hz, 1H), 1.78 (s, 1H), 1.64-1.60 (m, 2H), 1.39 (s, 3H), 1.35-1.22 (m, 13H), 097-0.93 (m, 6H).

Step 5

To a solution of rac-2-methyl-N-(2,3,3-trimethylbicyclo[2.2.1]heptan-2-yl)propane-2-sulfinamide (100 mg, 0.39 mmol, 1.0 eq) in anhydrous THF (10 mL) was added HCl (1 mL). The reaction mixture was stirred for 16 hours at rt. Once LCMS showed the reaction finished, solvent was removed under vacuum to get a residue, which was purified by prep-HPLC eluting with 0-90% ACN in water (0.1% TFA) to give rac-2,3,3-trimethylbicyclo[2.2.1]heptan-2-amine hydrogen chloride 242 (15 mg, 21%) as a white solid.

LCMS [M+H]–HCl]: 154.1

¹H NMR (400 Hz, CD₃OD) δ 2.14 (s, 1H), 1.98-1.96 (m, 1H), 1.87 (d, J=1.6 Hz, 1H), 1.76-1.74 (m, 1H), 1.59-1.47 (m, 3H), 1.35-1.32 (m, 4H), 1.08, (s, 3H), 1.06 (s, 3H).

Synthesis of rac-3-phenylspiro[bicyclo[2.2.1]heptane-2,1'-cyclopentan]-3-amine hydrochloride 250

Note: absolute configuration is unassigned and the configuration of the C1 of P1 is arbitrarily shown as (S).

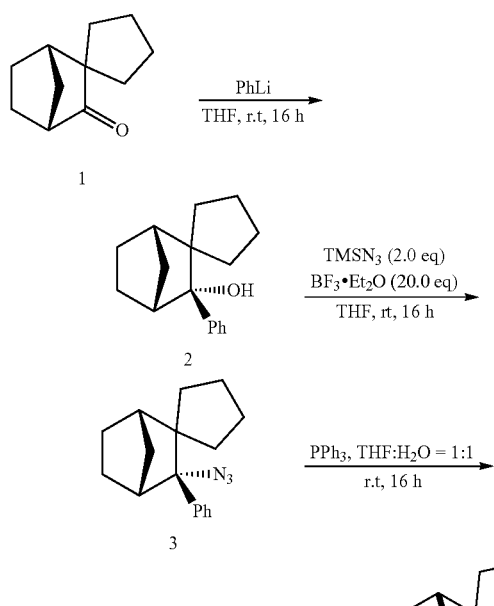

Step 1:
To a stirred solution of rac-spiro[bicyclo[2.2.1]heptane-2,1'-cyclopentan]-3-one (2.2 g, 13.40 mmol, 1.0 eq) in THF (15 mL) was added PhLi (40 mL, 40.21 mmol, 1.1 eq). The reaction mixture was stirred at room temperature for 16 hours. The reaction was quenched by sat.aq. NH₄Cl (50 mL), extracted with EtOAc (3×40 mL), dried over Na₂SO₄, and filtered. The filtration was concentrated under vacuum to give crude product, which was purified by silica gel chromatography eluting with 8%-10% EA in PE to afford rac-3-phenylspiro[bicyclo[2.2.1]heptane-2,1'-cyclopentan]-3-ol (3.4 g, 14.02 mmol) as a white oil.

¹H NMR (400 MHz, CDCl₃) δ 7.50-7.48 (m, 2H), 7.31-7.22 (m, 2H), 7.21-7.18 (m, 1H), 2.65 (d, J=2.0 Hz, 1H), 2.10-2.08 (m, 1H), 2.03-1.91 (m, 2H), 1.80-1.72 (m, 5H), 1.67-1.38 (m, 4H), 1.37-1.29 (m, 1H), 0.93-0.82 (m, 2H)

Step 2:
To a stirred solution of rac-3-phenylspiro[bicyclo[2.2.1]heptane-2,1'-cyclopentan]-3-ol (170 mg, 0.73 mmol, 1 eq) in Toluene (15 mL) was added TMSN₃ (3.4 g, 28.08 mmol, 2.0 eq) and BF₃.Et₂O (19.93 g, 140.4 mmol, 10.0 eq) under Ar atmosphere. The reaction mixture was stirred at rt for 16 hours. Once LCMS showed finished, the mixture was concentrated to dryness. The residue was concentrated and dissolved in EtOAc (150 mL), washed with water (100 mL) brine (100 mL), dried over Na₂SO₄. The filtration was concentrated under vacuum to give crude product (3.2 g, a white oil) which was used next step directly.

Step 3:
To a solution of rac-3-azido-3-phenylspiro[bicyclo[2.2.1]heptane-2,1'-cyclopentane] (3.2 g, 11.97 mmol, 1.0 eq) in THF/H₂O (7 mL/7 mL) was added PPh3 (6.23 g, 23.93 mmol, 2.0 eq) and stirred at 70° C. for 16 hours. Once LCMS showed the reaction finished, The mixture was adjusted with pH=3 by HCl (15%) and extracted with EtOAc (30 mL×4). The combined aqueous phase and adjusted the pH=11, extracted with EtOAc (100 mL×3). The organic layer was washed with brain (100 mL), dried over Na₂SO₄ and concentrated in vacuo. The residue was purified by prep-HPLC eluting with 0-90% ACN in water (0.1% TFA), and substituted by HCl to give 250 (116.18 mg, 0.48 mmol, 7%) as a white solid.

LCMS [M+H−HCl]:242.2

¹H NMR (400 MHz, CD₃OD) δ 7.61 (brs, 2H), 7.42-7.39 (m, 2H), 7.30-7.26 (m, 1H), 3.29-3.21 (m, 1H), 2.89-2.87 (m, 1H), 2.52-2.36 (m, 2H), 1.98-1.85 (m, 5H), 1.79-1.75 (m, 1H), 1.49-1.28 (m, 5H), 1.16-1.11 (m, 1H).

Synthesis of ((1S,3S,4R)-3-aminospiro[bicyclo[2.2.1]heptane-2,1'-cyclohexan]-3'-yl)(morpholino)methanone hydrochloride 226-1

Note: absolute configuration is unassigned and the configuration of the C1 of P1 is arbitrarily shown as (R). The relative stereochemistry of the cyclohexane substituent is unknown.

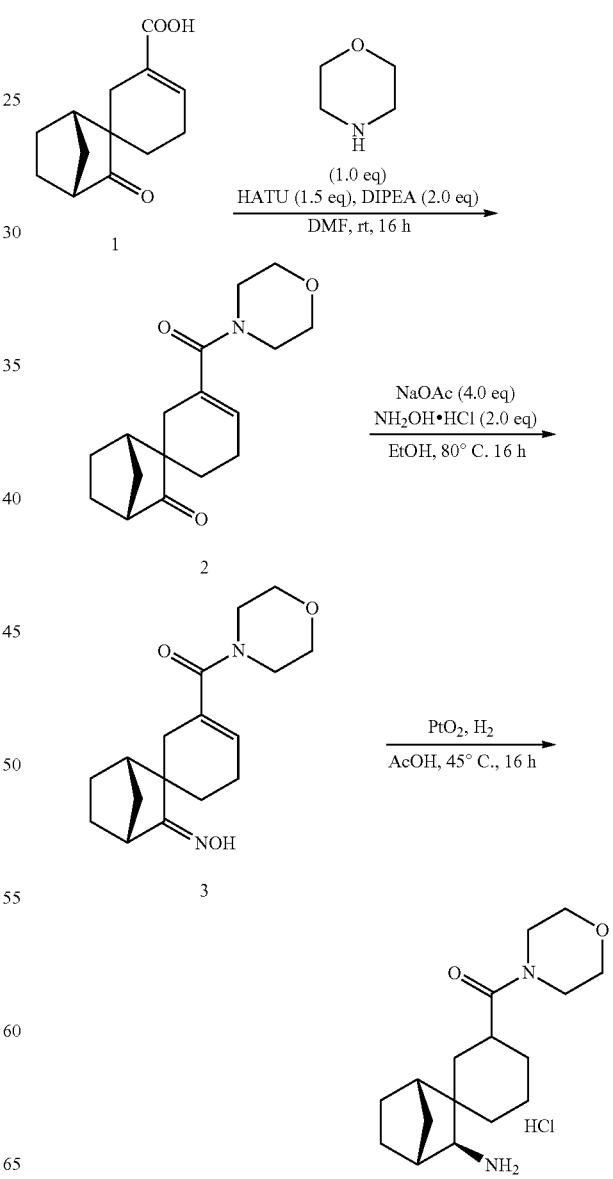

Step 1:

To a stirred solution of ethyl (1S,4R)-3-oxospiro[bicyclo[2.2.1]heptane-2,1'-cyclohexan]-3'-ene-3'-carboxylic acid (500 mg, 2.25 mmol, 1.0 eq) in DMF (10 mL) was added morpholine (196 mg 2.25 mmol 1.0 eq), HATU (1.28 g, 3.38 mmol, 1.5 eq) and DIPEA (582 mg 4.5 mmol 2.0 eq) at rt. The resulting mixture was stirred at rt for 16 hours. Extracted with EtOAc (3×20 mL), washed with water (1×50 mL), dried over $Na_2SO_4$, and filtered. The filtration was concentrated under vacuum to give crude product, which was purified by silica gel chromatography eluting with 2%-10% EA in PE to afford (1S,4R)-3'-(morpholine-4-carbonyl)spiro[bicyclo[2.2.1]heptane-2,1'-cyclohexan]-3'-en-3-one (Compound 1; 334 mg 1.09 mmol 49%) as a oil.

$^1$H NMR (400 MHz, MeOH) δ 5.86 (S, 1H), 3.65-3.54 (m, 8H), 2.62-2.60 (m, 1H), 2.44 (s, 1H), 2.23-2.19 (m, 3H), 2.04 (s, 1H), 1.96-1.93 (m, 2H), 1.70-1.56 (m, 3H), 1.54-1.49 (m, 3H).

Step 2:

To a stirred solution of (1S,4R)-3'-(morpholine-4-carbonyl)spiro[bicyclo[2.2.1]heptane-2,1'-cyclohexan]-3'-en-3-one (300 mg, 0.98 mmol, 1.0 eq) in EtOH (10 mL) was added $NH_2OH \cdot HCl$ (102.02 mg, 1.47 mmol, 1.5 eq) and NaOAc (241.17 mg, 2.94 mmol, 3.0 eq) in one portion at room temperature under nitrogen atmosphere. The reaction mixture was stirred at 80° C. for 16 hours. Once LCMS showed finished, the mixture was poured into water (50 mL) and stirred for 10 minutes. The aqueous was then extracted with EtOAc (3×20 mL). All the organic phases were collected, washed with brine 60 mL, dried over $Na_2SO_4$. and filtered The filtration was concentrated under vacuum to give ((1S,4R,Z)-3-(hydroxyimino)spiro[bicyclo[2.2.1]heptane-2,1'-cyclohexan]-3'-en-3'-yl)(morpholino)methanone (260 mg, 0.81 mmol, 82%) as a yellow oil.

LCMS [M+H]:305.2

Step 3:

To a stirred solution of ((1S,4R,Z)-3-(hydroxyimino)spiro[bicyclo[2.2.1]heptane-2,1'-cyclohexan]-3'-en-3'-yl)(morpholino)methanone (260 mg, 0.81 mmol, 1.0 eq, crude), in HOAc (4 mL) was added $PtO_2$ (26 mg, 0.089 mmol, 0.1 eq) in one portion at room temperature under nitrogen atmosphere. The suspension was degassed under vacuum and purged with $H_2$ several times. The mixture was stirred under $H_2$ (balloon) at 45° C. for 16 hours. LCMS showed major of desired compound. The residue was concentrated under vacuum to give crude product, which was purified by prep-HPLC eluting with 0-95% ACN in water (0.1% TFA), substituted with conc. HCl to afford ((1S,3S,4R)-3-aminospiro[bicyclo[2.2.1]heptane-2,1'-cyclohexan]-3'-yl)(morpholino)methanone hydrochloride 226-1 (4.5 mg, 0.014 mmol, 1.6% yield) as a white solid.

LCMS [M+H]:293.2

$^1$H NMR (400 MHz, MeOD) δ 3.66-3.50 (m, 8H), 3.00-2.95 (m, 1H), 2.92 (d, J=2.4 Hz, 1H), 2.52 (s, 1H), 2.45 (s, 1H), 1.77-1.71 (m, 4H), 1.64-1.61 (m, 2H), 1.55-1.38 (m, 8H), 1.09 (t, J=9.2 Hz, 1H).

Synthesis of ((1S,3S,4R)-3-aminospiro[bicyclo[2.2.1]heptane-2,1'-cyclohexan]-3'-yl)(piperidin-1-yl)methanone hydrochloride 227-1

Note: absolute configuration is unassigned and the configuration of the C1 of P1 is arbitrarily shown as (R). The relative stereochemistry of the cyclohexane substituents is unknown.

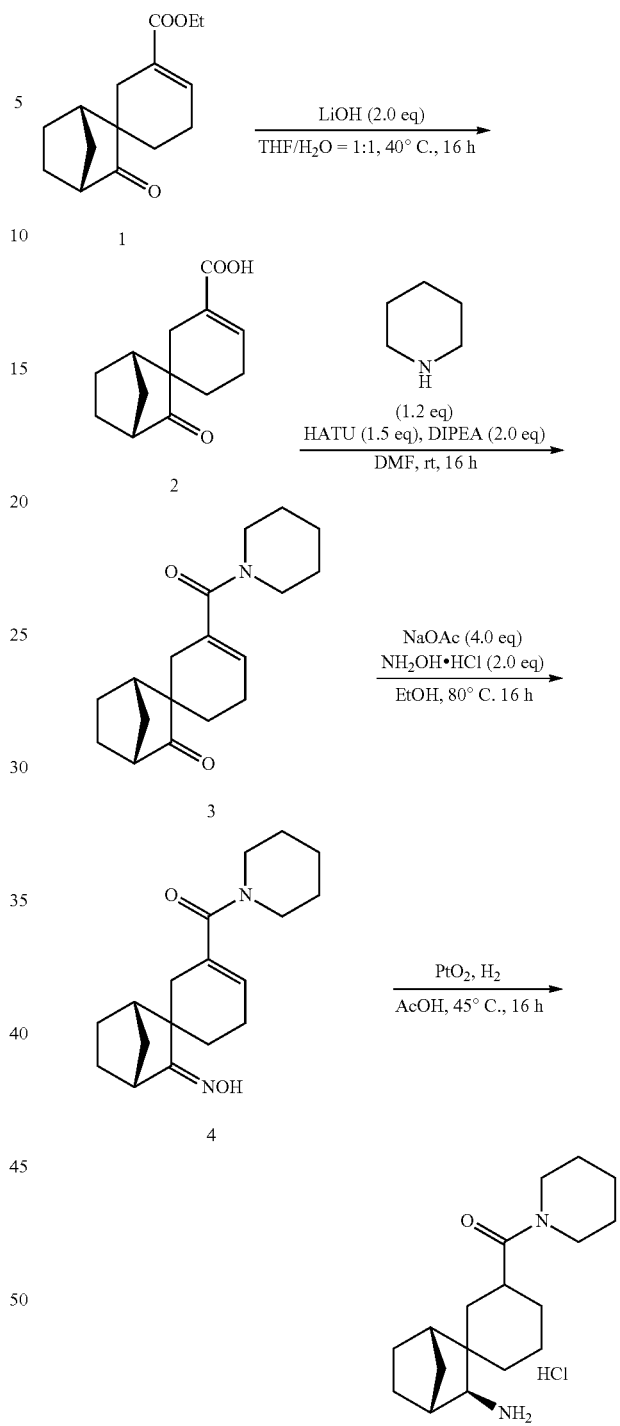

Step 1:

To a stirred solution of ethyl (1S,4R)-3-oxospiro[bicyclo[2.2.1]heptane-2,1'-cyclohexan]-3'-ene-3'-carboxylate (2 g, 8.0 mmol, 1.0 eq) in THF and $H_2O$ mixture solution (5 mL:5 mL) was added LiOH (670 mg, 16 mmol, 2.0 eq) at 40° C. under $N_2$. The resulting mixture was stirred at 40° C. for 16 hours. The mixture was adjusted pH=3 by HCl (10%), extracted with EtOAc (3×20 mL), washed with water (1×50 mL), dried over $Na_2SO_4$, and filtered. The filtration was concentrated under vacuum to afford (1S,4R)-3-oxospiro

[bicyclo[2.2.1]heptane-2,1'-cyclohexan]-3'-ene-3'-carboxylic acid (Compound 2 1.5 g, 6.75 mmol 87%) as a brown solid.

¹H NMR (400 MHz, MeOH) δ 7.04-7.03 (m, 1H), 2.56-2.55 (m, 1H), 2.36-2.32 (d, J=16H, 3H), 2.11-2.10 (m, 1H), 1.98-1.94 (m, 2H), 1.72-1.67 (m, 2H), 1.61-1.59 (m, 3H), 1.51-1.44 (m, 1H), 1.28-1.23 (m, 1H).

Step 2:

To a stirred solution of (1S,4R)-3-oxospiro[bicyclo[2.2.1]heptane-2,1'-cyclohexan]-3'-ene-3'-carboxylic acid (180 mg, 0.81 mmol, 1.0 eq) in DMF (7 mL) was added piperidine (69 mg 0.81 mmol 1.0 eq), HATU (463.8 mg, 1.22 mmol, 1.5 eq) and DIPEA (209 mg 1.62 mmol 2.0 eq) at rt. The resulting mixture was stirred at rt for 16 hours. Extracted with EtOAc (3×20 mL), washed with water (1×50 mL), dried over Na₂SO₄, and filtered. The filtration was concentrated under vacuum to give crude product, which was purified by silica gel chromatography eluting with 2%40% EA in PE to afford (1S,4R)-3'-(piperidine-1-carbonyl)spiro[bicyclo[2.2.1]heptane-2,1'-cyclohexan]-3'-en-3-one (Compound 2, 200 mg 0.66 mmol, 67%) as a yellow oil.

¹H NMR (400 MHz, MeOH) δ 5.84 (s, 1H), 4.10-4.08 (m, 1H), 2.55-2.46 (m, 2H), 2.28-2.24 (m, 1H), 2.15-2.14 (m, 3H), 2.00-1.94 (m, 3H), 1.75-1.56 (m, 13H), 1.25-1.21 (m, 1H).

Step 3:

To a stirred solution of (1S,4R)-3'-(piperidine-1-carbonyl)spiro[bicyclo[2.2.1]heptane-2,1'-cyclohexan]-3'-en-3-one (160 mg, 0.55 mmol, 1.0 eq) in EtOH (5 mL) was added NH₂OH·HCl (55.2 mg, 0.79 mmol, 1.5 eq) and NaOAc (130.4 mg, 1.59 mmol, 3.0 eq) in one portion at room temperature under nitrogen atmosphere. The reaction mixture was stirred at 85° C. for 16 hours. Once LCMS showed finished, the mixture was poured into water (50 mL) and stirred for 10 minutes. The aqueous was then extracted with EtOAc (3×20 mL). All the organic phases were collected, washed with brine 60 mL, dried over Na₂SO₄. and filtered The filtration was concentrated under vacuum to give ((1S,4R,Z)-3-(hydroxyimino)spiro[bicyclo[2.2.1]heptane-2,1'-cyclohexan]-3'-en-3'-yl)(piperidin-1-yl)methanone (160 mg, 0.53 mmol, 94%) as a yellow oil.

LCMS [M+H]:303.2

Step 4:

To a stirred solution of ((1S,4R,Z)-3-(hydroxyimino)spiro[bicyclo[2.2.1]heptane-2,1'-cyclohexan]-3'-en-3'-yl)(piperidin-1-yl)methanone (150 mg, 0.5 mmol, 1.0 eq, crude), in HOAc (3 mL) was added PtO₂ (15 mg, 0.066 mmol, 0.1 eq) in one portion at room temperature under nitrogen atmosphere. The suspension was degassed under vacuum and purged with H₂ several times. The mixture was stirred under H₂ (balloon) at 45° C. for 16 hours. LCMS showed major of desired compound. The residue was concentrated under vacuum to give crude product, which was purified by prep-HPLC eluting with 0-95% ACN in water (0.1% TFA), substituted with conc. HCl to afford ((1S,3R,4R)-3-aminospiro[bicyclo[2.2.1]heptane-2,1'-cyclohexan]-3'-yl)(piperidin-1-yl)methanone hydrochloride 227-1 (1.5 mg, 0.005 mmol, 1%) as a white solid.

LCMS [M+H]:291.2

¹H NMR (400 MHz, CD₃OD) δ 3.49-3.39 (m, 4H), 2.92-2.86 (m, 1H), 2.82 (d, J=3.6 Hz 1H), 2.42 (s, 1H), 2.35 (s, 1H), 1.69-1.57 (m, 6H), 1.53-1.51 (m, 4H) 1.44-1.36 (m, 5H), 1.34-1.28 (m, 4H), 1.02-0.96 (m, 1H).

Synthesis of (1S,3S,4R)-spiro[bicyclo[2.2.1]heptane-2,1'-cyclohexan]-3-amine hydrochloride 231

Note: absolute configuration is unassigned and the configuration of the C1 of P1 is arbitrarily shown as (S).

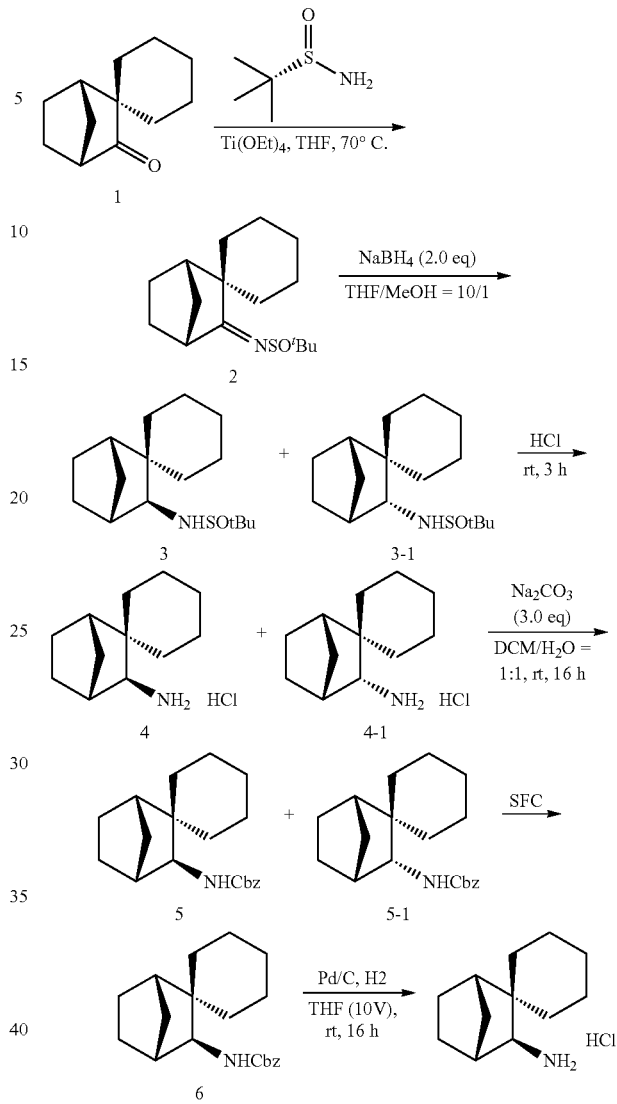

Step 1:

To a solution of (1S,4R)-spiro[bicyclo[2.2.1]heptane-2,1'-cyclohexan]-3-one (1.1 g, 6.28 mmol, 1.0 eq) in THF (30 mL) was added (S)-2-methylpropane-2-sulfinamide (913.4 mg, 7.54 mmol, 1.2 eq) and Ti(OEt)₄ (2.9 g, 12.6 mmol, 2.0 eq).The reaction mixture was stirred at 70° C. for 16 hours. Once LCMS showed the reaction finished. The reaction was quenched with aq.NaHCO₃ (20 mL), extracted with EtOAc (30 mL*3). The combined organic layer was concentrated and purified by silica gel column 10~30% EtOAc in PE to 2-methyl-N-((1S,4R,E)-spiro[bicyclo[2.2.1]heptane-2,1'-cyclohexan]-3-ylidene)propane-2-sulfinamide (370 mg, 21%) as a yellow solid.

LCMS [M+H]:282.2.

Step 2:

To a solution of 2-methyl-N-((1S,4R,E)-spiro[bicyclo[2.2.1]heptane-2,1'-cyclohexan]-3-ylidene)propane-2-sulfinamide (370 mg, 1.31 mmol, 1.0 eq) in THF:MeOH (10 mL: 1 mL) was added NaBH₄ (99.5 mg, 2.63 mmol, 2.0 eq), the reaction mixture was stirred at 25° C. for 16 hours. Once LCMS showed the reaction finished, the reaction was quenched with water (10 mL), extracted with EtOAc (20 mL*3), the combined organic layer was washed with brine, dried with Na$_2$SO$_4$ and concentrated to give 2-methyl-N-((1S,3S,4R)-spiro[bicyclo[2.2.1]heptane-2,1'-cyclohexan]-3-yl)propane-2-sulfinamide&2-methyl-N-((1S,3R,4R)-spiro[bicyclo[2.2.1]heptane-2,1'-cyclohexan]-3-yl)propane-2-sulfinamide (350 mg, crude) as a yellow oil.

LCMS [M+H]:284.2.

Step 3:

To a solution of 2-methyl-N-((1S,3S,4R)-spiro[bicyclo[2.2.1]heptane-2,1'-cyclohexan]-3-yl)propane-2-sulfinamide&2-methyl-N-((1S,3R,4R)-spiro[bicyclo[2.2.1]heptane-2,1'-cyclohexan]-3-yl)propane-2-sulfinamide (350 mg, 1.23 mmol, 1.0 eq) in THF (10.0 mL) was added HCl (5 mL, in dioxane, 4 M), and the reaction mixture was stirred at room temperature for 16 hours. Once LCMS showed the reaction finished, The reaction mixture was concentrated and washed with EtOAc (2 mL) to give (1S,3S,4R)-spiro[bicyclo[2.2.1]heptane-2,1'-cyclohexan]-3-amine hydrochloride& (1S,3R,4R)-spiro[bicyclo[2.2.1]heptane-2,1'-cyclohexan]-3-amine hydrochloride (250 mg, crude).

LCMS [M+H−HCl]: 180.1.

Step 4:

To a solution of (1S,3S,4R)-spiro[bicyclo[2.2.1]heptane-2,1'-cyclohexan]-3-amine hydrochloride& (1S,3R,4R)-spiro[bicyclo[2.2.1]heptane-2,1'-cyclohexan]-3-amine hydrochloride (250 mg, 1.16 mmol, 1.0 eq) in DCM (10.0 mL) was added Na$_2$CO$_3$ (368.8 mg, 3.48 mmol, 3.0 eq), and the reaction mixture was stirred at room temperature for 15 min, the CbzCl (296.8 mg, 1.74 mmol, 1.5 eq) was added. The reaction mixture was stirred for 16 h at rt. Once LCMS showed the reaction finished, The reaction mixture was added water (20 mL), extracted with DCM (20 mL*3). The combined organic layer was washed with brine, dried with Na$_2$SO$_4$, concentrated and purified by silica gel column 2%-10% EtOAc in PE to give benzyl ((1 S,3S,4R)-spiro[bicyclo[2.2.1]heptane-2,1'-cyclohexan]-3-yl)carbamate & benzyl ((1S,3R,4R)-spiro[bicyclo[2.2.1]heptane-2,1'-cyclohexan]-3-yl)carbamate (260 mg, 0.83 mmol, 60%).

LCMS [M+H−HCl]: 314.3.

Step 5:

SFC separation was carried out for compound 6 (260 mg). The SFC separation information are shown as following:

Analytical separation method:

Instrument: Waters UPCC, Column: ChiralPak AY, 250× 4.6 mm, 5 μm, Mobile phase: A for CO$_2$ and B for EtOH, Gradient: B 0-30%, Flow rate: 2.8 mL/min, Back pressure: 100 bar, Column temperature: 35° C., Wavelength: 214 nm Preparative separation method:

Instrument: Waters SFC80, Column: ChiralPak AY, 250× 25 mm, 10 μm, Mobile phase: A for CO$_2$ and B for EtOH, Gradient: B 30%, Flow rate: 7 g/min, Back pressure: 100 bar, Column temperature: 35° C., Wavelength: 214 nm, Cycle time: 8 min, Sample preparation: Compound was dissolved in 5 mL methanol, Injection: 2.5 ml per injection.

After separation, benzyl ((1S,3S,4R)-spiro[bicyclo[2.2.1]heptane-2,1'-cyclohexan]-3-yl)carbamate (compound 6; 130 mg, 50%) was obtained as a yellow solid.

Step 6

To a solution of benzyl ((1S,3S,4R)-spiro[bicyclo[2.2.1]heptane-2,1'-cyclohexan]-3-yl)carbamate (130 mg, 0.41 mmol, 1.0 eq) in EtOAc (100 mL) was added Pd/C (13 mg, 10% wt), and the reaction mixture was stirred at room temperature under H$_2$ atmosphere (1 atm) overnight. Once LCMS showed the reaction finished, the mixture was filtered through celite pad to get rid of Pd/C and the filtration was then concentrated to get the crude, which was then purified by prep-HPLC eluting with 0-90% ACN in water (0.1% TFA), and substituted by HCl to give 231 (108 mg, 84%) as a white solid LCMS [M+H−HCl]: 180.1

$^1$H NMR (400 MHz, MeOD) δ 2.87 (d, J=3.6 Hz, 1H), 2.44 (s, 1H), 2.42 (s, 1H), 1.793-1.43 (m, 12H), 1.39-1.23 (m, 5H), 1.16-1.11 (m, 1H).

Synthesis of rac-spiro[bicyclo[2.2.1]heptane-2, f-cyclopentan]-3-amine hydrochloride 232

Note: absolute configuration is unassigned and the configuration of the C1 of P1 is arbitrarily shown as (S).

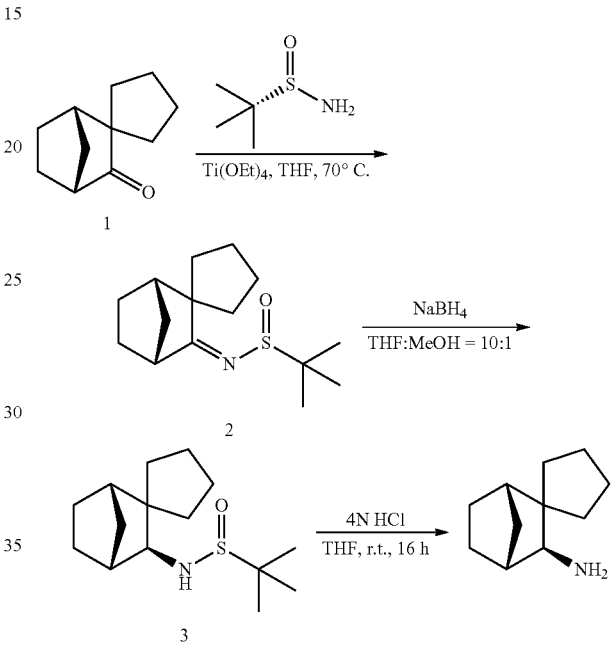

Step 1:

To a solution of rac-spiro[bicyclo[2.2.1]heptane-2,1'-cyclopentan]-3-one (2.0 g, 12.1 mmol, 1.0 eq) in THF (50 mL) was added (S)-2-methylpropane-2-sulfinamide (3.0 g, 24.2 mmol, 2.0 eq) and Ti(OEt)$_4$ (6.0 g, 12.1 mmol, 2.0 eq).The reaction mixture was stirred at 70° C. for 16 hours. Once LCMS showed the reaction finished, the reaction was purified by prep-HPLC eluting with 0-90% ACN in water (0.1% TFA) to give 2-methyl-N-((1S,4R,Z)-spiro[bicyclo[2.2.1]heptane-2,1'-cyclopentan]-3-ylidene)propane-2-sulfinamide (170 mg, 5%) as a colorless oil.

Step 2:

To a solution of 2-methyl-N-rac-spiro[bicyclo[2.2.1]heptane-2,1'-cyclopentan]-3-ylidene)propane-2-sulfinamide (170 mg, 0.64 mmol, 1.0 eq) in THF:MeOH (10 mL) was added NaBH$_4$ (50 mg, 1.28 mmol, 2.0 eq), the reaction mixture was stirred at 25° C. for 16 hours. Once LCMS showed the reaction finished, the reaction was purified by prep-HPLC eluting with 0-90% ACN in water (0.1% TFA) to give 2-methyl-N-rac-spiro[bicyclo[2.2.1]heptane-2,1'-cyclopentan]-3-yl)propane-2-sulfinamide (120 mg, 70%) as a colorless oil.

Step 3

To a solution of 2-methyl-N-rac-spiro[bicyclo[2.2.1]heptane-2,1'-cyclopentan]-3-yl)propane-2-sulfinamide (170 mg, 0.44 mmol, 1.0 eq) in THF (10.0 mL) was added HCl (5 mL, in dioxane, 4 M), and the reaction mixture was stirred at room temperature for 16 hours. Once LCMS showed the reaction finished, the reaction was purified by prep-HPLC eluting with 0-90% ACN in water (0.1% HCl) to give rac-spiro[bicyclo[2.2.1]heptane-2,1'-cyclopentan]-3-amine 232 (8.2 mg, 11%) as a white solid.

LCMS [M+H−HCl]: 166.1

$^1$H NMR (400 MHz, MeOD) δ 2.83 (s, 1H), 2.23 (d, J=4.3 Hz, 1H), 1.97 (d, J=2.0 Hz, 1H), 1.87-1.40 (m, 13H), 1.38-1.24 (m, 2H).

Synthesis of rac-3-methylspiro[bicyclo[2.2.1]heptane-2,1'-cyclopentan]-3-amine 233

Note: absolute configuration is unassigned and the configuration of the C1 of P1 is arbitrarily shown as (S).

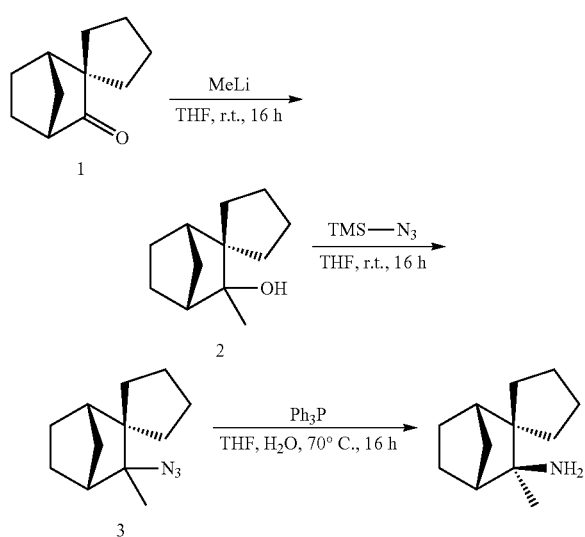

Step 1:
To a solution of rac-spiro[bicyclo[2.2.1]heptane-2,1'-cyclopentan]-3-one (1.0 g, 6.1 mmol, 1.0 eq) in THF (50 mL) was added MeLi (6.1 mL, 18.3 mmol, 3.0 eq) at 0° C. The reaction was stirred at 25° C. for 16 hours. Once LCMS showed the reaction finished, the reaction was purified by prep-HPLC eluting with 0-90% ACN in water (0.1% TFA) to rac-3-methylspiro[bicyclo[2.2.1]heptane-2,1'-cyclopentan]-3-ol (700 mg, 63%) as a colorless oil Step 2:
To a solution of rac-3-methylspiro[bicyclo[2.2.1]heptane-2,1'-cyclopentan]-3-ol (700 mg, 3.9 mmol, 1.0 eq) in THF (10 mL) was added TMS-N3 (7.8 mL, 7.8 mmol, 2.0 eq) at 0° C., the reaction mixture was stirred at 25° C. for 16 hours. Once LCMS showed the reaction finished, the reaction was purified by prep-HPLC eluting with 0-90% ACN in water (0.1% TFA) to give rac-3-azido-3-methylspiro[bicyclo[2.2.1]heptane-2,1'-cyclopentane] (120 mg, 15%) as a colorless oil Step 3:
To a solution of rac-3-azido-3-methylspiro[bicyclo[2.2.1]heptane-2,1'-cyclopentane] (120 mg, 0.59 mmol, 1.0 eq) in THF (10.0 mL) and H2O (10.0 mL) was added PPh3 (320 mg, 1.2 mmol, 2.0 eq), the reaction mixture was stirred at 70° C. for 16 hours. Once LCMS showed the reaction finished, the reaction was purified by prep-HPLC eluting with 0-90% ACN in water (0.1% HCl) to give rac-3-methylspiro[bicyclo[2.2.1]heptane-2,1'-cyclopentan]-3-amine 233 (2.7 mg, 3%) as a white solid.

LCMS [M+H−HCl]: 180.1

$^1$H NMR (400 MHz, MeOD) δ 3.07 (dd, J=8.7, 5.1 Hz, 1H), 1.94 (dt, J=13.3, 6.7 Hz, 2H), 1.80-1.38 (m, 12H), 1.29-1.16 (m, 2H), 1.02 (s, 3H).

Synthesis of (1S,3S,4R)-3-methylspiro[bicyclo[2.2.1]heptane-2,1'-cyclohexan]-3-amine hydrochloride 234

Note: absolute configuration is unassigned and the configuration of the C1 of P1 is arbitrarily shown as (S).

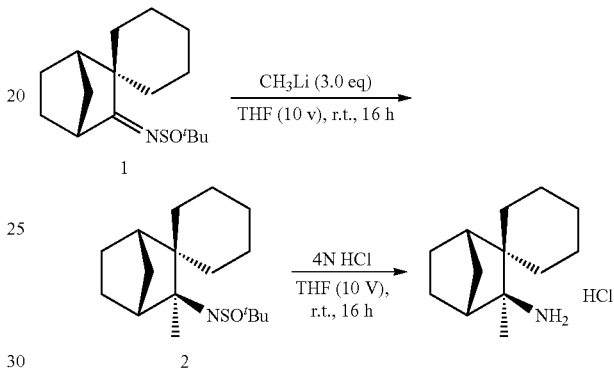

Step 1:
To a solution of rac-spiro[bicyclo[2.2.1]heptane-2,1'-cyclopentan]-3-one (650 mg, 2.31 mmol, 1.0 eq) in THF (20 mL) was added CH3Li (6.93 mL, 6.93 mmol, 3.0 eq) at 0° C. The reaction was stirred at 25° C. for 16 hours. Once LCMS showed the reaction finished, the reaction was purified by prep-HPLC eluting with 0-90% ACN in water (0.1% TFA) to 2-methyl-N-((1S,3 S,4R)-3-methylspiro[bicyclo[2.2.1]heptane-2,1'-cyclohexan]-3-yl)propane-2-sulfinamide (83 mg, 12%) as a colorless oil

LCMS [M+H]:298.2.

Step 2:
To a solution of 2-methyl-N-((1S,3S,4R)-3-methylspiro[bicyclo[2.2.1]heptane-2,1'-cyclohexan]-3-yl)propane-2-sulfinamide (80 mg, 0.27 mmol, 1.0 eq) in THF (10.0 mL) was added HCl (5 mL, in dioxane, 4 M), and the reaction mixture was stirred at room temperature for 16 hours. Once LCMS showed the reaction finished, The reaction mixture was concentrated and purified with by prep-HPLC eluting with 0-90% ACN in water (0.1% TFA), and substituted by HCl to give 234 (80 mg, 0.35 mmol, 93%) as a white solid.

LCMS [M+H−HCl]: 194.2.

$^1$H NMR (400 MHz, MeOD) δ 2.50 (s, 1H), 2.12 (s, 1H), 1.87 (d, J=10.8 Hz, 1H), 1.80 (d, J=12.4 Hz, 1H), 1.70-1.49 (m, 9H), 1.39-1.31 (m, 4H), 1.29 (s, 3H), 1.25-1.10 (m, 2H).

Synthesis of (1S,3R,4R)-spiro[bicyclo[2.2.1]heptane-2,2'-bicyclo[2.2.2]octan]-3-amine hydrochloride 239

Note: absolute configuration is unassigned and the configuration of the C1 of P1 is arbitrarily shown as (R). The relative stereochemistry of the [2,2,2]-bicycle is unassigned.

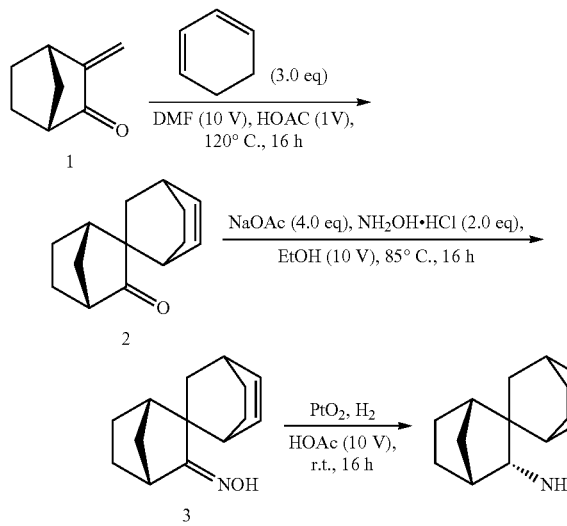

Step 1:

To a stirred solution of (1R,4S)-3-methylenebicyclo[2.2.1]heptan-2-one (200 mg, 1.639 mmol, 1.0 eq) and cyclohexa-1,3-diene (393 mg, 4.918 mmol, 3.0 eq) in DMF (2 mL) was HOAc (0.2 mL) and Sco(OTf)₃ (806 mg, 1.639 mmol, 1.0 eq). The reaction mixture was stirred at 120° C. for 16 hours. The reaction was quenched by H₂O (10 mL), extracted with EtOAc (3×10 mL), dried over Na₂SO₄, and filtered. The filtration was concentrated under vacuum to give (1S,4R)-spiro[bicyclo[2.2.1]heptane-2,2'-bicyclo[2.2.2]octan]-5'-en-3-one (210 mg, crude) as a yellow oil.

Step 2:

To a solution of (1S,4R)-spiro[bicyclo[2.2.1]heptane-2,2'-bicyclo[2.2.2]octan]-5'-en-3-one (200 mg, 1.64 mmol, 1.0 eq) in EtOH (5 mL) was added hydroxylamine hydrochloride (209 mg, 2.45 mmol, 1.5 eq) and NaOAc (404 mg, 4.92 mmol, 3.0 eq), and the reaction mixture was stirred at 80° C. overnight. Once LCMS showed the reaction finished, solvent was removed under vacuum to get a residue, which was diluted and extracted with EtOAc (10 mL×3). The organic phases were collected, washed with brine (10 mL), dried over Na₂SO₄, and filtered. The residue was purified with by prep-HPLC eluting with 0-90% ACN in water (0.1% TFA), and substituted by HCl to give (1S,4R,Z)-spiro[bicyclo[2.2.1]heptane-2,2'-bicyclo[2.2.2]octan]-5'-en-3-one oxime (15 mg, 0.069 mmol) as a white solid.

LCMS [M+H]:218.1

Step 3:

To a solution of (1S,4R,Z)-spiro[bicyclo[2.2.1]heptane-2,2'-bicyclo[2.2.2]octan]-5'-en-3-one oxime (15 mg, 0.069 mmol, 1.0 eq) in AcOH (3.0 mL) was added PtO₂ (0.01 g, 10% wt), and the reaction mixture was stirred at room temperature under H₂ atmosphere (1 atm) overnight. Once LCMS showed the reaction finished, solid was filtered and the filtration was concentrated. The residue was purified with by prep-HPLC eluting with 0-90% ACN in water (0.1% TFA), and substituted by HCl to give (1S,3R,4R)-spiro[bicyclo[2.2.1]heptane-2,2'-bicyclo[2.2.2]octan]-3-amine hydrochloride 239 (5.6 mg, 0.027 mmol) as a white solid.

LCMS [M+H−HCl]:206.2

¹H NMR (400 MHz, CD₃OD) δ 3.21-3.20 (m, 1H), 2.48 (s, 1H), 2.35 (s, 1H), 1.73-1.22 (m, 18H).

Synthesis of (1S,3R,3'S,4R)-3-aminospiro[bicyclo[2.2.1]heptane-2,1'-cyclohexan]-3'-ol hydrochloride 241-A Note: absolute configuration is unassigned and the configuration of the C1 of P1 is arbitrarily shown as (R). The relative stereochemistry of C3 and the alcohol are unassigned.

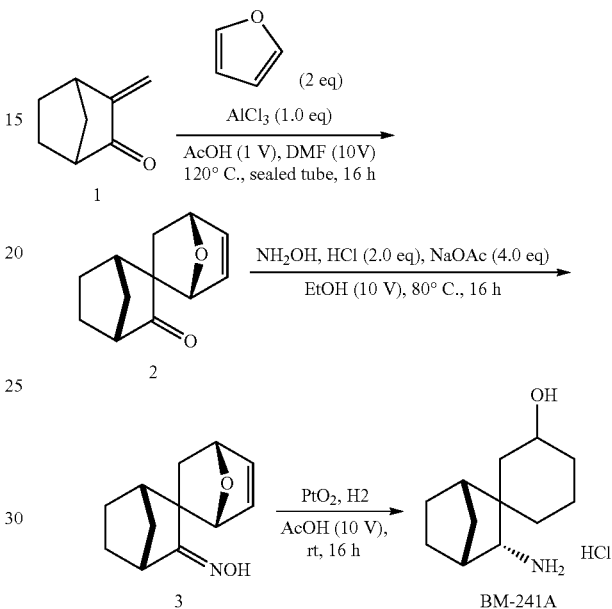

Step 1:

To a stirred solution of 3-methylenebicyclo[2.2.1]heptan-2-one (200 mg, 1.64 mmol, 1.0 eq) and furan (223.3 mg, 3.28 mmol, 2.0 eq) in DMF (2 mL) was HOAc (0.2 mL) and AlCl₃ (218.7 mg, 1.64 mmol, 1.0 eq). The reaction mixture was stirred at 120° C. for 16 hours. The reaction was quenched by H₂O (10 mL), extracted with EtOAc (3×10 mL), dried over Na₂SO₄, and filtered. The filtration was concentrated under vacuum to give (1R,1'S,4R,4'R)-7-oxa-2,2'-spirobi[bicyclo[2.2.1]heptan]-5-en-3'-one (205 mg, crude) as a yellow oil.

Step 2:

To a solution of (1R,1'S,4R,4'R)-7-oxa-2,2'-spirobi[bicyclo[2.2.1]heptan]-5-en-3'-one (205 mg, 1.08 mmol, 1.0 eq) in EtOH (5 mL) was added hydroxylamine hydrochloride (112.3 mg, 1.62 mmol, 1.5 eq) and NaOAc (265.7 mg, 3.24 mmol, 3.0 eq), and the reaction mixture was stirred at 80° C. overnight. Once LCMS showed the reaction finished, solvent was removed under vacuum to get a residue, which was diluted and extracted with EtOAc (10 mL×3). The organic phases were collected, washed with brine (10 mL), dried over Na₂SO₄, and filtered. The residue was purified with by prep-HPLC eluting with 0-90% ACN in water (0.1% TFA), and substituted by HCl to give (1R,1'S,4R,4'R,Z)-7-oxa-2,2'-spirobi[bicyclo[2.2.1]heptan]-5-en-3'-one oxime (40 mg, 0.19 mmol, 18.5%) as a white solid.

LCMS [M+H]:206.2.

Step 3:

To a solution of (1R,1'S,4R,4'R,Z)-7-oxa-2,2'-spirobi[bicyclo[2.2.1]heptan]-5-en-3'-one oxime (90 mg, 0.44 mmol, 1.0 eq) in AcOH (3.0 mL) was added PtO₂ (9 mg, 10% wt), and the reaction mixture was stirred at room temperature under H₂ atmosphere (1 atm) overnight. Once LCMS showed the reaction finished, solid was filtered and the filtration was concentrated. The residue was purified with by prep-HPLC eluting with 0-90% ACN in water (0.1% TFA), and substituted by HCl to give (1S,3R,3'S,4R)-3-aminospiro[bicyclo[2.2.1]heptane-2,1'-cyclohexan]-3'-ol hydrochloride 241-A (26 mg, 0.11 mmol, 25.6%) as a white solid.

LCMS [M+H–HCl]:196.1

¹H NMR (400 MHz, CDCl₃) δ 5.91-5.75 (m, 2H), 5.12-4.92 (m, 4H), 2.58 (d, J=5.2 Hz, 1H), 2.36 (s, 1H), 2.33-2.27 (m, 1H), 2.24-2.13 (m, 2H), 2.04-2.0 (m, 2H), 1.96-1.81 (m, 2H), 1.75-1.60 (m, 4H), 1.52-1.45 (m, 2H), 1.31-1.23 (m, 2H).

Synthesis of (1R,2R,4S)-3,3-diethyl-2-(thiophen-2-yl)bicyclo[2.2.1]heptan-2-amine hydrochloride 247

Note: absolute configuration is unassigned and the configuration of the C1 of P1 is arbitrarily shown as (S).

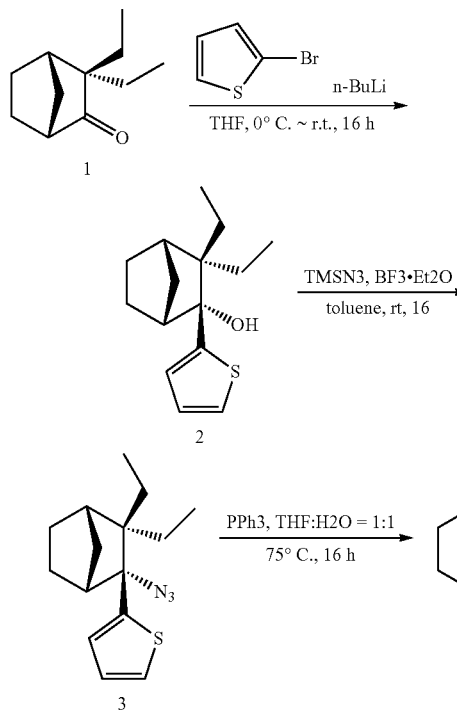

Step 1:

To a stirred solution of (1R,4S)-3,3-diethylbicyclo[2.2.1]heptan-2-one (1.0 g, 6.02 mmol, 1.0 eq) in THF (10 mL) was dropwise added n-BuLi (1.6 N, 5.7 mmL, 9.03 mmol, 1.5 eq) at 0° C. The reaction mixture was stirred at 0° C. for 2 hours. 2-bromothiophene (1.46 g, 9.03 mmol, 1.5 eq) was added. The reaction mixture was stirred at 25° C. for 16 hours. The reaction was quenched by sat.aq. NH₄Cl (30 mL), extracted with EtOAc (3×10 mL), dried over Na₂SO₄, and filtered. The filtration was concentrated under vacuum and purified with column chromatography (SiO₂, PE:EA=1000:1~500:1) to give (1R,2R,4S)-3,3-diethyl-2-(thiophen-2-yl)bicyclo[2.2.1]heptan-2-ol (1 g, 4.0 mmol, 66.7%) as a pink oil.

LCMS [M+H–OH]:233.2

Step 2:

To a solution of (1R,2R,4S)-3,3-diethyl-2-(thiophen-2-yl)bicyclo[2.2.1]heptan-2-ol (1.0 g, 4.0 mmol, 1.0 eq) and TMSN3 (921 mg, 8.0 mmol, 2.0 eq) in THF (15 mL) was added, BF3.Et₂O (460 mg, 40.0 mmol, 10.0 eq). The reaction mixture was stirred at 25° C. overnight. Once LCMS showed the reaction finished. The reaction was quenched by sat.aq. Na₂CO₃ (30 mL), extracted with EtOAc (3×10 mL), dried over Na₂SO₄, and filtered to give 2-((1R,2R,4S)-2-azido-3,3-diethylbicyclo[2.2.1]heptan-2-yl)thiophene (1.2 g, crude) as a brown oil.

Step 3:

To a solution of 2-((1R,2R,4S)-2-azido-3,3-diethylbicyclo[2.2.1]heptan-2-yl)thiophene (1.2 g, crude) in THF (15.0 mL) and H₂O (15.0 mL) was added PPh3 (3.4 g, 13.1 mmol, 3.0 eq). The reaction mixture was stirred at 75° C. overnight. Once LCMS showed the reaction finished. The mixture was reverse 3 times. The residue was purified with by prep-HPLC eluting with 0-90% ACN in water (0.1% TFA), and substituted by HCl to give (1R,2R,4S)-3,3-diethyl-2-(thiophen-2-yl)bicyclo[2.2.1]heptan-2-amine hydrochloride 247 (1.36 mg, 0.005 mmol) as a white solid.

LCMS [M+H–HCl]:250.1

¹H NMR (400 MHz, CD₃OD) δ 7.47-7.28 (m, 1H), 7.12-7.11 (m, 1H), 7.08-7.05 (m, 1H), 6.99-6.93 (m, 2H), 3.49-3.39 (m, 2H), 2.74-2.67 (m, 2H), 2.27-2.22 (m, 2H), 2.18-2.03 (m, 4H), 1.98-1.82 (m, 6H), 1.76-1.41 (m, 7H), 1.37-1.23 (m, 3H), 1.03-0.99 (m, 6H), 0.97-0.57 (m, 4H).

Synthesis of rac-3-aminospiro[bicyclo[2.2.1]heptane-2,1'-cyclopentan]-3'-ol 249A, 249B, 249C Note: absolute configuration is unassigned and the configuration of the C1 of P1 is arbitrarily shown as (R). The relative stereochemistry of C3 and the alcohol are unassigned. Three separate diastereomers are described.

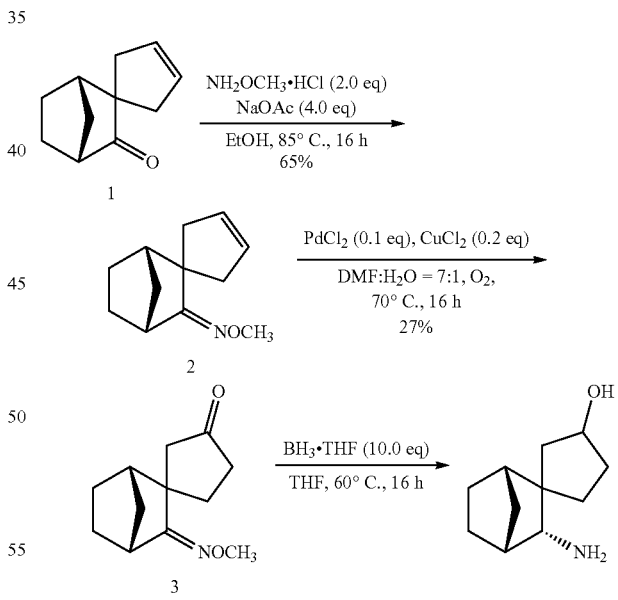

Step 1:

To a stirred solution of rac-spiro[bicyclo[2.2.1]heptane-2,1'-cyclopentan]-3'-en-3-one (3.2 g, 19.75 mmol, 1.0 eq) in EtOH (50.0 mL) was added NH₂OH·HCl (3.3 g, 39.51 mmol, 2.0 eq) and NaOAc (6.48 g, 79.01 mmol, 4.0 eq) in one portion at room temperature. The reaction mixture was stirred at 85° C. for 16 hours. Once LCMS showed finished, the mixture was concentrated to dryness. The residue was dissolved in EtOAc (80 mL×3), washed with water (100 mL), brine (100 mL), dried over $Na_2SO_4$. The filtration was concentrated under vacuum to give crude product, which was purified by silica gel chromatography eluting with 10%-50% EA in PE to afford rac-spiro[bicyclo[2.2.1]heptane-2,1'-cyclopentan]-3'-en-3-one O-methyl oxime (2.4 g, 12.54 mmol, 65%) as a colourless oil.

LCMS [M+H]:192.3

1H NMR (400 MHz, $CDCl_3$) δ 5.71-5.68 (m, 1H), 5.61-5.58 (m, 1H), 3.79 (s, 3H), 3.39 (dd, J=4.4, 1.6 Hz, 1H), 2.57-2.55 (m, 2H), 2.53-2.52 (m, 1H), 2.40-2.33 (m, 1H), 2.15 (dd, J=4.0, 2.0 Hz, 1H), 1.72-1.62 (m, 3H), 1.54-1.48 (m, 1H), 1.42-1.35 (m, 2H).

Step 2:

To a stirred solution of rac-spiro[bicyclo[2.2.1]heptane-2,1'-cyclopentan]-3'-en-3-one O-methyl oxime (2.4 g, 12.55 mmol, 1.0 eq) in DMF (14.0 mL):$H_2O$ (2.0 mL) was added $CuCl_2$ (248 mg, 2.51 mmol, 0.2 eq) and $PdCl_2$ (222 mg, 1.25 mmol, 0.1 eq) under O2 atmosphere at room temperature. The reaction mixture was stirred at 70° C. for 16 hours. Once LCMS showed finished, the mixture extracted in EtOAc (150 mL), washed with water (80 mL×3). The organic layer was washed with brine (80 mL×3), dried over $Na_2SO_4$. The filtration was concentrated under vacuum to give crude product, which was purified by silica gel chromatography eluting with 5%-20% EA in PE to afford rac-3-(methoxyimino)spiro[bicyclo[2.2.1]heptane-2,1'-cyclopentan]-3'-one (700 g, 3.38 mmol, 27%) as a yellow oil.

LCMS [M+H]:208.1

1H NMR (400 MHz, Chloroform-d) δ 3.76 (s, 3H), 3.40 (s, 1H), 2.71-2.59 (m, 1H), 2.41 (d, J=18.0 Hz, 1H), 2.29-2.13 (m, 4H), 2.01-1.66 (m, 4H), 1.47-1.38 (m, 3H).

Step 3:

To a stirred solution of rac-3-(methoxyimino)spiro[bicyclo[2.2.1]heptane-2,1'-cyclopentan]-3'-one (200 mg, 0.96 mmol, 1 eq) in THF (2.0 mL) was added $BH_3$/THF (9.65 mL, 9.65 mmol, 1.0 mol/L, 10 eq) under Argon atmosphere. The reaction was stirred at 60° C. for 16 hours. Once LCMS showed the reaction finished. The reaction was concentrated and purified by Prep-HPLC eluting with 0-90% ACN in water (0.1% TFA), and substituted by HCl to give 249A (16.11 mg, 0.09 mmol, 7.4%), 249B (26.61 mg, 0.15 mmol, 11.9%) and 249C (16.11 mg, 0.08 mmol, 6.1%) as a white solid.

249A: LCMS [M+H−HCl]: 182.1

1H NMR (400 MHz, $CDCl_3$) δ 8.12 (brs, 3H), 4.42 (s, 1H), 3.57 (s, 1H), 2.66 (s, 1H), 2.28 (d, J=76.0 Hz, 3H), 2.07-1.94 (m, 4H), 1.68-1.56 (m, 5H), 1.45-1.36 (m, 3H).

249B:LCMS [M+H−HCl]: 182.2

$^1$H NMR (400 MHz, $CDCl_3$) δ 7.96 (brs, 3H), 5.42 (s, 1H), 4.43 (s, 1H), 3.28 (s, 1H), 2.72-2.60 (m, 2H), 2.25-2.18 (m, 1H), 1.97-1.77 (m, 5H), 1.70-1.61 (m, 3H), 1.48-1.37 (m, 3H).

249C: LCMS [M+H−HCl]: 182.2

$^1$H NMR (400 MHz, $CDCl_3$) δ 7.85 (brs, 3H), 4.97 (s, 2H), 4.39 (s, 1H), 3.27 (s, 1H), 2.65 (s, 1H), 2.15 (d, J=14.8 Hz, 1H), 1.89-1.75 (m, 5H), 1.54-1.30 (m, 6H).

Synthesis of ((1S,2R,3R,3'S,4R)-3-aminospiro[bicyclo[2.2.1]heptane-2,1'-cyclohexan]-3'-yl)methanol hydrochloride & ((1S,2R,3R,3'R,4R)-3-aminospiro[bicyclo[2.2.1]heptane-2,1'-cyclohexan]-3'-yl)methanol hydrochloride 220-P1 & 220-P2

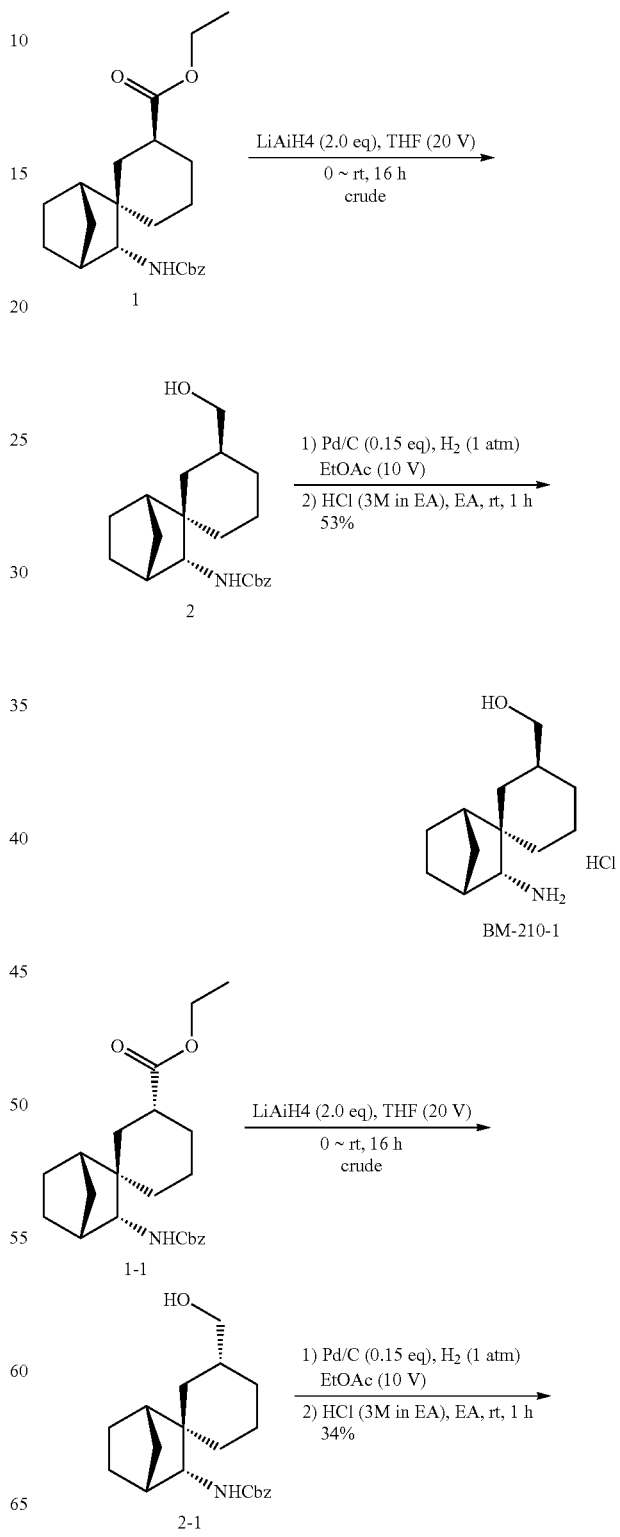

-continued

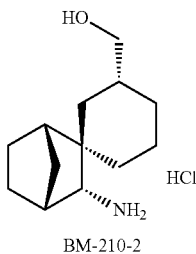

BM-210-2

Step 1:

To a solution of ethyl (1S,2R,3R,3'S,4R)-3-(((benzyloxy)carbonyl)amino)spiro[bicyclo[2.2.1]heptane-2,1'-cyclohexane]-3'-carboxylate (400 mg, 1.04 mmol, 1.0 eq) in THF (10 mL) was added LiAlH$_4$ (79 mg, 2.08 mmol, 2.0 eq) at 0° C. The mixture was stirred at room temperature for 16 hours. TLC was done to detect the process of the reaction. Once the reaction finished, 79 uL of H$_2$O, 79 uL of NaOH (15%) and 240 uL of H$_2$O was added in sequence at 0° C. to quench the reaction and the corresponding mixture was then stirred at room temperature for another 30 mins. Solid was filtered, and the filtration was dried over Na$_2$SO$_4$ to get rid of residual water and filtered. The filtration was then concentrated under vacuum to give benzyl ((1S,2R,3R,3'S,4R)-3'-(hydroxymethyl)spiro[bicyclo[2.2.1]heptane-2,1'-cyclohexan]-3-yl)carbamate (compound 2) (300 mg, crude) as a colorless oil.

$^1$H NMR (400 MHz, CD$_3$OD) δ 8.02 (s, 1H), 7.33-7.31 (m, 3H), 4.59 (s, 1H), 4.00 (d, J=4.0 Hz, 1H), 2.21 (s, 1H), 1.87-1.68 (m, 6H), 1.65-1.51 (m, 6H), 1.40-1.28 (m, 7H), 1.10-1.02 (m, 1H), 0.84-0.72 (m, 3H).

Step 2:

To a solution of benzyl ((1S,2R,3R,3'S,4R)-3'-(hydroxymethyl)spiro[bicyclo[2.2.1]heptane-2,1'-cyclohexan]-3-yl)carbamate (300 mg, crude) in EA (10.0 mL) was added Pd/C (30 mg, 10% wt), and the reaction mixture was stirred at room temperature under H$_2$ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 220-P1 (96.95 mg, 0.395 mmol, 53%) as a white solid.

LCMS [M–HCl–NH$_2$–OH–1]: 175.1

$^1$H NMR (400 MHz, CD$_3$OD) δ 8.08 (s, 1H), 4.01 (d, J=3.6 Hz, 1H), 3.36-3.32 (m, 2H), 2.24 (s, 1H), 1.88-1.84 (m, 3H), 1.81-1.75 (m, 2H), 1.68-1.62 (m, 2H), 1.55-1.48 (m, 2H), 1.42-1.32 (m, 3H), 1.25-1.22 (m, 1H), 1.12-1.03 (m, 1H), 0.83-0.76 (m, 2H).

Step 3:

To a solution of ethyl (1S,2R,3R,3'R,4R)-3-(((benzyloxy)carbonyl)amino)spiro[bicyclo[2.2.1]heptane-2,1'-cyclohexane]-3'-carboxylate (400 mg, 1.04 mmol, 1.0 eq) in THF (10 mL) was added LiAlH$_4$ (79 mg, 2.08 mmol, 2.0 eq) at 0° C. The mixture was stirred at room temperature for 16 hours. TLC was done to detect the process of the reaction. Once the reaction finished, 79 uL of H$_2$O, 79 uL of NaOH (15%) and 240 uL of H$_2$O was added in sequence at 0° C. to quench the reaction and the corresponding mixture was then stirred at room temperature for another 30 mins. Solid was filtered, and the filtration was dried over Na$_2$SO$_4$ to get rid of residual water and filtered. The filtration was then concentrated under vacuum to give benzyl ((1S,2R,3R,3'R,4R)-3'-(hydroxymethyl)spiro[bicyclo[2.2.1]heptane-2,1'-cyclohexan]-3-yl)carbamate (compound 2-1) (300 mg, crude) as a colorless oil.

Step 4:

To a solution of benzyl ((1S,2R,3R,3'R,4R)-3'-(hydroxymethyl)spiro[bicyclo[2.2.1]heptane-2,1'-cyclohexan]-3-yl)carbamate (300 mg, crude) in EA (10.0 mL) was added Pd/C (30 mg, 10% wt), and the reaction mixture was stirred at room temperature under H$_2$ atmosphere (1 atm) overnight. Once LCMS showed the reaction finished, solvent was removed to get the crude, which was then purified by prep-HPLC eluting with 0-90% ACN in water (0.1% TFA), and substituted by HCl to give 220-P2 (64.2 mg, 0.262 mmol, 34%) as a white solid.

LCMS [M–HCl–NH$_2$–OH–1]: 175.1

$^1$H NMR (400 MHz, CD$_3$OD) δ 8.15 (s, 1H), 3.75 (d, J=3.6 Hz, 1H), 3.34-3.33 (m, 2H), 2.36 (s, 1H), 2.23 (s, 1H), 1.85-1.58 (m, 8H), 1.53-1.41 (m, 3H), 1.31-1.22 (m, 2H), 1.04-0.77 (m, 3H).

Synthesis of rac-3-phenylspiro[bicyclo[2.2.1]heptane-2,1'-cyclopentan]-3-amine hydrochloride (Representative procedure D)

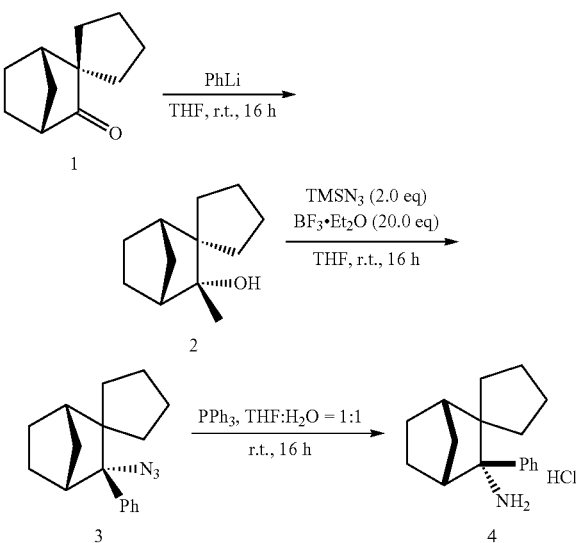

General procedure for preparation of rac-3-phenylspiro[bicyclo[2.2.1]heptane-2,1'-cyclopentan]-3-ol To a stirred solution of rac-spiro[bicyclo[2.2.1]heptane-2,1'-cyclopentan]-3-one (2.2 g, 13.40 mmol, 1.0 eq) in THF (15 mL) was added PhLi (40 mL, 40.21 mmol, 1.1 eq). The reaction mixture was stirred at room temperature for 16 hours. The reaction was quenched by sat.aq. NH$_4$Cl (50 mL), extracted with EtOAc (3×40 mL), dried over Na$_2$SO$_4$, and filtered. The filtration was concentrated under vacuum to give crude product, which was purified by silica gel chromatography eluting with 8%-10% EA in PE to afford rac-3-phenylspiro[bicyclo[2.2.1]heptane-2,1'-cyclopentan]-3-ol (3.4 g, 14.02 mmol) as a white oil.

$^1$H NMR (400 MHz, CDCl$_3$) δ 7.50-7.48 (m, 2H), 7.31-7.22 (m, 2H), 7.21-7.18 (m, 1H), 2.65 (d, J=2.0 Hz, 1H), 2.10-2.08 (m, 1H), 2.03-1.91 (m, 2H), 1.80-1.72 (m, 5H), 1.67-1.38 (m, 4H), 1.37-1.29 (m, 1H), 0.93-0.82 (m, 2H)

General procedure for preparation of rac-3-azido-3-phenylspiro[bicyclo[2.2.1]heptane-2,1'-cyclopentane] (compound 3)

To a stirred solution of rac-3-phenylspiro[bicyclo[2.2.1]heptane-2,1'-cyclopentan]-3-ol (170 mg, 0.73 mmol, 1 eq) in Toluene (15 mL) was added TMSN$_3$ (3.4 g, 28.08 mmol, 2.0 eq) and BF3.Et$_2$O (19.93 g, 140.4 mmol, 10.0 eq) under Ar atmosphere. The reaction mixture was stirred at rt for 16 hours. Once LCMS showed finished, the mixture was concentrated to dryness. The residue was concentrated and dissolved in EtOAc (150 mL), washed with water (100 mL) brine (100 mL), dried over Na$_2$SO$_4$. The filtration was concentrated under vacuum to give crude product (3.2 g, a white oil) which was used next step directly.

General procedure for preparation of rac-3-phenylspiro[bicyclo[2.2.1]heptane-2,1'-cyclopentan]-3-amine hydrochloride (compound 4)

To a solution of rac-3-azido-3-phenylspiro[bicyclo[2.2.1]heptane-2,1'-cyclopentane] (3.2 g, 11.97 mmol, 1.0 eq) in THF/H$_2$O (7 mL/7 mL) was added PPh3 (6.23 g, 23.93 mmol, 2.0 eq) and stirred at 70° C. for 16 hours. Once LCMS showed the reaction finished, The mixture was adjusted with pH=3 by HCl (15%) and extracted with EtOAc (30 mL×4). The combined aqueous phase and adjusted the pH=11, extracted with EtOAc (100 mL×3). The organic layer was washed with brain (100 mL), dried over Na$_2$SO$_4$ and concentrated in vacuo. The residue was purified by prep-HPLC eluting with 0-90% ACN in water (0.1% TFA), and substituted by HCl to give rac-3-phenylspiro[bicyclo[2.2.1]heptane-2,1'-cyclopentan]-3-amine hydrochloride (116.18 mg, 0.48 mmol, 7%) as a white solid.

LCMS [M+H−HCl]:242.2

$^1$H NMR (400 MHz, CD$_3$OD) δ 7.61 (br s, 2H), 7.42-7.39 (m, 2H), 7.30-7.26 (m, 1H), 3.29-3.21 (m, 1H), 2.89-2.87 (m, 1H), 2.52-2.36 (m, 2H), 1.98-1.85 (m, 5H), 1.79-1.75 (m, 1H), 1.49-1.28 (m, 5H), 1.16-1.11 (m, 1H).

TABLE 2

C2-amino-C3-spirocyclic disubstituted BRD4780 analogs. (Note, P1/P2 indicates a single enantiomer compound of undetermined absolute stereochemistry)

| Compound No.: | Structure | 1H-NMR, 400 MHz | LCMS [M + H]$^+$ | ee (%) | Procedure |
|---|---|---|---|---|---|
| 208 | (+/−) | (DMSO-d6) δ 8.07 (brs, 3H), 3.00 (t, J = 5.2 Hz, 1H), 2.33 (s, 1H), 2.17 (s, 1H), 2.00-1.98 (m, 1H), 1.87-1.74 (m, 5H), 1.39-1.25 (m, 6H). | 152.1 | NA | B |
| 208-P1 | 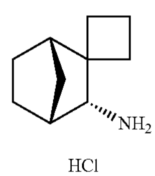 | (DMSO-d6) δ 8.01 (brs, 3H), 2.99 (d, J = 4.4 Hz, 1H), 2.33 (s, 1H), 2.17 (s, 1H), 2.00-1.98 (m, 1H), 1.87-1.74 (m, 5H), 1.39-1.25 (m, 6H). | 152.1 | P1: 99.9 | Chiral separation of derivatized compounds prepared in general procedure B |
| 208-P2 | 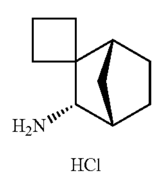 | | | P2: 99.0 | |
| 209 | (+/−) | (CDCl3) δ 8.35 (s, 3H), 3.20 (s, 1H), 2.64 (s, 1H), 1.91 (s, 1H), 1.83-1.77 (m, 2H), 1.67-1.59 (m, 3H), 1.58-1.56 (m, 2H), 1.53-1.49 (m, 3H), 1.47-1.46 (m, 1H), 1.44-1.38 (m, 2H), 1.35-1.33 (m, 1H). | 166.1 | NA | C |

TABLE 2-continued

C2-amino-C3-spirocyclic disubstituted BRD4780 analogs. (Note, P1/P2 indicates a single enantiomer compound of undetermined absolute stereochemistry)

| Compound No.: | Structure | 1H-NMR, 400 MHz | LCMS [M + H]+ | ee (%) | Procedure |
|---|---|---|---|---|---|
| 209-P1 | 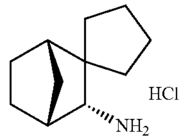 | (CDCl3) δ 8.37-8.34 (bs, 3H), 3.198 (m, 1H), 2.639 (m, 1H), 1.91 (m, 1H), 1.83-1.80 (m, 2H), 1.72-1.66 (m, 4H), 1.62-1.58 (m, 3H), 1.51-1.50 (m, 1H), 1.46-1.42 (m, 2H), 1.34 (d, J = 8 Hz, 1H), 1.253 (s, 1H). | 166.1 | P1: 100 | C |
| 209-P2 | 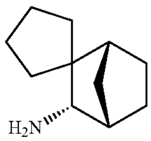 | | | P2: 100 | |
| 210 | 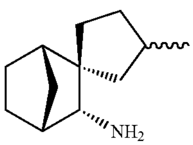 | (CD3OD) δ 3.19-3.16 (m, 1H), 2.47-2.43 (m, 1H), 2.03-1.40 (m, 10H), 1.33-1.24 (m, 1H), 1.09-1.01 (m, 3H). | 180.1 | NA | C |
| 210-P1-A | 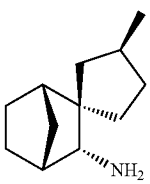 | (CDCl3) δ 8.36 (s, 3H), 3.15 (s, 1H), 2.67 (s, 1H), 2.19-1.94 (m, 3H), 1.81-1.65 (m, 3H), 1.59-1.54 (m, 1H), 1.42-1.11 (m, 7H), 1.05-0.98 (m, 3H). | 180.2 | 96.2 | C |
| 210-P1-B | 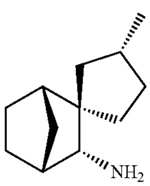 | (CDCl3) δ 8.41 (bs, 3H), 3.23 (s, 1H), 2.58 (s, 1H), 1.91-1.88 (m, 3H), 1.78-1.63 (m, 5H), 1.57-1.55 (m, 1H), 1.45-1.33 (m, 4H), 1.33-1.28 (m, 1H), 1.16-1.13 (m, 1H), 1.09-0.99 (m, 3H). | 180.2 | 98.3 | C |
| 210-P2-A | 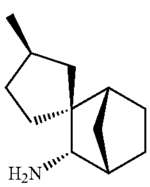 | (CDCl3) δ 8.36 (s, 3H), 3.15 (s, 1H), 2.67 (s, 1H), 2.19-1.94 (m, 3H), 1.81-1.65 (m, 3H), 1.59-1.54 (m, 1H), 1.42-1.11 (m, 7H), 1.05-0.98 (m, 3H). | 180.2 | 94.3 | C |
| 210-P2-B | 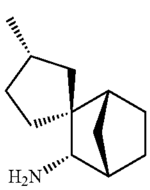 | (CDCl3) δ 8.41 (bs, 3H), 3.23 (s, 1H), 2.58 (s, 1H), 1.91-1.88 (m, 3H), 1.78-1.63 (m, 5H), 1.57-1.55 (m, 1H), 1.45-1.33 (m, 4H), 1.33-1.28 (m, 1H), 1.16-1.13 (m, 1H), 1.09-0.99 (m, 3H). | 180.2 | 98.9 | C |

TABLE 2-continued

C2-amino-C3-spirocyclic disubstituted BRD4780 analogs. (Note, P1/P2 indicates a single enantiomer compound of undetermined absolute stereochemistry)

| Compound No.: | Structure | 1H-NMR, 400 MHz | LCMS [M + H]+ | ee (%) | Procedure |
|---|---|---|---|---|---|
| 211-P1-A | 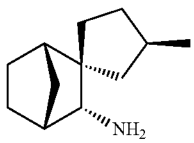 | (CD3OD) δ 3.15 (d, J = 4.0 Hz, 1H), 2.45 (s, 1H), 2.02-1.96 (m, 2H), 1.86-1.68 (m, 5H), 1.58-1.40 (m, 7H), 1.19-1.12 (m, 2H), 1.02 (d, J = 6.8 Hz, 4H). | 180.1 | 95 | C |
| 211-P1-B | 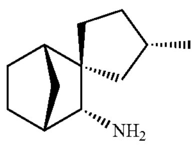 | (CD3OD) δ 3.20 (d, J = 4.4 Hz, 1H), 2.44 (s, 1H), 2.02 (s, 1H), 2.00-1.93 (m, 1H), 1.91-1.73 (m, 3H), 1.67-1.56 (m, 3H), 1.54-1.46 (m, 4H), 1.26-1.19 (m, 1H), 1.06 (d, J = 6.4 Hz, 3H), 0.93-0.87 (m, 1H). | 180.1 | 95 | C |
| 211-P2-A | 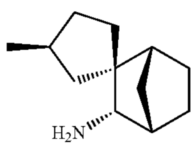 | (CD3OD) δ 3.15 (d, J = 4.0 Hz, 1H), 2.45 (s, 1H), 2.02-1.96 (m, 2H), 1.86-1.68 (m, 5H), 1.58-1.40 (m, 7H), 1.19-1.12 (m, 2H), 1.02 (d, J = 6.8 Hz, 4H). | 180.1 | 100 | C |
| 211-P2-B | 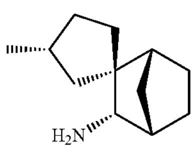 | CD3OD) δ 3.20 (d, J = 4.4 Hz, 1H), 2.44 (s, 1H), 2.02 (s, 1H), 2.00-1.93 (m, 1H), 1.91-1.73 (m, 3H), 1.67-1.56 (m, 3H), 1.54-1.46 (m, 4H), 1.26-1.19 (m, 1H), 1.06 (d, J = 6.4 Hz, 3H), 0.93-0.87 (m, 1H). | 180.1 | 97 | C |
| 212-P1 | 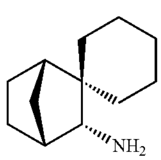 | (CDCl3) δ 2.61 (d, J = 3.6 Hz, 1H), 2.23 (s, 1H), 2.16-2.04 (m, 3H), 1.59-1.56 (m, 2H), 1.54-1.53 (m, 1H), 1.51-1.39 (m, 6H), 1.35-1.30 (m, 2H), 1.27-1.18 (m, 4H), 1.16-1.13 (m, 2H). | 180.1 | P1: 100 | C |
| 212-P2 | 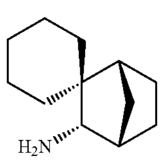 | | | P2: 100 | |
| 213 | 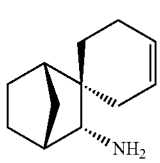 | (CD3OD) δ 5.75-5.69 (m, 1H), 5.65-4.88 (m, 1H), 2.98 (d, J = 3.2 Hz, 1H), 2.45 (s, 1H), 2.25-2.15 (m, 1H), 2.15-1.85 (m, 4H), 1.76-1.71 (m, 2H), 1.63-1.52 (m, 4H), 1.49-1.30 (m, 2H). | 178.1 | NA | C |

TABLE 2-continued

C2-amino-C3-spirocyclic disubstituted BRD4780 analogs. (Note, P1/P2 indicates a single enantiomer compound of undetermined absolute stereochemistry)

| Compound No.: | Structure | 1H-NMR, 400 MHz | LCMS [M + H]$^+$ | ee (%) | Procedure |
|---|---|---|---|---|---|
| 214-P1-A | 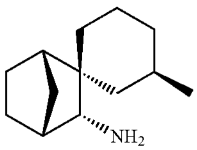 | (CDCl3) δ 8.38 (brs, 3H), 3.09 (s, 1H), 2.76 (s, 1H), 2.06 (m, 1H), 1.83-1.51 (m, 9H), 1.50-1.36 (m, 1H), 1.34-1.06 (m, 3H), 0.89-0.66 (m, 5H). | 194.2 | 100 | C |
| 214-P1-B | 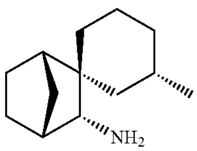 | (CDCl3) δ 8.33 (brs, 3H), 2.93 (s, 1H), 2.58 (s, 1H), 2.34 (s, 1H), 1.94 (s, 1H), 1.79 (s, 1H), 1.75-1.34 (m, 8H), 1.34-1.04 (m, 4H), 0.93-0.79 (m, 4H). | 194.1 | 99.6 | C |
| 214-P2-A | 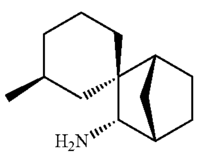 | (CDCl3) δ 8.39 (brs, 3H), 3.09 (s, 1H), 2.78 (s, 1H), 2.06 (d, J = 13.6 Hz, 1H), 1.88-1.50 (m, 9H), 1.50-1.04 (m, 4H), 0.92-0.64 (m, 5H). | 194.1 | 98.9 | C |
| 214-P2-B | 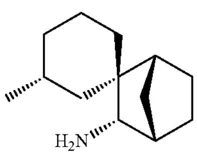 | (CDCl3) δ 8.34 (brs, 3H), 2.92 (s, 1H), 2.57 (s, 1H), 2.33 (s, 1H), 1.93 (s, 1H), 1.79 (s, 1H), 1.75-1.34 (m, 8H), 1.34-1.04 (m, 4H), 0.93-0.79 (m, 4H). | 194.2 | 98.2 | C |
| 215 | 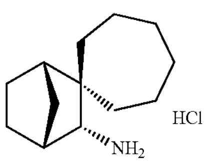 | (CD3OD) δ 2.95-2.94 (m, 1H), 2.43 (s, 1H), 2.22 (s, 1H), 2.00 (s, 1H), 1.84-1.59 (m, 7H), 1.556-1.44 (m, 9H), 1.39-1.34 (m, 1H). | 194.2 | NA | C |
| 215-P1 | 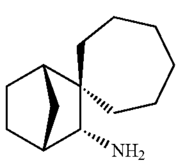 | (CDCl3) δ 2.99 (s, 1H), 2.61 (s, 1H), 2.13 (s, 2H), 1.76-1.50 (m, 10H), 1.49-1.43 (m, 3H), 1.42-1.31 (m, 3H), 1.29-1.26 (m, 1H). | 194.2 | P1: 100 | C |
| 215-P2 | 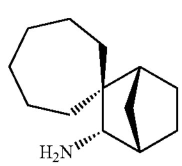 | | | P2: 100 | |

TABLE 2-continued

C2-amino-C3-spirocyclic disubstituted BRD4780 analogs. (Note, P1/P2 indicates a single enantiomer compound of undetermined absolute stereochemistry)

| Compound No.: | Structure | 1H-NMR, 400 MHz | LCMS [M + H]⁺ | ee (%) | Procedure |
|---|---|---|---|---|---|
| 216-P1 | 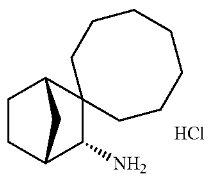 | (CD3OD) δ 3.03 (d, J = 3.6 Hz, 1H), 2.44 (s, 1H), 2.16 (s, 1H), 1.83-1.81 (d, J = 8.0 Hz, 1H), 1.67-1.43 (m, 19H), 1.36-1.34 (m, 1H). | 208.2 | P1: 99 | C |
| 216-P2 | 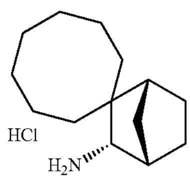 | | | P2: 100 | |
| 217-P1-A | 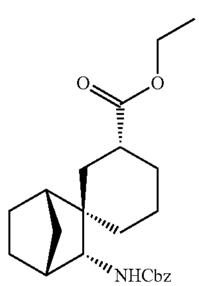 | (CD3OD) δ 4.06-4.00 (m, 2H), 2.99 (d, J = 3.2 Hz, 1H), 2.39-2.37 (m, 2H), 1.84 (s, 1H), 1.78-1.69 (m, 3H), 1.62-1.47 (m, 6H), 1.42-1.24 (m, 6H), 1.15 (t, J = 6.8 Hz, 3H). | 252.2 | P1: 100 | C |
| 217-P2-A | 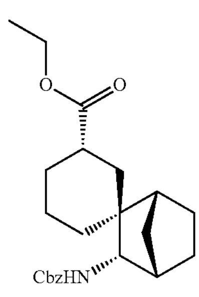 | | | P2: 99.9 | |

TABLE 2-continued

C2-amino-C3-spirocyclic disubstituted BRD4780 analogs. (Note, P1/P2 indicates a single enantiomer compound of undetermined absolute stereochemistry)

| Compound No.: | Structure | 1H-NMR, 400 MHz | LCMS [M + H]$^+$ | ee (%) | Procedure |
|---|---|---|---|---|---|
| 217-P3-B | 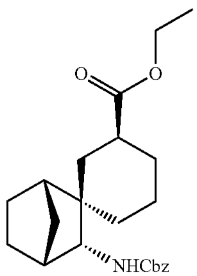 | (CD3OD) δ 4.03-3.98 (m, 2H), 2.80 (d, J = 4.0 Hz, 1H), 2.54-2.47 (m, 1H), 2.33-2.30 (m, 2H), 1.85-1.73 (m, 2H), 1.69-1.62 (m, 4H), 1.51-1.35 (m, 4H), 1.32-1.21 (m, 4H), 1.14 (t, J = 7.2 Hz, 3H), 1.00-0.95 (m, 1H). | 252.2 | P3: 100 | C |
| 217-P4-B | 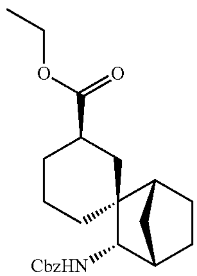 | | | P4: 96.3 | |

Note:
Compounds labeled "A" are pure enantiomers with identical relative configuration of the substituent in the spirocyclic ring. Compounds labeled "B" are enantiomeric pairs of the other relative configuration (opposite of "A") at the substituted spirocyclic position. The relative configuration of the C2/C3 substituents is known, whereas the relative configuration of the substituent in the spirocyclic ring is unknown and arbitrarily assigned.

Example 2: Exemplary Biological Activity of Compounds of the Disclosure

P cells were seeded 24 hr prior to compound treatment at a density of 12,000 cells/well in 384 well Cell Carrier Ultra plates (6057308, Perkin Elmer), pre-coated with 0.25 mg/mL Synthemax II SC Substrate (3535, Corning). Compounds were used at 5 doses (35, 3.5, 0.35, 0.035 and 0.0035 µM) for the primary screen and 10 doses (16, 5.6, 1.8, 0.6, 0.21, 0.07, 0.02, 0.008, 0.002 and 0.0008 µM) for the following screens. The compounds, in two replicates, were transferred from compound source plates to the cell plates using the HighRes Pin Tool. DMSO was used as a negative control and JQ1 (250 nM) (a bromodomain inhibitor) was chosen as a positive control, based on earlier studies showing its potent effect on reducing total MUC1 mRNA levels (data not shown). After 48 hr incubation, cells were fixed for 20 min in 4% PFA (Electron Microscopy Sciences) in PBS, washed twice, then permeabilized (10 min) with 0.5% Triton-X100 (X100-100ML, Sigma-Aldrich) in PBS and washed once more. Cells were blocked for 10 min at RT with Blocking solution (100 mM Tris HCL pH8; 150 mM NaCL; 5 g/L Blocking Reagent [11096176001, Roche]), then incubated 90 min at RT with one of the following primary antibodies in Roche Blocking solution: 1:500, monoclonal Fab-A-VSH anti-MUC1-fs, AbD22655.2, Bio-Rad; 1:2000, monoclonal mouse anti-MUC1 (214D4), 05-652-KC, Millipore; 1:1000, monoclonal, Rabbit anti-GM130 (D6B1) XP, 12480, Cell signaling technology. The primary antibody cocktail was incubated at RT for 1.5 hr, followed by four PBS wash cycles. The secondary antibody cocktail contained four components that were all prepared at a 1:1000 dilution in the Roche blocking solution and consisted of Alexa Fluor® 488-conjugated AffiniPure F(ab')2 Fragment Goat anti-Human IgG, 109-546-097, Jackson Immunoresearch; Alexa Fluor® 647-conjugated Goat anti-Rabbit IgG, A-21246, Thermo Fisher Scientific®; Alexa Fluor® 546 Goat anti-mouse IgG, A-21123, Thermo Fisher Scientific® and Hoechst 33342 stain (62249, Thermo Fisher Scientific®). The secondary antibody cocktail was incubated at RT for 45 min, followed by four PBS wash cycles. Finally, plates were sealed with a Plate Loc plate and stored in Liconic incubator at 10° C. until imaging. Following image analysis, three parameters were selected, i) MUC1-fs and ii) MUC1-wt total cytoplasm intensity (averaged per cell) and iii) cell number as was detected by Hoechst 33342 stained nuclei. The levels of MUC1-fs and MUC1-wt found following DMSO and JQ1 were defined as 0 and −100% activity, respectively. The values obtained for all compounds were normalized accordingly. Cell number was normalized to DMSO control.

| Compound No. | EC$_{50}$(Spot) (µM) | EC$_{Max}$ (%) | WT EC$_{50}$ (Cytoplasm) (µM) | WT EC$_{Max}$ (%) |
|---|---|---|---|---|
| 201-P1 | 0.088 | −94.91 | 10.31 | 63 |
| 201-P2 | 0.470 | −85.5 | 11.9 | 68.51 |
| 202-rac | 0.050 | −76.19 | 2.11 | 125.82 |
| 202-P1 | 0.040 | −77.14 | 4.04 | ~150 |
| 202-P2 | 0.020 | −76 | >1.8 | ~175 |
| 203-P1 | 0.050 | −76.02 | 2.7 | 91.48 |
| 203-P2 | 0.040 | −75 | 2.6 | 95 |
| 204 | 0.010 | −85.02 | 1.01 | 190.26 |
| 204-P1 | 0.030 | −118.54 | 3.32 | 197.55 |

| Compound No. | EC$_{50}$(Spot) (μM) | EC$_{Max}$ (%) | WT EC$_{50}$ (Cytoplasm) (μM) | WT EC$_{Max}$ (%) |
|---|---|---|---|---|
| 204-P2 | 0.020 | −90.34 | 1.09 | 65.02 |
| 205 | >32 | −3.08 | >32 | −12.24 |
| 205-P1 | 18.5 | −49.33 | >32 | −5.77 |
| 205-P2 | 8.07 | −64.37 | >32 | 7.55 |
| 206-P1 | >32 | 16.41 | >32 | −11.84 |
| 206-P2 | >32 | −10.5 | >32 | −3.86 |
| 207 | >32 | −25.6 | >32 | 5.9 |
| 207-P1 | >32 | −23.63 | >32 | −11.78 |
| 207-P2 | >32 | −27.46 | >32 | −12.69 |
| 208 | 0.130 | −65.35 | >5.6 | ~125 |
| 208-P1 | 0.670 | −−84.54 | >16 | 20.55 |
| 208-P2 | 0.030 | −65.69 | 8.04 | 157.02 |
| 209-P1 | 0.040 | −70.66 | >5.6 | −210 |
| 209-P2 | 0.010 | −64.28 | 2.06 | −210 |
| 210 | 0.120 | −62.47 | >32 | −10.67 |
| 210-P1-A | 26.8984 | −33.62 | >32 | 0.73 |
| 210-P1-B | 15.5 | −26.85 | >32 | −4.05 |
| 210-P2-A | 1.04 | −62.63 | >32 | −8.9 |
| 210-P2-B | 0.100 | −66.02 | >16 | 30.21 |
| 211-P1-A | 1.22 | −87.44 | >5.6 | 9.39 |
| 211-P1-B | 5 | −61.55 | >32 | 9.31 |
| 211-P2-A | 20.1 | −23.56 | >32 | 3.22 |
| 211-P2-B | >32 | −10.93 | >32 | 4.75 |
| 212-P1 | 1.57 | −65.18 | 3.01 | 110.73 |
| 212-P2 | 0.010 | −68.36 | 2.6 | 183.41 |
| 213 | 0.020 | −86.49 | >1.8 | ~175 |
| 214-P1-A | 10.5 | −26.27 | >32 | 3.96 |
| 214-P1-B | 12.1 | −58.73 | >32 | −12.08 |
| 214-P2-A | 24.0 | −24.69 | >32 | −7.57 |
| 214-P2-B | 15.1 | −29.12 | >32 | −4.96 |
| 215 | 0.110 | −56.54 | 8.87 | 63 |
| 215-P1 | 7.16 | −29.45 | 11.98 | 40.5 |
| 215-P2 | 0.120 | −63.45 | 8.74 | 189.48 |
| 216-P1 | 20.2 | −38.24 | >32 | 0.16 |
| 216-P2 | 1.07 | −82.5 | 9.89 | 92.77 |
| 217-P1-A | >32 | −19.6 | >32 | 8.1 |
| 217-P2-A | >32 | −8.81 | >32 | −8.08 |
| 217-P3-B | >32 | 15.96 | >32 | −9.06 |
| 217-P4-B | >32 | 7.10 | >32 | 4.42 |

| Compound No. | EC$_{50}$ uM | E$_{max}$ | WT EC$_{50}$ | WT E$_{Max}$ |
|---|---|---|---|---|
| 218 | 13.5 | −54.7 | >16 | −15.4 |
| 219-P1 | >16 | 5.6 | >16 | 12.4 |
| 219-P2 | >16 | −10.3 | >16 | 11.3 |
| 220-P1 | >16 | 6.0 | N/A | N/A |
| 220-P2 | >16 | 9.4 | N/A | N/A |
| 221 | >16 | 16.2 | >16 | 15.6 |
| 222-P1 | >16 | −17.9 | N/A | N/A |
| 222-P2 | >16 | 19.0 | N/A | N/A |
| 223 | >16 | −12 | >16 | 25.7 |
| 224 | >16 | −17.0 | >16 | −24.4 |
| 225-2 | 10.1 | −20.7 | >16 | −11.1 |
| 225-1 | >16 | −13.3 | >16 | −15.8 |
| 226 | >16 | 7.8 | >16 | 9.0 |
| 226-1 | >16 | −32.0 | >16 | −24.5 |
| 227 | >16 | −39.9 | >16 | 4.6 |
| 227-1 | 3.6 | −79.5 | >16 | −7.0 |
| 228 | >16 | −15.1 | >16 | −10.2 |
| 229 | 15.5 | −48.1 | >16 | 10.3 |
| 230 | >16 | −12.8 | >16 | −16.1 |
| 231 | 1.63 | −76.5 | >16 | −7.0 |
| 232 | 5.99 | −68.6 | >16 | 6.6 |
| 233 | 0.077 | −86.9 | >16 | 21.8 |
| 234 | 4.83 | −96 | >16 | 6.7 |
| 235 | 1.77 | −88.6 | >16 | −6.6 |
| 236 | 0.962 | −89.6 | >16 | −20.3 |
| 237 | 13.3 | −45.1 | >16 | −10.0 |
| 238 | 0.032 | −96.4 | 0.74 | 68.9 |
| 238-A | 0.006 | −108.1 | 1.8 | 38.7 |
| 238-B | 0.029 | −106.4 | 5.6 | 40.7 |
| 239 | 2.29 | −83.1 | 13.5 | 62.7 |
| 240 | >16 | −34.8 | >16 | −11.1 |
| 241-A | >16 | −11.4 | >16 | −5.7 |
| 242 | 2.43 | −67.4 | >16 | 27.7 |
| 243-A | >16 | −40.4 | >16 | 3.2 |
| 244 | >16 | −35.0 | >16 | −9.0 |
| 245 | 0.011 | −90.2 | 4.5 | 106.2 |
| 246-A | 1.90 | −67.8 | >16 | 20.7 |
| 246-B | 6.99 | −69.3 | >16 | 6.2 |
| 247 | >16 | −45.8 | >16 | 5.7 |
| 248 | 0.110 | −83.1 | 9.8 | 36.5 |
| 249A | 2.2 | −98.1 | >16 | −7.2 |
| 249B | 4.14 | −72.5 | >16 | −6.7 |
| 249C | 6.38 | −74.4 | >16 | −11.9 |
| 250 | 7.83 | −86.3 | >16 | 8.2 |

Example 3: Exemplary Biological Activity of Compounds of the Disclosure

Prepared Renal Life Media by adding the supplements provided in the kit, substituting the FBS provided with Tet system approved FBS, and filtering the media (not including provided kit antibiotics). Thawed P6 vial(s) into T175 flasks 2 weeks prior to screening. Cells have to be passaged at least once after thaw before they can be used for screening. Hyperflasks can be used depending on the cell number needed. One confluent T175 flask should give at least 25 million cells. Cells should not be split beyond 1:2-1:4 and should only be trypsinized 1x/week. Cells must be spun down after each typsinization. Flasks must be confluent at time of plating. Flasks were incubated at 37° C., 5% $CO_2$, 98% humidity. Cells can only be cultured for up to 10 passages before a new vial will need to be thawed.

Assay Timeline Overview:
Day 1: Cells are plated.
Day 2: Compounds are transferred into assay plates with Echo (24 hours post-seeding)
Day 3: Begin preparing reagents for fixation and staining.
Day 4: Plates are fixed and stained (48 hour treatment time) on automated system and subsequently imaged on Opera Phenix.
Day 5: Data analysis and reporting is performed.

Plate Preparation:
Barcoded Cell Carrier 384 Ultra plates with compound management's VCode Barcoder. Coated plates with Synthemax II Substrate using Multidrop Combi in Room 3052A with designated Combi cassette. Resuspended powder in 10 ml of sterile water (1 mg/ml stock). Diluted 10 ml stock by adding 390 ml sterile water for 400 ml total (0.25 mg/ml final conc.). Dispensed 30 μl per well (Thoroughly rinsed Combi cassettes with 70% Ethanol followed by Sterile Water before and after every use). Incubated at RT for two hours in hood. Flicked out Synthemax II and blot plates on KIMwipes prior to seeding. Plates may be stored at 4° C. for up to 3 months or used immediately for seeding cells. Seal up stored plates well so they remain sterile.

Day 1: Cell plating (Done in 3052A Tissue Culture Hood w/Combi):
Calculated cell number needed and media volume needed for the run (MAX 20 plates/run). Cells were seeded into Synthemax-coated 384-well Cell Carrier plates at a density of 12,000 cells/well in 40 ul of Renal Life Media/well. Calculated for an extra 2-3 plate volumes to account for volume needed to fill the Combi cassette lines and left dead volume of cell suspension. (20 ul added with Combi after compound addition for total 60 ul assay volume, due to volume constraints of Echo transfer process). Trypsinized cells with 3 ml/T175 flask of TrypLE™ Express Enzyme 1X. Then spun down cells and resuspend in 10 ml media. Counted the cells using Nexcelom Cellometer K2. Prepared a mixture of 20 ul cell suspension/20 ul Cellometer AOPI Stain (#CS2-0106) and then add 20 ul of the 2 fold diluted mixture onto a Cellometer slide. Counted the cells by using the Dual Stain option and following the prompts. Recorded the live cell density, viability, and current passage number and date in notebook. Used the live cell density in calculating how to prepare the cell seeding suspension. Mixed the cell suspension thoroughly but gently. Once Combi cassette cleaned and cell suspension was made, dispensed 40 ul of cell suspension per well into the Synthemax-coated Cell Carrier assay plates. Immediately after seeding, stored the assay plates in the Liconic Incubator on the enclosed system in the 3100 automation lab, spaced plates out every other slot in stackers to maximize air flow.

Day 2: Automated Echo Compound Transfer:

Generated Arxspan Run ID to record compound transfer in CBIP. Spun down compound plates and assay plates 2000 RPM 10 sec. Load assay plates into Echo system incubator. Coordinated plate locations and record RUN ID with automation team member. Ran protocol for 100 nl transfer according to designated plate layout/template. When run was completed, added 20 ul of media/well for all assay plates with Combi in hood in Tissue culture room. Returned plates to the incubator in the enclosed system for 48 hour treatment time.

Day 3/4: Fixation/staining reagent preparation:
Combi 1: Dilute PFA 32% to 4%

| Reagent | 1 Plate Volume (ml) |
|---|---|
| FORMALDEHYDE 16% SOL | 1.92 |
| 1XPBS | 13.44 |
| Total | 15.36 |

Combi 2: Dilute TritonX100 to 0.5%: Can be made in large batches (2 L) and store at room temp.

| Reagent | 1 Plate Volume (ml) |
|---|---|
| TritonX100 | 0.0768 |
| 1XPBS | 15.283 |
| Total | 15.36 |

Combi 3: Prepare Roche Block: 1 Liter=54 plates

| Reagent | 1 L Amount |
|---|---|
| 1M Tris | 100 ml |
| 5M NaCl | 30 ml |
| Roche Powder | 5 g |
| DI Water | 870 ml |
| Total | 1000 ml |

Heated up solution (100° C. on stir plate) and dissolved Roche Blocking reagent by stirring. The resulting solution was cloudy. Stored at 4° C. and used within one week or froze aliquots at −20° C. Combi 4: 1° Antibody Cocktail: Prepared the day of experiment. Swirled to mix. Do not shake to avoid damaging the antibody or causing bubbles in the Combi lines. Prepared solution in Corning 250 ml conical flask and covered with tinfoil to protect from light.

| Reagent | Dilution | 1 Plate Volume |
|---|---|---|
| 1° Antibody: mutant VNTR selective AbD22655.2 | 1:500 | 23 µl |
| 1° Antibody: WT Muc1 214D4 | 1:2000 | 5.75 µl |
| 1° Antibody: Anti-NUCB1 | 1:500 | 23 µl |
| Roche Block | | 11.5 ml |
| Total | | 11.5 ml |

Combi 5: 2° Antibody Cocktail: Prepared the day of experiment. Swirlrf to mix. Do not shake to avoid damaging the antibody or causing bubbles in the Combi lines. Prepared solution in Corning 250 ml conical flask and covered with tinfoil to protect from light.

| Reagent | Dilution | 1 Plate Volume |
|---|---|---|
| 2° anti-human 488 [bottle] | 1:1000 | 11.5 µl |
| 2° Alexa Fluor 647 goat anti-Rb | 1:1000 | 11.5 µl |
| 2° Alexa Fluor anti-mu 546 | 1:1000 | 11.5 µl |
| Hoechst 33342 | 1:1000 | 11.5 µl |
| Roche Block | | 11.5 µl |
| Total | | 11.5 µl |

Day 4: Setting Up Automated Run:

Attached all reagent designated Combi cassettes to their designated Combis. Set up all reagent bottles next to designated Combi and prime the cassettes with fluid. Both Antibody cocktails needed to be set up on magnetic stir plates. Placed the magnetic stir bars into each solution and brung to a gentle stir. Then primed the cassette lines.

Day 4: Run Automated Fixation and Staining Protocol

Automation protocol consisted of the following steps:
Fix Cells with 4% PFA

Removed media using BioTek plate washer. (PEKASP62) Moved plates to Combi. Combi 1. Dispensed 40 µl of 4% PFA (Combi on MEDIUM Speed). Incubated plates 20 minutes. Washed two times on BioTek plate washer. (PEK26X2)

Permeabilization, Blocking and Staining

Moved plates to Combi. Combi 2. Dispensed 40 µl of 0.5% Triton designated by plate maps (Combi on MEDIUM Speed). Incubated for 10 min at RT. Washed 1× with PBS (PEK26). Dispensed 40 µl Roche Block. Combi 3 (Combi on MEDIUM Speed). Incubated room temperature for 10 min. Aspirated block on BioTek plate washer (PEKASP62). Dispensed 30 µl of 1° Ab in dilutions according to plate maps in Roche Block Combi 4 (Combi on MEDIUM Speed). Incubated for 1.5 hours at room temperature. Protected from light. Ran a maintenance wash with PBS in between steps. Washed 5× with PBS using BioTek plate washer (PEK26X4). Dispensed 30 µl secondary antibody solution Combi 4 (Combi on MEDIUM Speed). Incubated at room temperature for 45 min. Protected from light. Ran a maintenance wash with PBS in between steps. Washed 5× with PBS using BioTek plate washer (PEK4F). Sealed with plate loc. (169° C., 1.9S).

Day 4/5: Plate Imaging and Analysis: Fluorescence Image Acquisition

All fluorescence imaging performed in this study was done using the Opera Phenix High-Content Screening System (HH14000000, PerkinElmer). For fluorescence imaging of cells (live cell or fixed cell imaging), CellCarrier Ultra microplates (6055302, Perkin Elmer) were used, and a minimum of nine fields was acquired per well using 20× or 63× water immersion objectives in a confocal mode. Image analysis for all imaging experiments was performed using Harmony software (PerkinElmer). Cell nuclei were first identified using the DAPI channel, and cell number was calculated. Cytoplasmic regions were then detected in individual cells based on all combined channels and eliminating the nucleus area. Subsequently, the total signal intensity value for each fluorophore was calculated separately in the cell cytoplasm and the average signal per cell was calculated for each well.

| Compound No | STRUCTURE | FS MUC1 Spot Cytoplasm Avg IC50 | FS MUC1 Spot Cytoplasm Avg Emax | NUCB1 Intensity Avg EC50 | NUCB1 Intensity Avg Emax |
|---|---|---|---|---|---|
| 251 | Single enantiomer* | 0.2405 | −72.07 | | |
| 252 | Single enantiomer* | 7.8324 | −86.32 | 11.21 | −72.37 |
| 242 | Racemic | 2.4338 | −67.4 | 4.93 | −85.46 |
| 253 | Racemic | *8.5785 | −52.28 | 32 | −21.51 |
| 254 | Racemic | 8.5211 | −69.07 | | |
| 255 | Racemic | 8.2526 | −67.5 | | |

-continued

| Compound No | STRUCTURE | FS MUC1 Spot Cytoplasm Avg IC50 | FS MUC1 Spot Cytoplasm Avg Emax | NUCB1 Intensity Avg EC50 | NUCB1 Intensity Avg Emax |
|---|---|---|---|---|---|
| 256 | 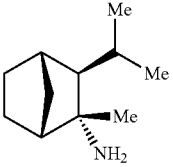 Racemic | 6.4451 | −65.11 | | |
| 257 | 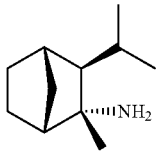 Single enantiomer* | 0.0969 | −74.94 | | |
| 258 | 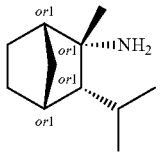 Single enantiomer* | 5.8717 | −67.73 | 9.77 | −89.37 |
| 259 | 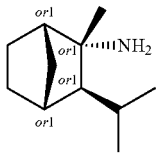 Racemic | 2.9396 | −59.03 | 14.61 | −53 |

*Absolute stereochemistry not known.

Example 4: Pharmacodynamic Study to Evaluate the Effect of Exemplary Compounds on the Clearance of Misfolded MUC1 Protein from the Kidney of Transgenic C57BL/6 Mice A frameshift in the MUC1 gene causes mucin 1 kidney disease (MKD). The human wild type MUC1 gene or a variant with a frameshift mutation have been introduced into the C57BL/6 mice. The transgenic mice carrying the frameshift mutations accumulate misfolded MUC1-fs protein in their kidneys, resulting in a kidney disease similar to MKD in humans.

BRD4780 treatment of C57BL/6 MUC1-fs knock-in mice results in the clearance of MUC1-fs at 50 mg/kg, oral dosing, once a day for 7 days (Dvela-Levitt M. et al., 2019, Cell 178, 521-535).

Compounds 1 to 6 (below) had in vitro cellular potencies in the range of 10-50 nM. (see Table A below)

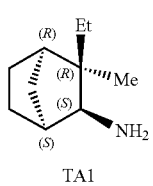

(203-P2)

TA1

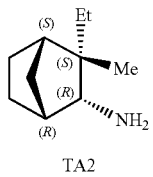

(203-P1)

TA2

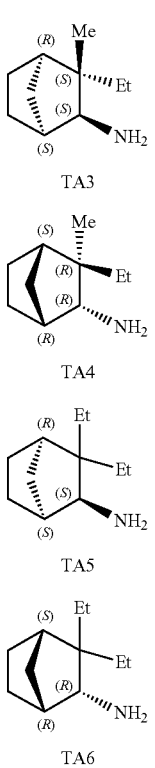

TA3 (202-P2)

TA4 (202-P1)

TA5 (204-P2)

TA6 (204-P1)

The above compounds were tested in MUC1-fs knock-in mice for clearance of mutant MUC1-fs protein from the kidneys at oral doses of 10, 3 and 1 mg/kg.

After 7-day treatment of C57BL/6 MUC1-fs mice by oral gavage once a day, test compounds showed an efficacious effect on MUC1-fs removal. At a 10 mg/kg dose, kidney lysates analyzed by western blots showed a complete removal to partial removal of MUC1-fs, depending on the compound. At a 3 or 1 mg/kg dose, removal of MUC1-fs was also observed, but to a lesser degree (see Western Blots images FIG. 1).

These compounds showed excellent in vitro cellular potency and in vivo efficacy on a mg/kg dose basis. The clearance of MUC1-fs by the test compounds was dose-dependent.

Results

TABLE A in vitro cellular potency of TA compounds determined in P cells

| Compound ID | in vitro potency (nM) |
| --- | --- |
| TA1 | 46 |
| TA2 | 40 |
| TA3 | 14 |
| TA4 | 26 |

Conclusion

These studies demonstrated:
Test compounds showed excellent in vitro cell potency of approximately 10-50 nM
Test compounds cleared MUC1-fs misfolded protein from mice kidneys at low doses (10, 3 and 1 mg/kg)
Test compounds cleared MUC1-fs from mice kidney in a dose-dependent manner Study Design Fifty-two MUC1-fs mutant C57BL/6 mice were divided into fourteen groups of four mice as shown in Table B. Groups 1 to 13 were treated with TA1, 2, 3, or 4, once daily for 7 days at doses of 1, 3, or 10 mg/kg as shown in Table 1. Group 13 was administered the vehicle as a control group. On Day 7, all mice were sacrificed at 4 h post-dose and EDTA plasma prepared and both kidneys were harvested; plasma was stored at −80° C. until shipped for bioanalysis. One kidney was processed immediately to lysate for Western blot.

Kidney lysates were prepared and analyzed by Western blot for MUC1-fs and wt MUC1.

TABLE B

| Group | Number of Animals | Treatment | Dose (mg/kg) | Treatment Schedule[1] | Route[2] | Day 7 collection: time post-last dose (h) |
| --- | --- | --- | --- | --- | --- | --- |
| 1 | 4 (Male) C57BL/6 MUC1-fs | TA1 (203-P2) | 10 | qd Days 1-7 | PO | 4 |
| 2 | 4 (Male) C57BL/6 MUC1-fs | TA1 (203-P2) | 3 | qd Days 1-7 | PO | 4 |
| 3 | 4 (Male) C57BL/6 MUC1-fs | TA1 (203-P2) | 1 | qd Days 1-7 | PO | 4 |
| 4 | 4 (Male) C57BL/6 MUC1-fs | TA2 (203-P1) | 10 | qd Days 1-7 | PO | 4 |
| 5 | 4 (Male) C57BL/6 MUC1-fs | TA2 (203-P1) | 3 | qd Days 1-7 | PO | 4 |
| 6 | 4 (Male) C57BL/6 MUC1-fs | TA2 (203-P1) | 1 | qd Days 1-7 | PO | 4 |
| 7 | 4 (Male) C57BL/6 MUC1-fs | TA3 (202-P2) | 10 | qd Days 1-7 | PO | 4 |
| 8 | 4 (Male) C57BL/6 MUC1-fs | TA3 (202-P2) | 3 | qd Days 1-7 | PO | 4 |

TABLE B-continued

| Group | Number of Animals | Treatment | Dose (mg/kg) | Treatment Schedule[1] | Route[2] | Day 7 collection: time post-last dose (h) |
|---|---|---|---|---|---|---|
| 9 | 4 (Male) C57BL/6 MUC1-fs | TA3 (202-P2) | 1 | qd Days 1-7 | PO | 4 |
| 10 | 4 (Male) C57BL/6 MUC1-fs | TA4 (202-P1) | 10 | qd Days 1-7 | PO | 4 |
| 11 | 4 (Male) C57BL/6 MUC1-fs | TA4 (202-P1) | 3 | qd Days 1-7 | PO | 4 |
| 12 | 4 (Male) C57BL/6 MUC1-fs | TA4 (202-P1) | 1 | qd Days 1-7 | PO | 4 |
| 13 | 4 (Male) C57BL/6 MUC1-fs | Vehicle | 0 | qd Days 1-7 | PO | 4 |

[1]qd = once a day;
[2]PO = oral gavage;
(h) = hours

Body Weights

Animal body weights was measured at D0 pre-dose, at D3 and D7 post-dose. If animals lost more than 10% body weight during the dosing period, compound dosing was halted.

Clinical Observations/Signs

Animals were observed daily for significant clinical signs, moribundity and mortality.

Animals Found Dead or Moribund

Percentage of animal mortality and time to death was recorded for every animal on the study. Moribund animals were sacrificed if they show prolonged or excessive pain or distress as defined by clinical observations such as: prostrate, hunched posture, paralysis/paresis, distended abdomen, diarrhea, seizures and/or hemorrhages. Plasma and kidneys were harvested and processed as described in the Materials and Methods section.

Materials And Methods

Test System

Species/strain: C57BL/6 mice: MUC1-fs
Physiological state: normal
Age/weight range at start of study: Animals aged 8-10 weeks
Number/sex of animals: 52/male
Identification: Ear Notch
Randomization: Animals were randomized prior to assignment to treatment groups
Justification: Standard Protocol
Replacement: Animals were not replaced during course of the study Animal Housing and Environment Housing: Microisolator cage system.
Acclimation: 2 days minimum
Environmental conditions: 12-hour light cycle at 21-22° C. (70-72° F.) and 40%-60% humidity.
Food/water: ad libitum Test Agent Identity and lot number: TA1, TA2, TA3, and TA4; lot # 01 for all compounds
Storage conditions: 4° C.
Stability/expiration date: Stable when refrigerated and at room temperature for few hours Test compounds were prepared daily by dissolving the right amount of compounds in the adequate volume of Vehicle, 5% dextrose:95% water solution Administration of Test Agents Route and method of administration: oral gavage (PO)
Justification for route of previous oral gavage PK information is available, administration: and it is also the intended route of administration in clinical trial
Frequency and duration of dosing: qd (once a day), for 7 consecutive days
Administered doses: 1, 3, or 10 mg/kg
Administered volume(s): 10 mL/kg, adjusted per animal weight
Justification for dose levels: To establish an optimal dose profile in this model Kidney and Lysate Processing for Western Blot Analysis of Muc1-fs Protein Abundance Before extraction of the kidneys, the mice were quickly perfused with 100 mM PBS pH 7.4 to flush the blood. For each mouse, one kidney was processed immediately to lysate. Freshly harvested kidneys were put on ice and immediatley processed for lysate. Kidney tissues were lysed by tissue homogenizer (Tissue-Tearor™, BioSpec Products) in lysing buffer solution (Cell Signaling Technology) containing protease inhibitors (Roche) and phosphatase inhibitors (Roche); homogenates were incubated for 20 min at 4° C. on a shaking or rocking table, before centrifugation at 16,000 g at 4° C. for 5 min. To normalize the protein concentration, proteins from kidney lysate supernatants were quantified using the Pierce BCA Protein Assay Kit (Thermo Fisher Scientific).

SDS-PAGE Gel Electrophoresis and Western Blot

General Information:
This assay was developed to quantify MUC1-WT and MUC1-fs proteins in mouse kidney lysate samples.

Materials and Equipment:

Cell Lines
N and P cells

Compounds
Test article compounds

Reagents
Primary antibody: Anti-MUC1/episialin Antibody, clone 214D4: Millipore Sigma, Cat. #05-652-KC Primary antibody: Anti-MUC1-fs clone ABD22655-Lot9, BioRad
Secondary Antibodies: V5 Tag Monoclonal Antibody: Invitrogen, Cat. #R96025
Tertiary Antibodies: IRDye® 800CW Goat anti-Mouse IgG Secondary Antibody: Li-Cor, Cat. #926-32210
Anti-β-Actin primary antibody will be used as internal control
Pierce™ BCA Protein Assay Kit: Thermo Scientific, Cat. #23225
NuPAGE™ Sample Reducing Agent (10×): Invitrogen, Cat. #NP0009
NuPAGE™ LDS Sample Buffer (4×): Invitrogen, Cat. #NP0007
NuPAGE™ 3 to 8%, Tris-Acetate, 1.0 mm, Mini Protein Gel, 12-well: Invitrogen, Cat. #EA03752BOX
iBlot™ Transfer Stack, nitrocellulose, regular size: Invitrogen, Cat. #IB23001
Phosphate Buffered Saline (PBS): Gibco, Cat. #10010-023
Tween™ 20: Fisher BioReagents, BP337-100

Equipment
Mini Gel Tank: Life Technologies, Cat. #A25977
iBlot 2 Dry Blotting System
Li-Cor Odyssey Experimental procedure:
Sample Preparation
1. Mouse kidney lysates were thawed on ice prior to BCA and western blot sample preparation
2. Total protein concentration was quantified using Pierce BCA kit
3. Samples were prepared such that 20 ug of protein is added per lane of gel
   a. NuPage Sample Reducing Agent 1× final concentration
   b. NuPage LDS Sample Buffer 1× final concentration
   c. Cell Culture grade water used as diluent
4. Samples and corresponding ladder added to 3-8% Tris-Acetate gels
   a. MUC1-fs expected protein bands are ~100-170 kDa
      i. Chameleon® Duo Pre-stained Protein Ladder
   b. MUC1-WT expected ~260 kDa
      i. HiMark™ Pre-stained Protein Standard
5. Gels were run according to specified time and voltage for protein of interest
   a. MUC1-fs run at 125V for 45 minutes or until loading dye reaches bottom of gel
   b. MUC1-WT run at 150V for 50 minutes or until separation of high kDa ladder reaches desired separation
6. Gels were loaded on to iBlot 2 transfer apparatus
   a. P0 protocol used for MUC1-fs
   b. P3 protocol extended to 9 minutes for MUC1-WT
7. Nitrocellulose membranes were cut and briefly washed with PBS+0.05% Tween-20
8. Membranes were blocked in 5% non-fat milk in PBS+0.05% Tween-20 for 1-2 hours at RT or overnight at 4° C.
9. Washes were performed 3× with PBS+0.05% Tween-20, ~5 minutes per wash
10. Primary Antibodies were diluted in 5% non-fat milk in PBS+0.05% Tween-20 overnight at 4° C.
    a. MUC1-fs: 2.5 ug/mL lot 9
    b. MUC1-WT: 1 ug/mL Anti-MUC1/episialin Antibody, clone 214D4
11. Washes were performed 3× with PBS+0.05% Tween-20, ~5 minutes per wash
12. Secondary Antibodies were diluted in 5% non-fat milk in PBS+0.05% Tween-20
    a. MUC1-fs: 1:5000 anti-V5 tag
    b. MUC1-WT: IRDye® 800CW Goat anti-Mouse IgG Secondary Antibody: Li-Cor, Cat. #926-32210
13. Washes were performed 3× with PBS+0.05% Tween-20, ~5 minutes per wash
14. Tertiary Antibodies
    a. MUC1-fs: IRDye® 800CW Goat anti-Mouse IgG Secondary Antibody: Li-Cor, Cat. #926-32210
15. Washes were performed 3× with PBS+0.05% Tween-20, ~5 minutes per wash
16. Image on Li-Cor Odyssey
17. Export to Image Studio and Empiria Studio for band quantification

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A compound having a structure represented by formula IVo:

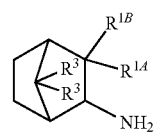

or a stereoisomer or pharmaceutically acceptable salt thereof, wherein:
$R^{1A}$ is ethyl and $R^{1B}$ is $C_{1-6}$ alkyl, $C_{2-6}$ alkenyl, or $C_{2-6}$ alkynyl; or
$R^{1A}$ is methyl and $R^{1B}$ is ethyl;
wherein $R^{1A}$ and $R^{1B}$ are each independently and optionally substituted with 1, 2, 3, 4, 5, or 6 deuterium or halogen atoms;
both instances of $R^3$ are H or are $C_{1-6}$ alkyl.

2. The compound of claim 1, wherein both instances of $R^3$ are H.

3. The compound of claim 1, wherein both $R^{1A}$ and $R^{1B}$ are ethyl.

4. The compound of claim 1, wherein $R^{1A}$ is methyl.

5. The compound of claim 1, wherein $R^{1A}$ is ethyl.

6. The compound of claim 1, wherein $R^{1A}$ is methyl and $R^{1B}$ is ethyl.

7. The compound of claim 1, wherein $R^{1A}$ and $R^{1B}$ are each independently substituted with 1, 2, or 3 deuterium or halogen atoms.

8. The compound of claim 1, wherein $R^{1A}$ and $R^{1B}$ are each unsubstituted.

9. The compound of claim 1, wherein the compound is represented by formula VIa or VIb:

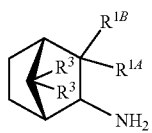

VIa

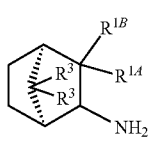

VIb or a pharmaceutically acceptable salt thereof.

10. The compound of claim 1, wherein the compound is represented by formula VIc or VId:

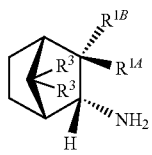

VIc

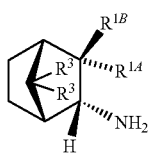

VId or a pharmaceutically acceptable salt thereof.

11. The compound of claim 1, wherein the compound is represented by formula VIe or VIf:

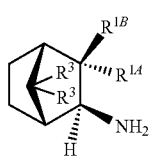

VIe

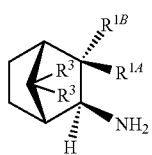

VIf or a pharmaceutically acceptable salt thereof.

12. The compound of claim 1, wherein the compound is represented by formula VIg or VIh:

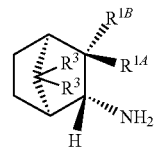

VIg

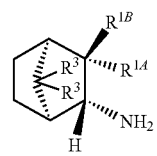

VIh or a pharmaceutically acceptable salt thereof.

13. The compound of claim 1, wherein the compound is represented by formula VIi or VIj:

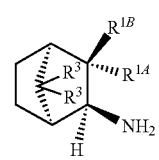

VIi

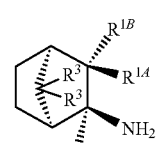

VIj or a pharmaceutically acceptable salt thereof.

14. A compound selected from:

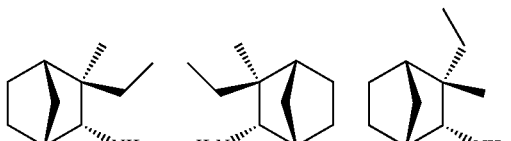

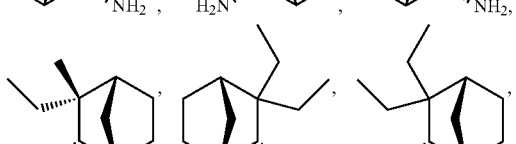

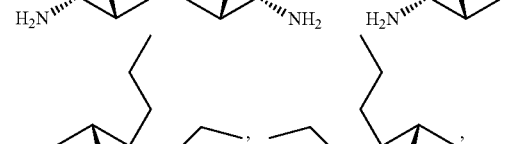

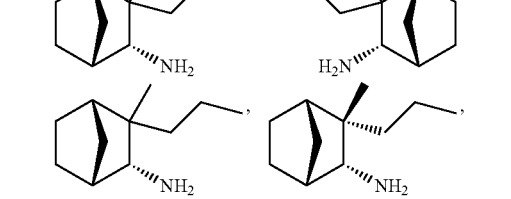

-continued

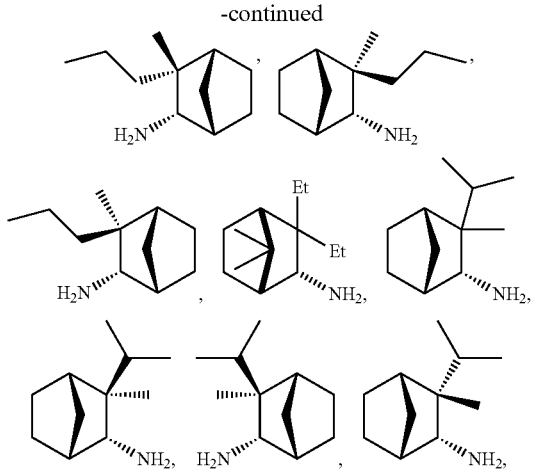

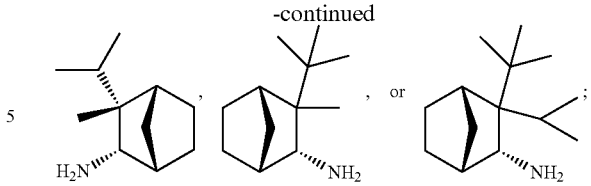

or a pharmaceutically acceptable salt thereof.

15. A pharmaceutical composition comprising a compound of claim 1, or a pharmaceutically acceptable salt thereof, and a pharmaceutically acceptable excipient.

16. A method of treating a disorder selected from a MUC1-associated kidney disease, retinitis pigmentosa, or a uromodulin kidney disease, in a subject in need thereof, comprising administering to the subject a compound of claim 1, or a pharmaceutically acceptable salt thereof.

* * * * *

UNITED STATES PATENT AND TRADEMARK OFFICE
CERTIFICATE OF CORRECTION

PATENT NO. : 11,840,495 B2
APPLICATION NO. : 17/560997
DATED : December 12, 2023
INVENTOR(S) : Brian T. Chamberlain et al.

Page 1 of 1

It is certified that error appears in the above-identified patent and that said Letters Patent is hereby corrected as shown below:

In the Claims

Columns 198, 199, 200, Lines 40-10, In Claim 1, Line 1, cancel the text beginning with "14. A compound selected from" to and ending "or a pharmaceutically acceptable salt thereof." and insert the following claim:

14. A compound selected from:

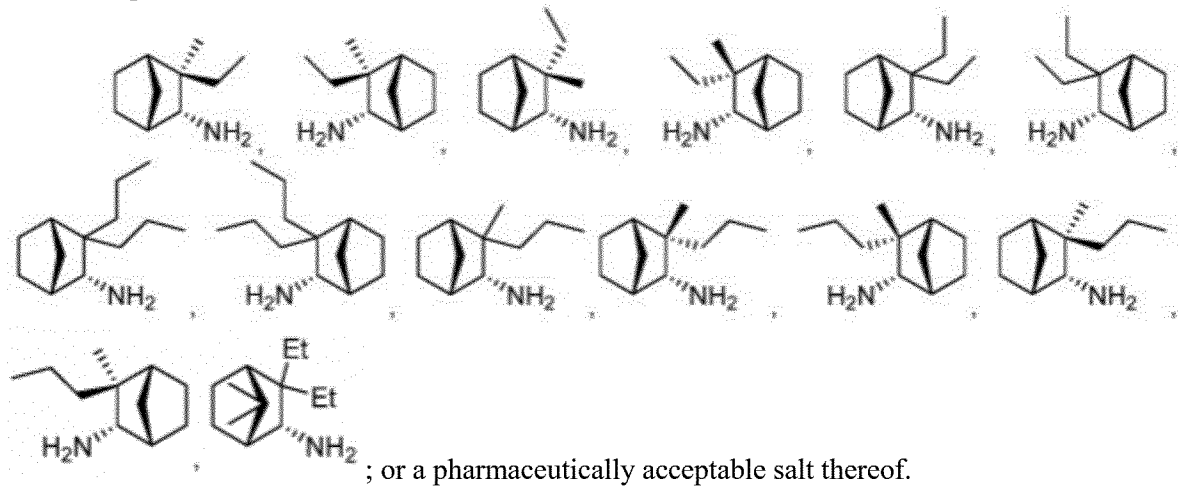

; or a pharmaceutically acceptable salt thereof.

Signed and Sealed this
Sixteenth Day of July, 2024

Katherine Kelly Vidal
*Director of the United States Patent and Trademark Office*